(12) United States Patent (10) Patent No.: US 7,935,704 B2
Palladino et al. (45) Date of Patent: May 3, 2011

(54) DEHYDROPHENYLAHISTINS AND ANALOGS THEREOF AND THE SYNTHESIS OF DEHYDROPHENYLAHISTINS AND ANALOGS THEREOF

(75) Inventors: Michael A. Palladino, Olivenhain, CA (US); George Kenneth Lloyd, Poway, CA (US); Yoshio Hayashi, Shiga (JP); Benjamin Nicholson, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 832 days.

(21) Appl. No.: 11/051,268

(22) Filed: Feb. 4, 2005

(65) Prior Publication Data

US 2005/0197344 A1 Sep. 8, 2005

Related U.S. Application Data

(63) Continuation-in-part of application No. 10/632,531, filed on Aug. 1, 2003, now Pat. No. 7,064,201.

(60) Provisional application No. 60/542,073, filed on Feb. 4, 2004, provisional application No. 60/624,262, filed on Nov. 1, 2004.

(51) Int. Cl.
*A61K 31/497* (2006.01)
(52) U.S. Cl. .......... 514/252.19; 514/253.09; 514/254.05
(58) Field of Classification Search .................. None
See application file for complete search history.

(56) References Cited

U.S. PATENT DOCUMENTS

| | | | |
|---|---|---|---|
| 5,607,934 A | 3/1997 | Tone et al. |
| 5,733,888 A | 3/1998 | Carver et al. |
| 5,852,018 A | 12/1998 | Bryans et al. |
| 5,874,443 A | 2/1999 | Kiely et al. |
| 5,886,210 A | 3/1999 | Rayle et al. |
| 5,891,877 A | 4/1999 | Brocchini et al. |
| 5,922,683 A | 7/1999 | Or et al. |
| 6,069,146 A | 5/2000 | Fenical et al. |
| 6,350,759 B1 | 2/2002 | Casara et al. |
| 6,358,957 B1 | 3/2002 | Fukumoto et al. |
| 6,500,825 B2 | 12/2002 | Lan et al. |
| 6,506,787 B2 | 1/2003 | Fujishita et al. |
| 6,509,331 B1 | 1/2003 | Audia et al. |
| 6,583,143 B2 | 6/2003 | Haddach |
| 6,713,480 B2 | 3/2004 | Fukumoto et al. |
| 6,972,289 B1 | 12/2005 | Kanzaki et al. |
| 7,026,322 B2 | 4/2006 | Hayashi et al. |
| 7,064,201 B2 | 6/2006 | Hayashi et al. |
| 7,674,903 B2 | 3/2010 | Hayashi et al. |
| 2002/0028819 A1 | 3/2002 | Teng et al. |
| 2002/0143021 A1 | 10/2002 | Fukumoto et al. |
| 2004/0102454 A1 | 5/2004 | Hayashi et al. |
| 2005/0090667 A1 | 4/2005 | Hayashi et al. |
| 2005/0197344 A1 | 9/2005 | Palladino et al. |
| 2006/0079953 A1 | 4/2006 | Kanzaki et al. |
| 2006/0167010 A1 | 7/2006 | Hayashi et al. |
| 2006/0217553 A1 | 9/2006 | Hayashi et al. |
| 2006/0223822 A1 * | 10/2006 | Hayashi et al. .......... 514/253.09 |
| 2006/0223823 A1 * | 10/2006 | Hayashi et al. .......... 514/253.09 |
| 2007/0078138 A1 * | 4/2007 | Palladino et al. ............. 514/249 |
| 2008/0221122 A1 | 9/2008 | Palladino et al. |

FOREIGN PATENT DOCUMENTS

| | | |
|---|---|---|
| CA | 2403790 | 7/2001 |
| EP | 0655060 B1 | 1/1998 |
| EP | 1 264 831 A1 | 11/2002 |
| GB | 2143823 | 2/1985 |
| JP | 5009164 | 1/1993 |
| JP | 10-130266 | 5/1998 |
| WO | WO 95/21832 | 8/1995 |
| WO | WO 96/20190 | 7/1996 |
| WO | WO 99/38844 | 8/1999 |
| WO | WO 99/48889 | 9/1999 |
| WO | WO 01/53290 | 7/2001 |
| WO | WO2004054498 | * 1/2004 |
| WO | WO 2004/054498 A2 | 7/2004 |
| WO | WO 2005/077940 | 8/2005 |

OTHER PUBLICATIONS

Dorwald F. A. Side Reactions in Organic Synthesis, 2005, Wiley: VCH, Weinheim p. IX of Preface.*
Cecil Textbook of Medicine, 21st Edition (2000), Goldman & Bennett (Editors), W.B. Saunders Company (Publisher), Chapter 198, pp. 1060-1074.*
Internal Medicine, 4th Edition, Editor-in-Chief Jay Stein, Chapters 71-72, pp. 699-715.*

(Continued)

*Primary Examiner* — James O Wilson
*Assistant Examiner* — Jeffrey H Murray
(74) *Attorney, Agent, or Firm* — Knobbe Martens Olson & Bear LLP

(57) ABSTRACT

Compounds represented by the following structure (I) are disclosed:

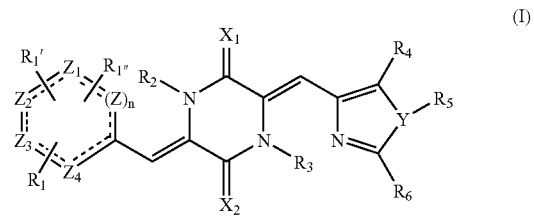

(I)

as are methods for making such compounds, wherein said methods comprise reacting a diacyldiketopiperazine with a first aldehyde to produce an intermediate compound; and reacting the intermediate compound with a second aldehyde to produce the class of compounds with the generic structure, where the first aldehyde and the second aldehydes are selected from the group consisting of an oxazolecarboxaldeyhyde, imidazolecarboxaldehyde, a benzaldehyde, imidazolecarboxaldehyde derivatives, and benzaldehyde derivatives, thereby forming the above compound wherein $R_1$, $R_1'$, $R_1''$, $R_2$, $R_3$, $R_4$, $R_5$, and $R_6$, $X_1$ and $X_2$, Y, Z, $Z_1$, $Z_2$, $Z_3$, and $Z_4$ may each be separately defined in a manner consistent with the accompanying description. Compositions and methods for treating vascular proliferation are also disclosed.

7 Claims, 58 Drawing Sheets

OTHER PUBLICATIONS http://scienceandresearch.homeoffice.gov.uk/animal-research/publications-and-reference/001-abstracts/abstracts2-2006/02november-2006/457?view=Html; "Abstract #457, Animals in Scientific Procedures (2006)." (accessed on Nov. 19, 2008.).*
Mahindroo, et. al., Expert Opin. Ther. Patents (2006) 16(5), 647-691.*
Abstracts of The 1999 Joint Chubu and Kansai Branch Conference and Symposium of Japan Society for Bioscience, Biotechnology, and Agrochemistry, p. 48 (1999) (in Japanese).
Abstracts of The 1999 Joint Chubu and Kansai Branch Conference and Symposium of Japan Society for Bioscience, Biotechnology, and Agrochemistry, p. 48 (1999) (translated to English).
Akerlund et al., "Diketopiperazine-Based Polymers from Common Amino Acids," Journal of Applied Polymer Science (2000), 78 (12), 2213-2218.
Amendment and Response to Written Opinion submitted in International Application No. PCT/US03/024232 on Jan. 20, 2005.
Augustin, M. "Die Umsetzung des 2,5-Diketopiperazins mit Aldehyden und Nitrosoverbindungen" Journal für Praktische Chemie, vol. 32(4) pp. 158-166 (1966).
European Supplementary Search Report dated Oct. 11, 2005 for Application No. 00963011.2-2117 PCT/JP0006807.
Fukushima et al., "Biological Activities of Albonoursin," J. Antibiotics, 26: 175 (1973).
Goldfarb et al., "Synthesis of β-2-thienylalanine" Izvestiya Akademii Nauk SSSR, Seriya Khimicheskaya, pp. 98-100 (1958), as abstracted by CAPLUS.
Hayashi, et al., "Total Synthesis of Anti-microtubule Diketopiperazine Derivatives: Phenylahistin and Aurantiamine," J. Org. Chem. 2000, 65: 8402-8405.
Hyun, et al., "Valine dehydrogenase from Streptomyces albus: gene cloning, heterologous expression and identification of active site by site-directed mutagenesis," FEMS Microbiology Letters 182 (2000) 29-34.
International Search Report, International Application No. PCT/US03/24232, Sep. 27, 2004.
Kanoh et al., "(−)-Phenylahistin: A New Mammalian Cell Cycle Inhibitor Produced by Aspergillus USTUS," Bioorganic & Medicinal Chemistry Letters, 7: 2847-2852 (1997).
Kanoh et al., "Synthesis and Biological Activities of Phenylahistin Derivatives," Bioorganic & Medicinal Chemistry, 7: 1451-1457 (1999).
Kanoh et al., "Antitumor Activity of Phenylahistin in Vitro and in Vivo," Bioscience Biotechnology Biochemistry, 63: 1130-1133 (1999).
Kanoh et al., "(−)-Phenylahistin Arrests Cells in Mitosis by Inhibiting Tubulin Polymerization", The Journal of Antibiotics, 52: 134-141 (1999).
Kanzaki et al., A Novel Potent Cell Cycle Inhibitor Dehydrophenylahistin-Enzymatic Synthesis and Inhibitory Activity toward Sea Urchin Embryo, The Journal of Antibiotics, 55: 1042-1047 (Dec. 2002).
Kanzaki et al., "Effective Production of Dehydro Cyclic Dipeptide Albonoursin Exhibiting Pronuclear Fusion Inhibitory Activity, I. Taxonomy and Fermentation" The Journal of Antibiotics, 52: 1017-1022 (1999).
Kanzaki et al., "Effective Production of Dehydro Cyclic Dipeptide Albonoursin Exhibiting Pronuclear Fusion Inhibitory Activity, II. Biosynthetic and Bioconversion Studies" The Journal of Antibiotics, 53: 58-62 (2000).
Kanzaki, et al., "Novel Cyclic Dipeptide Dehydrogenase and Assay Method for Its Activity," Scientific Reports of the Faculty of Agriculture, Okayama University, 88:7-11 (1999). (in Japanese).
Kanzaki, et al., "Novel Cyclic Dipeptide Dehydrogenase and Assay Method for Its Activity," Scientific Reports of the Faculty of Agriculture, Okayama University, 88:7-11 (1999). (translated into English).
Kanzaki et al., "Enzymatic Synthesis of Physiologicall Actve Substances Utilizing a Novel System for the Synthesis of Diketopiperazines Comprising Dehydroamino Acids as Constituents" Abstracts of Papers Presented at the 1999 Meeting of the Society for Actinomycetes Japan, p. 42 (1999).

Kanzaki et al., "Enzymatic dehydrogenation of cyclo(L-Phe-L-Leu) to a bioactive derivative, albonoursin,"Journal of Molecular Catalysis B: Enzymatic 6 (1999) 265-270.
Kobayashi et al., "Microtubule Assembly Regulators of Microbial Origin" Abstract of Paper Read at the 1989 Symposium on the Chemistry of Natural Products, p. 51 (1989).
Kopple et al., "A Convenient Synthesis of 2,5-Piperazinediones1a," The Journal of Organic Chemistry, 33: 862-864 (1967).
Küster and Köppenhofer, "Über eininge Pyrrolderivate" Z. Physiol, Chem., vol. 172, pp. 126-137 (1927).
Lastly, Asahina, T. Bulletin of the Chemical Society of Japan, vol. 5, pp. 354-365 (1930).
Niemann et al, "The Synthesis of the Three Isomeric dl-β-Pyridylalanines" Journal of the American Chemical Society, vol. 64(7), pp. 1678-1682 (1942).
Nitecki et al., "A Simple Route to Sterically Pure Diketopiperazines1," The Journal of Organic Chemistry, 33: 864-866 (1968).
PCT International Preliminary Examination Report, International Application No. PCT/JP00/06807, Dec. 7, 2001.
PCT International Preliminary Report, International Application No. PCT/US2005/003636, mailed Aug. 17, 2006.
PCT International Search Report from PCT/US2005/003636, mailed Jul. 19, 2005.
"Prosecution History of U.S. Appl. No. 10/632,531."
"Prosecution History of U.S. Appl. No. 10/181,786."
Saito et al., Synthesis of novel octahydro-1, 5-imino-3-benzazocin-4, 7, 10-trione derivatives having a methyl group at the C-2 position as ABC ring models of saframycins. Chemical & Pharmaceutical Bulletin (1997), 45(7), 1120-1129.
Sezaki and Shoten, "Drug Delivery Systems", Drug Development, 13: 116, Table 2. 29, (Jul. 1989).
Yokio et al, "Neihumicin, A New Cytotoxic Antibiotic From Micromonospora Neihuensis" The Journal of Antibiotics, vol. 41(4), pp. 494-501 (Apr. 1988).
PCT International Search Report and Written Opinion from PCT/US2006/036736, mailed Feb. 5, 2007.
"Prosecution History as of Mar. 27, 2009 of U.S. Appl. No. 11/448,924, filed Jun. 7, 2006."
Office Action dated Oct. 19, 2009 for U.S. Appl. No. 11/448,924.
Office Action dated Jun. 15, 2009 for U.S. Appl. No. 11/524,772.
Office Action dated Nov. 27, 2009 for U.S. Appl. No. 11/524,772.
Notice of Allowance dated Oct. 19, 2009 for U.S. Appl. No. 11/448,948.
Cai, "Small molecule vascular disrupting agents: potential new drugs for cancer treatment." Recent Pat Anticancer Drug Discov. (2007) 2(1):79-101.
Ahmed et al. "A new rapid and simple non-radioactive assay to monitor and determine the proliferation of lymphocytes: an alternative to [$^3$ H]thymidine incorporation assay." J. Immunol. Methods. 170, 211-224 (1994).
Algaier et al. "The effects of dimethyl sulfoxide on the kinetics of tubulin assembly." Biochim. Biophys. Acta. 954, 235-43 (1988).
Ali et al. "Toxicity of echinulin from Aspergillus chevalieri in rabbits." Toxicology Letters. (1989) 48: 235-41.
Bergman et al., Ariloxy Substituted N-arylpiperazinones as Dual Inhibitors of Farnesyltransferase and Geranylgeranyltransferase-1, Bioorg & Med Chem Lttrs. (Mar. 2001) 11: 1411-1415.
Bond et al. "The Synthesis of Viridamine, a Penicillium Viridicatum Mycotoxin." Synthetic Commun. 19 (13&14), 2551-2566 (1989).
Borisy, G.G. "A Rapid Method for Quantitative Determination of Microtubule Protein using DEAE-Cellulose Filters." Anal. Biochem. 50, 373-385 (1972).
Burtles, Sally, "Transition from Preclinical to first-in-man Phase", Expert Scientific Group on Phase One Clinical Trials Final Report, Presentation Jun. 19, 2006, pp. 35-38.
Cai, Sui X., "Small Molecule Vascular Disrupting Agents: Potential New Drugs for Cancer Treatment", Recent Pat Anticancer Drug Discov. (2007) 2(1): 79-101.
Cui et al. "Novel Mammalian Cell Cycle Inhibitors, Tryprostatins A, B and Other Diketopiperazines Produced by Aspergillus fumigatus." J. Antibiotics. 49(6), 534-40 (1996).

Cui et al. "Novel Mammalian Cell Cycle Inhibitors, Tryprostatins A, B and Other Diketopiperazines Produced by *Aspergillus fumigatus*." J. Antibiotics. 49(6): 527-33 (1996).

Dandan et al., JP 5009164, Chemical Abstract 119: 8514 (1993).

Folkes et al., Synthesis and In Vitro Evaluation of a Series of Diketopiperazine Inhibitors of Plasminogen Activator Inhibitor-1, Bioorg & Med Chem Lttrs., (Jul. 2001) 11: 2589-2592.

Goldani et al. "Treatment of murine pulmonary mucormycosis with SCH 42427, a broad-spectrum triazole antifungal drug", Correspondence, J Antimicrob Chemother. 33, 369-372 (1994).

Gordon et al. "Reductive Alkylation on a Solid Phase: Synthesis of a Piperazinedione Combinatorial Library." J. Bioorg. Med. Chem. Letters. 5, 47-50 (1995).

Gura, Trisha, "Cancer Models: Systems for Identifying New Drugs are Often Faulty", Science 7(Nov. 1997) 278(5340): 1041-1042.

Hamel, E. "Antimitotic Natural Products and Their Interactions with Tubulin." Med. Res. Rev. (1996) 16(2): 207-31.

Hartwell et al. "Checkpoints: Controls that Ensure the Order of Cell Cycle Events." Science. 246, 629-34 (1989).

Horak et al. "Structures of the Austalides A-E, Five Novel Toxic Metabolites from *Aspergillus ustus*." J Chem Soc Chem Commun. (1981) 1265-67.

International Search Report dated Oct. 25, 2004 from Application No. PCT/US04/024940, filed Jul. 29, 2004.

International Preliminary Report on Patentability and Written Opinion dated Nov. 16, 2005 from Application No. PCT/US2004/024940, filed Jul. 29, 2004.

International Preliminary Report on Patentability and Written Opinion dated Mar. 26, 2008 from PCT/US2006/036736, filed Sep. 20, 2006.

International Search Report dated Dec. 6, 2006 from PCT/US2006/011206, filed Mar. 27, 2006.

Iwasaki, S. "Antimitotic Agents: Chemistry and Recognition of Tubulin Molecule." Med Res Rev. (1993) 13: 183-198.

Iwasaki, S. "Bioactive Natural Products Interfering with Microtubule Function." Kagaku to Seibutsu. 32(3): 153-159 (1994).

Johnson et al. "Kinetic Analysis of Microtubule Self-assembly in Vitro." *J. Mol. Biol.* 117, 1-31 (1977).

Kamb, Alexander, "What's wrong with our cancer models?", Nature Reviews Drug Discovery (Feb. 2005) 4: 161-165.

Keepers et al. "Comparison of the Sulforhodamine B Protein and Tetrazolium (MTT) Assays for in vitro Chemosensitivity Testing." Eur. J. Cancer. 27, 897-900 (1991).

Kim et al. "Polymer attached cyclic peptides, tetrahedron: Asymmetry." 3(11):1421-1430 (1992).

Kola et al., "Can the pharmaceutical industry reduce attrition rates?", Nature Reviews Drug Discovery (2004) 3: 711-715.

Kondoh et al. "Effects of Tryprostatin Derivatives on Microtubule Assembly In Viro and In Situ." J. Antibiotics. 51, 801-04 (1998).

Krishan, A. "Rapid Flow Cytofluorometric Analysis of Mammalian Cell Cycle by Propidium Iodide Staining." J. Cell Biol. 66, 188-193 (1975).

Kupchan et al. "Steganacin and Steganangin, Novel Antileukemic Lignan Lactones from *Steganotaenia araliacea* 1-3." J. Am. Chem. Soc. (1973) 95(4): 1335-36.

Lacey et al. "Interaction of Phomopsin A and Related Compounds with Purified Sheep Brain Tubulin." Biochem. Pharmacol. 36, 2133-38 (1987).

Laemmli, U.K. "Cleavage of Structural Proteins during the Assembly of the Head of Bacteriophage T4." Nature. 227, 680-85 (1970).

Larsen et al. "Aurantiamine, A Kiketopiperazine from Two Varieties of Penicillium Aurantiogriseum." Phytochemistry. 31, 1613-1615 (1992).

Leaf, Clifton, "Why are we losing the war on cancer (And how to win it)?", Health Administrator (2005) XVII(1): 172-183.

Lee et al. "The Reconstitution of Microtubules from Purified Calf Brain Tubulin." Biochemistr. 14(23), 5183-87 (1975).

Li, Y., et al. "Interaction of marine toxin dolastatin 10 with porcine brain tubulin: competitive inhibition of rhizoxin and phomopsin A binding." Chem. Biol. Interact. 93, 175-83 (1994).

Liwo et al. "Origin of the Ring-Ring Interaction in Cyclic Dipeptides Incorporating an Aromatic Amino Acid." Tetrahedron Lett. 26, 1873-1876 (1985).

Luduena, R.F. "Contrasting Roles of Tau and Microtubule-associated Protein 2 in the Vinblastine-induced Aggregation of Brain Tubulin." J. Biol. Chem. 259:12890-98 (1984).

Neidle, Stephen, ed., Cancer Drug Design and Discovery, 9th Edition, Elsevier/Academic Press, (2008) Chapter 18, pp. 427-431.

Pettit et al. "Antineoplastic Agents. 291. Isolation and Synthesis of Combretastatins A-4, A-5, and A-6 1a." J. Med. Chem. (1995) 38: 1666-1672.

Prosecution History of U.S. Appl. No. 11/448,924, filed Jun. 7, 2006 as of Sep. 1, 2010.

Prosecution History of U.S. Appl. No. 11/934,677, filed Nov. 2, 2007 as of Aug. 30, 2010.

Prosecution History of U.S. Appl. No. 11/524,772, filed Sep. 20, 2006 as of Jul. 15, 2010.

Roberge et al. "Antitumor Drug Fostriecin Inhibits the Mitotic Entry Checkpoint and Protein Phospatases 1 and 2A." Cancer Res. 54, 6115-21 (1994).

Roberts et al, "Trends in the Risks and Benefits to Patients with Cancer Participating in Phase 12 Clinical Trials", JAMA (2004) 292(17): 2130-2140.

Rowinski et al. "Taxol: A Novel Investigational Antimicrotubule Agent." J. Natl. Cancer Inst. 82(15): 1247-59 (1990).

Sackett, D.L. "Podophyllotoxin, Steganacin and Combretastatin: Natural Products that Bind at the Colchicine Site of Tubulin." Pharmacol. Ther. (1993) 59: 163-228.

Sherline et al. "Binding of Colchicine to Purifiied Microtubule Protein." J. Biol. Chem. 250, 5481-86 (1975).

Siwicka et al., "Diastereodivergent Synthesis of 2,5-diketopiperazine Derivatives of Beta-Carboline and Isoquinoline from L-amino Acids," Tetrahedron: Asymmetry (Mar. 7, 2005) 16(5): 975-993.

Smedsgaard et al. "Using direct electrospray mass spectrometry in taxonomy and secondary metabolite profiling of crude fungal extracts." J. Microbiol. Meth. (1996) 25: 5-17.

Sölter et al., Barettin, Revisited? Tetrahed Lttrs. (Mar. 2002) 43: 3385-3386.

Steyn, P.S. "The Structures of Five Diketopiperazines from *Aspergillus ustus*." Tetrahedron. 29, 107-120 (1973).

Sugar et al. "Comparison of Three Methods of Antifungal Susceptibility Testing with the Proposed NCCLS Standard Broth Macrodilution Assay: Lack of Effect of Phenol Red." Diagn Micro and Infect Diseases. 21, 129-133 (1995).

Takahashi et al. "Rhizoxin binding to tubulin at the maytansine-binding site." Biochim. Biophys. Acta. 926, 215-23 (1987).

Tiwari et al. "A pH- and Temperature-Dependent Cycling Method that doubles the Yield of Microtubule Protein." Anal. Biochem. 215, 96-103 (1993).

Turner et al. "Recent Advances in the Medicinal Chemistry of Antifungal Agents." Current Pharmaceutical Design. 2, 209-224 (1996).

Usui et al. "Tryprostatin A, a specific and novel inhibitor of microtubule assembly." Biochem J. 333, 543-48 (1998).

Van der Waerden, B.L., "Wirksamkeits- und Konzentrationsbestimmung durch Tierversuche." Arch Exp Pathol Pharmakol. 195, 389-412, (1940).

Verdier-Pinard et al., "Structure-Activity Analysis of the Interaction of Curacin A, the Potent Colchicine Site Antimitotic Agent, with Tubulin and Effects of Analogs on the Growth of MCF-7 breast Cancer Cells." Mol. Pharmacol., 53, 62-76 (1998).

Voskoglou-Nomikos et al., Clinical predictive value of the in vitro cell line, human xenograft, and mouse allograft preclinical cancer models, National Cancer Institute of Canada Clinical Trials Group et al., 2003, vol. 9, pp. 4227-4239.

Weisenberg et al. "The Colchicine-Binding Protein of Mammalian Brain and its Relation to Microtubules." Biochemistry (1968) 7(12): 4466-79.

Yahara et al. "Microtubule Organization of Lymphocytes and its Modulation by Patch and Cap Formation." Cell. 15, 251-259 (1978).

Yamazaki et al. "Crystal Structure and Absolute Configuration of Fumitremorgin B, a Tremorgenic Toxin from *Aspergillus Fumigatus* Fres." Tetrahedron Lett. 1, 27-28 (1975).

Yamori T., "A Human Cell Line Panel for Screening Anti-Cancer Drugs", Jap. J. Cancer Chemother. 24, 129-35 (1997).

Yoshida, M.M. Protein Nucleic Acid Enzymes. 38, 1753-1765 (1993).

Yoshimatsu et al. "Mechanism of Action of E7010, an Orally Active Sulfonamide Antitumor Agent: Inhibition of Mitosis by Binding to the Colchicine Site of Tubulin." Cancer Res. 57, 3208-13 (1997).

Zawadzka et al., "Diastereoselective Synthesis of 1-Benzyltetrahydroisoquinoline Derivatives from Amino Acids by 1,4 Chirality Transfer", Euro J Org Chem., (Jul. 2003) 2003(13): 2443-2453.

* cited by examiner

* p<0.01 vs Control
# p<0.05 vs CPT Alone
## p<0.01 vs CPT Alone

*p<0.05 vs Control ANOVA
**p<0.01 vs Control ANOVA
# p<0.05 vs CPT Alone t-test

\* p <0.05 vs Control
\*\* p <0.01 vs Control
\# p <0.05 vs CPT Alone
\#\# p <0.01 vs CPT Alone \* $p<0.05$ vs Control, ANOVA
\*\* $p<0.01$ vs Control, ANOVA
\# $p<0.05$ vs Taxotere alone, t-test
\+ $p<0.05$ vs Control t-test
\+\+ $p<0.01$ vs Control t-test \* $p<0.05$ vs Control, ANOVA
\*\* $p<0.01$ vs Control, ANOVA
\+ $p<0.05$ vs Control t-test
\+\+ $p<0.01$ vs Control t-test
\# $p<0.05$ vs Taxotere t-test
\#\# $p<0.01$ vs Taxotere t-test \*\* p<0.01 vs Control ANOVA
\# p<0.05 vs Control t-test
\#\# p<0.01 vs Control t-test
\+ p<0.05 vs Paclitaxel, t-test

FIGURE 35 Effect of KPU-02 on Tumor Blood Flow in the P22 Rat Sarcoma Model Using the $^{125}$I-IAP Technique FIGURE 36  Effect of KPU-02 15 mg/kg IP (Expressed as % Vehicle Control) on Blood Flow in Different Tissues 1 and 24 hours Post-Dose FIGURE 37  Tumor Necrosis Induced by KPU-02 7.5 and 15.0 mg/kg IP in the P22 Rat Sarcoma Model
1. KPU-02 7.5 mg/kg  2. KPU-02 15.0 mg/kg  3. Vehicle Control

Modification of the phenyl ring of KPU-2 (tBu-ΔPLH, NPI-2358)

R = Ph: IC$_{50}$ = 16.8 nM (KPU-2)

| compd. | R | IC$_{50}$ / HT-29 cells (nM) | compd. | R | IC$_{50}$ / HT-29 cells (nM) | compd. | R | IC$_{50}$ / HT-29 cells (nM) | compd. | R | IC$_{50}$ / HT-29 cells (nM) |
|---|---|---|---|---|---|---|---|---|---|---|---|
| 1 | | 75.5 ± 24.7 | 1 | | 819 | 1 | | 30 ± 16.5 | 3 | | 53.4 ± 4.85 |
| 2 | | 20.1 ± 8.54 | 1 | | 45.8 ± 11.5 | 2 | | 131 ± 45.2 | 3 | | 20.3 ± 2.12 |
| 3 | | 657 | 1 | | 46.7 ± 9.64 | 2 | | 501 ± 84.8 | 3 | | > 20000 |
| 4 | | 86 | 1 | | 483 ± 61.5 | 2 | | 46.3 ± 13.5 | 4 | | 103 ± 11.6 |
| 5 | | 508 | 1 | | 45.9 ± 10.2 | 2 | | 24.5 ± 8.73 | 4 | | 54 |
| 6 | | 97 | 1 | | 17.0 ± 1.52 | 2 | | 70 | 4 | | 149 ± 2.12 |
| 7 | | 517 | 1 | | 6160 ± 1230 | 2 | | 40.5 ± 10.9 | 4 | | 173 |
| 8 | | 202 | 1 | | 364 ± 187 | 2 | | 31.1 ± 7.29 | 4 | | 78.9 ± 14.1 |
| 9 | | 45.4 ± 12.1 | 1 | | 52 | 2 | | 71 | paclitaxel | | 16.2 ± 3.04 |

Compounds 20 (KPU-35), 34 (KPU-80) and 42 (KPU-66) showed potent anti-cytotoxic activity similar to paclitaxel.

FIGURE 39

3D-QSAR (CoMFA)

CoMFA Fields

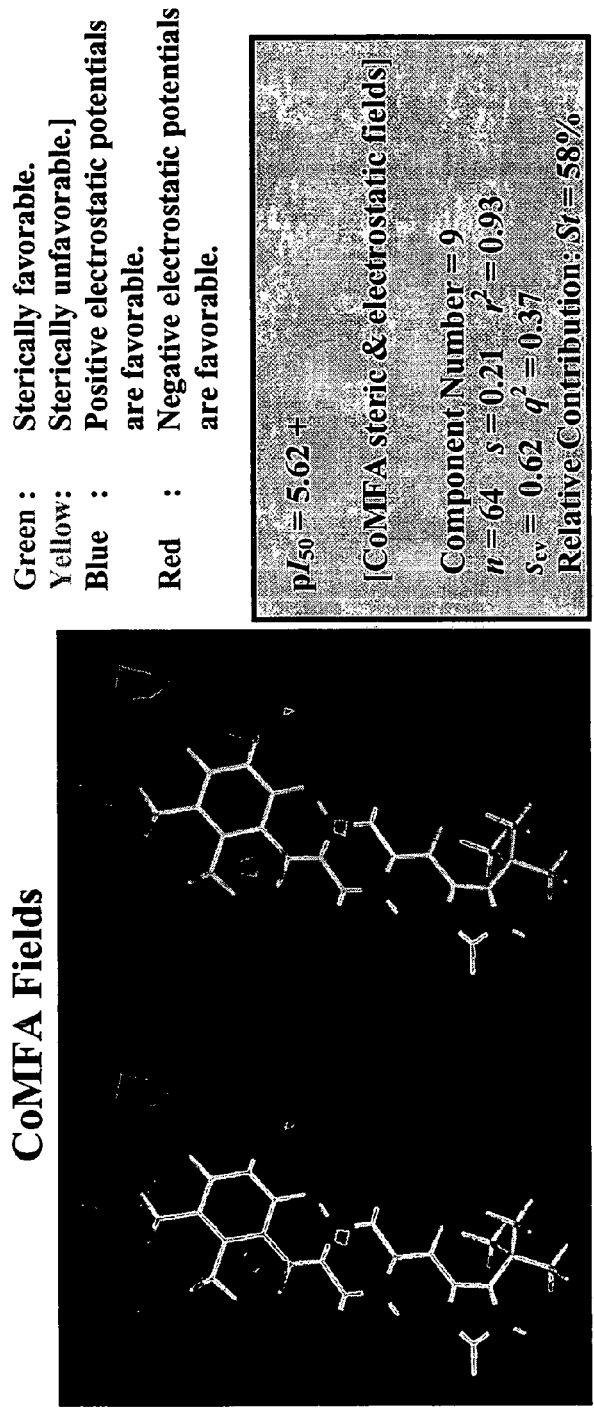

Green : Sterically favorable.
Yellow: Sterically unfavorable.
Blue : Positive electrostatic potentials are favorable.
Red : Negative electrostatic potentials are favorable.

$pI_{50} = 5.62 +$

[CoMFA steric & electrostatic fields]

Component Number = 9
$n = 64$   $s = 0.21$   $r^2 = 0.93$
$s_{cv} = 0.62$   $q^2 = 0.37$
Relative Contribution: $St = 58\%$
$El = 42\%$ Molecular Models : Structures of compounds were optimized by the molecular orbital method, PM3.
    Atomic charges:  Calculated by MNDO-ESP.

CoMFA: Carried out with the Advanced CoMFA module of SYBYL 6.8.
    Probe: C(sp$^3$) for the calculation of the steric Interaction potential.
    +1.0 charge for the calculation of the electrostatic potential.

FIGURE 41 Biological activity of phenylahistin derivatives

| compound | structure | IC₅₀ (μM) tubulin polymerization | IC₅₀ (nM, cytotoxicity) | | |
|---|---|---|---|---|---|
| | | | HT-29 | PC-3 | P- |
| (−)-PLH | | 31.3 | 394 | n.t. | 388 / 180 |
| ΔPLH | | 20.9 | 43 | 4.7 | 36 |
| KPU-2 (NPI-2358) | | 16.8 | 14.9 | 1.0 | 2.8 |
| colchicine | | 96.7 | n.t. | n.t. | 210 |

Cytoskeleton Immunofluorescence Staining of PC-3 Cells

Untreated     KPU-2 (1μM)     colchicine (1μM)

KPU-2 showed more potent activity than ΔPLH.

FIGURE 43

Effect of PLH derivatives on drug-sensitive and -resistant tumor cell lines

| compound | MES-SA uterine sarcoma cyclosporin pretreatment | | MES-SA/DX-5 (resistant) cyclosporin pretreatment | |
|---|---|---|---|---|
| | (−) | (+) | (−) | (+) |
| ΔPLH | 116 ± 15 | 114 ± 32 | 98 ± 24 | 88 ± 15 |
| KPU-2 | 34 ± 10 | 31 ± 5 | 23 ± 7 | 38 ± 2 |
| paclitaxel | 13 ± 4 | 8 ± 1 | >100 | 27 ± 2 |

FIGURE 46A
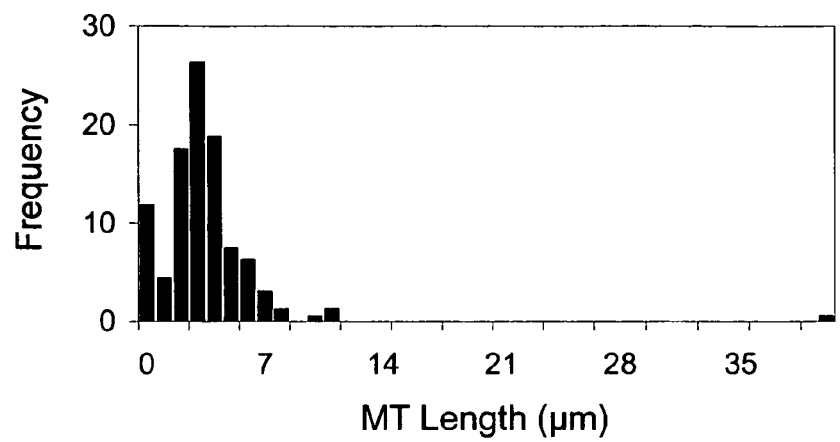
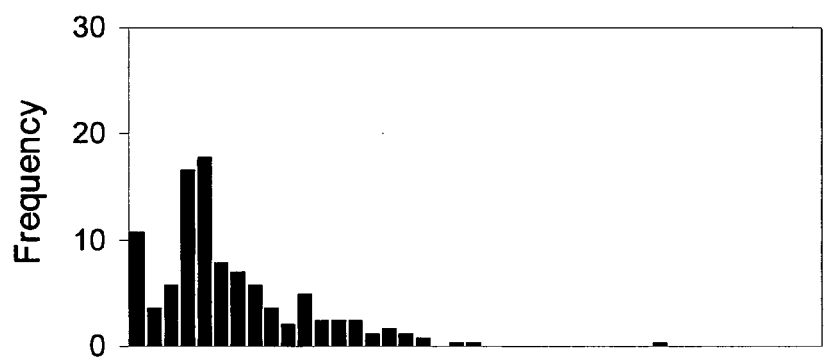
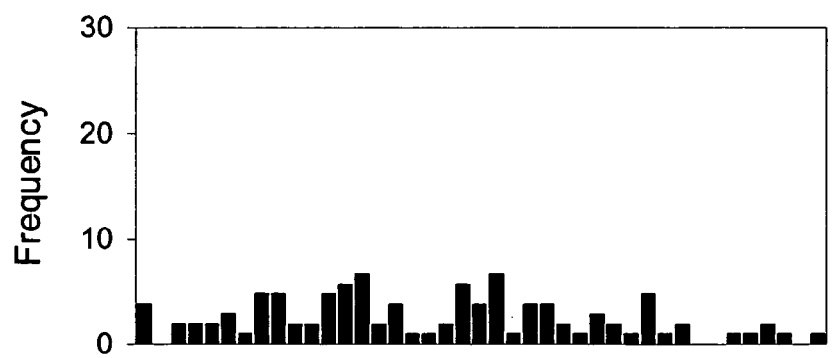

10 μm

10 μm

FIGURE 47C
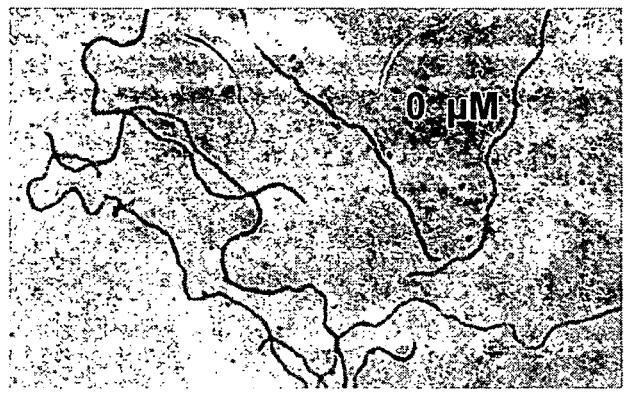
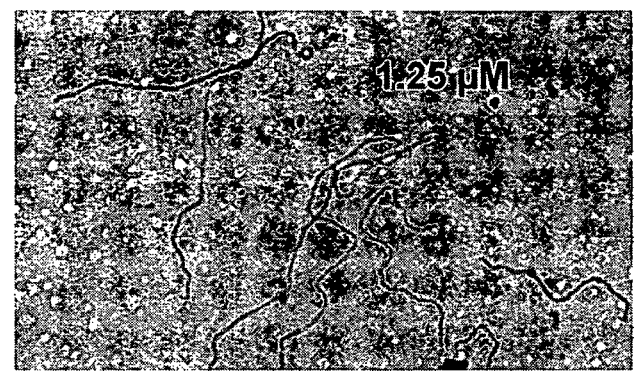
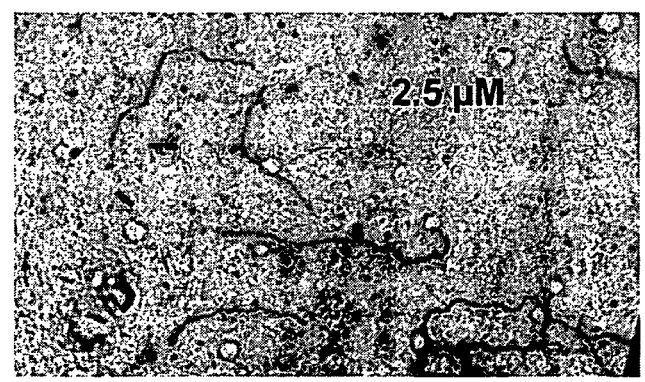
10 µm

DEHYDROPHENYLAHISTINS AND ANALOGS THEREOF AND THE SYNTHESIS OF DEHYDROPHENYLAHISTINS AND ANALOGS THEREOF

RELATED APPLICATIONS

This application is a continuation-in-part of U.S. patent application Ser. No. 10/632,531 filed on Aug. 1, 2003, now U.S. Pat. No. 7,064,201, and claims priority to U.S. Provisional Application No. 60/542,073 filed Feb. 4, 2004 and to U.S. Provisional Application No. 60/624,262 filed Nov. 1, 2004, all of which are entitled DEHYDROPHENYLAHISTINS AND ANALOGS THEREOF AND THE SYNTHESIS OF DEHYDROPHENYLAHISTINS AND ANALOGS THEREOF; and each of which is incorporated herein by reference in its entirety.

BACKGROUND OF THE INVENTION

1. Field of the Invention

The present invention relates to compounds and methods of synthetic preparation in the fields of chemistry and medicine. More specifically, the present invention relates to compounds and procedures for making compounds useful in the treatment of cancer and the treatment of fungal infections.

2. Brief Description of the Related Art

It is thought that a single, universal cellular mechanism controls the regulation of the eukaryotic cell cycle process. See, e.g., Hartwell, L. H. et al., Science (1989), 246: 629-34. It is also known that when an abnormality arises in the control mechanism of the cell cycle, cancer or an immune disorder may occur. Accordingly, as is also known, antitumor agents and immune suppressors may be among the substances that regulate the cell cycle. Thus, new methods for producing eukaryotic cell cycle inhibitors are needed as antitumor and immune-enhancing compounds, and should be useful in the treatment of human cancer as chemotherapeutic, anti-tumor agents. See, e.g., Roberge, M. et al., Cancer Res. (1994), 54, 6115-21.

Fungi, especially pathogenic fungi and related infections, represent an increasing clinical challenge. Existing antifungal agents are of limited efficacy and toxicity, and the development and/or discovery of strains of pathogenic fungi that are resistant to drugs currently available or under development. By way of example, fungi that are pathogenic in humans include among others *Candida* spp. including *C. albicans, C. tropicalis, C. kefyr, C. krusei* and *C. galbrata; Aspergillus* spp. including *A. fumigatus* and *A. flavus; Cryptococcus neoformans; Blastomyces* spp. including *Blastomyces dermatitidis; Pneumocystis carinii; Coccidioides immitis; Basidiobolus ranarum; Conidiobolus* spp.; *Histoplasma capsulatum; Rhizopus* spp. including *R. oryzae* and *R. microsporus; Cunninghamella* spp.; *Rhizomucor* spp.; *Paracoccidioides brasiliensis; Pseudallescheria boydii; Rhinosporidium seeberi;* and *Sporothrix schenckii* (Kwon-Chung, K. J. & Bennett, J. E. 1992 Medical Mycology, Lea and Febiger, Malvern, Pa.).

Recently, it has been reported that tryprostatins A and B (which are diketopiperazines consisting of proline and iso-prenylated tryptophan residues), and five other structurally-related diketopiperazines, inhibited cell cycle progression in the M phase, see Cui, C. et al., 1996 *J Antibiotics* 49:527-33; Cui, C. et al. 1996 *J Antibiotics* 49:534-40, and that these compounds also affect the microtubule assembly, see Usui, T. et al. 1998 *Biochem J* 333:543-48; Kondon, M. et al. 1998 *J Antibiotics* 51:801-04. Furthermore, natural and synthetic compounds have been reported to inhibit mitosis, thus inhibit the eukaryotic cell cycle, by binding to the colchicine binding-site (CLC-site) on tubulin, which is a macromolecule that consists of two 50 kDa subunits (α-and β-tubulin) and is the major constituent of microtubules. See, e.g., Iwasaki, S., 1993 *Med Res Rev* 13:183-198; Hamel, E. 1996 *Med Res Rev* 16:207-31; Weisenberg, R. C. et al., 1969 *Biochemistry* 7:4466-79. Microtubules are thought to be involved in several essential cell functions, such as axonal transport, cell motility and determination of cell morphology. Therefore, inhibitors of microtubule function may have broad biological activity, and be applicable to medicinal and agrochemical purposes. It is also possible that colchicine (CLC)-site ligands such as CLC, steganacin, see Kupchan, S. M. et al., 1973 *J Am Chem Soc* 95:1335-36, podophyllotoxin, see Sackett, D. L., 1993 *Pharmacol Ther* 59:163-228, and combretastatins, see Pettit, G. R. et al., 1995 *J Med Chem* 38:166-67, may prove to be valuable as eukaryotic cell cycle inhibitors and, thus, may be useful as chemotherapeutic agents.

Although diketopiperazine-type metabolites have been isolated from various fungi as mycotoxins, see Horak R. M. et al., 1981 *JCS Chem Comm* 1265-67; Ali M. et al., 1898 Toxicology Letters 48:235-41, or as secondary metabolites, see Smedsgaard J. et al., 1996 *J Microbiol Meth* 25:5-17, little is known about the specific structure of the diketopiperazine-type metabolites or their derivatives and their antitumor activity, particularly in vivo. Not only have these compounds been isolated as mycotoxins, the chemical synthesis of one type of diketopiperazine-type metabolite, phenylahistin, has been described by Hayashi et al. in *J. Org. Chem.* (2000) 65, page 8402. In the art, one such diketopiperazine-type metabolite derivative, dehydrophenylahistin, has been prepared by enzymatic dehydrogenation of its parent phenylahistin. With the incidences of cancer on the rise, there exists a particular need for chemically producing a class of substantially purified diketopiperazine-type metabolite-derivatives having animal cell-specific proliferation-inhibiting activity and high antitumor activity and selectivity. There is therefore a particular need for an efficient method of synthetically producing substantially purified, and structurally and biologically characterized, diketopiperazine-type metabolite-derivatives.

Also, PCT Publication WO/0153290 (Jul. 26, 2001) describes a non-synthetic method of producing dehydrophenylahistin by exposing phenylahistin or a particular phenylahistin analog to a dehydrogenase obtained from *Streptomyces albulus*.

SUMMARY OF THE INVENTION

Compounds, and methods for the synthetic manufacture of compounds, are disclosed for a class of compounds having the structure of Formula (I):

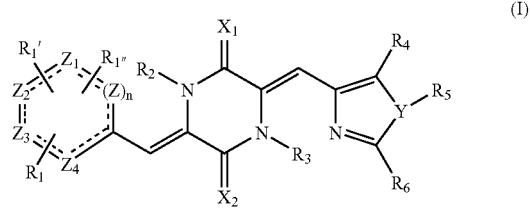

The disclosed compounds have the structure of Formula (I) wherein:

$R_1$, $R_4$, and $R_6$, are each separately selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

$R_1'$ and $R_1''$ are independently selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

$R_2$, $R_3$, and $R_5$ are each separately selected from the group consisting of a hydrogen atom, a halogen atom, and saturated $C_1$-$C_{12}$ alkyl, unsaturated $C_1$-$C_{12}$ alkenyl, acyl, cycloalkyl, alkoxy, cycloalkoxy, aryl, substituted aryl, heteroaryl, substituted heteroaryl, amino, substituted amino, nitro, and substituted nitro groups, sulfonyl and substituted sulfonyl groups;

$X_1$ and $X_2$ are separately selected from the group consisting of an oxygen atom, a nitrogen atom, and a sulfur atom, each either unsubstituted or substituted with a $R_5$ group, as defined above;

Y is selected from the group consisting of a nitrogen atom, a substituted nitrogen atom with a $R_5$ group from above, an oxygen atom, a sulfur atom, a oxidized sulfur atom, a methylene group and a substituted methylene group;

n is an integer equal to zero, one or two;

Z, for each separate n, if non-zero, and $Z_1$, $Z_2$, $Z_3$ and $Z_4$ are each separately selected from a carbon atom, a sulfur atom, a nitrogen atom or an oxygen atom; and the dashed bonds may be either single or double bonds;

with the proviso that, in a particular compound, if $R_1$, $R_1'$, $R_2$, $R_3$, $R_4$ and $R_5$ are each a hydrogen atom, then it is not true that $X_1$ and $X_2$ are each an oxygen atom and $R_6$ is either 3,3-dimethylbutyl-1-ene or a hydrogen atom.

The methods comprise the steps of:

reacting a diacyldiketopiperazine with a first aldehyde to produce an intermediate compound; and reacting said intermediate compound with a second aldehyde to produce said class of compounds with said generic structure, wherein said first aldehyde and said second aldehydes are selected from the group consisting of an oxazolecarboxaldeyhde, imidazolecarboxaldehyde, a benzaldehyde, imidazolecarboxaldehyde derivatives, and benzaldehyde derivatives, thereby forming a compound wherein The disclosed compounds have the structure of Formula (I) wherein:

$R_1$, $R_4$, and $R_6$, are each separately selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

$R_1'$ and $R_1''$ are independently selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

$R_2$, $R_3$, and $R_5$ are each separately selected from the group consisting of a hydrogen atom, a halogen atom, and saturated $C_1$-$C_{12}$ alkyl, unsaturated $C_1$-$C_{12}$ alkenyl, acyl, cycloalkyl, alkoxy, cycloalkoxy, aryl, substituted aryl, heteroaryl, substituted heteroaryl, amino, substituted amino, nitro, and substituted nitro groups, sulfonyl and substituted sulfonyl groups;

$X_1$ and $X_2$ are separately selected from the group consisting of an oxygen atom, a nitrogen atom, and a sulfur atom, each either unsubstituted or substituted with a $R_5$ group, as defined above;

Y is selected from the group consisting of a nitrogen atom, a substituted nitrogen atom with a $R_5$ group from above, an oxygen atom, a sulfur atom, a oxidized sulfur atom, a methylene group and a substituted methylene group;

n is an integer equal to zero, one or two;

Z, for each separate n, if non-zero, and $Z_1$, $Z_2$, $Z_3$ and $Z_4$ are each separately selected from a carbon atom, a sulfur atom, a nitrogen atom or an oxygen atom; and the dashed bonds may be either single or double bonds.

In preferred embodiments of the compound and method, the imidazolecarboxaldehyde is 5-(1,1-dimethyl-2-ethyl) imidazole-4-carboxaldehyde and the benzaldehyde comprises a single methoxy group. Additional preferred embodiments of the compounds described herein include compounds having a t-butyl group, a dimethoxy group, a chloro-group, and a methylthiophen group, and methods of making such compounds, as well as the compounds described in Tables 2, 3 and 4, as well as methods of making such compounds.

Also disclosed are methods and materials for treating neoplastic tissue or preventing cancers or infection by a pathogenic fungus. These methods and materials are particularly well suited for treatment of mammalian subjects, more particularly humans, and involve administering to the subject a dehydrophenylahistin or its analog. The method comprises administering to the subject a composition comprising an effective antitumor or antifungal amount of a dehydrophenylahistin or its analog.

Further embodiments relate to methods for treating a condition in an animal, which methods can include administering to the animal a compound as described herein in an amount that is effective to reduce vascular proliferation or in an amount that is effective to reduce vascular density. Exemplary conditions include neoplasms, such as cancers, as well as other conditions associated with or which rely upon vascularization, including for example, immune and non-immune inflammation, rheumatoid arthritis, chronic articular rheumatism, psoriasis, diabetic retinopathy, neovascular glaucoma, retinopathy of prematurity, macular degeneration, corneal graft rejection, retrolental fibroplasia, rubeosis, capillary proliferation in atherosclerotic plaques, osteoporosis, and the like. In some embodiments, the disease is not cancer.

Other embodiments relate to methods of inducing vascular collapse in an animal. The methods can include treating said animal with a therapeutically effective amount of a compound of the Formula (I) as described herein, for example. The therapeutically effective amount of said compound can cause tubulin depolymerization in the vasculature.

Preferably the animal can be a human. Preferably the disease can be a tumor, a diabetic retinopathy, an age-related macular degeneration, and the like. In some aspects the disease is not cancer or cancer can be specifically excluded from the methods and uses. Preferably, the compound is KPU-02.

Still further embodiments relate to pharmaceutical compositions for treating or preventing vascular proliferation comprising a pharmaceutically effective amount of a compound disclosed herein together with a pharmaceutically acceptable carrier therefor. The vascular proliferation can be a symptom of a disease, for example, cancer, age-related macular degeneration and diabetic retinopathy.

Some embodiments relate to methods of preferentially targeting tumor vasculature over non-tumor tissue vasculature. The methods can include the step of administering to an animal, preferably a human, a compound having the structure of Formula (I) as described herein. The non-tumor tissue can be, for example, skin, muscle, brain, kidney, heart, spleen, gut, and the like. The tumor vasculature can be preferentially targeted over non-tumor tissue vasculature, for example, by about 10%, 20%, 30%, 40%, 50%, 60%, 70%, 80% and 90%.

Other embodiments relate to methods of preferentially targeting tumor vasculature over non-tumor tissue vasculature, which methods can include administering to an animal an agent that preferentially targets tumor vasculature over non-tumor tissue vasculature.

Further embodiments relate to uses of a compound having the structure of Formula (I) in the preparation of a medicament for the treatment of a condition associated with increased vasculature or which relies upon vasculature. In some aspects the condition can be cancer, while in others, cancers particular types or all cancers are specifically excluded. The condition can be any other that is associated with hypervascularization, associated with vasculature or which relies upon vasculature. Examples include immune and non-immune inflammation, rheumatoid arthritis, chronic articular rheumatism, psoriasis, diabetic retinopathy, neovascular glaucoma, retinopathy of prematurity, macular degeneration, corneal graft rejection, retrolental fibroplasia, rubeosis, capillary proliferation in atherosclerotic plaques, osteoporosis, and the like.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings:

FIG. 30 depicts effects of KPU-35 and KPU-02 on tumor vasculature in the dorsal skinfold chamber of FIG. 30.

FIG. 31 depicts effect of KPU-02 in combination with CPT-11 on the estimated tumor weight in the HT-29 human colon tumor xenograft model.

FIG. 39 depicts 3D QSAR (CoMFA) analysis of tBu-dehydro-PLH derivatives.

FIG. 43 depicts the effect of dehydro-PLH and tBu-dehydro-PLH (KPU-2) on drug-sensitive and drug-resistant tumor cell lines as compared to paclitaxel.

FIG. 46A depicts frequency histograms of mean microtubule lengths in vitro at steady state in the presence of KPU-02.

FIG. 47C depicts electron micrographs of MAP-rich microtubules formed in vitro at steady state in the presence of CLC.

Figure 1:
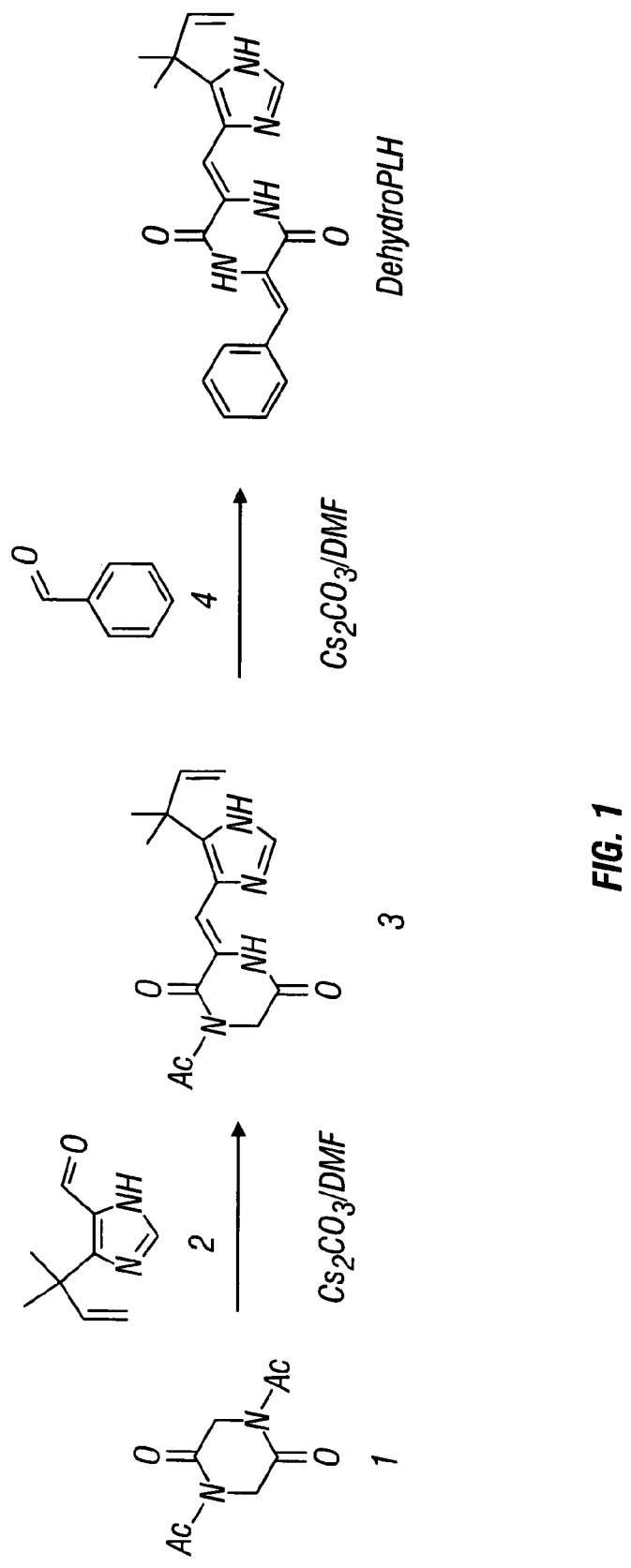
FIG. 1 illustrates a reaction scheme for producing dehydrophenylahistins by reacting a diacyldiketopiperazine 1 with an imidazolecarboxaldeheyde 2 to yield an intermediate compound 3 which is reacted with a benzaldehyde 4 to produce a dehydrophenylahistin.

In certain Figures, compounds are identified using an alternative designation. A complete chart to convert these alternative designations is as follows:

| Alternative designation | Designation used herein |
|---|---|
| NPI-2350 | (−)-phenylahistin |
| NPI-2352 | KPU-01 |
| NPI-2353 | KPU-03 |
| NPI-2354 | KPU-04 |
| NPI-2355 | KPU-05 |
| NPI-2356 | KPU-06 |
| NPI-2357 | KPU-07 |
| NPI-2358 | KPU-02 |
| NPI-2359 | KPU-08 |
| NPI-2360 | KPU-09 |
| NPI-2361 | KPU-10 |
| NPI-2362 | KPU-11 |
| NPI-2363 | KPU-12 |
| NPI-2364 | KPU-13 |
| NPI-2365 | KPU-14 |
| NPI-2366 | KPU-15 |
| NPI-2367 | KPU-16 |
| NPI-2368 | KPU-17 |
| NPI-2369 | KPU-18 |
| NPI-2370 | KPU-19 |
| NPI-2371 | KPU-21 |
| NPI-2372 | KPU-22 |
| NPI-2373 | KPU-23 |
| NPI-2374 | KPU-24 |
| NPI-2375 | KPU-25 |
| NPI-2376 | KPU-28 |
| NPI-2377 | KPU-26 |
| NPI-2378 | KPU-27 |
| NPI-2379 | KPU-29 |
| NPI-2380 | KPU-20 |
| NPI-2381 | KPU-30 |
| NPI-2382 | KPU-31 |
| NPI-2383 | KPU-32 |
| NPI-2384 | KPU-33 |
| NPI-2385 | KPU-34 |
| NPI-2386 | KPU-35 |
| NPI-2387 | KPU-36 |
| NPI-2388 | KPU-37 |
| NPI-2389 | KPU-38 |
| NPI-2390 | KPU-39 |
| NPI-2391 | KPU-40 |
| NPI-2392 | KPU-41 |
| NPI-2393 | KPU-42 |
| NPI-2394 | KPU-43 |
| NPI-2395 | KPU-44 |
| NPI-2396 | KPU-45 |
| NPI-2397 | KPU-46 |
| NPI-2398 | KPU-47 |
| NPI-2399 | KPU-48 |
| NPI-2400 | KPU-49 |
| NPI-2401 | KPU-50 |
| NPI-2402 | KPU-51 |
| NPI-2403 | KPU-52 |
| NPI-2404 | KPU-53 |
| NPI-2405 | KPU-54 |
| NPI-2406 | KPU-55 |
| NPI-2407 | KPU-56 |
| NPI-2408 | KPU-57 |
| NPI-2409 | KPU-58 |
| NPI-2410 | KPU-59 |
| NPI-2411 | KPU-60 |
| NPI-2412 | KPU-61 |
| NPI-2413 | KPU-62 |
| NPI-2414 | KPU-63 |
| NPI-2415 | KPU-64 |
| NPI-2416 | KPU-65 |
| NPI-2417 | KPU-66 |
| NPI-2418 | KPU-67 |
| NPI-2419 | KPU-68 |
| NPI-2420 | KPU-69 |
| NPI-2421 | KPU-70 |
| NPI-2422 | KPU-71 |
| NPI-2423 | KPU-72 |
| NPI-2424 | KPU-73 |
| NPI-2425 | KPU-74 |
| NPI-2426 | KPU-75 |
| NPI-2427 | KPU-76 |
| NPI-2428 | KPU-77 |
| NPI-2429 | KPU-79 |
| NPI-2430 | KPU-80 |
| NPI-2431 | KPU-81 |
| NPI-2432 | KPU-82 |
| NPI-2433 | KPU-83 |
| NPI-2434 | KPU-84 |
| NPI-2435 | KPU-86 |
| NPI-2436 | KPU-87 |
| NPI-2437 | KPU-88 |
| NPI-2438 | KPU-89 |
| NPI-2439 | KPU-90 |
| NPI-2440 | KPU-91 |
| NPI-2441 | KPU-92 |
| NPI-2442 | KPU-80 |
| NPI-2455 | KPU-94 |
| NPI-2456 | KPU-95 |
| NPI-2457 | KPU-96 |
| NPI-2458 | KPU-97 |
| NPI-2459 | KPU-98 |
| NPI-2460 | t-butyl phenylahistin |

DETAILED DESCRIPTION OF THE PREFERRED EMBODIMENT

Each reference cited herein, including the U.S. patents cited herein, is to be considered incorporated by reference in its entirety into this specification, to the full extent permissible by law. U.S. patent application Ser. No. 10/632,531, and PCT Application No. PCTUS03/24232, both filed on Aug. 1, 2003, and both entitled, "DEHYDROPHENYLAHISTINS AND ANALOGS THEREOF AND THE SYNTHESIS OF DEHYDROPHENYLAHISTINS AND ANALOGS THEREOF," are incorporated herein by reference in their entireties.

The disclosure provides methods for the synthetic preparation of compounds, including novel compounds, including dehydrophenylahistin and dehydrophenylahistin analogs, and provides methods for producing pharmaceutically acceptable cell cycle inhibitors, antitumor agents and antifungal agents in relatively high yield, wherein said compounds and/or their derivatives are among the active ingredients in these cell cycle inhibitors, antitumor agents and antifungal agents. Other objects include providing novel compounds not obtainable by currently available, non-synthetic methods. It is also an object to provide a method of treating cancer, particularly human cancer, comprising the step of administering an effective tumor-growth inhibiting amount of a member of a class of new anti-tumor compounds. This invention also provides a method for preventing or treating a pathogenic fungus in a subject which involves administering to the subject an effective anti-fungal amount of a member of a class of new anti-fungal compounds, e.g., administering a dehydrophenylahistin or its analog in an amount and manner which provides the intended antifungal effect. In the preferred embodiment of the compounds and methods of making and using such compounds disclosed herein, but not necessarily in all embodiments of the present invention, these objectives are met.

Disclosed herein, also, are compounds, and methods of producing a class of compounds, wherein the compounds are represented by Formula (I):

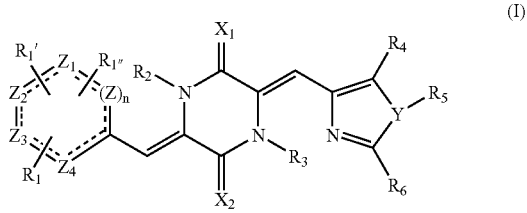

(I)

wherein:

$R_1$, $R_4$, and $R_6$, are each separately selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

$R_1'$ and $R_1''$ are independently selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

R, $R_1'$ and $R_1''$ are either covalently bound to one another or are not covalently bound to one another;

$R_2$, $R_3$, and $R_5$ are each separately selected from the group consisting of a hydrogen atom, a halogen atom, and saturated $C_1$-$C_{12}$ alkyl, unsaturated $C_1$-$C_{12}$ alkenyl, acyl, cycloalkyl, alkoxy, cycloalkoxy, aryl, substituted aryl, heteroaryl, substituted heteroaryl, amino, substituted amino, nitro, and substituted nitro groups, sulfonyl and substituted sulfonyl groups;

$X_1$ and $X_2$ are separately selected from the group consisting of an oxygen atom, a nitrogen atom, and a sulfur atom, each either unsubstituted or substituted with a $R_5$ group, as defined above;

Y is selected from the group consisting of a nitrogen atom, a substituted nitrogen atom with a $R_5$ group from above, an oxygen atom, a sulfur atom, a oxidized sulfur atom, a methylene group and a substituted methylene group;

n is an integer equal to zero, one or two;

Z, for each separate n, if non-zero, and $Z_1$, $Z_2$, $Z_3$ and $Z_4$ are each separately selected from a carbon atom, a sulfur atom, a nitrogen atom or an oxygen atom; and the dashed bonds may be either single or double bonds.

The method comprises a method of producing compounds of Formula (I) by the steps of:

reacting a diacyldiketopiperazine with a first aldehyde to produce an intermediate compound; and reacting said intermediate compound with a second aldehyde to produce said class of compounds with said generic structure, wherein said first aldehyde and said second aldehydes are selected from the group consisting of an oxazolecarboxaldeyhyde, imidazolecarboxaldehyde, a benzaldehyde, imidazolecarboxaldehyde derivatives, and benzaldehyde derivatives, thereby forming a compound of Formula (I) wherein $R_1$, $R_4$, and $R_6$, are each separately selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

$R_1'$ and $R_1''$ are independently is selected from the group consisting of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, alkylthio, halogenated alkyl including polyhalogenated alkyl, halogenated carbonyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups;

$R_2$, $R_3$, and $R_5$ are each separately selected from the group consisting of a hydrogen atom, a halogen atom, and saturated $C_1$-$C_{12}$ alkyl, unsaturated $C_1$-$C_{12}$ alkenyl, acyl, cycloalkyl, alkoxy, cycloalkoxy, aryl, substituted aryl, heteroaryl, substituted heteroaryl, amino, substituted amino, nitro, and substituted nitro groups, sulfonyl and substituted sulfonyl groups;

$X_1$ and $X_2$ are separately selected from the group consisting of an oxygen atom, a nitrogen atom and a sulfur atom, and Y is selected from the group consisting of a nitrogen atom, a substituted nitrogen atom with a $R_5$ group from above, an oxygen atom, a sulfur atom, a oxidized sulfur atom, a methylene group and a substituted methylene group;

Z, for each separate n, if non-zero, and $Z_1$, $Z_2$, $Z_3$ and $Z_4$ are each separately selected from a carbon atom, a sulfur atom, a nitrogen atom or an oxygen atom; and the dashed bonds may be either single or double bonds.

Also provided are pharmaceutically acceptable salts and pro-drug esters of the compound of Formulae (I) and (II) and provides methods of synthesizing such compounds by the methods disclosed herein.

The term "pro-drug ester," especially when referring to a pro-drug ester of the compound of Formula (I) synthesized by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups).

The term "pro-drug ester," as used herein, also refers to a chemical derivative of the compound that is rapidly transformed in vivo to yield the compound, for example, by hydrolysis in blood. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as pro-drugs for compounds containing carboxyl groups).

The term "pharmaceutically acceptable salt," especially when referring to a pharmaceutically acceptable salt of the compound of Formula (I) synthesized by the methods disclosed herein, refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds synthesized by the method that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

The term "pharmaceutically acceptable salt," as used herein, also refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compound of Formula (I) synthesized by the method disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

In preferred embodiments of the methods of the compounds disclosed herein, a relatively rigid, planar pseudo three-ring structure may be formed. To stabilize such a relatively rigid, planar pseudo three-ring structure, $R_3$ may preferably be chosen to be hydrogen.

In other preferable embodiments of the compounds and methods described herein, n is equal to zero or one, more preferable one, and $Z_2$, $Z_3$, and $Z_4$, and each separately selected from an oxygen atom, a nitrogen atom, and a carbon atom, more preferable at one least one of $Z_2$, $Z_3$, and $Z_4$ being a carbon atom, and most preferable at least two of $Z_2$, $Z_3$, and $Z_4$ being a carbon atom. All Z's may simultaneous be carbon atoms.

Still other preferred embodiments of the methods and compositions disclosed herein involve compounds having the structures of Formulae (Ia) and (Ib), below:

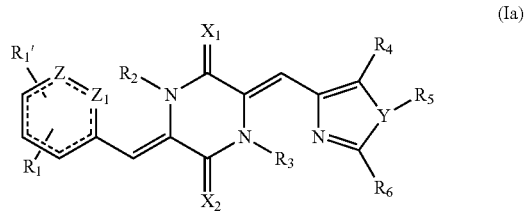

(Ia)

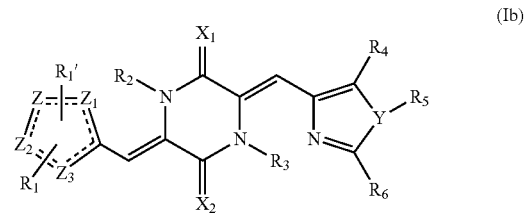

(Ib)

wherein the variable groups are as defined herein.

The term "halogen atom," as used herein, means any one of the radio-stable atoms of column 7 of the Periodic Table of the Elements, i.e., fluorine, chlorine, bromine, or iodine, with fluorine and chlorine being preferred.

The term "alkyl," as used herein, means any unbranched or branched, substituted or unsubstituted, saturated hydrocarbon, with $C_1$-$C_6$ unbranched, saturated, unsubstituted hydrocarbons being preferred, with methyl, ethyl, iosbutyl, and tert-butyl being most preferred. Among the substituted, saturated hydrocarbons, $C_1$-$C_6$ mono- and di- and per-halogen substituted saturated hydrocarbons and amino-substituted hydrocarbons are preferred, with perfluromethyl, perchloromethyl, perfluoro-tert-butyl, and perchloro-tert-butyl being the most preferred. The term "substituted" has its ordinary meaning, as found in numerous contemporary patents from the related art. See, for example, U.S. Pat. Nos. 6,583,143, 6,509,331; 6,506,787; 6,500,825; 5,922,683; 5,886,210; 5,874,443; and 6,350,759. Specifically, the definition of substituted is as broad as that provided in U.S. Pat. No. 6,583,143, which defines the term substituted as any groups such as alkyl, aryl, arylalkyl, heteroaryl, heteroarylalkyl, heterocycle and heterocyclealkyl, wherein at least one hydrogen atom is replaced with a substituent. The term "substituted" is also as broad as the definition provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. The other above-listed patents also provide standard definitions for the term "substituted" that are well-understood by those of skill in the art. The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$-$C_6$ unbranched, mono-unsaturated and di-unsaturated, unsubstituted hydrocarbons being preferred, and mono-unsaturated, di-halogen substituted hydrocarbons being most preferred. In the $R_1$ and $R_4$ positions, of the compound of structure (I) a z-isoprenyl moiety is particularly preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

The terms "purified," "substantially purified," and "isolated" as used herein refer to the compound being free of other, dissimilar compounds with which the compound is normally associated in its natural state, so that the compound of the invention comprises at least 0.5%, 1%, 5%, 10%, or 20%, and most preferably at least 50% or 75% of the mass, by weight, of a given sample.

The compound of Formula (I) may be chemically synthesized or produced from reagents known and available in the art. For example, modifications of diacyldiketopiperazine (diacetyldiketopiperazine) have been described, for example, by Loughlin et al., 2000 *Bioorg Med Chem Lett* 10:91 or by Brocchini et al. in WO 95/21832. The diacyldiketopiperazine (diacetyldiketopiperazine) may be prepared, for example, by diacetylation of inexpensive 2,5-piperazinedione (TCI Cat. No. G0100, 25 g) with sodium acetate and sodium anhydride. The diacetyl structure of the activated deketopiperazine can be replaced with other acyl groups, to include carbamates such as Boc (t-butoxycarbonyl), Z (benzoyloxycarbonyl).

The imidazolecarboxaldehyde may be prepared, for example, according the procedure disclosed in Hayashi et al., 2000 *J Organic Chem* 65: 8402 as depicted below:

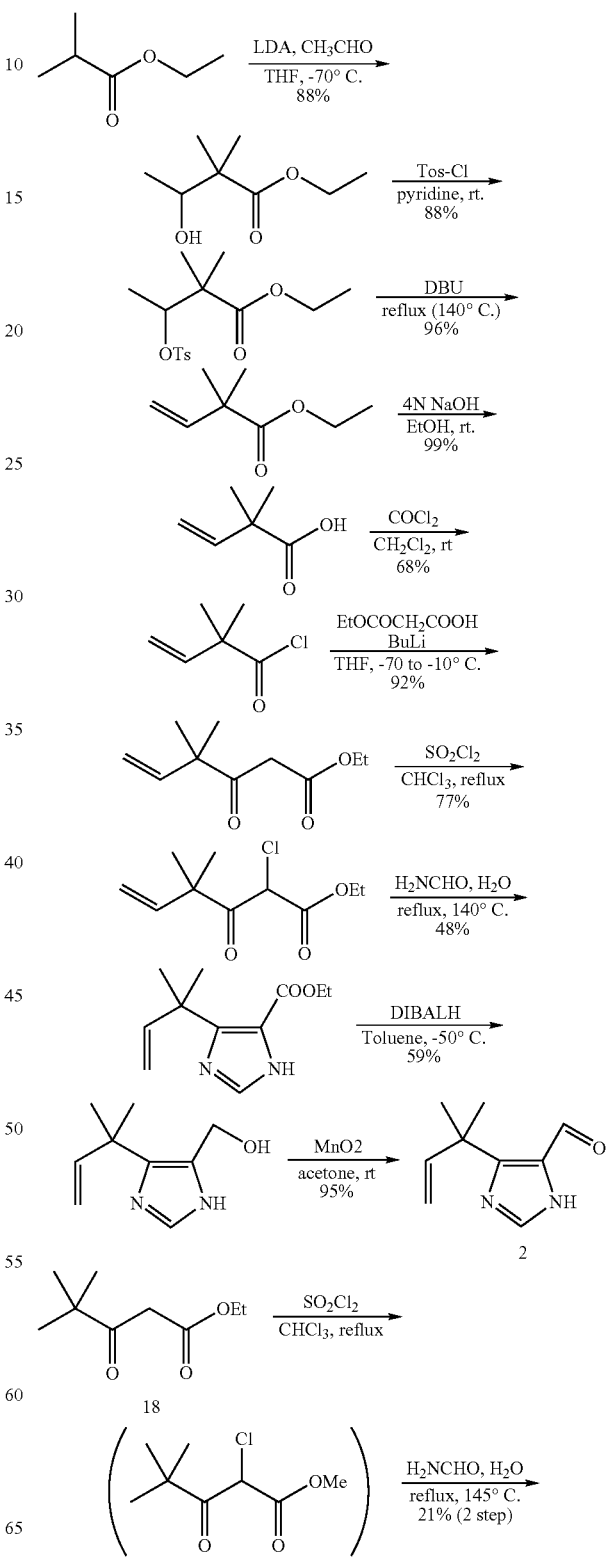

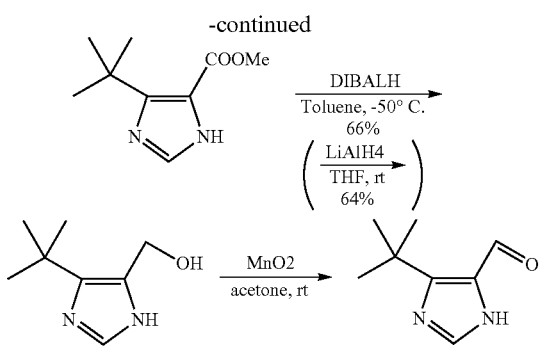

The synthetic method disclosed herein may be preferably performed in the presence of cesium carbonate as a base in DMF and in a deoxygenated atmosphere. The inert atmosphere circumvents the probable oxidation of activated a-carbon atoms of the diketopiperazine ring during the treatment with cesium carbonate (see below) as reported, for example, by Watanabe et al., 18$^{th}$ *International Congress of Heterocyclic Chemistry in Yokohama, Japan* (30 Jul. 2001), Abstract, page 225.

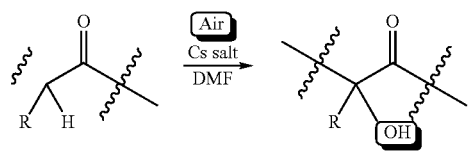

Air-oxidation of Activated Carbonyl Compounds with Cesium Salts

Other embodiments of the synthetic method involve modifications to the compounds used in or otherwise involved in the synthesis of compounds represented by Formula (I). Such derivatives may include modifications to the phenyl ring, introduction of other aromatic ring systems, position of the aromatic ring, alterations to the imidazole ring system and/or further modifications to the 5-position on the imidazole ring. Examples of such modifications are discussed, for example, in Example 4. The result of such modifications includes increased nitrogen content of the phenyl ring and/or the compound which may increase compound solubility. Other modifications may incorporate derivatives of known tubulin inhibitors, thereby mimicking the activity of the tubulin inhibitors. Other modifications may simplify the synthesis of the β-ketoester involved in the production of the imidazolecarboxaldehyde used in the methods disclosed herein.

Pharmaceutical Compositions

The present invention also encompasses the compounds disclosed herein, optionally and preferably produced by the methods disclosed herein, in pharmaceutical compositions comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

The dehydrophenylahistin or dehydrophenylahistin analog compositions may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection or infusion, or as emulsions. Suitable excipients are, for example, water, saline, dextrose, mannitol, lactose, lecithin, albumin, sodium glutamate, cysteine hydrochloride, human serum albumin and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use may be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809

(lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations).

Further disclosed herein are various pharmaceutical compositions well known in the pharmaceutical art for uses that include intraocular, intranasal, and intraauricular delivery. Pharmaceutical formulations include aqueous ophthalmic solutions of the active compounds in water-soluble form, such as eyedrops, or in gellan gum (Shedden et al., 2001 *Clin Ther* 23(3):440-50) or hydrogels (Mayer et al., 1996 *Ophthalmologica* 210:101-3); ophthalmic ointments; ophthalmic suspensions, such as microparticulates, drug-containing small polymeric particles that are suspended in a liquid carrier medium (Joshi, A., 1994 *J Ocul Pharmacol* 10:29-45), lipid-soluble formulations (Alm et al., 1989 *Prog Clin Biol Res* 312:447-58), and microspheres (Mordenti, 1999 *Toxicol Sci* 52:101-6); and ocular inserts. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences (Mack Publishing, 18$^{th}$ Edition), and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

When used as a cell cycle inhibitor, a tumor-growth-inhibiting, or a fungus-growth-inhibiting compound, the compound of Formula (I) can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection or infusion, subcutaneously, intreperitoneally, intravenously, intramuscularly, or the like. Similarly, it may be administered topically, rectally, or vaginally, as deemed appropriate by those of skill in the art for bringing the compound into optimal contact with a tumor, thus inhibiting the growth of the tumor. Local administration at the site of the tumor is also contemplated, either before or after tumor resection, as are controlled release formulations, depot formulations, and infusion pump delivery.

Methods of Administration

The present invention also encompasses methods for making and for administering the disclosed chemical compounds and the disclosed pharmaceutical compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection or infusion, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the dehydrophenylahistin or dehydrophenylahistin analog composition required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods, the products or compositions can be used alone or in combination with one another, or in combination with other therapeutic or diagnostic agents. For example, as disclosed herein, the compounds disclosed herein are effective in the treatment of cancer when used in combination with other actives, specifically other chemotherapeutics, for example biologics and the specific chemotherapeutics CPT-11, Taxotene (docataxel) and paclitaxel. The compounds disclosed herein are also effective in the treatment of cancer when used in combination with other actives, including anti-vascular agents, anti-angiogenenic agents, such as Erbuitux (Imclone/bristol-Myers) and Iressa (AstraZeneca), other VEGF inhibitors and biologics, more specifically, at least one anti-VEGF antibodies, especially monoclonal antibodies to the VEGF receptor, including DC101, a rat monoclonal antibody, which blocks the mouse VEGF receptor 2 (flk-1). Such combinations may be utilized in vivo, ordinarily in a mammal, preferably in a human, or in vitro. In employing them in vivo, the disclosed compounds, alone or in combination with other chemotherapeutics or other biologic products, may be administered to the mammal in a variety of ways, including parenterally, intravenously, via infusion or injection, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration may be oral on an every third day, every other day, daily, twice daily, or thrice daily basis.

The exact formulation, route of administration and dosage can be chosen by the individual physician in view of the patient's condition. See for example, Fingl et al., in The Pharmacological Basis of Therapeutics, 1975. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990). Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, via infusion, intraperitoneal, intranasal, or intraocular injections.

For injection or infusion, the agents may be formulated in aqueous solutions, for example, in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions disclosed herein, in particular, those formulated as solutions, may be administered parenterally, such as by intravenous injection or infusion. The compounds can be formulated readily using pharmaceutically acceptable carriers well known in the art into dosages suitable for oral administration. Such carriers enable the compounds to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions may be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several art recognized methods, such as in vitro methods, animal models, or human clinical trials. Art-recognized in vitro models exist for nearly every class of condition, including the conditions abated by the compounds disclosed herein, including cancer, cardiovascular disease and various fungal infections. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-cancer agent, or a tumor-growth-inhibiting compound, the compounds disclosed herein may be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection or infusion, subcutaneously, intreperitoneally, intravenously, intramuscularly, intradermally, or the like. Similarly, it may be administered topically, rectally, or vaginally, as deemed appropriate by those of skill in the art for bringing the compound into optimal contact with a tumor, thus inhibiting the growth of the tumor. Local administration at the site of the tumor or other disease condition is also contemplated, either before or after tumor resection, or as part of an art-recognized treatment of the disease condition. Controlled release formulations, depot formulations, and infusion pump delivery are similarly contemplated.

When used as an anti-cancer agent or an anti-tumor agent, may be orally or non-orally administered to a human patient in the amount of about 0.0007 mg/day to about 7,000 mg/day of the active ingredient, and more preferably about 0.07 mg/day to about 70 mg/day of the active ingredient at, preferably, one time per day or, less preferably, over two to about ten times per day. Alternatively and also preferably, the compound may preferably be administered in the stated amounts continuously by, for example, an intravenous drip. Thus, for a patient weighing 70 kilograms, the preferred daily dose of the active anti-tumor ingredient would be about 0.0007 mg/kg/day to about 35 mg/kg/day including 1.0 mg/kg/day and 0.5 mg/kg/day, and more preferable, from 0.007 mg/kg/day to about 0.050 mg/kg/day, including 0.035 mg/kg/day. Nonetheless, as will be understood by those of skill in the art, in certain situations it may be necessary to administer the anti-tumor compound in amounts that excess, or even far exceed, the above-stated, preferred dosage range to effectively and aggressively treat particularly advanced or lethal tumors.

When used as an antifungal agent the preferable amount of the dehydrophenylahistin or its analog effective in the treatment or prevention of a particular fungal pathogen will depend in part on the characteristics of the fungus and the extent of infection, and can be determined by standard clinical techniques. In vitro or in vivo assays may optionally be employed to help identify optimal dosage ranges. Effective doses may be extrapolated from dose-response curves derived from in vitro analysis or preferably from animal models. The precise dosage level should be determined by the attending physician or other health care provider and will depend upon well known factors, including route of administration, and the age, body weight, sex and general health of the individual; the nature, severity and clinical stage of the infection; the use (or not) of concomitant therapies.

The effective dose of the dehydrophenylahistin or its analog will typically be in the range of about 0.01 to about 50 mg/kgs, preferably about 0.1 to about 10 mg/kg of mammalian body weight per day, administered in single or multiple doses. Generally, the compound may be administered to patients in need of such treatment in a daily dose range of about 1 to about 2000 mg per patient.

To formulate the dosage including the compounds disclosed herein as a tumor-growth-inhibiting compound, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methyiacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound, particularly when the compound is to be administered orally.

The compositions disclosed herein in a pharmaceutical compositions may also comprise a pharmaceutically acceptable carrier. Such compositions may be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions may be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection or infusion, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions, as described above, may be used alone or in combination with one another, or in combination with other therapeutic or diagnostic agents. Specifically, the disclosed compounds products may be used alone or in combination with other chemotherapeutics or biologics, including antibodies, for the treatment of cancer, or in combination with other anti-infective for the treatment of fungal infection. These products or compositions can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions may be formulated and administered either systemically or locally. A variety of techniques for formulation and administration may be found in Remington's Pharmaceutical Sciences, 18th ed., Mack Publishing Co., Easton, Pa. (1990).

To formulate the compounds of Formula (I), preferably synthetically produced according to the methods disclosed herein, as a cell cycle inhibitor, a tumor-growth-inhibiting, or an antifungal compound, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methyiacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound produced by the method, particularly when the compound is to be administered orally.

The cell cycle inhibitors, the antitumor agents, and the antifungal agents that may be produced by the method may be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, once every three days on a cyclic basis, once every other day, one time per day, twice per day, or less preferably, over two to about ten times per day. Alternatively and also preferably, the compound produced by the method may preferably be administered in the stated amounts continuously by, for example, an intravenous drip. Thus, for the example of a patient weighing 70 kilograms, the preferred daily dose of the active anti-tumor ingredient would be about 0.07 mg/day to about 700 grams/day, and more preferable, 7 mg/day to about 7 grams/day. Nonetheless, as will be understood by those of skill in the art, in certain situations it may be necessary to administer the anti-tumor compound produced by the method in amounts that excess, or even far exceed, the above-stated, preferred dosage range to effectively and aggressively treat particularly advanced or lethal tumors.

In the case of using the cell cycle inhibitor produced by methods as a biochemical test reagent, the compound produced by methods of the invention inhibits the progression of the cell cycle when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the invention for use as a cell cycle inhibitor is generally in the range of about 1 to about 100 μg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

From a pharmaceutical perspective, certain embodiments provide methods for preventing or treating fungal infections and/or a pathogenic fungus in a subject, involve administering to the subject a composition including a dehydrophenylahistin or its analog, for example, administering the dehydrophenylahistin or its analog in an amount and manner which provides the intended antifungal effect.

Other embodiments include the treatment or prevention of infection in a patient by a pathogenic fungus such as those listed above or referred to below.

Another embodiment relates to the treatment or prevention of infection in a patient by a pathogenic fungus which is resistant to one or more other antifungal agents, especially an agent other than dehydrophenylahistin or its analog, including e.g. amphotericin B or analogs or derivatives thereof (including 14(s)-hydroxyamphotericin B methyl ester, the hydrazide of amphotericin B with 1-amino-4-methylpiperazine, and other derivatives) or other polyene macrolide antibiotics, including, e.g., nystatin, candicidin, pimaricin and natamycin; flucytosine; griseofulvin; echinocandins or aureobasidins, including naturally occurring and semi-synthetic analogs; dihydrobenzo[a]napthacenequinones; nucleoside peptide antifungals including the polyoxins and nikkomycins; allylamines such as naftifine and other squalene epoxidase inhibitors; and azoles, imidazoles and triazoles such as, e.g., clotrimazole, miconazole, ketoconazole, econazole, butoconazole, oxiconazole, terconazole, itraconazole or fluconazole and the like. For additional conventional antifungal agents and new agents under development, see e.g. Turner and Rodriguez, 1996 Current Pharmaceutical Design, 2:209-224. Another embodiment involves the treatment or prevention of infection in a patient by a pathogenic fungus in cases in which the patient is allergic to, otherwise intolerant of, or nonresponsive to one or more other antifungal agents or in whom the use of other antifungal agents is otherwise contraindicated. Those other antifungal agents include, among others, those antifungal agents disclosed above and elsewhere herein.

In the foregoing methods for treatment or prevention, a dehydrophenylahistin or its analog, is administered to the subject in an effective antifungal amount.

Other embodiments relate to the treatment or prevention of infection by a pathogenic fungus in a patient by administration of a dehydrophenylahistin or its analog, in conjunction with the administration of one or more other antifungal agents, including for example, any of the previously mentioned agents or types of agents (e.g. in combination with treatment with amphotericin B, preferably in a lipid or liposome formulation; an azole or triazole such as fluconazole, for example; an aureobasidin; dihydrobenzo[a]napthacenequinone; or an echinocardin) as well as with a different dehydrophenylahistin or its analog.

The dehydrophenylahistin or its analog may be administered before, after or at the same time the other antifungal agent is administered. In certain embodiments, the combination therapy will permit the use of reduced amounts of one or both antifungal components, relative to the amount used if used alone.

Still other embodiments relate to administration of a dehydrophenylahistin or its analog to a subject for the treatment or prevention of infection by a pathogenic fungus, where the subject is immunosuppressed or immunocompromised, e.g. as the result of genetic disorder, disease such as diabetes or HIV or other infection, chemotherapy or radiation treatment for cancer or other disease, or drug- or otherwise induced immunosuppression in connection with tissue or organ transplantation or the treatment of an autoimmune disorder. Where the patient is being or will be treated with an immunosuppressive agent, e.g., in connection with a tissue or organ transplantation, a dehydrophenylahistin or its analog may be co-administered with the immunosuppressive agent(s) to treat or prevent a pathogenic fungal infection.

Another aspect of this invention is the treatment or prevention of infection by a pathogenic fungus in a patient infected, or suspected of being infected, with HIV, by administration of an antifungal dehydrophenylahistin or its analog, in conjunction with the administration of one or more anti-HIV therapeutics (including e.g. HIV protease inhibitors, reverse transcriptase inhibitors or anti-viral agents). The dehydrophenylahistin or its analog may be administered before, after or at the same time as administration of the anti-HIV agent(s).

Another aspect of this invention is the treatment or prevention of infection by a pathogenic fungus in a patient by administration of an antifungal dehydrophenylahistin or its analog, in conjunction with the administration of one or more other antibiotic compounds, especially one or more antibacterial agents, preferably in an effective amount and regiment to treat or prevent bacterial infection. Again, the dehydrophenylahistin or its analog may be administered before, after or at the same time as administration of the other agent(s).

Pathogenic fungal infections which may be treated or prevented by the disclosed methods include, among others, Aspergillosis, including invasive pulmonary aspergillosis;

Blastomycosis, including profound or rapidly progressive infections and blastomycosis in the central nervous system; Candidiasis, including retrograde candidiasis of the urinary tract, e.g. in patients with kidney stones, urinary tract obstruction, renal transplantation or poorly controlled diabetes mellitus; Coccidioidomycosis, including chronic disease which does not respond well to other chemotherapy; Cryptococcosis; Histopolasmosis; Mucormycosis, including e.g. craniofacial mucormycosis and pulmonary mucormnycosis; Paracoccidioidomycosis; and Sporotrichosis. It should be noted that administration of a composition comprising an antifungal amount of one or more dehydrophenylahistin or its analogs may be particularly useful for treating or preventing a pathogenic fungal infection in a mammalian subject where the fungus is resistant to one or more other antifungal therapies, or where the use of one or more other antifungal therapies is contraindicated, e.g., as mentioned above.

Antifungal pharmaceutical compositions containing at least one antifungal dehydrophenylahistin or its analog, are also provided for use in practicing the disclosed methods. Those pharmaceutical compositions may be packaged together with an appropriate package insert containing, inter alia, directions and information relating to their antifungal use. Pharmaceutical compositions are also provided which contain one or more dehydrophenylahistin or its analog together with a second antifungal agent.

Methods of Treating Fungal Infections

Certain embodiments disclosed herein relate to methods for treating or preventing a pathogenic fungal infection, including for example Aspergillosis, including invasive pulmonary aspergillosis; Blastomycosis, including profound or rapidly progressive infections and blastomycosis in the central nervous system; Candidiasis, including retrograde candidiasis of the urinary tract, e.g. in patients with kidney stones, urinary tract obstruction, renal transplantaion or poorly controlled diabetes mellitus; Coccidioidomycosis, including chronic disease which does not respond well to other chemotherapy; Cryptococcosis; Histopolasmosis; Mucormycosis, including e.g. craniofacial mucormycosis and pulmonary mucormycosis; Paracoccidioidomycosis; and Sporotrichosis. The methods may involve administering at least one antifungal dehydrophenylahistin or its analog, as described above, to a human subject such that the fungal infection is treated or prevented. In certain embodiments the dehydrophenylahistin or its analog may be administered in conjunction with administration of one or more non-dehydrophenylahistin or its analog antifungal agents such as amphotericin B, or an imidazole or triazole agent such as those mentioned previously.

The pathogenic fungal infection may be topical, e.g., caused by, among other organisms, species of *Candida, Trichophyton, Microsporum* or *Epiderinophyton* or mucosal, e.g., caused by *Candida albicans* (e.g. thrush and vaginal candidiasis). The infection may be systemic, e.g., caused by *Candida albicans, Cryptococcus neoformans, Aspergillus fumigatus, Coccidiodes, Paracocciciodes, Histoplasma* or *Blastomyces* spp. The infection may also involve eumycotic mycetoma, chromoblastomycosis, cryptococcal meningitits or phycomycosis.

Further embodiments relate to methods for treating or preventing a pathogenic fungal infection selected from the group consisting of *Candida* spp. including *C. albicans, C. tropicalis, C. kefyr, C. krusei* and *C. galbrata; Aspergillus* spp. including *A. fumigatus* and *A. flavus; Cryptococcus neoibrmans; Blastomyces* spp. including *Blastomyces dermatitidis; Pneumocvstis carinii; Coccidioides immitis; Basidiobolus ranarum; Conidiobolus* spp.; *Histoplasma capsulatum; Rhizopus* spp. including *R. oryzae* and *R. microsporus; Cunninghamella* spp.; *Rhizoniucor* spp.; *Paracoccidioides brasiliensis; Pseudallescheria boydii; Rhinosporidium seeberi*; and *Sporothrix schenckii*. Again, the method may involve administering a non-immunosuppressive antifungal dehydrophenylahistin or its analog to a patient in need thereof such that the fungal infection is treated or prevented without inducing an untoward immunosuppressive effect.

Further embodiments relate to methods for treating or preventing a pathogenic fungal infection which is resistant to other antifungal therapy, including pathogenic fungal infections which are resistant to one or more antifungal agents mentioned elsewhere herein such as amphotericin B, flucytosine, one of the imidazoles or triazoles (including e.g. fluconazole, ketoconazole, itraconazole and the other previously mentioned examples). The methods may involve administering to the patient one or more antifungal dehydrophenylahistin or its analog, in an amount and dosing regimen such that a fungal infection resistant to another antifungal therapy in the subject is treated or prevented.

Further embodiments relate to methods for treating or preventing a pathogenic fungal infection in a patient who is allergic to, intolerant of or not responsive to another antifungal therapy or in whom the use of other antifungal agents is otherwise contra-indicated, including one or more other antifungal agents mentioned elsewhere herein such as amphotericin B, flucytosine, one of the imidazoles or triazoles (including e.g. fluconazole, ketoconazole, itraconazole and the other previously mentioned examples). The methods may involve administering to such patient one or more antifungal dehydrophenylahistin or its analog, in an amount such that a fungal infection is treated or prevented.

Packaged Dehydrophenylahistin or its Analogs

Certain embodiments relate to packaged dehydrophenylahistin or its analogs, preferably packaged nonimmunosuppressive antifungal dehydrophenylahistin or its analogs, which term is intended to include at least one dehydrophenylahistin or its analog, as described above, packaged with instructions for administering the dehydrophenylahistin or its analog(s) as an antifungal agent without causing a untoward immunosuppressive effects within a human subject. In some embodiments, the non-immunosuppressive antifungal dehydrophenylahistin or its analog is a member of one of the preferred subsets of compounds described above. The dehydrophenylahistin or its analog can be packaged alone with the instructions or can be packaged with another dehydrophenylahistin or its analog, raparnycin or another ingredient or additive, e.g., one or more of the ingredients of the pharmaceutical compositions. The package can contain one or more containers filled with one or more of the ingredients of the phan-naceutical compositions. Optionally associated with such container(s) can be a notice in the form prescribed by a governmental agency regulating the manufacture, use or sale of pharmaceutical or biological products, which notice reflects approval by the agency of manufacture, use or sale for human administration.

The following non-limiting examples are meant to describe the preferred methods using certain preferred embodiments. Variations in the details of the particular methods employed and in the precise chemical compositions obtained will undoubtedly be appreciated by those of skill in the art.

EXAMPLE 1

A. Synthesis of Dehydrophenylahistin

Dehydrophenylahistin was synthesized by condensation according to the following basic reaction scheme, as shown in FIG. 1:

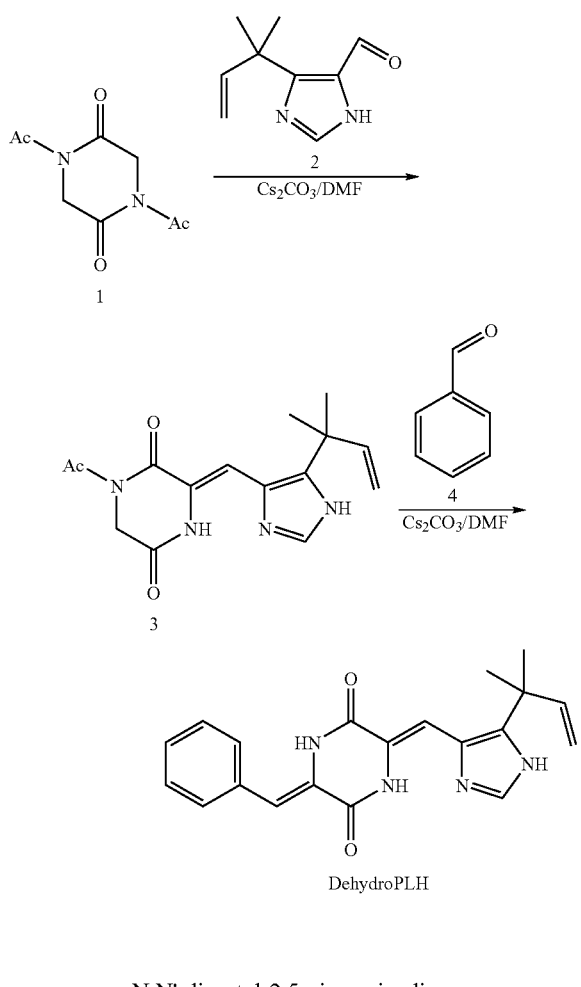

N,N'-diacetyl-2,5-piperazinedione 25.0 g of global 2,5-piperazinedione 1 [2,5-piperazinedione (Aldrich G640-6), 25.0 g, 0.218 mol] in 100 mL of acetic anhydride (Ac₂O) was mixed with sodium acetate (NaOAc) (17.96 g, 0.0218 mol). The mixture was heated at 110° C. for 8 h using a double coiled condenser under an Ar atmosphere. After Ac₂O was removed by evaporation, the residue was dissolved in AcOEt, washed with 10% citric acid, 10% NaHCO₃ and saturated NaCl (three times each), dried over Na₂SO₄, and concentrated in vacuo. The residue was triturated with ether to form a solid. This solid was recrystallized from EtOAc with ether-hexane to afford 26.4 g (61%) of N,N'-diacetyl-2,5-piperazinedione 1.

1-Acetyl-3-{(Z)-1-[5-(1,1-dimethyl-2-propenyl)-1H-4-imidazolyl]methylidenel}]-2,5-piperazinedione 2

To a solution of 5-(1,1-dimethyl-2-propenyl)imidazole-4-carboxaldehyde (100 mg, 0.609 mmol) in DMF (2 mL) was added compound 1 (241 mg, 1.22 mmol) and the solution was repeatedly evacuated in a short time to remove oxygen and flushed with Ar, followed by the addition of Cs₂CO₃ (198 mg, 0.609 mmol) and the evacuation-flushing process was repeated again. The resultant mixture was stirred for 5 h at room temperature. After the solvent was removed by evaporation, the residue was dissolved in the mixture of EtOAc and 10% Na₂CO₃, and the organic phase was washed with 10% Na₂CO₃ again and saturated NaCl for three times, dried over Na₂SO₄ and concentrated in vacuo. The residual oil was purified by column chromatography on silica using CHCl₃-MeOH (100:0 to 50:1) as an eluant to give 60 mg (33%) of a pale yellow solid 2.

Dehydrophenylahistin

Figure 2:
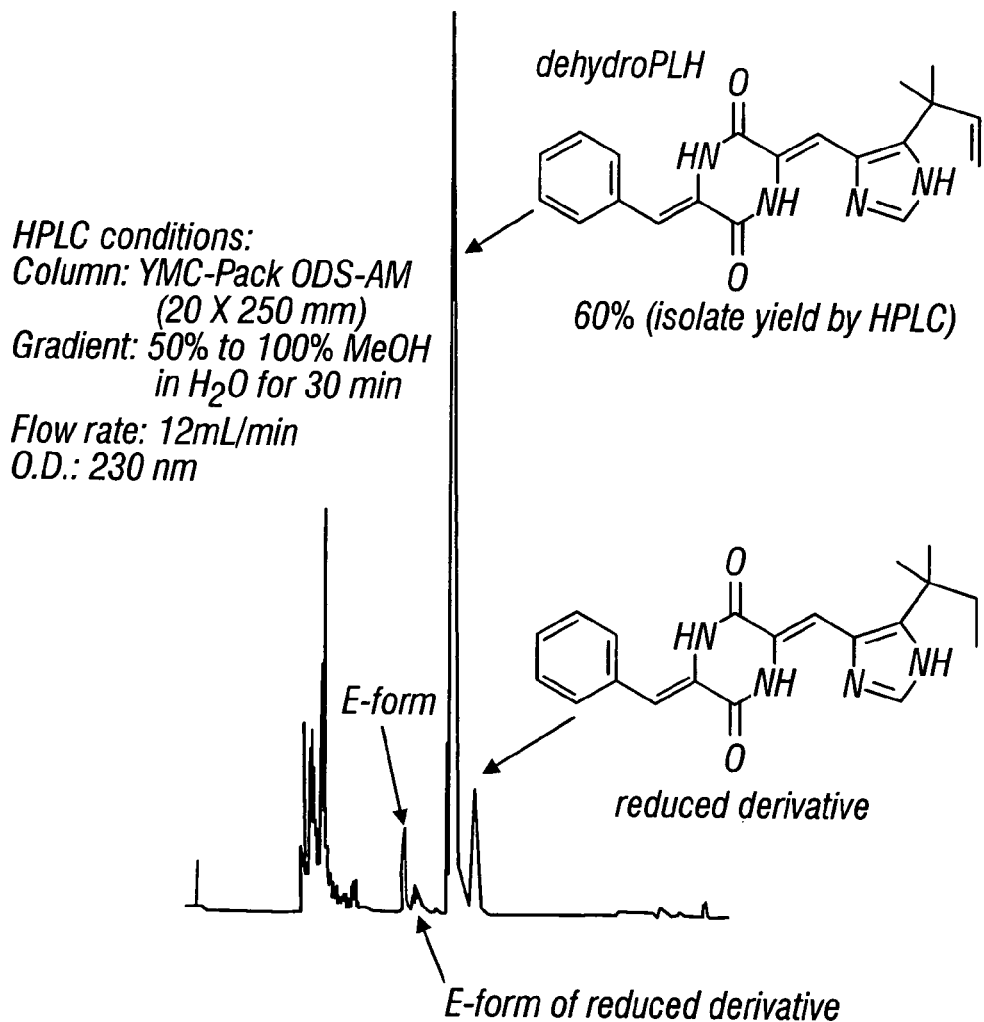
FIG. 2 depicts the HPLC profile of the synthetic crude dehydrophenylahistin.
Figure 3:
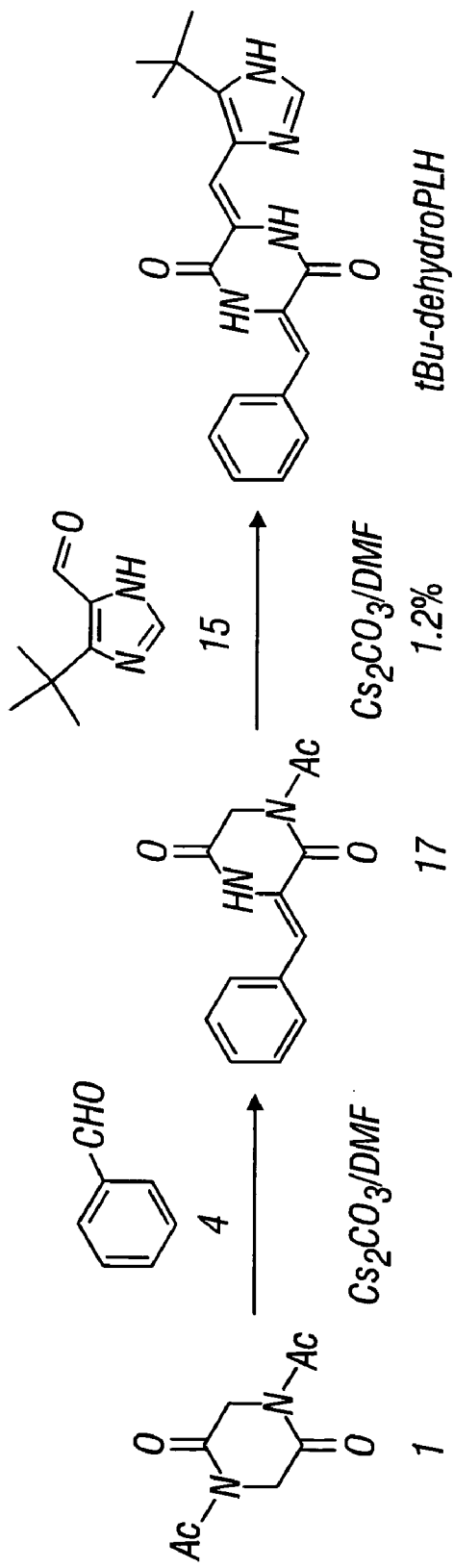
FIG. 3 illustrates a reaction scheme for producing dehydrophenylahistins by reacting a diacyldiketopiperazine 1 with a benzaldehyde 4 to yield an intermediate compound 17 which is reacted with an imidazolecarboxaldeheyde 15 to produce a dehydrophenylahistin.

To a solution of 2 (30 mg, 0.099 mmol) in DMF (0.8 mL) was added benzaldehyde (51 µL, 0.496 mmol, 5 eq) and the solution was repeatedly evacuated in a short time to remove oxygen and flushed with Ar, followed by the addition of Cs₂CO₃ (53 mg, 0.149 mmol, 1.5 eq) and the evacuation-flushing process was repeated again. The resultant mixture was heated for 2.5 h at 80° C. (The temperature must be increased slowly. Rapid heating increases the production of E-isomer at the benzylidene moiety.) After the solvent was removed by evaporation, the residue was dissolved in EtOAc, washed with water for two times and saturated NaCl for three times, dried over Na₂SO₄ and concentrated in vacuo. On TLC using CHCl₃-MeOH (10:1), you can observe a spot with bright green-yellow luminescence at 365 nm WV. The purity of this crude product was more than 75% from HPLC analysis. The resulting residue was dissolved in 90% MeOH aq and applied to reverse-phase HPLC column (YMC-Pack, ODS-AM, 20×250 mm) and eluted using a linear gradient from 70 to 74% MeOH in water over 16 min at a flow rate of 12 mL/min, and the desired fraction was collected and concentrated by evaporation to give a 19.7 mg (60%) of yellow colored dehydrophenylahistin. The HPLC profile of the synthetic crude dehydrophenylahistin is depicted in FIG. 2.

Figure 4:
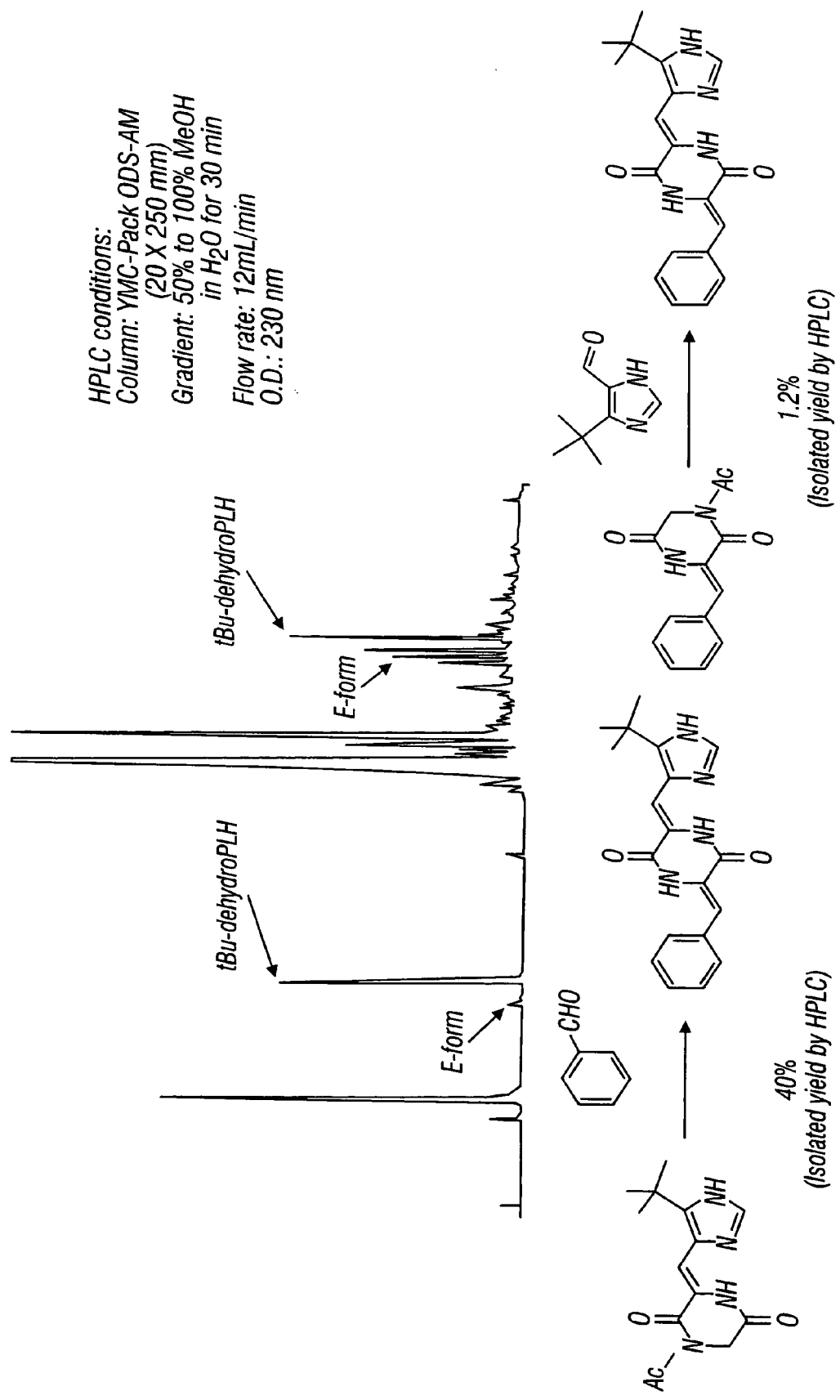
FIG. 4 depicts the HPLC profiles of the crude synthetic tBu-dehyrophenylahistin produced from Route A and from Route B.

In the purification of dehydrophenylahistin, as shown in FIG. 4, a major peak was the desired Z- form compound of dehydrophenylahistin. The formation of an E-isomer was observed as a minor component (about 10%), which was eluted as a more polar peak than Z-isomer. As other minor peaks, the reduced Z- and E-compounds, in which the dimethylallyl part of dehydrophenylahistin was reduced, was also observed. The formation of these reduced compounds was due to the aldehyde 2 with a reduced impurity, which was generated during the reduction of with DIBAL-H and was not separated in the subsequent process.

These minor compounds could be removed by preparative HPLC purification, afforded dehydrophenylahistin with the Z-configuration at the benzylidene part in a 60% yield (20% yield in two steps) with more than 95% purity. The compounds with E-configuration at the imidazole side of the diketopiperazine ring were not observed in this HPLC chart, suggesting that the first reaction from compound 1 to 3 in FIG. 1 is Z-selective.

B. Chemical Characteristics:

The above dehydrophenylahistin compound is a pale yellow solid. Its structure is confirmed by standard NMR analyses.

EXAMPLE 2

Synthesis and Physical Characterization of tBu-dehydrophenylahistin Derivatives

Structural derivatives of dehydrophenylahistin were synthesized according to the following reaction schemes to produce tBu-dehydrophenylahistin. Synthesis by Route A (see FIG. 1) is similar in certain respects to the synthesis of the dehydrophenylahistin synthesized as in Example 1.

Route A

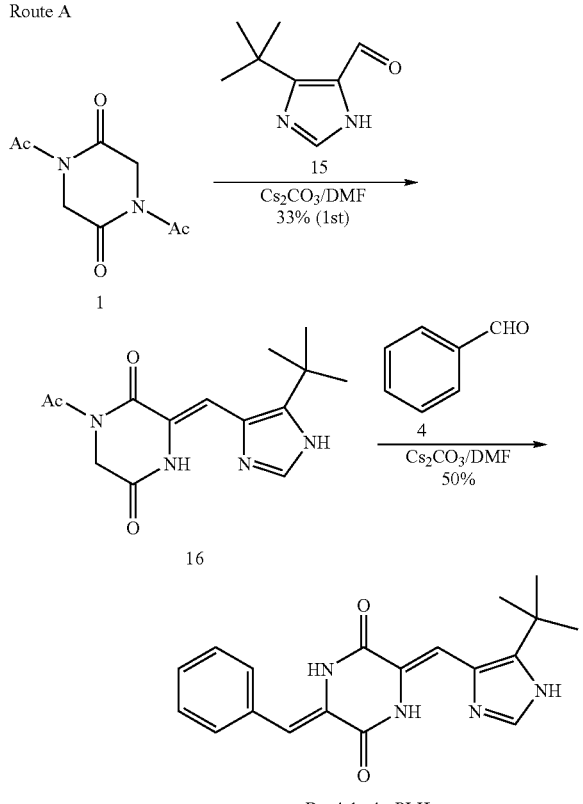

Route B

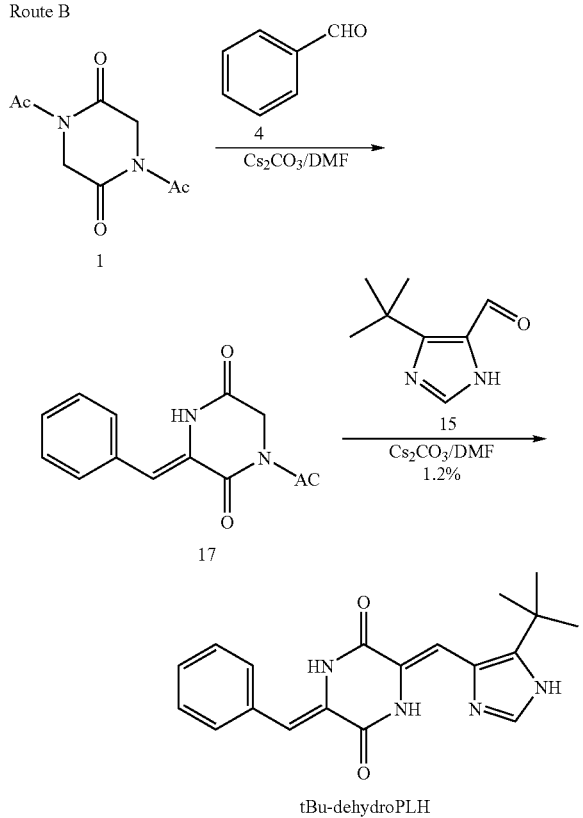

Route A:
N,N'-diacethyl-2,5-piperazinedione 1 was prepared as in Example 1.

1) 1-Acetyl-3-{(Z)-1-[5-tert-butyl-1H-4-imidazolyl]methylidenel}]-2,5-piperazinedione (16)

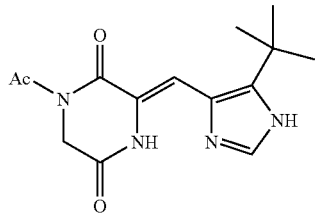

To a solution of 5-tert-butylimidazole-4-carboxaldehyde 15 (3.02 g, 19.8. mmol) in DMF (30 mL) was added compound 1 (5.89 g, 29.72 mmol) and the solution was repeatedly evacuated in a short time to remove oxygen and flushed with Ar, followed by the addition of $Cs_2CO_3$ (9.7 g, 29.72 mmol) and the evacuation-flushing process was repeated again. The resultant mixture was stirred for 5 h at room temperature. After the solvent was removed by evaporation, the residue was dissolved in the mixture of EtOAc and 10% $Na_2CO_3$, and the organic phase was washed with 10% $Na_2CO_3$ again and saturated NaCl for three times, dried over $Na_2SO_4$ and concentrated in vacuo. The residual oil was purified by column chromatography on silica using $CHCl_3$-MeOH (100:0 to 50:1) as an eluant to give 1.90 g (33 %) of a pale yellow solid 16. $^1$H NMR (270 MHz, $CDCl_3$) δ 2.14 (d, br-s, 1H), 9.22 (br-s, 1H), 7.57 (s, 1H), 7.18, (s, 1H), 4.47 (s, 2H), 2.65 (s, 3H), 1.47 (s, 9H).

2) t-Bu-dehydrophenylahistin

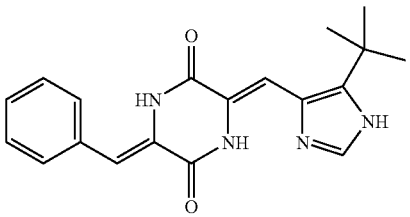

To a solution of 1-Acetyl-3-{(Z)-1-[5-tert-butyl-1H-4-imidazolyl]methylidene}]-2,5-piperazinedione (16) (11 mg, 0.038 mmol) in DMF (1.0 mL) was added benzaldehyde (19 µL, 0.19 mmol, 5 eq) and the solution was repeatedly evacuated in a short time to remove oxygen and flushed with Ar, followed by the addition of $Cs_2CO_3$ (43 mg, 0.132 mmol, 3.5 eq) and the evacuation-flushing process was repeated again. The resultant mixture was heated for 2.5 h at 80° C. After the solvent was removed by evaporation, the residue was dissolved in EtOAc, washed with water for two times and saturated NaCl for three times, dried over $Na_2SO_4$ and concentrated in vacuo. The resulting residue was dissolved in 90% MeOH aq and applied to reverse-phase HPLC column (YMC-Pack, ODS-AM, 20×250 mm) and eluted using a linear gradient from 70 to 74% MeOH in water over 16 min at a flow rate of 12 mL/min, and the desired fraction was collected and concentrated by evaporation to give a 6.4 mg (50%) of yellow colored tert-butyl-dehydrophenylahistin. $^1$H NMR (270 MHz, $CDCl_3$) δ 12.34 br-s, 1H), 9.18 (br-s, 1H), 8.09 (s, 1H), 7.59 (s, 1H), 7.31-7.49 (m, 5H), 7.01 s, 2H), 1.46 (s, 9H).

The dehydrophenylahistin reaction to produce tBu-dehydrophenylahistin is identical to Example 1.

The total yield of the tBu-dehydrophenylahistin recovered was 16.5%.

Route B:
N,N'-diacethyl-2,5-piperazinedione 1 was prepared as in Example 1.

1) 1-Acetyl-3-[(Z)-benzylidene]-
2,5-piperazinedione (17)

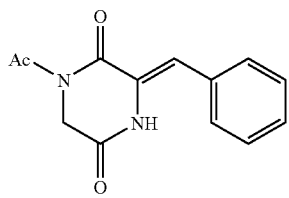

To a solution of benzaldehyde 4 (0.54 g, 5.05. mmol) in DMF (5 mL) was added compound 1 (2.0 g, 10.1 mmol) and the solution was repeatedly evacuated in a short time to remove oxygen and flushed with Ar, followed by the addition of $Cs_2CO_3$ (1.65 g, 5.05 mmol) and the evacuation-flushing process was repeated again. The resultant mixture was stirred for 3.5 h at room temperature. After the solvent was removed by evaporation, the residue was dissolved in the mixture of EtOAc and 10% $Na_2CO_3$, and the organic phase was washed with 10% $Na_2CO_3$ again and saturated NaCl for three times, dried over $Na_2SO_4$ and concentrated in vacuo. The residual solid was recrystalized from MeOH-ether to obtain a off-white solid of 17; yield 1.95 g (79%).

2) t-Bu-dehydrophenylahistin

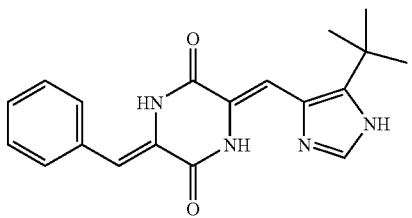

To a solution of 1-Acetyl-3-[(Z)-benzylidenel]-2,5-piperazinedione (17) (48 mg, 0.197 mmol) in DMF (1.0 mL) was added 5-tert-butylimidazole-4-carboxaldehyde 15 (30 mg, 0.197 mmol) and the solution was repeatedly evacuated in a short time to remove oxygen and flushed with Ar, followed by the addition of $Cs_2CO_3$ (96 mg, 0.296 mmol) and the evacuation-flushing process was repeated again. The resultant mixture was heated for 14 h at 80° C. After the solvent was removed by evaporation, the residue was dissolved in EtOAc, washed with water for two times and saturated NaCl for three times, dried over $Na_2SO_4$ and concentrated in vacuo. The resulting residue was dissolved in 90% MeOH aq and applied to reverse-phase HPLC column (YMC-Pack, ODS-AM, 20×250 mm) and eluted using a linear gradient from 70 to 74% MeOH in water over 16 min at a flow rate of 12 mL/min, and the desired fraction was collected and concentrated by evaporation to give a 0.8 mg (1.2%) of yellow colored tert-butyl-dehydrophenylahistin.

The total yield of the tBu-dehydrophenylahistin recovered was 0.9%.

The HPLC profile of the crude synthetic tBu-dehyrophenylahistin from Route A and from Route B is depicted in FIG. 4.

Two other tBu-dehydrophenylahistin derivatives were synthesized according to the method of Route A. In the synthesis of the additional tBu-dehydrophenylahistin derivatives, modifications to the benzaldehyde compound 4 were made.

FIG. 4 illustrates the similarities of the HPLC profiles (Column: YMC-Pack ODS-AM (20×250 mm); Gradient: 65% to 75% in a methanol-water system for 20 min, then 10 min in a 100% methanol system; Flow rate: 12 mL/min; O.D. 230 nm) from the synthesized dehydrophenylahistin of Example 1 (FIG. 2) and the above exemplified tBu-dehydrophenylahistin compound produced by Route A.

The sequence of introduction of the aldehydes is a relevant to the yield and is therefore aspect of the synthesis. An analogue of dehydrophenylahistin was synthesized, as a control or model, wherein the dimethylallyl group was changed to the tert-butyl group with a similar steric hindrance at the 5-position of the imidazole ring.

The synthesis of this "tert-butyl (tBu)-dehydrophenylahistin" using "Route A" was as shown above: Particularly, the sequence of introduction of the aldehyde exactly follows the dehydrophenylahistin synthesis, and exhibited a total yield of 16.5% tBu-dehydrophenylahistin. This yield was similar to that of dehydrophenylahistin (20%). Using "Route B", where the sequence of introduction of the aldehydes is opposite that of Route "A" for the dehydrophenylahistin synthesis, only a trace amount of the desired tBu-dehydroPLH was obtained with a total yield of 0.9%, although in the introduction of first benzaldehyde 4 gave a 76% yield of the intermediate compound 17. This result indicated that it may be difficult to introduce the highly bulky imidazole-4-carboxaldehydes 15 with a substituting group having a quatemary-carbon on the adjacent 5-position at the imidazole ring into the intermediate compound 17, suggesting that the sequence for introduction of aldehydes is an important aspect for obtaining a high yield of dehydrophenylahistin or an analog of dehydrophenylahistin employing the synthesis disclosed herein.

From the HPLC analysis of the final crude products, as shown in FIG. 4, a very high content of tBu-dehydrophenylahistin and small amount of by-product formations were observed in the crude sample of Route A (left). However, a relatively smaller amount of the desired tBu-dehydrophenylahistin and several other by-products were observed in the sample obtained using Route B (right).

EXAMPLE 3

Alternative, Larger-Scale Synthesis of Dehydrophenylahistin and Analogs

Synthesis of 3-Z-Benzylidene-6-[5"-(1,1-dimethylal-lyl)-1H-imidazol-4"-Z-ylmethylene]-piperazine-2,5-dione [Dehydrophenylahistin] (1)

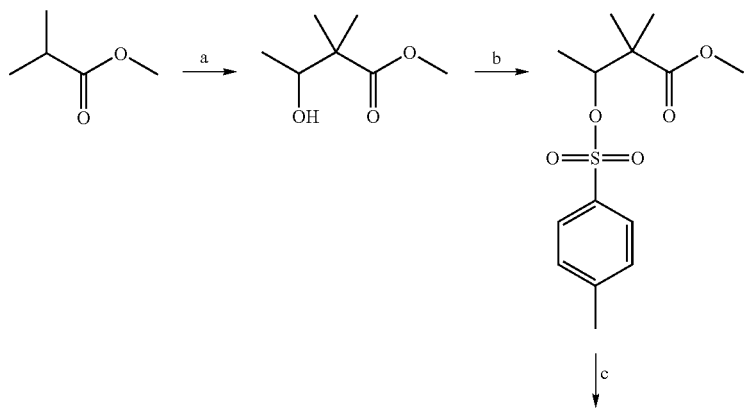

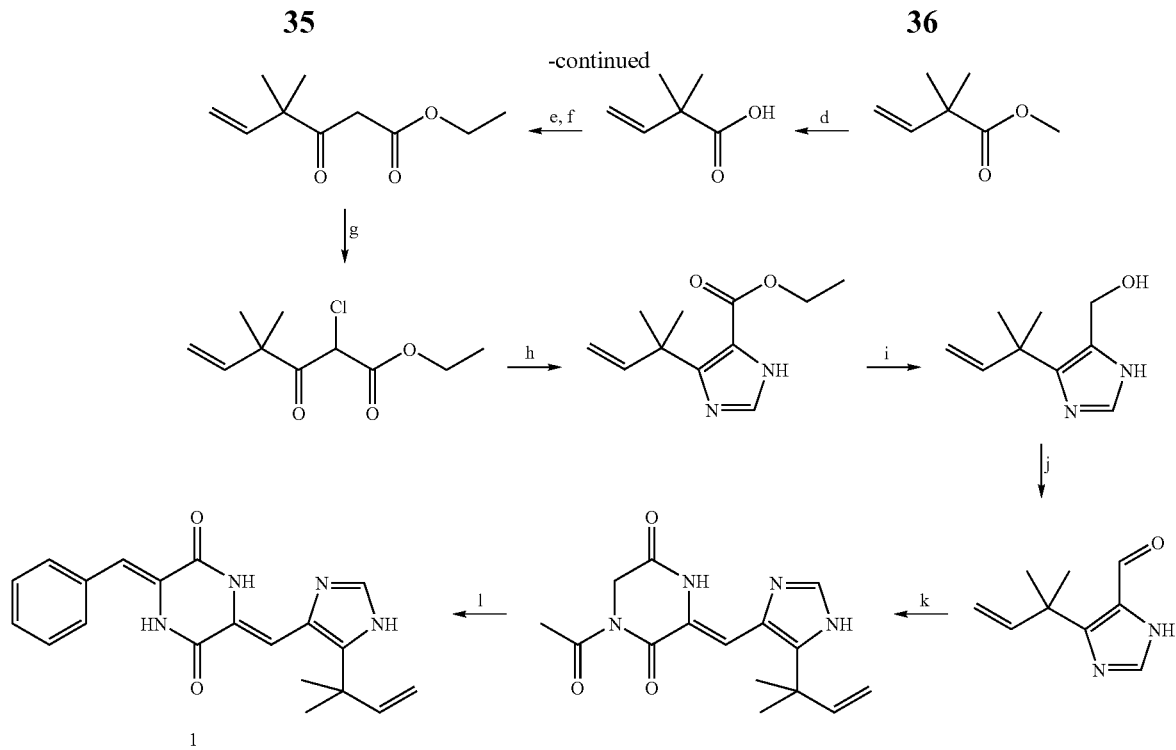

Reagents: a) LDA, CH$_3$CHO; b) Tos-Cl, pyridine; c) DBU; d) NaOH; e) C$_2$Cl$_2$O$_2$; f) KOOCCH$_2$COOEt, BuLi; g) SO$_2$Cl$_2$; h) H$_2$NCHO, H$_2$O; i) LiAlH$_4$; j) MnO$_2$; k) 1,4-diacetyl-piperazine-2,5-dione, Cs$_2$CO$_3$; l) benzaldehyde, Cs$_2$CO$_3$ 3-Hydroxy-2,2-dimethyl-butyric acid methyl ester

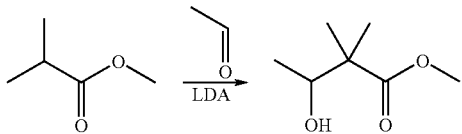

A solution of LDA in heptane/THF/ethylbenzene (2 M, 1,96 ml, 0.39 mol) was added under argon to a solution of methyl isobutyrate (45 ml, 0.39 mol) in THF (270 ml) at −60° and the resultant mixture was stirred for 30 min. A solution of acetaldehyde (27 ml, 0.48 in THF (45 ml), precooled to −60°, was added slowly and the resulting solution stirred for a further 30 min. Saturated ammonium chloride (50 ml) was added and the solution was allowed to warm to room temperature. The reaction mixture was extracted with ethyl acetate, and the extracts were washed with HCl (2 M), sodium bicarbonate, then brine. The organic layer was dried over magnesium sulfate, filtered, then evaporated to give a clear oil (52.6 g). Distillation 76-82°/30 mmHg gave pure 3-hydroxy-2,2-dimethyl-butyric acid methyl ester (42.3 g, 74%). (Burke et al., *J. Am. Chem. Soc.*, 117:4423-4424 (1995)).

$^1$H NMR (400 MHz, CDCl$_3$) δ 1.15 (d, J=6.2 Hz, 3H); 1.17 (s, 6H); 2.66 (d, J=6.2 Hz, 1H, —OH); 3.71 (s, 3H, -OMe); 3.87 (app quintet, J=6.4 Hz, 1H, H3).

2,2-Dimethyl-3-(toluene-4-sulfonyloxy)-butryic acid methyl ester

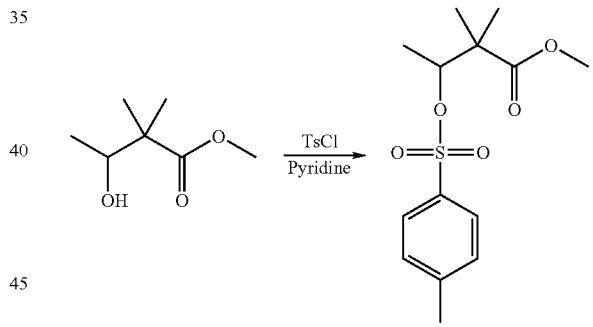

To a cooled (0°) solution of 3-hydroxy-2,2-dimethyl-butyric acid methyl ester (52.0 g, 0.36 mol) in pyridine (100 ml) was added gradually, p-toluene sulfonyl chloride (69.0 g, 0.36 mol). The mixture was allowed to warm to room temperature and was stirred for 60 h. The reaction was again cooled in ice and was acidified by addition of HCl (2 M). The resultant solution was extracted with ethyl acetate, the extracts were washed with HCl, then brine, dried and evaporated to give an oil which formed a white precipitate upon standing. This mixture was dissolved in the minimum amount of ethyl acetate and then light petroleum was added to afford a white precipitate which was collected and washed with more light petroleum. The filtrate was partially evaporated and a second crop of crystals was collected and added to the first to afford 2,2-dimethyl-3-(toluene-4-sulfonyloxy)-butyric acid methyl ester (81.2 g, 76%).

$^1$H NMR (400 NMz, CDCl$_3$) δ 1.12 (s, 3H); 1.13 (s, 3H); 1.24 (d, J=6.4 Hz, 3H); 2.45 (s, 3H, -OMe) 3.58 (s, 3H, -OMe); 4.94 (quartet, J=6.4 Hz, 1H, H3), 7.33 (d, J=8.0 Hz, 2H), 7.78 (d, J=8.0 Hz, 2H).

Evaporation of the final filtrate afforded additional crude 2,2-dimethyl-3-(toluene-4-sulfonyloxy)-butyric acid methyl ester (19.0 g, 18%).

2,2-Dimethyl-but-3-enoic acid methyl ester

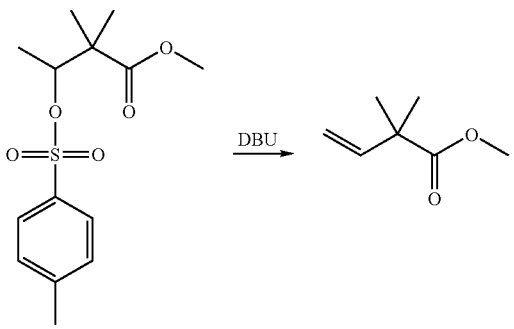

A solution of 2,2-dimethyl-3-(toluene-4-sulfonyloxy)-butyric acid methyl ester (18.06 g, 0.06 mol) in DBU (15 ml) was heated at 140-160° for 3.5 h. The mixture was allowed to cool to room temperature and was then diluted with ether. The mixture was washed with HCl (1 M), sodium bicarbonate, then brine. The ethereal layer was dried and partially evaporated to give a concentrated solution of 2,2-dimethyl-but-3-enoic acid methyl ester (10 g). (Savu and Katzenellenbogen, *J. Org. Chem*, 46:239-250 (1981)). Further evaporation was avoided due to the volatility of the product (bp 102°). (Tsaconas et al., *Aust. J. Chem.*, 53:435-437 (2000)).

$^1$H NMR (400 NMz, CDCl$_3$) δ 1.31 (s, 6H); 3.68 (s, 3H); 5.06 (d, J=17.1 Hz, 1H, —CH═CH$_2$); 5.11 (d, J=10.7 Hz, 1H, —CH═CH$_2$); 6.03 (dd, J=17.1, 10.7 Hz, 1H, —CH═CH$_2$).

2,2-Dimethyl-but-3-enoic acid

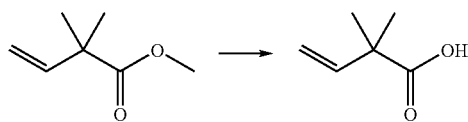

The above ethereal solution of 2,2-dimethyl-but-3-enoic acid methyl ester (10 g) was diluted with ethanol (25 ml), sodium hydroxide (4 M, 22 ml) was added and the mixture was stirred overnight. The solution was partially evaporated to remove the ethanol and the resultant mixture was added to HCl (1M, 100 ml). The product was extracted with ethyl acetate and the extracts were dried and evaporated to give 2,2-dimethyl-but-3-enoic acid (6.01 g, 88% 2 steps). (Hayashi et al., *J. Org. Chem.*, 65:8402-8405 (2000).

$^1$H NMR (400 MHz, CDCl$_3$) δ 1.33 (s, 6H); 5.11 (d, J=10.8 Hz, 1H, —CH═CH$_2$); 5.15 (d, J=17.2 Hz, 1H, —CH═CH$_2$); 6.05 (dd, J=17.2, 10.8 Hz, 1H, —CH═CH$_2$).

Monoethyl hydrogen malonate (Wierenga and Skulnick, "Aliphatic and Aromatic β-keto Esters from Monoethyl Malonate: Ethyl 2-Butyrylacetate," *Organic Syntheses Collective Volume 7*, 213).

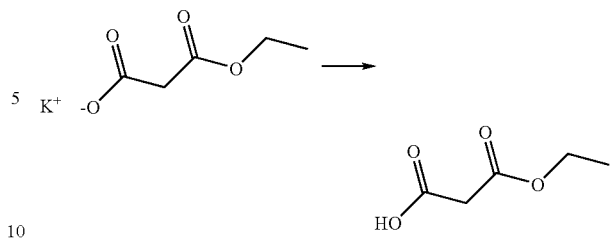

Ethyl potassium malonate (25.0 g, 0.15 mol) was suspended in water (15.6 ml) and cooled in an ice bath. Concentrated HCl (12.5 ml) was added dropwise over 30 min, then the mixture was stirred for a further 10 min. The precipitate was filtered, then washed twice with ether. The filtrate was separated and the aqueous phase was extracted with ether. The combined ethereal solutions were dried (MgSO$_4$) and evaporated to afford, as an oil, monoethyl hydrogen malonate (19.2 g, 99%) which was dried under vacuum overnight (or 50°/1 mm for 1 h) prior to use.

4,4-Dimethyl-3-oxo-hex-5-enoic acid ethyl ester

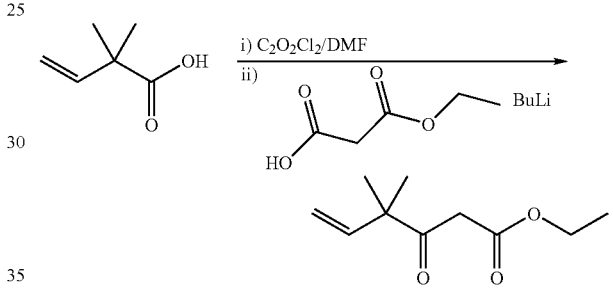

Oxalyl chloride (3.83 ml, 43.9 mmol) was added dropwise to a cooled (0°) solution of 2,2-dimethyl-but-3-enoic acid (5.0 g, 43.9 mmol) and DMF (1 drop) in anhydrous dichloromethane (25 ml). The mixture was stirred for 1 h at 0°, then for 16 h at room temperature. Fractional distillation (121°/760 mmHg) afforded 2,2-dimethyl-but-3-enoyl chloride (4.1 g, 71%).

Monoethyl hydrogen malonate (7.2 g, 0.05 mol) and bipyridyl (few milligrams) were dissolved in THF (90 ml) and the system was flushed with nitrogen. The solution was cooled to –70°, then BuLi (2.5 M in hexanes, 37 ml, 0.09 mol) was added. After the addition of only ~10 ml of BuLi the solution turned pink and additional THF (15 ml) was required to enable magnetic stirring. The cooling bath was removed and the remaining BuLi was added, the temperature was allowed to reach –10°, upon which the solution turned colorless. The mixture was again cooled to –60° and a solution of 2,2-dimethyl-but-3-enoyl chloride (4.1 g, 0.03 mol) in THF (12 ml) was added dropwise. After addition was complete the mixture was allowed to warm to 0° and stir for 3 h, then it was added to a 1:1 mixture of ether/1M HCl (260 ml) at 0° and stirred for a further 1.5 h. The organic layer was removed, washed with HCl (1 M), sodium bicarbonate solution, brine then dried and evaporated to give 4,4-dimethyl-3-oxo-hex-5-enoic acid ethyl ester (5.6 g, 98%). (Hayashi et al., *J. Org. Chem.*, 65:8402-8405 (2000). Distillation with a Kugelrohr oven (160°/1 mmHg) afforded pure material.

$^1$H NMR (400 MHz, CDCl$_3$) δ 1.26 (s, 6H); 1.27 (t, J=6.9 Hz, 3H, —CH$_2$CH$_3$); 3.51 (s, 2H); 4.18 (q, J=6.9 Hz, 2H, —CH$_2$CH$_3$); 5.20 (d, J=17.7 Hz, 1H, —CH═CH$_2$); 5.21 (d, J=9.6 Hz, 1H, —CH═CH$_2$); 5.89 (dd, J=17.7, 9.6 Hz, 1H, 1H, —CH═CH$_2$).

2-Chloro-4,4-dimethyl-3-oxo-hex-5-enoic acid ethyl ester

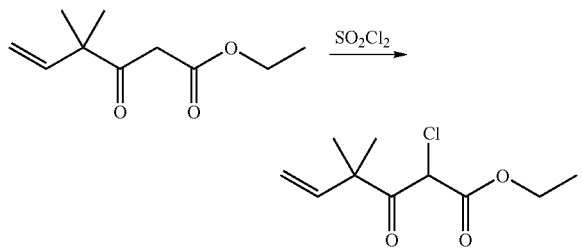

Sulfuryl chloride (0.84 ml, 10.4 mmol) was added to a cooled (0°) solution of 4,4-dimethyl-3-oxo-hex-5-enoic acid ethyl ester (1.83 g, 9.93 mmol) in chloroform (7 ml). The resulting mixture was allowed to warm to room temperature and stir for 30 min, after which it was heated under reflux for 2 h. After cooling to room temperature the reaction mixture was diluted with chloroform, then was washed with sodium bicarbonate, water then brine. The organic phase was dried and evaporated to afford, as a brown oil, 2-chloro-4,4-dimethyl-3-oxo-hex-5-enoic acid ethyl ester (2.01 g, 93%). (Hayashi et al., *J. Org. Chem.*, 65:8402-8405 (2000)).

$^1$H NMR (400 MHz, CDCl$_3$) δ 1.28 (t, J=7.0 Hz, 3H, —CH$_2$CH$_3$); 1.33 (s, 3H); 1.34 (s, 3H); 4.24 (q, J=7.0 Hz, 2H, —CH$_2$CH$_3$); 5.19 (s, 1H; 5.28 (d, J=16.9 Hz, 1H, —CH=CH$_2$); 5.29 (d, J=10.9 Hz, 1H, —CH=CH$_2$); 5.96 (dd, J=16.9, 10.9 Hz, 1H, —CH=CH$_2$)

LC/MS $t_R$=8.45 [M(Cl$^{37}$)+H]$^+$ min.

This material was reacted without further purification.

5-(1,1-Dimethyl-allyl)-3H-imidazole-4-carboxylic acid ethyl ester

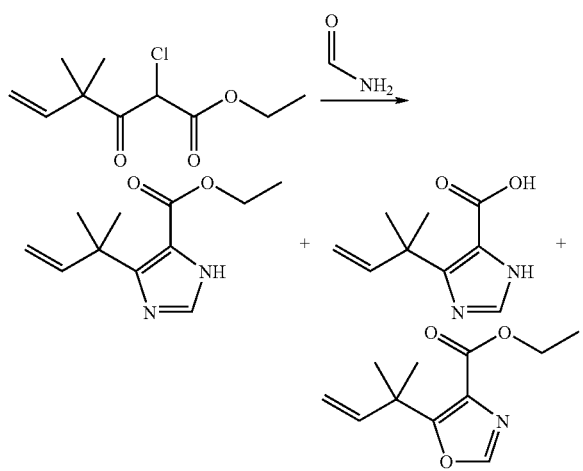

A suspension of 2-chloro-4,4-dimethyl-3-oxo-hex-5-enoic acid ethyl ester (19.4 g, 0.09 mol) and water (1.94 ml, 0.11 mol) in formamide (36.8 ml) was shaken briefly, then dispensed into 15×18 ml vials. The vials were sealed and heated at 150° for 5 h. After cooling to room temperature, the vials' contents were combined and extracted exhaustively with chloroform. The extracts were dried and evaporated to afford a concentrated formamide solution (14.7 g). This was added to a silica column (7 cm diameter, 11 cm height) packed in 1% MeOH/1% Et$_3$N in chloroform. Elution of the column with 2 L of this mixture followed by 2 L of 2% MeOH/1% Et$_3$N in chloroform afforded, in the early fractions, a compound suspected of being 5-(1,1-dimethyl-allyl)-oxazole-4-carboxylic acid ethyl ester (1.23 g, 7%).

HPLC (214 nm) $t_R$=8.68 (50.4%) min.

$^1$H NMR (400 MHz, CDCl$_3$) δ 1.40 (t, J=7.2 Hz, 3H, —CH$_2$CH$_3$); 1.54 (s, 6H); 4.38 (t, J=7.2 Hz, 2H, —CH$_2$CH$_3$); 5.03 (d, J=17.4 Hz, 1H, —CH=CH$_2$); 5.02 )d, J=10.4 Hz, 1H, —CH=CH$_2$); 6.26 (dd, J=17.4, 10.4 Hz, 1H, —CH=CH$_2$); 7.83 (s, 1H).

LCMS $t_R$=8.00 (210.1 [M+H]$^+$, 361.1 [2M+H]$^+$) min.

Recovered from later fractions was the desired 5-(1,1-dimethyl-allyl)-3H-imidazole-4-carboxylic acid ethyl ester (3.13 g, 17%). (Hayashi et al., *J. Org. Chem.*, 65:8402-8405 (2000)).

HPLC (214 nm) $t_R$=5.52 (96.0%) min.

$^1$H NMR (400 MHz, CDCl$_3$) δ 1.38 (t, J=7.0 Hz, 3H); 1.57 (s, 6H); 4.35 (q, J=7.0 Hz, 2H); 5.04-5.14 (m, 2H, —CH=CH$_2$); 6.28 (dd, J=18.0, 10.4 Hz, 1—CH=CH$_2$); 7.52 (s, 1H).

LC/MS $t_R$=5.30 (209.1 [M+H]$^+$, 417.2 [2M+H]$^+$) min.

Additional 5-(1,1-dimethyl-allyl)-3H-imidazole-4-carboxylic acid ethyl ester was also recovered from the column (3.59 g, 19%) which was of lower purity but still sufficient for further reaction.

Another byproduct isolated from a similar reaction (smaller scale) by further elution of the column with 5% MeOH/1% Et$_3$N in chloroform was a compound suspected of being 5-(1,1-dimethyl-allyl)-3H-imidazole-4-carboxylic acid (0.27 g, 9%).

HPLC (245 nm) $t_R$=5.14 (68.9%) min. $^1$H NMR (400 MHz, CD$_3$OD) δ 1.45 (s, 6H); 4.97 (d, J=10.6 Hz, 1H, —CH=CH$_2$); 5.01 (d, J=17.7 Hz, 1H, —CH=CH$_2$); 6.28 (dd, J=17.7, 10.6 Hz, 1H, —CH=CH$_2$); 7.68 (s, 1H).

LCMS $t_R$=4.72 (181.0 [M+H]$^+$, 361.1 [2M+H]$^+$) min.

[5-(1,1-Dimethyl-allyl)-3H-imidazol-4-yl]-methanol

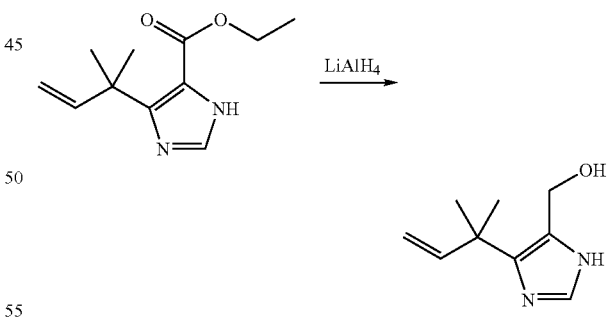

A solution of 5-(1,1-dimethyl-allyl)-3H-imidazole-4-carboxylic acid ethyl ester (3.13 g, 15.0 mmol) in THF (60 ml) was added dropwise to a suspension of lithium aluminium hydride (95% suspension, 1.00 g, 25.0 mmol) in THF (40 ml) and the mixture was stirred at room temperature for 4 h. Water was added until the evolution of gas ceased, the mixture was stirred for 10 min, then was filtered through a sintered funnel. The precipitate was washed with THF, then with methanol, the filtrate and washings were combined, evaporated, then freeze-dried to afford [5-(1,1-dimethyl-allyl)-3H-imidazol-4-yl]-methanol (2.56 g, 102%). Residual water was removed by azeotroping with chloroform prior to further reaction. (See Hayashi et al., *J. Org. Chem.*, 65:8402-8405 (2000)).

HPLC (240 nm) $t_R$=3.94 (56.8%) min.

$^1$H NMR (400 MHz, CD$_3$OD) δ 1.43 (s, 6H); 4.57 (s, 2H); 5.01 (d, J=10.5 Hz, 1H, —CH═CH$_2$); 5.03 (d, J=17.7 Hz, 1H, —CH═CH$_2$); 6.10 (dd, J=17.7, 10.5 Hz, 1H, —CH═CH$_2$); 7.46 (s, 1H).

LC/MS $t_R$=3.77 (167.3 [M+H]$^+$) min.

5-(1,1-Dimethyl-allyl)-3H-imidazole-4-carbaldehyde

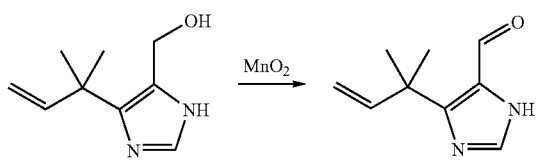

Manganese dioxide (20 g, 0.23 mol) was added to a solution of [5-(1,1-dimethyl-allyl)-3H-imidazol-4-yl]-methanol (2.56 g, 0.02 mol) in acetone (300 ml) and the resulting mixture was stirred at room temperature for 5 h. The mixture was filtered through filter paper and the residue was washed with acetone. The filtrate and washings were combined and evaporated to afford 5-(1,1-dimethyl-allyl)-3H-imidazole-4-carbaldehyde (1.82 g, 51%). (Hayashi et al., *J. Org. Chem.*, 65:8402-8405 (2000)).

HPLC (240 nm) $t_R$=4.08 (91.5%) min.

$^1$H NMR (400 MHz, CDCl$_3$) δ 1.56 (s, 6H); 5.16 (d, J=10.6 Hz, 1H, —CH═CH$_2$); 5.19 (d, J=17.3 Hz, 1H, CH═CH$_2$); 6.22 (dd, J=17.3, 10.6 Hz, 1H, —CH═CH$_2$); 7.75 (s, 1H), 10.02 (s, 1H, HCO).

LC/MS $t_R$=3.75 (165.2 [M+H]$^+$) min.

1-Acetyl-3-[5'-(1,1-dimethyl-allyl)-1H-imidazol-4'-Z-ylmethylene]-piperazine-2,5-dione

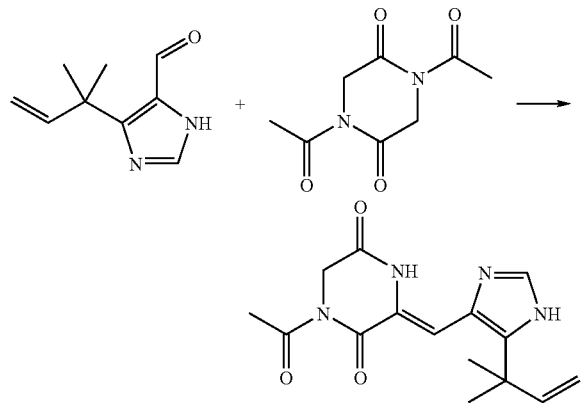

To a solution of 5-(1,1-dimethyl-allyl)-3H-imidazole-4-carbaldehyde (1.78 g, 0.01 mol) in DMF (35 ml) was added 1,4-diacetyl-piperazine-2,5-dione (8.59 g, 0.04 mol) and the mixture was evacuated, then flushed with argon. The evacuation-flushing process was repeated a further two times, then cesium carbonate (3.53 g, 0.01 mol) was added. The evacuation-flushing process was repeated a further three times, then the resultant mixture was heated at 45° for 5 h. The reaction mixture was partially evaporated (heating under high vacuum) until a small volume remained and the resultant solution was added dropwise to ice-water (50 ml). The yellow precipitate was collected, washed with water, then freeze-dried to afford 1-acetyl-3-[5'-(1,1-dimethyl-allyl)-1H-imidazol-4'-ylmethylene]-piperazine-2,5-dione (1.18 g, 36%). (Hayashi, Personal Communication (2001)).

HPLC (214 nm) $t_R$=6.01 (72.6%) min.

$^1$H NMR (400 MHz, CDCl$_3$) δ 1.53 (s, 6H); 2.64 (s, 3H); 4.47 (s, 2H); 5.19 (d, J=17.3 Hz, 1H, —CH═CH$_2$); 5.23 (d, J=10.7 Hz, 1H, —CH═CH$_2$); 6.06 (dd, J=17.3, 10.7 Hz, 1H, —CH═CH$_2$); 7.16 (s, 1H), 7.59 (s, 1H), 9.47 (bs, 1H); 12.11 (bs, 1H) [observed ~2% 1,4-diacetyl-piperazine-2,5-dione contamination δ 2.59 (s, 6H); 4.60 (s, 4H).]

LC/MS $t_R$=6.65 (303.3 [M+H]$^+$, 605.5 [2M+H]$^+$) min. (n.b. different system used).

3-Z-Benzylidene-6-[5''-(1,1-dimethylallyl)-1H-imidazol-4''-Z-ylmethylene]-piperazine-2,5-dione

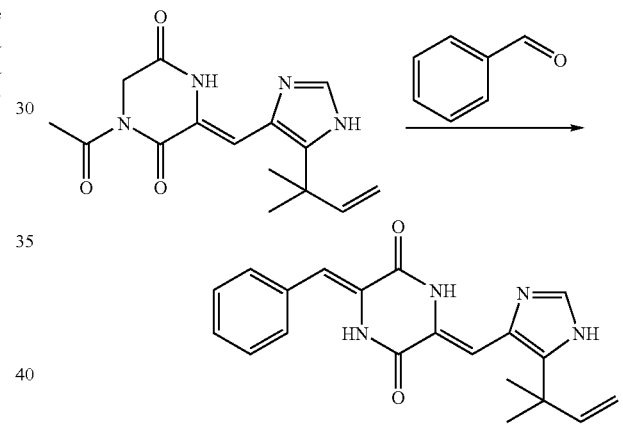

To a solution of 1-acetyl-3-[5'-(1,1-dimethyl-allyl)-1H-imidazol-4'-ylmethylene]-piperazine-2,5-dione (2.91 g, 9.62 mmol) in DMF (70 ml) was added benzaldehyde (4.89 ml, 48.1 mmol) and the solution was evacuated, then flushed with Argon. The evacuation-flushing process was repeated a further two times, then cesium carbonate (4.70 g, 14.4 mmol) was added. The evacuation-flushing process was repeated a further three times, then the resultant mixture was heated under the temperature gradient ad shown below.

After a total time of 5 h the reaction was allowed to cool to room temperature and the mixture was added to ice-cold water (500 ml). The precipitate was collected, washed with water (300 ml), then freeze-dried to afford a yellow solid (2.80 g). This material was dissolved in chloroform (250 ml) filtered through filter paper and evaporated to azeotrope remaining water. The residual yellow precipitate (2.70 g, HPLC (214 nm) $t_R$=7.26 (93.6%) min.) was partially dissolved in chloroform (20 ml), the suspension was sonicated for 5 min, then the solid was collected and air dried to afford 3-Z-benzylidene-6-[5''-(1,1-dimethylallyl)-1H-imidazol-4''-Z-ylmethylene]-piperazine-2,5-dione (1.82 g, 54%) (Hayashi, Personal Communication (2001)), m.p. 239-240° (dec.).

HPLC (214 nm) $t_R$=6.80 (1.92) min, 7.33 (95.01%).

$^1$H NMR (400 MHz, CDCl$_3$) δ 1.53 (s, 6H); 5.18 (d, J=17.6 Hz, 1H, —CH═CH$_2$); 5.21 (d, J=11.0 Hz, 1H, —CH═CH$_2$); 6.06 (dd, J=17.6, 11.0 Hz, 1H, —CH═CH$_2$); 6.99 (s, 1H, —C—C═CH); 7.00 (s, 1H, —C—C═CH); 7.30-7.50 (m, 5×ArH); 7.60 (s, H2"); 8.07 (bs, NH); 9.31 (bs, NH); 12.30 (bs, NH).

LC/MS t$_R$=6.22 (349.3 [M+H]$^+$, E isomer), 6.73 (349.5 [M+H]$^+$, 697.4 [2M+H]$^+$, Z isomer) min.

ESMS m/z 349.5 [M+H]$^+$, 390.3 [M+CH$_4$CN]$^+$.

Evaporation of the chloroform solution gave additional 3-Z-benzylidene-6-[5"-(1,1-dimethylallyl)-1H-imidazol-4"-Z-ylmethylene]-piperazine-2,5-dione (0.76 g, 29%).

HPLC (214 nm) t$_R$=7.29 (84.5%) min.

3-E-Benzylidene-6-[5"-(1,1-dimethylallyl)-1H-imidazol-4"-Z-ylmethylene]-piperazine-2,5-dione

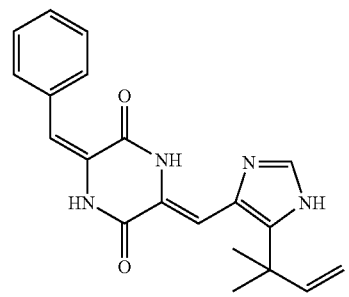

Preparative HPLC purification of a crude sample of material synthesized as above afforded the geometric isomer 3-E-Benzylidene-6-[5"-(1,1-dimethylallyl)-1H-imidazol-4"-Z-ylmethylene]-piperazine-2,5-dione (1.7 mg).

HPLC (214 nm) t$_R$=6.75 (87.79) min.

$^1$H NMR (400 MHz, CDCl$_3$) δ 1.52 (s, 6H); 5.19 (d, J=20.8 Hz, 1H, CH═CH$_2$); 5.22 (d, J=14.0 Hz, 1H, CH═CH$_2$); 6.05 (dd, J=18.0, 10.4 Hz, 1H, CH═CH$_2$); 6.33 (s, 1H, C—C═CH); 6.90-7.65 (m, 7H).

ESMS m/z 349.5 [M+H]$^+$, 390.4 [M+CH$_4$CN]$^+$.

Synthesis of 3-Z-Benzylidene-6-(5"-tert-butyl-1H-imidazol-4"-Z-ylmethylene)-piperazine-2,5-dione (2)

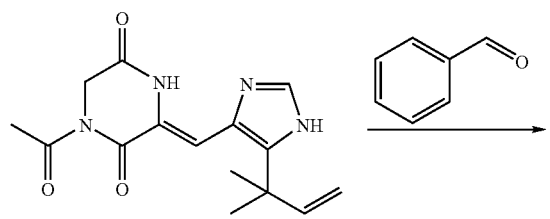

↓g

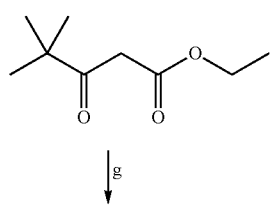

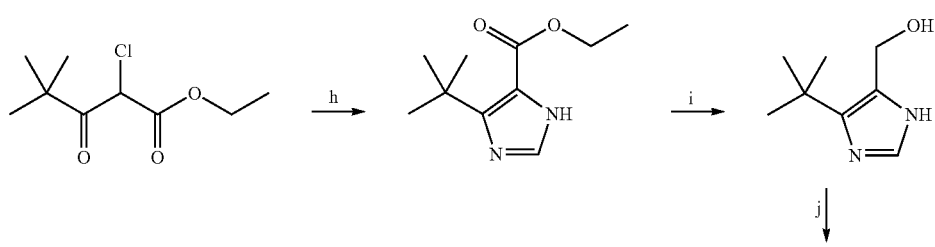

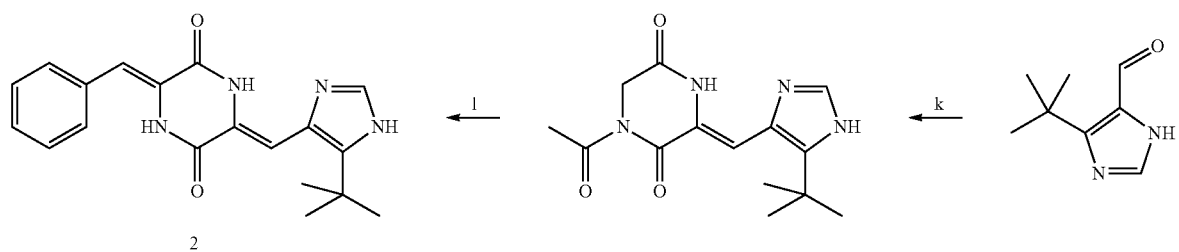

2

Reagents: g) SO$_2$Cl$_2$; h) H$_2$NCHO, H$_2$O; I)LiAlH$_4$; j) MnO$_2$; k) 1,4-diacetyl-piperazine-2,5-dione, Cs$_2$CO$_3$; l) benzaldehyde, Cs$_2$CO$_3$ 2-Chloro-4,4-dimethyl-3-oxo-pentanoic acid ethyl ester

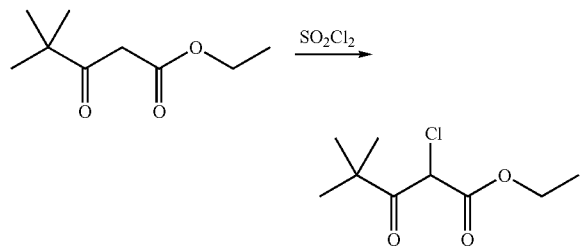

Sulfuryl chloride (14.0 ml, 0.17 mol) was added to a cooled (0°) solution of ethyl pivaloylacetate (27.17 g, 0.16 mol) in chloroform (100 ml). The resulting mixture was allowed to warm to room temperature and was stirred for 30 min, after which it was heated under reflux for 2.5 h. After cooling to room temperature, the reaction mixture was diluted with chloroform, then washed with sodium bicarbonate, water then brine.

The organic phase was dried and evaporated to afford, as a clear oil, 2-chloro-4,4-dimethyl-3-oxo-pentanoic acid ethyl ester (33.1 g, 102%). (Durant et al., "Aminoalkylimidazoles and Process for their Production." Patent No. GB1341375 (Great Britain, 1973)).

HPLC (214 nm) $t_R$=8.80 (92.9%) min.
$^1$H NMR (400 MHz, CDCl$_3$) δ 1.27 (s, 9H); 1.29 (t, J=7.2 Hz, 3H); 4.27 (q, J=7.2 Hz, 2H); 5.22 (s, 1H).
$^{13}$C NMR (100 MHz, CDCl$_3$) δ 13.8, 26.3, 45.1, 54.5, 62.9, 165.1, 203.6.

5-tert-Butyl-3H-imidazole-4-carboxylic acid ethyl ester

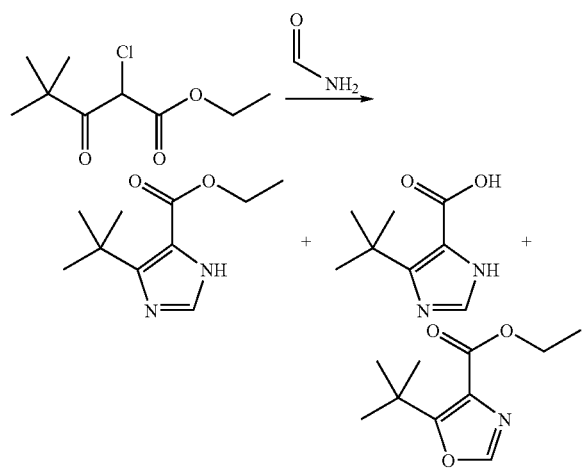

A solution of 2-chloro-4,4-dimethyl-3-oxo-pentanoic acid ethyl ester (25.0 g, 0.12 mol) in formamide (47.5 ml) and water (2.5 ml) was shaken, then dispensed into 15×8 ml vials. All vials were sealed and then heated at 150° for 3.5 h. The vials were allowed to cool to room temperature, then water (20 ml) was added and the mixture was exhaustively extracted with chloroform. The chloroform was removed to give a concentrated formamide solution (22.2 g) which was added to a flash silica column (6 cm diameter, 12 cm height) packed in 1% MeOH/1% Et$_3$N in chloroform. Elution of the column with 2.5 L of this mixture followed by 1 L of 2% MeOH/1% Et$_3$N in chloroform gave, in the early fractions, a product suspected of being 5-tert-butyl-oxazole-4-carboxylic acid ethyl ester (6.3 g, 26%).

HPLC (214 nm) $t_R$=8.77 min.
$^1$H NMR (400 MHz, CDCl$_3$) δ 1.41 (t, J=7.2 Hz, 3H); 1.43 (s, 9H); 4.40 (q, J=7.2 Hz, 2H); 7.81 (s, 1H).
$^{13}$C NMR (100 MHz, CDCl$_3$) δ 14.1, 28.8, 32.5, 61.3, 136.9, 149.9, 156.4, 158.3.
ESMS m/z 198.3 [M+H]$^+$, 239.3 [M+CH$_4$CN]$^+$.
LC/MS $t_R$=7.97 (198.1 [M+H]$^+$) min.

Recovered from later fractions was 5-tert-butyl-3H-imidazole-4-carboxylic acid ethyl ester (6.20 g, 26%). (Durant et al., "Aminoalkylimidazoles and Process for their Production." Patent No. GB1341375 (Great Britain, 1973)).

HPLC (214 nm) $t_R$=5.41 (93.7%) min.
$^1$H NMR (400 MHz, CDCl$_3$) δ 1.38 (t, J=7.0 Hz, 3H); 1.47 (s, 9H); 4.36 (q, J=7.2H); 7.54 (s, 1H).
$^{13}$C NMR (100 MHz, CDCl$_3$) δ 13.7, 28.8, 32.0, 59.8, 124.2, 133.3, 149.2,
ESMS m/z 197.3 [M+H]$^+$, 238.3 [M+CH$_4$CN]$^+$.

Further elution of the column with 1L of 5% MeOh/1% Et$_3$N gave a compound suspected of being 5-tert-butyl-3H-imidazole-4-carboxylic acid (0.50 g, 2%).

HPLC (245 nm) $t_R$=4.68 (83.1%) min.
$^1$H NMR (400 MHz, CD$_3$OD) δ 1.36 (s, 9H); 7.69 (s, 1H).
$^1$H NMR (400 MHz, CDCl$_3$) δ 1.37 (s, 9H); 7.74 (s, 1H).
$^1$H NMR (400 MHz, CD$_3$SO) δ 1.28 (s, 9H); 7.68 (s, 1H).
ESMS m/z 169.2 [M+H]$^+$, 210.4 [M+CH$_4$CN]$^+$.

(5-tert-Butyl-3H-imidazol-4-yl)-methanol

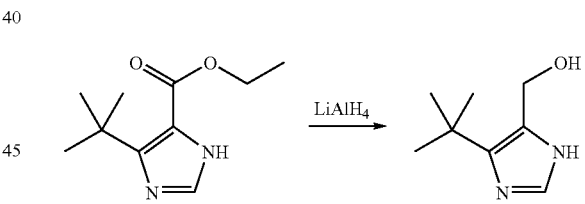

A solution of 5-tert-butyl-3-imidazole-4-carboxylic acid ethyl ester (3.30 g, 16.8 mmol) in THF (60 ml) was added dropwise to a suspension of lithium aluminium hydride (95% suspension, 0.89 g, 22.2 mmol) in THF (40 ml) and the mixture was stirred at room temperature for 3 h. Water was added until the evolution of gas ceased, the mixture was stirred for 10 min, then was filtered through a sintered funnel. The precipitate was washed with THF, then with methanol, the filtrate and washings were combined and evaporate. The residue was freeze-dried overnight to afford, as a white solid (5-tert-butyl-3H-imidazol-4-yl)-methanol (2.71 g, 105%). (Durant et al., "Aminoalkylimidazoles and Process for their Production." Patent No. GB1341375 (Great Britain, 1973)).

HPLC (240 nm) $t_R$=3.70 (67.4%) min.
$^1$H NMR (400 MHz, CD$_3$OD) δ 1.36 (s, 9H); 4.62 (s, 2H); 7.43 (s, 1H).
$^{13}$C NMR (100 MHz, CD$_3$OD) δ 31.1, 33.0, 57.9, 131.4, 133.9, 140.8.
LC/MS $t_R$=3.41 (155.2 [M+H]$^+$) min.

This material was used without further purification.

5-tert-Butyl-3H-imidazole-4-carbaldehyde

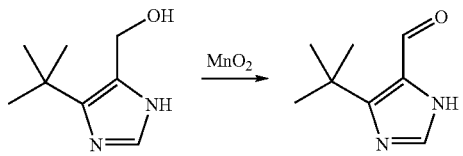

Manganese dioxide (30 g, 0.35 mol) was added to a heterogeneous solution of (5-tert-butyl-3H-imidazol-4-yl)-methanol (4.97 g, 0.03 mol) in acetone (700 ml) and the resulting mixture was stirred at room temperature for 4 h. The mixture was filtered through a pad of Celite and the pad was washed with acetone. The filtrate and washings were combined and evaporated. The residue was triturated with ether to afford, as a colorless solid, 5-tert-butyl-3H-imidazole-4-carbaldehyde (2.50 g, 51%). (Hayashi, Personal Communication (2000)).

HPLC (240 nm) $t_R$=3.71 (89.3%) min.
$^1$H NMR (400 MHz, CDCl$_3$) δ 1.48 (s, 9H); 7.67 (s, 1H); 10.06 (s, 1H).
LC/MS $t_R$=3.38 (153.2 [M+H]$^+$) min.

Evaporation of the filtrate from the trituration gave additional 5-tert-butyl-3H-imidazole-4-carbaldehyde (1.88 g, 38%).

1-Acetyl-3-(5'-tert-butyl-1H-imdazol-4'-Z-ylmethylene)-piperazine-2,5-dione

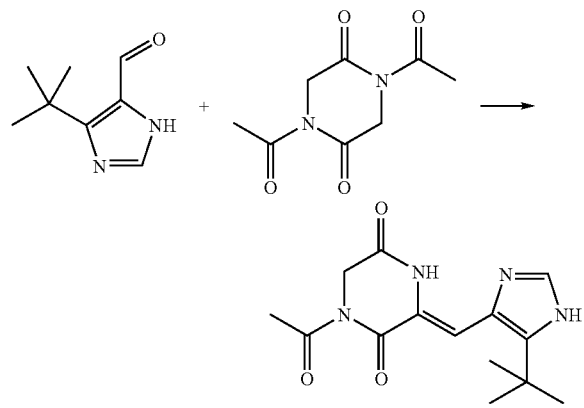

To a solution of 5-tert-butyl-3H-imidazole-4-carbaldehyde (2.50 g, 164.4 mmol) in DMF (50 ml) was added 1,4-diacetyl-piperazine-2,5-dione (6.50 g, 32.8 mmol) and the solution was evacuated, then flushed with argon. The evacuation-flushing process was repeated a further two times, then cesium carbonate (5.35 g, 16.4 mmol) was added. The evacuation-flushing process was repeated a further three times, then the resultant mixture was stirred at room temperature for 5 h. The reaction mixture was partially evaporated (heat and high vacuum) until a small volume remained and the resultant solution was added dropwise to water (100 ml). The yellow precipitate was collected, then freeze-dried to afford 1-acetyl-3-(5'-tert-butyl-1H-imidazol-4'-Z-ylmethylene)-piperazine-2,5-dione (2.24 g, 47%). (Hayashi, Personal Communication (2000)).

HPLC (214 nm) $t_R$=5.54 (94.4%) min.
$^1$H NMR (400 MHz, CDCl$_3$) δ 1.47 (s, 9H); 2.65 (s, 3H), 4.47 (s, 2H); 7.19 (s, 1H); 7.57 (s, 1H), 9.26 (s, 1H), 12.14 (s, 1H).
$^{13}$C NMR (100 MHz, CDCl$_3$+CD$_3$OD) δ 27.3, 30.8, 32.1, 46.5, 110.0, 123.2, 131.4, 133.2, 141.7, 160.7, 162.8, 173.0
LC/MS $t_R$=5.16 (291.2 [M+H]$^+$, 581.6 [2M+H]$^+$) min.

3-Z-Benzylidene-6-(5''-tert-butyl-1H-imidazol-4''-Z-ylmethylene)-piperazine-2,5-dione

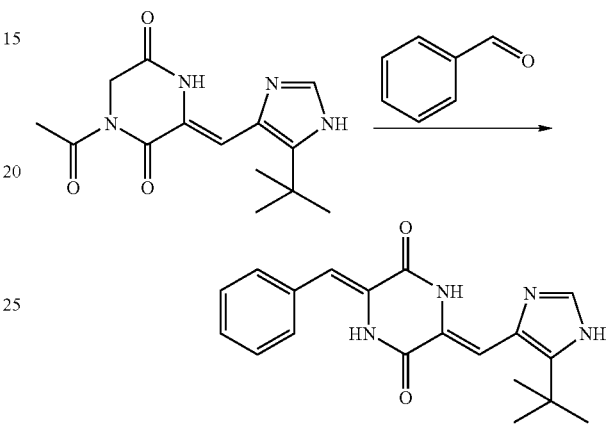

To a solution of 1-acetyl-3-(5'-tert-butyl-1H-imidazol-4'-ylmethylene)-piperazine-2,5-dione (2.43 g, 8.37 mmol) in DMF (55 ml) was added benzaldehyde (4.26 ml, 41.9 mmol) and the solution was evacuated, then flushed with nitrogen. The evacuation-flushing process was repeated a further two times, then cesium carbonate (4.09 g, 12.6 mmol) was added. The evacuation-flushing process was repeated a further three times, then the resultant mixture was heated under the temperature gradient as shown below. After a total time of 5 h the reaction was allowed to cool to room temperature and the mixture was added to ice-cold water (400 ml). The precipitate was collected, washed with water, then freeze-dried to afford a yellow solid (2.57 g, HPLC (214 nm) $t_R$=6.83 (83.1%) min.). This material was dissolved in chloroform (100 ml) and evaporated to azeotrope remaining water, resulting in a brown oil. This was dissolved in chloroform (20 ml) and cooled in ice. After 90 min the yellow precipitate was collected and air-dried to afford 3-Z-benzylidene-6-(5''-tert-butyl-1H-imidazol-4''-Z-ylmethylene)-piperazine-2,5-dione (1.59 g, 56%). (Hayashi, Personal Communication (2000)).

HPLC (214 nm) $t_R$=6.38 (2.1%), 6.80 (95.2) min.
$^1$H NMR (400 MHz, CDCl$_3$) δ 1.46 (s, 9H); 7.01 (s, 1H, —C—C=CH); 7.03 (s, 1H, —C—C=CH); 7.30-7.50 (m, 5H, Ar); 7.60 (s, 1H); 8.09 (bs, NH); 9.51 (bs, NH); 12.40 (bs, NH).
LC/MS $t_R$=5.84 (337.4 [M+H]$^+$, E isomer), 6.25 (337.4 [M+H]$^+$, 673.4 [2M+H]$^+$, Z isomer) min.
ESMS m/z 337.3 [M+H]$^+$, 378.1 [M+CH$_4$CN]$^+$.

Evaporation of the chloroform solution gave additional 3-Z-benzylidene-6-(5''-tert-butyl-1H-imidazol-4''-Z-ylmethylene)-piperazine-2,5-dione (0.82 g, 29%). HPLC (214 nm) $t_R$=6.82 (70.6%) min.

General Experimental

Sodium bicarbonate refers to a 5% solution.
Organic solvents were dried over sodium sulfate unless otherwise stated.

49

Analytical Conditions

NMR Conditions $^1$H NMR (400 MHz) analysis was performed on a Varian Inova Unity 400 MHz NMR machine. Samples were run in deuterated chloroform containing 0.1% TMS (unless otherwise specified). Chemical shifts (ppm) are referenced relative to TMS (0.00 ppm) or CH$_3$OH at 3.30 ppm for samples run CD$_3$OD. Coupling constants are expressed in hertz (Hz).

Analytical HPLC Conditions

System 6 conditions:

RP-HPLC was done on a Rainin Microsorb-MV C18 (5 μm, 100 Å) 50×4.6 mm column.

Buffer A: 0.1% aqueous TFA

Buffer B: 0.1% TFA in 90% aqueous MeCN

Gradient: 0-100% Buffer B over 11 min

Flow rate: 1.5 mL/min

LCMS Conditions

LCMS were run on a Perkin-Elmer Sciex API-100 instrument.

LC conditions:

Reverse Phase HPLC analysis

Column: Monitor 5 μm C18 50×4.6 mm

Solvent A: 0.1% TFA in water

Solvent B: 0.085% TFA in 90% aqueous MeCN

Gradient: 0-100% B over 11.0 min

Flow rate: 1.5 mL/min

Wavelength: 214 nm

MS conditions:

Ion Source: Ionspray

Detection: Ion counting

Flow rate to the mass spectrometer: 300 μL/min after split from column (1.5 mL/min).

ESMS Conditions

ESMS was done on a Perkin Elmer/Sciex-API III LC/MS/MS using an electrospray inlet.

Solvent: 0.1% AcOH in 60% aqueous MeCN

Flow rate: 25 μL/min

Ionspray: 5000 V

Orifice plate: 55 V

Acquisition time: 2.30 min

Scan range: 100-1000 amu/z

Scan step size: 0.2 amu/z

Preparative RP-HPLC Purification Conditions

Reverse phase HPLC purification was carried out using Nebula with the Waters XterraMS column (19×50 mm, 5 μm, C18) using the following conditions:

Solvent A: 0.1% aqueous TFA

Solvent B: 0.1% TFA in 90% aqueous MeCN

Gradient: 5-95% B over 4 min

Flow rate: 20 mL/min

Wavelength: 214 nm

Abbreviations are as follows: br s: broad singlet; BuLi: n-butyl lithium; d: doublet; DBU: 1,8-diazabicyclo[5.4.0]undec-7-ene; ESMS: electrospray mass spectrometry; HCl: hydrochloric acid; HPLC: high performance liquid chromatography; LCMS: liquid chromatography mass spectrometry; LD: lithium diisopropylamide; M+: molecular ion; m: multiplet; MeCN: acetonitrile; M: mass spectrometry; MW: molecular weight; NMR: nuclear magnetic resonance; q: quartet; s: singlet; : triplet; $t_R$: retention time; TFA: trifluoroacetic acid; THF: tetrahydrofuran Detailed Procedure for the Synthesis of Dehydrophenylahistin

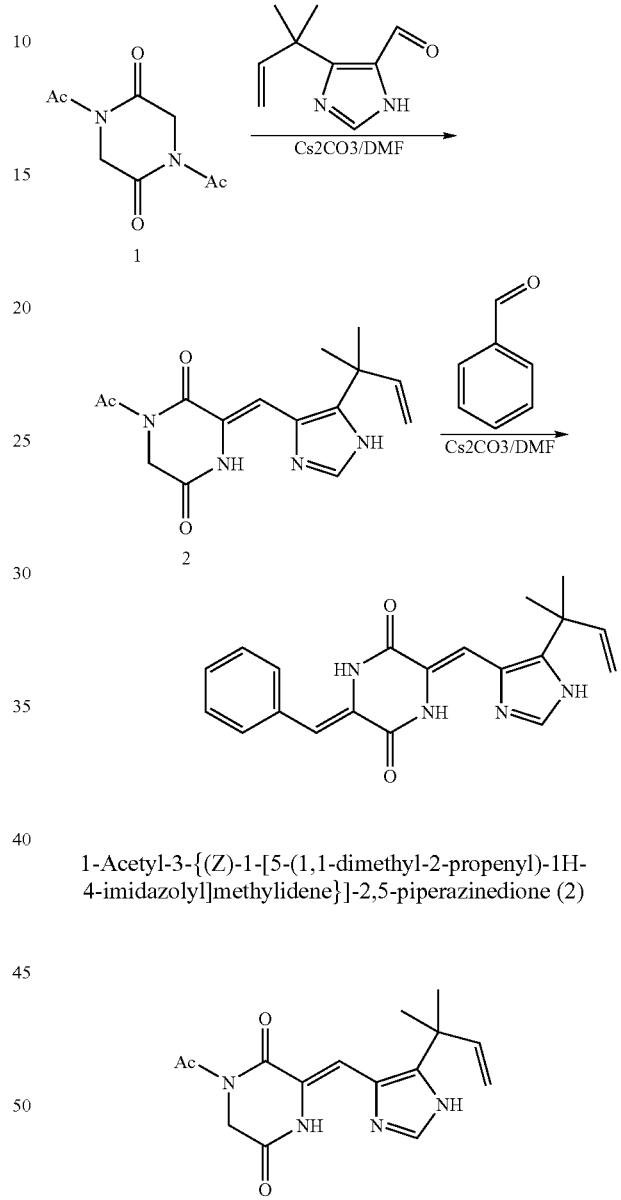

1-Acetyl-3-{(Z)-1-[5-(1,1-dimethyl-2-propenyl)-1H-4-imidazolyl]methylidene}]-2,5-piperazinedione (2)

To a solution of 5-(1,1-dimethyl-2-propenyl)imidazole-4-carboxaldehyde (100 mg, 0.609 mmol) in DMF (2 mL) was added compound 1 (241 mg, 1.22 mmol) and the solution was repeatedly evacuated in a short time to remove oxygen and flushed with Ar, followed by the addition of Cs$_2$CO$_3$ (198 mg. 0.609 mmol) and the evacuation-flushing process was repeated again. The removal of oxygen is preferred because such removal is believed to decrease oxidation of alpha-carbon at the position 6 of the diketopiperazine ring. The resultant mixture was stirred for 5 h at room temperature. After the solvent was removed by evaporation, the residue was dissolved in the mixture of EtOAc and 10% Na$_2$CO$_3$, and the organic phase was washed with 10% $Na_2CO_3$ again and saturated NaCl for three times, dried over $Na_2CO_3$ and concentrated in vacuo. The residual oil was purified by column chromatography on silica using $CHCl_3$-MeOH (100:0 to 50:1) as an eluant to give 60 mg (33%) of a pale yellow solid 2.

Dehydrophenylahistin

To a solution of 2 (30 mg, 0.099 mmol) in DMF (0.8 mL) was added benzaldehyde (51 µL, 0.496 mmol, 5 eq) and the solution was repeatedly evacuated in a short time to remove oxygen and flushed with Ar, followed by the addition of $Cs_2CO_3$ (53 mg, 0.149 mmol, 1.5 eq) and the evacuation-flushing process was repeated again. The resultant mixture was heated for 2.5 h at 80° C. (The temperature must be increased slowly. Rapid heating increases the production of E-isomer at the benzylidene moiety.) After the solvent was removed by evaporation, the residue was dissolved in EtOAc, washed with water for two times and saturated NaCl for three times, dried over $Na_2SO_4$ and concentrated in vacuo. On TLC using $CHCl_3$-MeOH (10:1), you can observe a spot with bright green-yellow luminescence at 365 nm UV. The purity of this crude product was more than 75% from HPLC analysis. The resulting residue was dissolved in 90% MeOH aq and applied to reverse-phase HPLC colunm (YMC-Pack, ODS-AM, 20×250 mm) and eluted using a linear gradient from 70 to 74% MeOH in water over 16 min at a flow rate of 12 mL/min, and the desired fraction was collected and concentrated by evaporation to give a 19.7 mg (60%), although the yields are not optimized for each step,. of yellow colored dehydrophenylahistin.

EXAMPLE 4

Biological Characteristics of Dehydrophenylahistin and Dehydrophenylahistin Analogs A. Biological Evaluation The biological characteristics of synthesized tBu-dehydrophenylahistin and dehydrophenylahistin were evaluated in both HT29 human colon cells, and PC-3 prostatic adenocarcinoma cells.

HT-29 (ATCC HTB-38) a human colorectal adenocarcinoma was maintained in McCoy's complete medium (McCoy's 5A medium with L-glutamine and 25 mM HEPES supplemented with 10% FBS, lmM Na pyruvate, 1X NEAA, 2 mM L-glutamine, and Pen/Strep at 100IU/ml and 100 µg/ml, respectively). PC-3 (ATCC CRL-1435), a human prostate adenocarcinoma, was maintained in F12K complete medium (F12K medium supplemented with 10% FBS; 2mM Glutamine; 1% HEPES; and Pen/Strep at 100IU/ml and 100 µg/ml, respectively). Cell lines were cultured at 37° C., 5% $CO_2$ in a 95% humidified incubator.

For tumor cytotoxicity assays HT-29 or PC-3 cells were seeded at 5,000 cells/well in 90 µl complete media into a Coming 3904 black-walled, clear-bottom tissue culture plate and the plate were incubated overnight to allow cells to establish and enter log phase growth. 20 mM stock solutions of dehydrophenylahistin and tBu-dehydrophenylahistin were prepared in 100% DMSO and stored at −20° C. 10× concentrated serial dilutions of the two compounds were prepared in appropriate culture medium for final concentrations ranging from $2.0\times10^{-5}$ M to $2.0\times10^{-10}$ M. Ten µl volumes of the 10× serial dilutions were added to the test wells in triplicate and the plates returned to the incubator for 48 hours. The final concentration of DMSO was 0.25% in all samples.

Following 48 hours of drug exposure 10 µl of 0.2 mg/ml resazurin (obtained from Sigma-Aldrich Chemical Co.) in $Mg^{2+}$, $Ca^{2+}$ free PBS was added to each well and the plates were returned to the incubator for 3-4 hours. The plates were removed and resazurin fluorescence was measured using 530 nm excitation and 590 nm emission filters in a Fusion fluorimeter (Packard Instruments). Resazurin dye without cells was used to determine the background, which was subtracted from the data for all experimental wells. The data were analyzed using Prism software (GraphPad Software). The data were normalized to the average of the cells treated with media only (100% cell growth) and $EC_{50}$ values were determined using a standard sigmoidal dose response curve fitting algorithm.

As indicated in Table 1 below, tBu-dehydrophenylahistin demonstrates about a 4-times greater cytotoxic activity in comparison with dehydrophenylahistin.

TABLE 1

Cytotoxic Effect of dehydrophenylahistin and derivative.

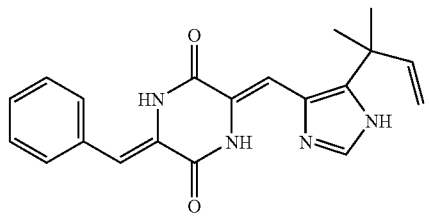

Dehydrophenylahistin

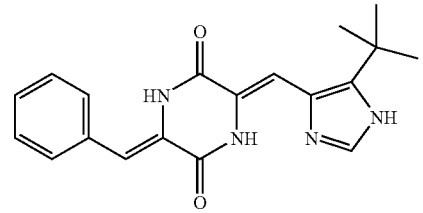

tBu-dehydrophenylahistin

| cell | $EC_{50}$ (nM) | |
|---|---|---|
| | ΔPLH | tBu-ΔPLH |
| HT29 | 48 | 13 |
| PC-3 | 5.4 | 1.0 |

Figure 41:
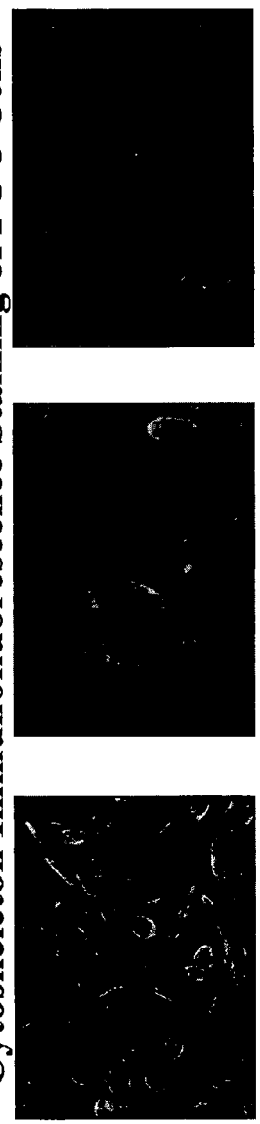
FIG. 41 depicts the biologically activity of various phenylahistin derivatives compared to colchicine.

See also FIG. 41 for additional data at HT-29, PC-3, and P-388 cells.

B. Structure and Activity Study of Dehydrophenylahistin Derivatives

The cytotoxic effects of phenylahistin, dehydrophenylahistin and various derivatives of dehydrophenylahistin were examined in P388 murine leukemia cells, HT-29 human colon cells, and PC-3 prostatic adenocarcinoma cells.

As explained above, HT-29 a human colorectal adenocarcinoma was maintained in McCoy's complete medium (McCoy's 5A medium with L-glutamine and 25 mM HEPES supplemented with 10% FBS, 1 mM Na pyruvate, 1X NEAA, 2 mM L-glutamine, and Pen/Strep at 100IU/ml and 100 µg/ml, respectively). PC-3, a human prostate adenocarcinoma, was maintained in F12K complete medium (F12K medium supplemented with 10% FBS; 2 mM Glutamine; 1% HEPES; and Pen/Strep at 100IU/ml and 100 µg/ml, respectively). Cell lines were cultured at 37° C., 5% $CO_2$ in a 95% humidified incubator.

For tumor cytotoxicity assays HT-29 or PC-3 cells were seeded at 5,000 cells/well in 90 µl complete media into a Corning 3904 black-walled, clear-bottom tissue culture plates and the plates were incubated overnight to allow cells to establish and enter log phase growth. 20 mM stock solutions of dehydrophenylahistin and tBu-dehydrophenylahistin were prepared in 100% DMSO and stored at −20 °C. 10× concentrated serial dilutions of the two compounds were prepared in appropriate culture medium for final concentrations ranging from $2.0 \times 10^{-5}$ M to $2.0 \times 10^{-10}$ M. Ten µl volumes of the 10× serial dilutions were added to the test wells in triplicate and the plates returned to the incubator for 48 hours. The final concentration of DMSO was 0.25% in all samples.

Following 48 hours of drug exposure 10 µl of 0.2 mg/ml resazurin (obtained from Sigma-Aldrich Chemical Co.) in $Mg^{2+}$, $Ca^{2+}$ free PBS was added to each well and the plates were returned to the incubator for 3-4 hours. The plates were removed and resazurin fluorescence was measured using 530 nm excitation and 590 nm emission filters in a Fusion fluorimeter (Packard Instruments). Resazurin dye without cells was used to determine the background, which was subtracted from the data for all experimental wells. The data were analyzed using Prism software (GraphPad Software). The data were normalized to the average of the cells treated with media only (100% cell growth) and $EC_{50}$ values were determined using a standard sigmoidal dose response curve fitting algorithm.

$EC_{50}$ and $IC_{50}$ values of phenylahistin, dehydrophenylahistin and dehydrophenylahistin derivatives are summarized in Table 2 below.

TABLE 2

SAR study of phenylahistin or dehydrophenylahistin and of dehydrophenylahistin derivatives

| COMPOUNDS | STRUCTURE | $EC_{50}$ (nM) HT-29 | $EC_{50}$ (nM) PC-3 | $IC_{50}$ (nM) P-388 |
|---|---|---|---|---|
| (−)-Phenylahistin | | 1600 | n.t. | 833 ± 153 (n = 5) |
| KPU-1 ΔPLH | | 48 | 4.7 | 36 ± 12.8 (n = 5) |
| KPU-2 tBu-ΔPLH | | 13 | 1 | 31.8 ± 5.0 (n = 5) |
| KPU-6 tBu-ΔPLH-p-OMe | | >2000 | n.t. | 9333 ± 5457 (n = 3) |

TABLE 2-continued

SAR study of phenylahistin or dehydrophenylahistin and of dehydrophenylahistin derivatives

| COMPOUNDS | STRUCTURE | $EC_{50}$ (nM) HT-29 | PC-3 | $IC_{50}$ (nM) P-388 |
|---|---|---|---|---|
| KPU-8<br>tBu-ΔPLH-o-OMe | (structure) | 89 | | 315 ± 137<br>(n = 4) |
| KPU-9<br>tBu-ΔPLH-M-OMe | (structure) | 31 | | 20.8 ± 68<br>(n = 4) |
| Colchicine | — | | | 208 ± 68<br>(n = 4) |

Modifications to the phenyl ring have a significant effect of the cytotoxic activities. In comparison with the activity of tBu-dehydrophenylahistin (#6), the activity of the methoxy group at the meta-position (KPU-9) exhibited the highest activity than the other derivatives with an $IC_{50}$ of 20.8±3.3 nM in P388 cells. The KPU-9 derivative also exhibited cytotoxicity in HT-29 cells ($EC_{50}$ 31 nM). Dehydrophenylahistin, tBu-dehydrophenylahistin (KPU-2) and the KPU-9 derivative all exhibited cytotoxicity in P388 cells.

C. Structure and Activity Study of Additional Dehydrophenylahistin Derivatives The cytotoxic effects of phenylahistin, dehydrophenylahistin and various additional derivatives of dehydrophenylahistin were examined in HT-29 human colon cells and PC-3 prostatic adenocarcinoma cells using the methodology described above.

TABLE 3

SAR study of phenylahistin, dehydrophenylahistin and of additional dehydrophenylahistin derivatives

| COMPOUNDS | STRUCTURE | SALT FORM | M.W. | $EC_{50}$ (nM) HT-29 | PC-3 |
|---|---|---|---|---|---|
| (−)-Phenylahistin | (structure) | — | 350.41 | 1600 | n.t. |
| KPU-1<br>ΔPLH | (structure) | — | 348.40 | 48 | 4.7 |

TABLE 3-continued

SAR study of phenylahistin, dehydrophenylahistin and of additional dehydrophenylahistin derivatives

| COMPOUNDS | STRUCTURE | SALT FORM | M.W. | EC$_{50}$ (nM) HT-29 | PC-3 |
|---|---|---|---|---|---|
| KPU-2 tBu-ΔPLH | | — | 336.39 | 13 | 1 |
| KPU-6 tBu-ΔPLH-p-OMe | | — | 366.41 | >2000 | n.t. |
| KPU-8 tBu-ΔPLH-o-OMe | | — | 366.41 | 89 | |
| KPU-9 tBu-ΔPLH-m-OMe | | — | 366.41 | 31 | |
| KPU-14 tBu-ΔPLH-2,3-diOMe | | TFA | 396.44 510.46 (+TFA) | 610 | 96% |
| KPU-12 tBu-ΔPLH-2,4-diOMe | | — | 396.44 | 4980 | |

TABLE 3-continued

SAR study of phenylahistin, dehydrophenylahistin
and of additional dehydrophenylahistin derivatives

| COMPOUNDS | STRUCTURE | SALT FORM | M.W. | EC$_{50}$ (nM) HT-29 | PC-3 |
|---|---|---|---|---|---|
| KPU-10 tBu-ΔPLH-2,5-diOMe | | — | 396.44 | 1350 | |
| KPU-15 tBu-ΔPLH-2,6-diOMe | | TFA | 396.44 510.46 (+TFA) | 4430 | 96% |
| KPU-13 tBu-ΔPLH-3,4-diOMe | | — | 396.44 | 2130 | |
| KPU-16 tBu-ΔPLH-3,5-diOMe | | — | 396.44 | 42 | 82% |
| KPU-11 tBu-ΔPLH-3,4,5-triOMe | | — | 426.47 | >20 μM | |
| KPU-17 tBu-ΔPLH-2,3,4-triOMe | | TFA | 426.47 540.49 (+TFA) | 4060 | 94% |

TABLE 3-continued
SAR study of phenylahistin, dehydrophenylahistin and of additional dehydrophenylahistin derivatives
| COMPOUNDS | STRUCTURE | SALT FORM | M.W. | EC$_{50}$ (nM) HT-29 | PC-3 |
|---|---|---|---|---|---|
| KPU-18 tBu-ΔPLH-o-Cl | 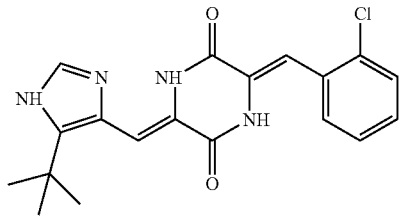 | TFA | 370.83 484.86 (+TFA) | 42 | 100% |
| KPU-19 tBu-ΔPLH-m-Cl | 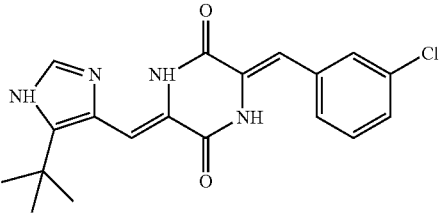 | TFA | 370.83 484.86 (+TFA) | 20 | 98% |
| KPU-20 tBu-ΔPLH-p-Cl | 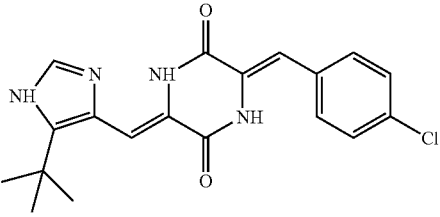 | TFA | 370.83 484.86 (+TFA) | 545 | |
| KPU-21 tBu-ΔPLH-2Cl-5-NO$_2$ | 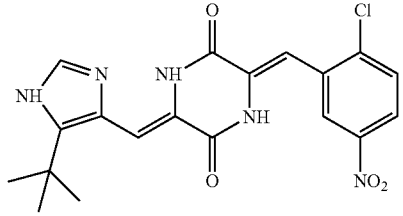 | TFA | 415.83 529.85 (+TFA) | 51 | 100% |
| KPU-22 tBu-ΔPLH-3,4-methylene-dioxy | 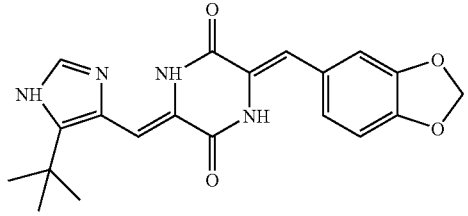 | TFA | 380.40 494.42 (+TFA) | 82 | 95% |
| KPU-23 tBu-ΔPLH-2-OH-3-OMe (o-vanillin) | 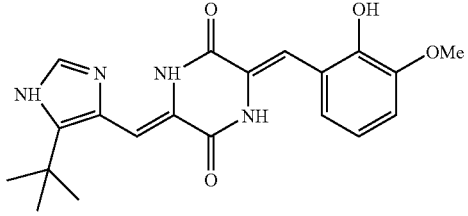 | TFA | 382.41 494.44 (+TFA) | 5870 | 86% |

TABLE 3-continued

SAR study of phenylahistin, dehydrophenylahistin and of additional dehydrophenylahistin derivatives

| COMPOUNDS | STRUCTURE | SALT FORM | M.W. | EC$_{50}$ (nM) HT-29 | PC-3 |
|---|---|---|---|---|---|
| KPU-24 tBu-ΔPLH-cyclized-3-MeO | 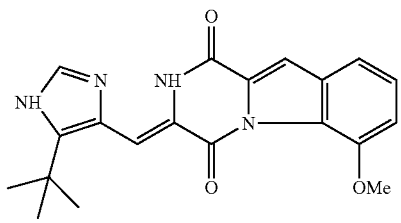 | TFA | 364.40 487.42 (+TFA) | 7040 | 100% |
| KPU-25 tBu-ΔPLH-4-pyridyl | 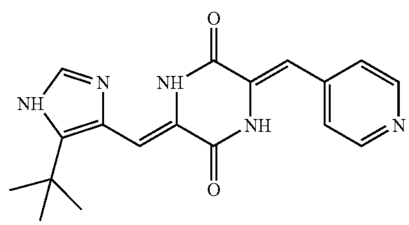 | TFA | 337.38 565.42 (+2TFA) | 544 | 98% |
| KPU-28 tBu-ΔPLH-2-pyridyl | 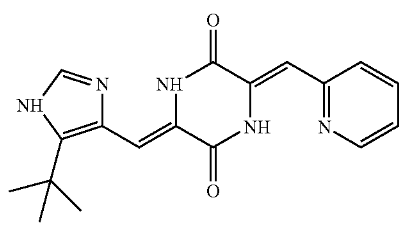 | TFA | 337.38 565.42 (+2TFA) | >20 μM | 99% |
| KPU-26 tBu-ΔPLH-2-furyl | 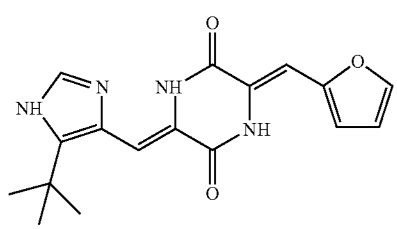 | TFA | 326.35 440.37 (+TFA) | 600 | 88% |
| KPU-27 tBu-ΔPLH-5-Me-2-thienyl | 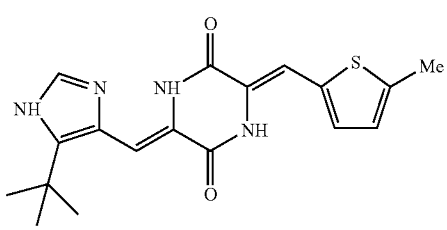 | TFA | 356.44 470.47 (+TFA) | 80 | 97% |
| KPU-29 tBu-ΔPLH-3-Me-2-thienyl | 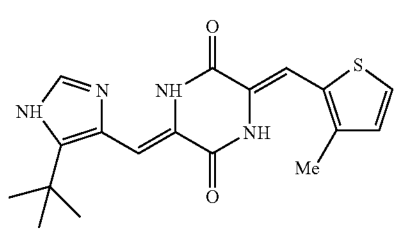 | TFA | 356.44 470.47 (+TFA) | 44 | 81% |

Additional cytotoxicity assays were performed as described above under this example, using Resazurin fluorescence as an indicator of cell viability. The results are shown below in Table 3.1.

TABLE 3.1

Study of phenylahistin, dehydrophenylahistin and of additional dehydrophenylahistin derivatives

| NPI | Structure | Chemical name | EC$_{50}$ (M) Mean | SD | % cytotox Mean | SD | n |
|---|---|---|---|---|---|---|---|
| 2350 | 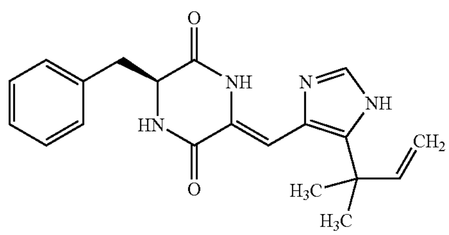 | (−)-(S)-Halimide, (−)-(S)-Phenylahistin, (−)-(S)-PLH | 3.94E−07 | 9.49E−08 | 87 | 2 | 5 |
| 2352 | 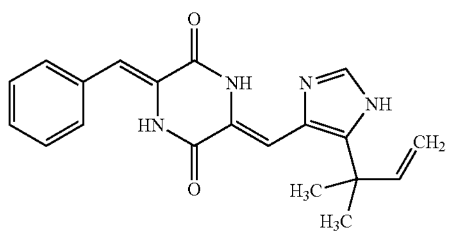 | Dehydophenylahistin, delta-PLH, KPU-1 | 4.26E−08 | 1.08E−08 | 86 | 2 | 5 |
| 2354 | 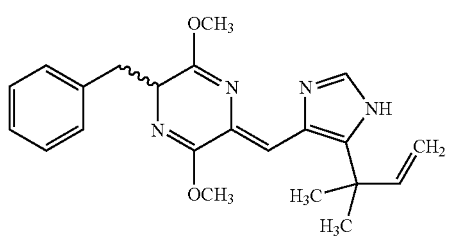 | KPU-4, D,L-bislactim-PLH | >2E−05 | NA | 4 | NA | 2 |
| 2355 | 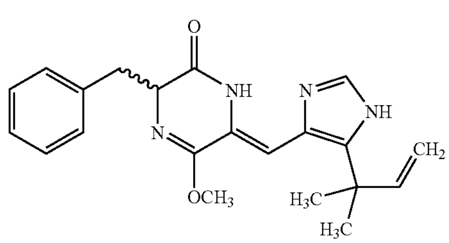 | KPU-5, D,L-monolactim-PLH | >2E−05 | NA | 13 | NA | 2 |
| 2356 | 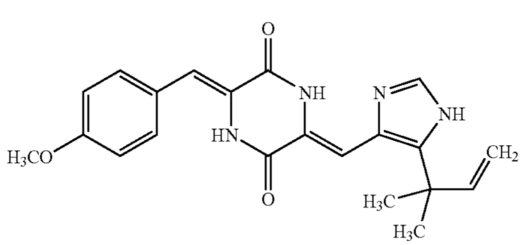 | KPU-6 | 6.57E−06 | NA | 63 | NA | 2 |

TABLE 3.1-continued

Study of phenylahistin, dehydrophenylahistin and of additional dehydrophenylahistin derivatives

| NPI | Structure | Chemical name | $EC_{50}$ (M) Mean | SD | % cytotox Mean | SD | n |
|---|---|---|---|---|---|---|---|
| 2357 | 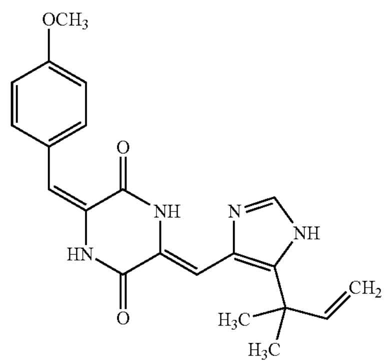 | KPU-7 | 8.25E−06 | NA | 63 | NA | 2 |
| 2358 | 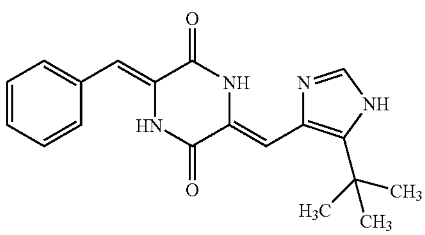 | t-butyl-delta-PLH, KPU-2 | 1.49E−08 | 3.77E−09 | 86 | 2 | 5 |
| 2359 | 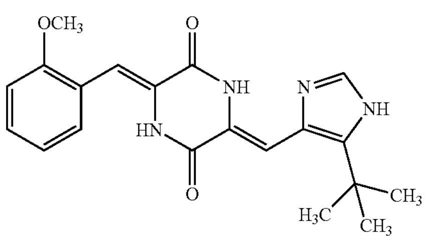 | KPU-8 | 7.55E−08 | 2.47E−08 | 87 | 3 | 3 |
| 2360 | 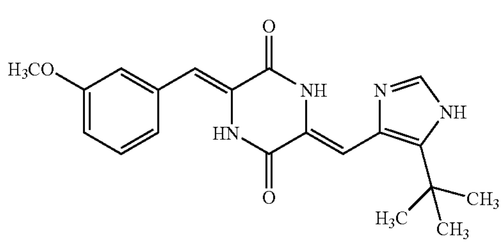 | KPU-9 | 2.61E−08 | 8.54E−09 | 87 | 3 | 3 |
| 2361 | 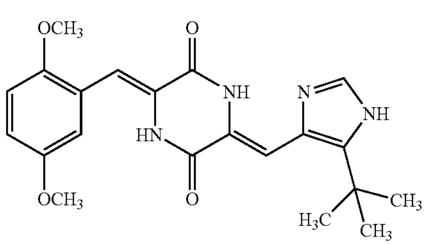 | KPU-10 | 9.70E−07 | NA | 86 | NA | 2 |

TABLE 3.1-continued

Study of phenylahistin, dehydrophenylahistin and of additional dehydrophenylahistin derivatives

| NPI | Structure | Chemical name | EC$_{50}$ (M) Mean | SD | % cytotox Mean | SD | n |
|---|---|---|---|---|---|---|---|
| 2362 | 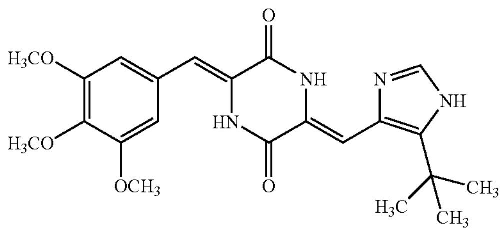 | KPU-11 | 8.19E−06 | NA | 78 | NA | 2 |
| 2363 | 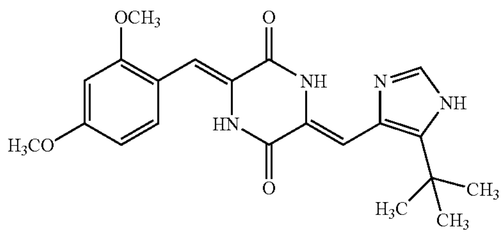 | KPU-12 | 5.08E−06 | NA | 79 | NA | 2 |
| 2364 | 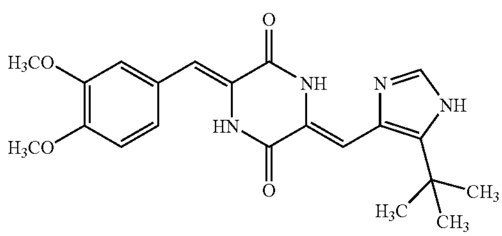 | KPU-13 | 2.02E−06 | NA | 76 | NA | 2 |
| 2365 | 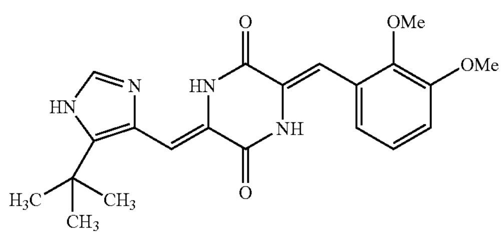 | KPU-14, tBu-delta-PLH-2,3-diOMe | 8.68E−07 | NA | 84 | NA | 2 |
| 2366 | 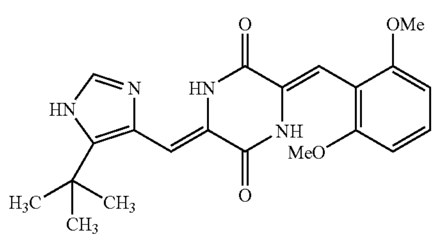 | KPU-15, tBu-delta-PLH-2,6-diOMe | 5.17E−06 | NA | 81 | NA | 2 |
| 2367 | 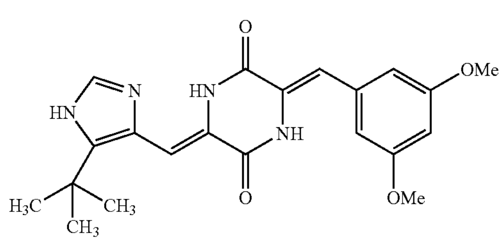 | KPU-16, tBu-delta-3,5-diOMe | 4.54E−08 | 1.21E−08 | 87 | 2 | 3 |

TABLE 3.1-continued

Study of phenylahistin, dehydrophenylahistin and of
additional dehydrophenylahistin derivatives

| NPI | Structure | Chemical name | EC$_{50}$ (M) Mean | SD | % cytotox Mean | SD | n |
|---|---|---|---|---|---|---|---|
| 2368 | 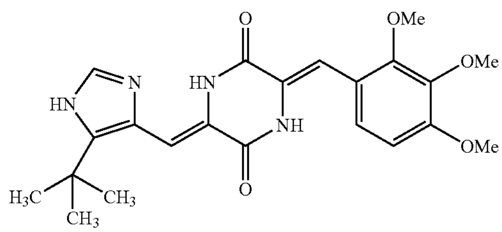 | KPU-17, tBu-delta-PLH-2,3,4-triOMe | 4.80E−06 | NA | 78 | NA | 2 |
| 2369 | 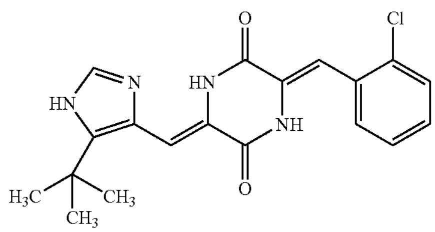 | KPU-18, tBu-delta-PLH-o-Cl | 4.63E−08 | 1.35E−08 | 86 | 3 | 3 |
| 2370 | 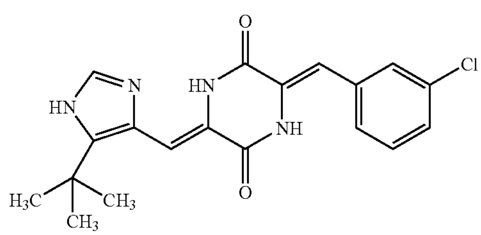 | KPU-19, tBu-delta-PLH-m-Cl | 2.45E−08 | 8.73E−09 | 85 | 3 | 3 |
| 2371 | 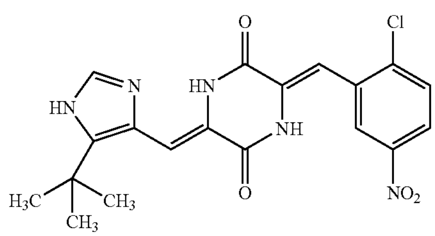 | KPU-21, tBu-delta-PLH-2-Cl-5-NO2 | 5.34E−08 | 4.85E−09 | 86 | 3 | 3 |
| 2372 | 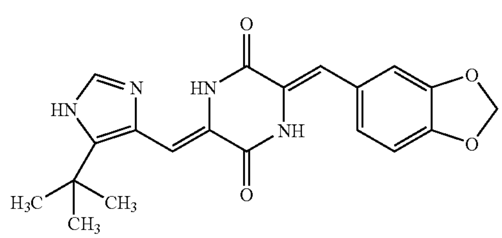 | KPU-22, tBu-delta-PLH-3,4-methylene-dioxy | 8.73E−08 | 1.10E−08 | 84 | 4 | 3 |
| 2373 | 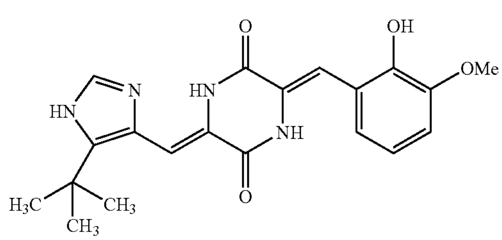 | KPU-23, tBu-delta-PLH-2-OH-3-OMe (o-vanillin) | 5.36E−06 | NA | 79 | NA | 2 |

TABLE 3.1-continued

Study of phenylahistin, dehydrophenylahistin and of additional dehydrophenylahistin derivatives

| NPI | Structure | Chemical name | EC₅₀ (M) Mean | SD | % cytotox Mean | SD | n |
|---|---|---|---|---|---|---|---|
| 2374 | 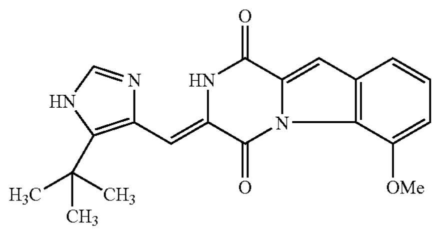 | KPU-24, tBu-delta-PLH-cyclized-3-MeO | 6.92E−06 | NA | 58 | NA | 2 |
| 2375 | 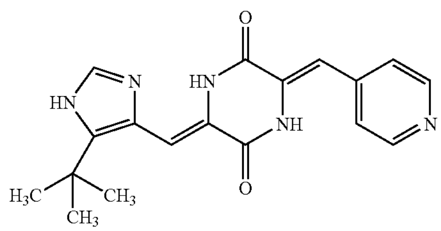 | KPU-25, tBu-delta-PLH-4-pyridyl | 5.48E−07 | NA | 82 | NA | 2 |
| 2376 | 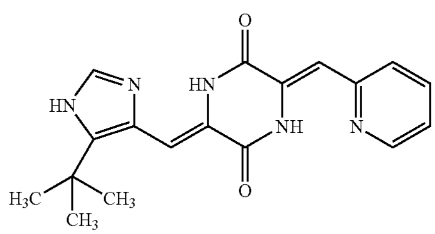 | KPU-28, tBu-delta-PLH-2-pyridyl | >2E−05 | NA | 39 | NA | 2 |
| 2377 | 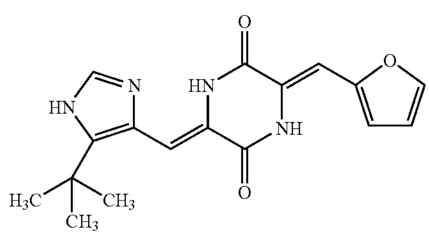 | KPU-26, tBu-delta-PLH-2-furyl | 7.12E−07 | NA | 80 | NA | 2 |
| 2378 | 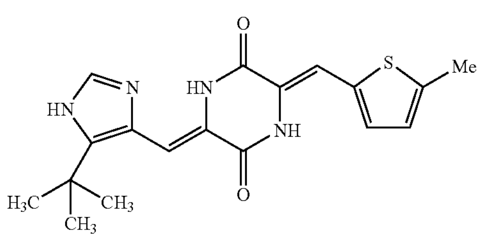 | KPU-27, tBu-delta-PLH-5-Me-2-thienyl | 8.52E−08 | 1.35E−08 | 85 | 3 | 3 |
| 2379 | 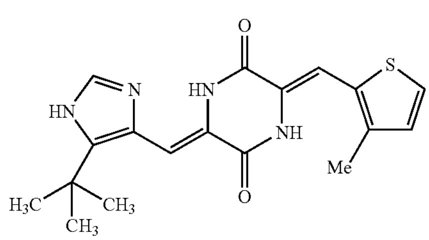 | KPU-29, tBu-delta-PLH-3-Me-2-thienyl | 4.70E−08 | 1.30E−08 | 86 | 3 | 3 |

TABLE 3.1-continued

Study of phenylahistin, dehydrophenylahistin and of
additional dehydrophenylahistin derivatives

| NPI | Structure | Chemical name | $EC_{50}$ (M) Mean | SD | % cytotox Mean | SD | n |
|---|---|---|---|---|---|---|---|
| 2380 | 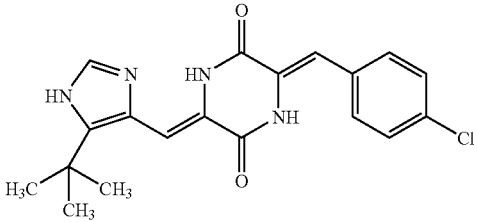 | KPU-20; t-butyl-delta-PLH-p-Cl + TFA salt (MW: 484) | 7.09E−07 | NA | 81 | NA | 2 |
| 2381 | 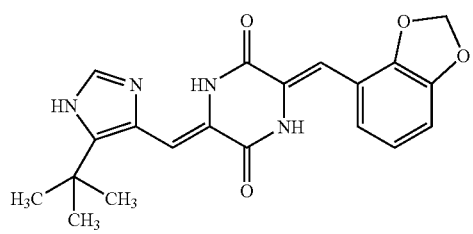 | KPU-30, tBu-delta-PLH-2,3-methylendioxy; TFA salt (MW: 494.42) | 5.20E−07 | NA | 82 | NA | 2 |
| 2382 | 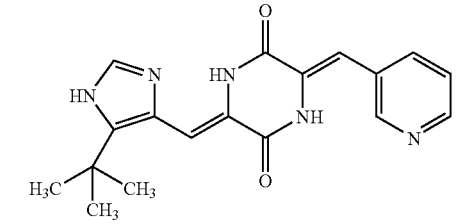 | KPU-31, tBu-delta-PLH-3-pyridyl; 2TFA salt (MW: 565.42) | 1.03E−07 | 1.16E−08 | 86 | 3 | 3 |
| 2383 | 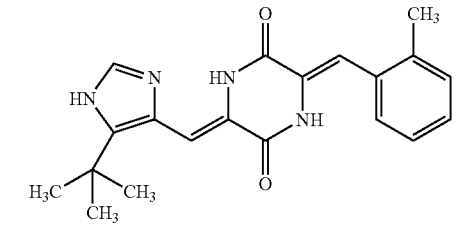 | KPU-32, tBu-delta-PLH-o-Me; TFA salt (MW: 464.44) | 4.58E−08 | 1.15E−08 | 86 | 3 | 3 |
| 2384 | 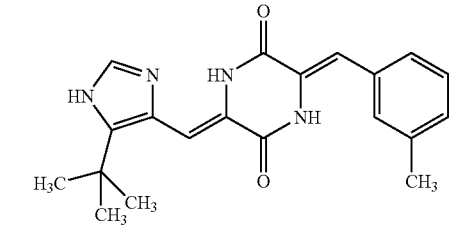 | KPU-33, tBu-delta-PLH-3-Me-2-pyridyl; 2TFA salt (MW: 579.45) | >2E−05 | NA | 37 | NA | 2 |
| 2385 | 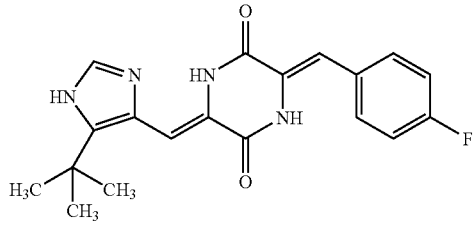 | KPU-34, tBu-delta-PLH-4-F; TFA salt (MW: 468.40) | 5.01E−07 | 8.48E−08 | 81 | 5 | 3 |

TABLE 3.1-continued

Study of phenylahistin, dehydrophenylahistin and of additional dehydrophenylahistin derivatives

| NPI | Structure | Chemical name | EC$_{50}$ (M) Mean | SD | % cytotox Mean | SD | n |
|---|---|---|---|---|---|---|---|
| 2386 | 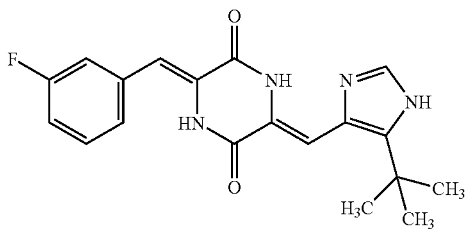 | KPU-35, tBu-delta-PLH-m-F; TFA salt (MW: 468.40) | 1.31E−08 | 5.32E−09 | 85 | 2 | 5 |
| 2387 | 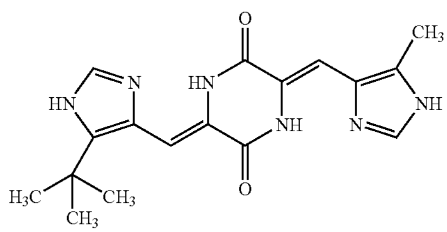 | KPU-36, tBu-delta-PLH-5-Me-4-im; 2TFA salt (MW: 584.47) | 2.35E−06 | NA | 84 | NA | 2 |
| 2388 | 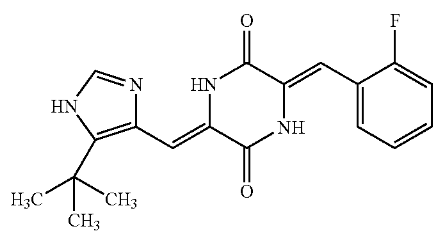 | KPU-37, tBu-delta-PLH-o-F, TFA salt (MW: 468.40) | 3.00E−08 | 1.65E−08 | 86 | 3 | 3 |
| 2389 | 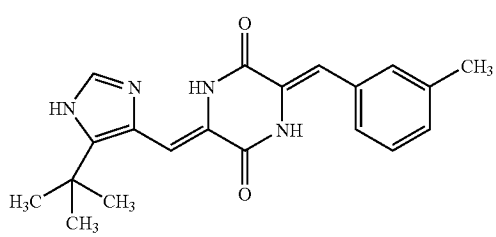 | KPU-38, tBu-delta-PLH-m-Me; TFA salt (MW: 464.44) | 4.67E−08 | 9.64E−09 | 86 | 3 | 3 |
| 2390 | 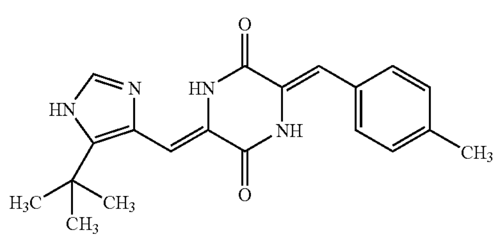 | KPU-39, tBu-delta-PLH-p-Me; TFA Salt (MW: 464.44) | 4.83E−07 | 6.15E−08 | 84 | 4 | 3 |
| 2391 | 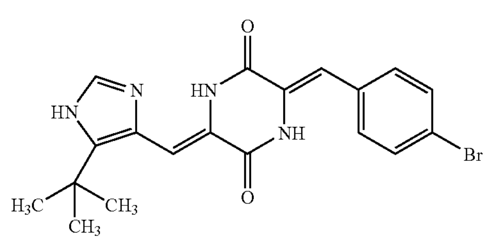 | KPU-40, tBu-delta-PLH-p-Br; TFA Salt (MW: 529.31) | 7.14E−07 | NA | 82 | NA | 2 |

TABLE 3.1-continued

Study of phenylahistin, dehydrophenylahistin and of additional dehydrophenylahistin derivatives

| NPI | Structure | Chemical name | EC$_{50}$ (M) Mean | SD | % cytotox Mean | SD | n |
|---|---|---|---|---|---|---|---|
| 2392 | | KPU-41, tBu-delta-PLH-m-Br; TFA Salt (MW: 529.31) | 3.11E−08 | 7.29E−09 | 87 | 3 | 3 |
| 2393 | | KPU-42, tBu-delta-PLH-3-thienyl; TFA Salt (MW: 456.44) | 5.58E−08 | 6.23E−09 | 86 | 3 | 3 |
| 2394 | | KPU-43, tBu-delta-PLH-p-CN; TFA Salt (MW: 475.42) | >2E−05 | NA | 14 | NA | 2 |
| 2395 | | KPU-44, tBu-delta-PLH-m-EtO; TFA Salt (MW: 494.46) | 4.59E−08 | 1.02E−08 | 85 | 4 | 3 |
| 2396 | | KPU-45, tBu-delta-PLH-2,4,6-TriOMe; TFA Salt (MW: 540.49) | >2E−05 | NA | 2 | NA | 2 |
| 2397 | | KPU-46, tBu-delta-PLH-o-NO2; TFA Salt (MW: 495.41) | 5.03E−08 | 1.24E−08 | 86 | 4 | 3 |

TABLE 3.1-continued

Study of phenylahistin, dehydrophenylahistin and of additional dehydrophenylahistin derivatives

| NPI | Structure | Chemical name | $EC_{50}$ (M) Mean | SD | % cytotox Mean | SD | n |
|---|---|---|---|---|---|---|---|
| 2398 | 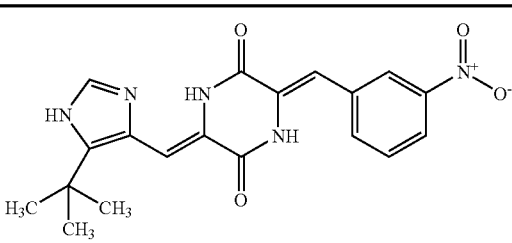 | KPU-47, tBu-delta-PLH-m-NO2; TFA Salt (MW: 495.41) | 4.47E−08 | 1.19E−08 | 86 | 3 | 3 |
| 2399 | 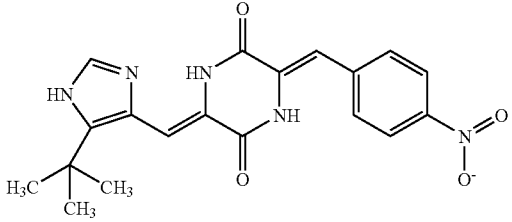 | KPU-48, tBu-delta-PLH-p-NO2; TFA Salt (MW: 495.41) | >2E−05 | NA | 23 | NA | 2 |
| 2400 | 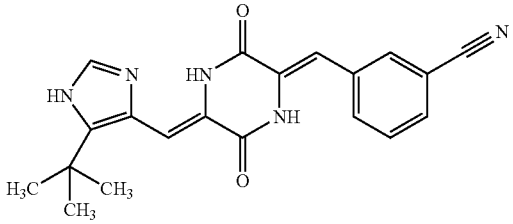 | KPU-49, tBu-delta-PLH-m-CN; TFA Salt (MW: 475.42) | 3.56E−08 | 1.40E−08 | 85 | 3 | 3 |
| 2401 | 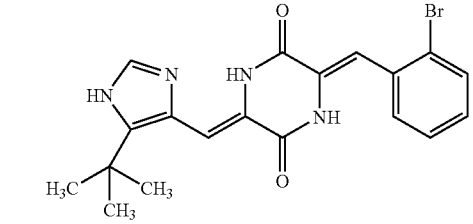 | KPU-50, tBu-delta-PLH-o-Br; TFA Salt (MW: 529.31) | 4.05E−08 | 1.09E−08 | 86 | 3 | 3 |
| 2402 | 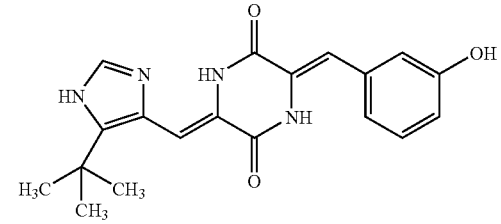 | KPU-51, tBu-delta-PLH-m-OH; TFA Salt (MW: 466.41) | 3.64E−07 | 1.86E−07 | 86 | 2 | 4 |
| 2403 | 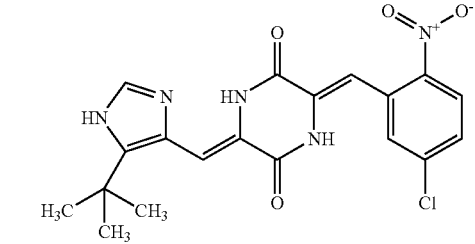 | KPU-52, tBu-delta-PLH-2-NO2-5-Cl; TFA salt (MW: 529.85) | 9.97E−08 | 2.63E−08 | 86 | 2 | 5 |

TABLE 3.1-continued

Study of phenylahistin, dehydrophenylahistin and of
additional dehydrophenylahistin derivatives

| NPI | Structure | Chemical name | EC$_{50}$ (M) Mean | SD | % cytotox Mean | SD | n |
|---|---|---|---|---|---|---|---|
| 2403 | 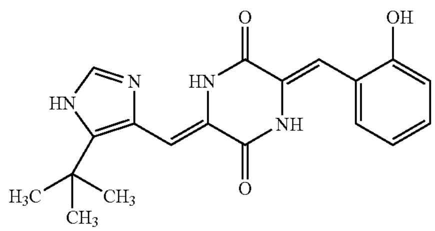 | KPU-53, tBu-delta-PLH-o-OH; TFA Salt (MW: 466.41) | 6.10E−06 | 1.23E−06 | 66 | 10 | 3 |
| 2405 | 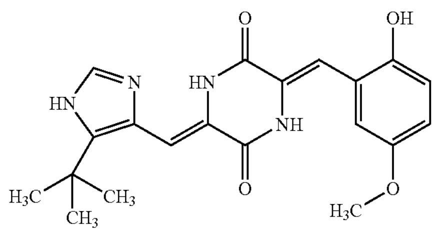 | KPU-54, tBu-delta-PLH-2-OH-5-OMe; TFA Salt (MW: 496.44) | >2E−05 | NA | 25 | 12 | 4 |
| 2406 | 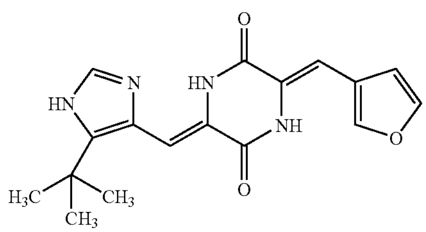 | KPU-55, tBu-delta-PLH-3-furanyl; TFA Salt (MW: 440.37) | 3.59E−08 | 1.03E−08 | 86 | 2 | 5 |
| 2407 | 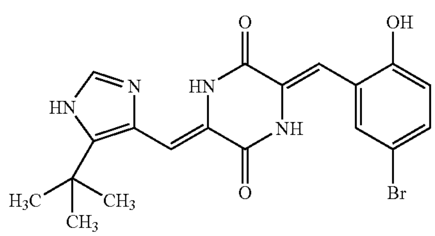 | KPU-56, tBu-delta-PLH-2-OH-5-Br; TFA Salt (MW: 545.31) | >2E−05 | NA | 13 | 6 | 3 |
| 2408 | 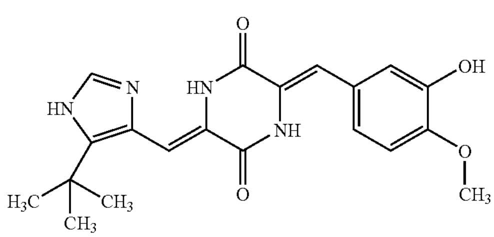 | KPU-57, tBu-delta-PLH-3-OH-4-OMe; TFA Salt (MW: 496.44) | 7.48E−06 | 8.62E−07 | 66 | 4 | 3 |
| 2409 | 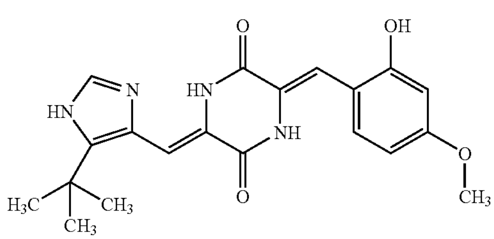 | KPU-58, tBu-delta-PLH-2-OH-4-OMe; TFA Salt (MW: 496.44) | >2E−05 | NA | 8 | 10 | 4 |

TABLE 3.1-continued

Study of phenylahistin, dehydrophenylahistin and of additional dehydrophenylahistin derivatives

| NPI | Structure | Chemical name | EC$_{50}$ (M) Mean | SD | % cytotox Mean | SD | n |
|---|---|---|---|---|---|---|---|
| 2410 | 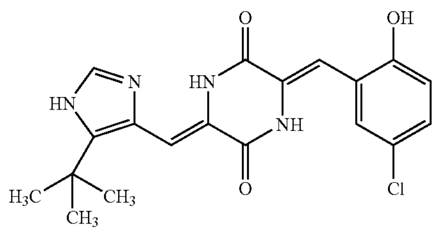 | KPU-59, tBu-delta-PLH-2-OH-5-Cl; TFA Salt (MW: 500.86) | >2E−05 | NA | 37 | 17 | 3 |
| 2411 | 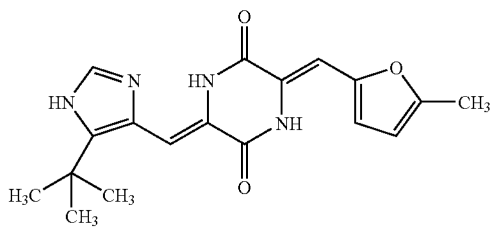 | KPU-60, tBu-delta-PLH-5-Me-2-furanyl; TFA Salt (MW: 454.40) | 5.72E−08 | 2.00E−08 | 85 | 2 | 5 |
| 2412 | 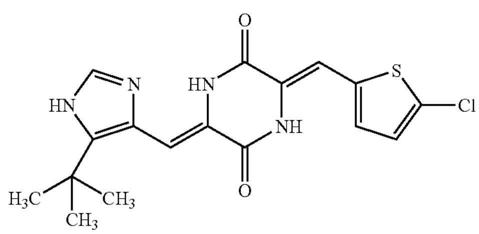 | KPU-61, tBu-delta-PLH-5-Cl-2-thionyl; TFA Salt (MW: 490.88) | 1.65E−07 | 3.32E−08 | 85 | 3 | 3 |
| 2413 | 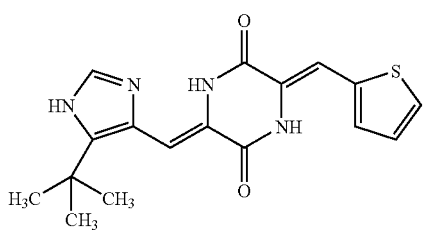 | KPU-62, tBu-delta-PLH-2-thionyl; TFA Salt (MW: 456.44) | 2.74E−08 | 6.29E−09 | 88 | 2 | 3 |
| 2414 | 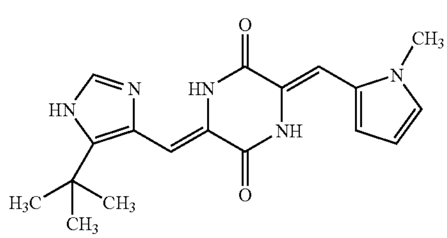 | KPU-63, tBu-delta-PLH-N-Me-2-pyrrole; TFA Salt (MW: 453.42) | 1.17E−07 | 3.14E−08 | 88 | 3 | 3 |
| 2415 | 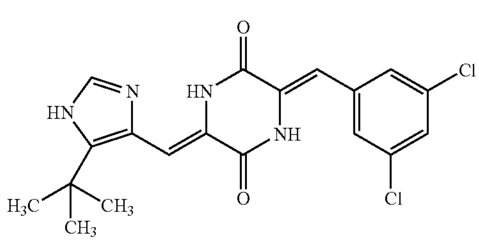 | KPU-64, tBu-delta-PLH-3,5-diCl; TFA Salt (MW 519.30) | 9.49E−08 | 5.05E−09 | 87 | 3 | 3 |

TABLE 3.1-continued

Study of phenylahistin, dehydrophenylahistin and of
additional dehydrophenylahistin derivatives

| NPI | Structure | Chemical name | EC$_{50}$ (M) Mean | SD | % cytotox Mean | SD | n |
|---|---|---|---|---|---|---|---|
| 2416 | 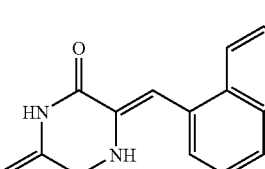 | KPU-65, tBu-delta-PLH-m-CF3; TFA Salt (MW 518.41) | 4.40E−08 | 7.40E−09 | 87 | 2 | 3 |
| 2417 | 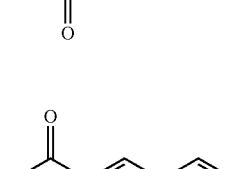 | KPU-66, tBu-delta-PLH-1-napthalene; TFA Salt (MW 500.47) | 1.49E−08 | 2.12E−09 | 88 | 2 | 3 |
| 2418 | 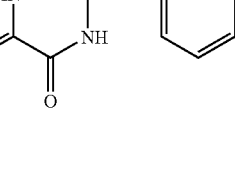 | KPU-67, tBu-delta-PLH-2-napthalene; TFA Salt (MW 500.47) | 1.73E−06 | NA | 83 | NA | 2 |
| 2419 | 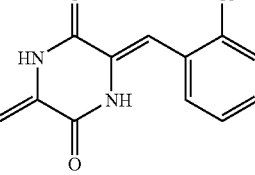 | KPU-68, tBu-delta-PLH-2,3-diCl; TFA Salt (MW 519.30) | 2.99E−08 | 4.46E−09 | 88 | 2 | 3 |
| 2420 | 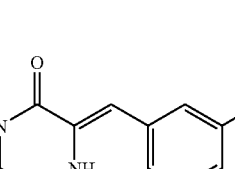 | KPU-69, tBu-delta-PLH-m-Vinyl; TFA Salt (MW 476.45) | 1.70E−08 | 1.52E−09 | 88 | 2 | 3 |
| 2421 | 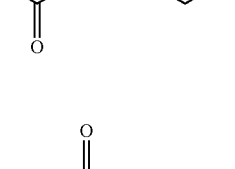 | KPU-70, tBu-delta-PLH-oxazole; TFA Salt (MW 451.40) | 2.22E−08 | 3.28E−09 | 88 | 2 | 3 |

TABLE 3.1-continued

Study of phenylahistin, dehydrophenylahistin and of additional dehydrophenylahistin derivatives

| NPI | Structure | Chemical name | $EC_{50}$ (M) Mean | SD | % cytotox Mean | SD | n |
|---|---|---|---|---|---|---|---|
| 2422 | 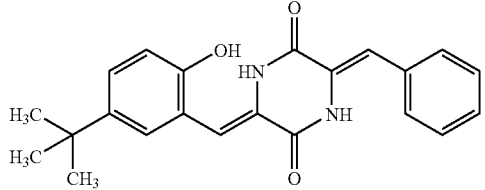 | KPU-71, tBu-delta-PLH-2-Hydroxybenzyl; TFA Salt (MW 495.91) | >2E−05 | NA | 14 | NA | 2 |
| 2423 | 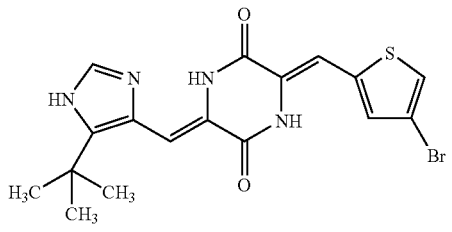 | KPU-72, tBu-delta-PLH-4-Br-2-thionyl; TFA Salt (MW 484.49) | 1.71E−07 | 1.86E−08 | 86 | 3 | 3 |
| 2424 | 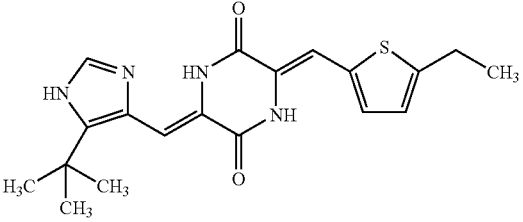 | KPU-73, tBu-delta-PLH-5-Et-2-thionyl; TFA Salt (MW 535.34) | 1.32E−07 | 2.56E−08 | 87 | 3 | 3 |
| 2425 | 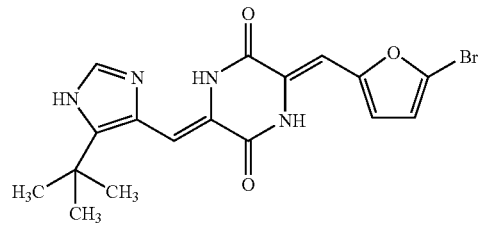 | KPU-74, tBu-delta-PLH-5-Br-2-furyl; TFA Salt (MW 519.27) | 3.05E−08 | 8.71E−09 | 87 | 3 | 3 |
| 2426 | 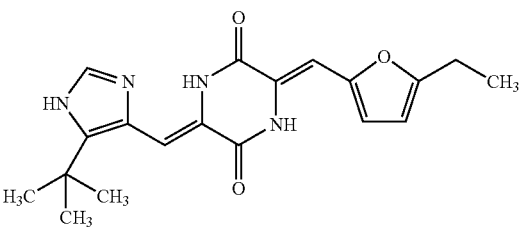 | KPU-75, tBu-delta-PLH-5-Et-2-furyl; TFA Salt (MW 468.43) | 2.42E−07 | NA | 86 | NA | 2 |
| 2427 | 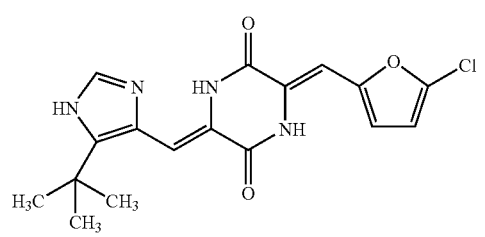 | KPU-76, tBu-delta-PLH-5-Cl-2-furyl; TFA Salt (MW 474.82) | 3.82E−08 | 8.88E−09 | 87 | 2 | 3 |

TABLE 3.1-continued

Study of phenylahistin, dehydrophenylahistin and of
additional dehydrophenylahistin derivatives

| NPI | Structure | Chemical name | EC$_{50}$ (M) Mean | SD | % cytotox Mean | SD | n |
|---|---|---|---|---|---|---|---|
| 2428 | 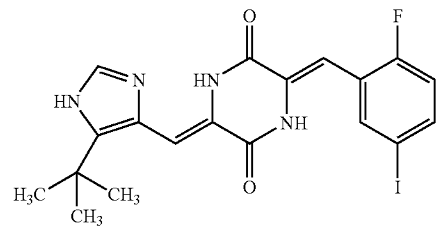 | KPU-77, tBu-delta-PLH-2-F-5-I; TFA Salt (MW 594.30) | 4.17E−08 | 7.78E−09 | 87 | 2 | 3 |
| 2429 | 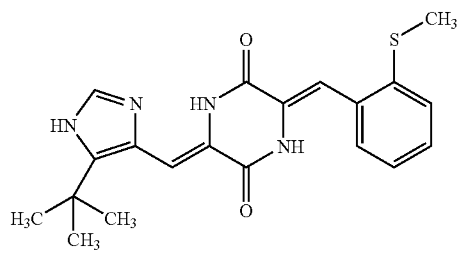 | KPU-79, tBu-delta-PLH-2-(Methylthio); TFA Salt (MW 496.50) | 2.86E−08 | 3.59E−09 | 87 | 2 | 3 |
| 2430 | 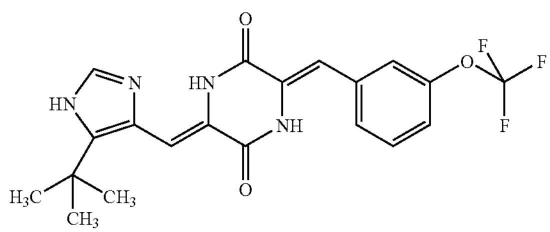 | KPU-80, tBu-delta-PLH-m-OCF3; TFA Salt (MW) | 1.43E−08 | 4.93E−09 | 87 | 2 | 3 |
| 2431 | 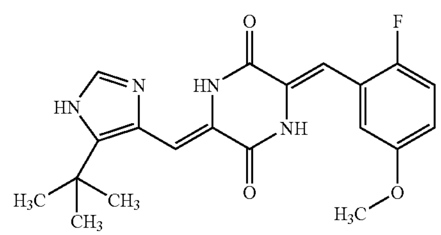 | KPU-81, tBu-delta-PLH-2-F5-OMe; TFA Salt (MW) | 2.03E−08 | 2.12E−09 | 88 | 2 | 3 |
| 2432 | 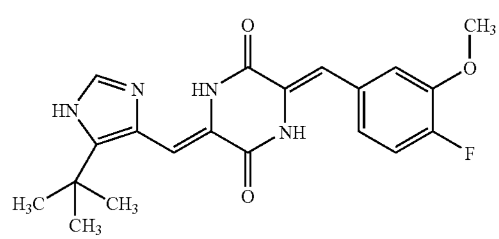 | KPU-82, tBu-delta-PLH-4-F-3-OMe; TFA Salt (MW) | 4.93E−07 | NA | 85 | NA | 2 |
| 2433 | 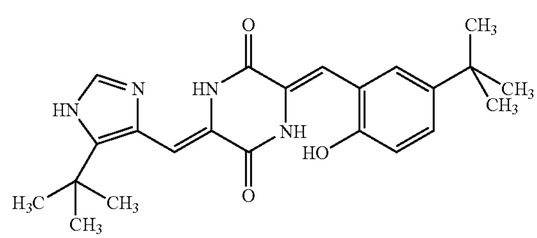 | KPU-83, tBu-delta-PLH-2-OH-5-tBU; TFA Salt (MW) | 8.53E−06 | NA | 80 | NA | 2 |

TABLE 3.1-continued

Study of phenylahistin, dehydrophenylahistin and of
additional dehydrophenylahistin derivatives

| NPI | Structure | Chemical name | EC$_{50}$ (M) Mean | SD | % cytotox Mean | SD | n |
|---|---|---|---|---|---|---|---|
| 2434 | 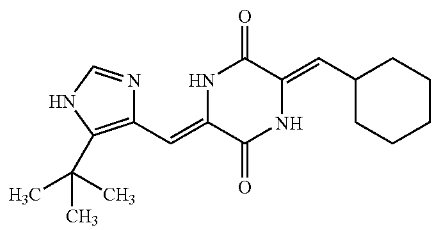 | KPU-84, tBu-delta-PLH-cyclohexane; TFA Salt (MW) | 7.89E−08 | 1.41E−08 | 87 | 3 | 3 |
| 2435 | 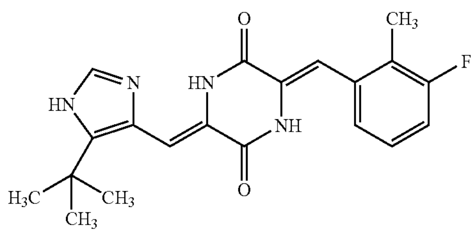 | KPU-86, tBu-delta-PLH-2-Me-3-F; TFA Salt (MW) | 3.34E−08 | 6.66E−09 | 86 | 3 | 3 |
| 2436 | 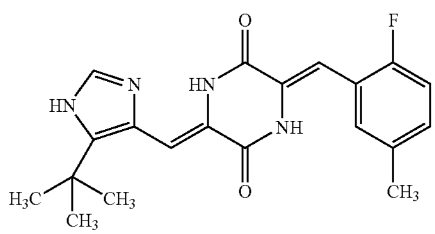 | KPU-87, tBu-delta-PLH-2-F-5-Me; TFA Salt (MW) | 2.50E−08 | 3.52E−10 | 86 | 3 | 3 |
| 2437 | 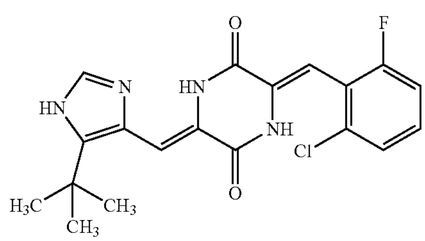 | KPU-88, tBu-delta-PLH-2-Cl-6-F; TFA Salt (MW) | 2.49E−08 | 1.31E−09 | 86 | 2 | 3 |
| 2438 | 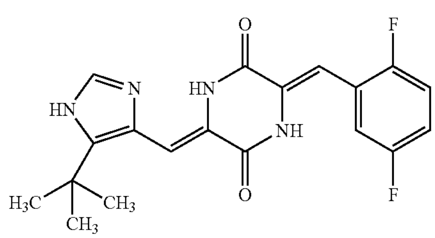 | KPU-89, tBu-delta-PLH-2,5-di-F; TFA Salt (MW) | 3.07E−08 | 2.14E−09 | 87 | 3 | 3 |
| 2439 | 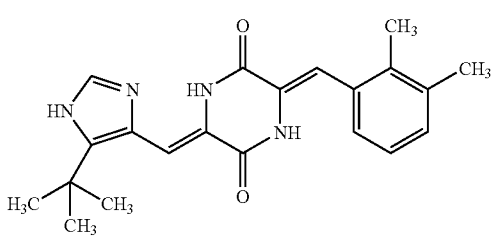 | KPU-90, tBu-delta-PLH-2,3-di-Me; TFA Salt (MW) | 2.96E−09 | 2.27E−10 | 87 | 3 | 3 |

TABLE 3.1-continued

Study of phenylahistin, dehydrophenylahistin and of additional dehydrophenylahistin derivatives

| NPI | Structure | Chemical name | $EC_{50}$ (M) Mean | SD | % cytotox Mean | SD | n |
|---|---|---|---|---|---|---|---|
| 2440 | 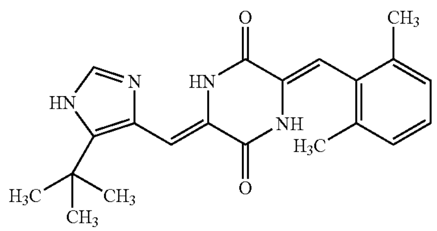 | KPU-91 tBu-delta-PLH-2,6-di-Me; TFA Salt (MW) | 4.30E−07 | NA | 85 | NA | 2 |
| 2441 | 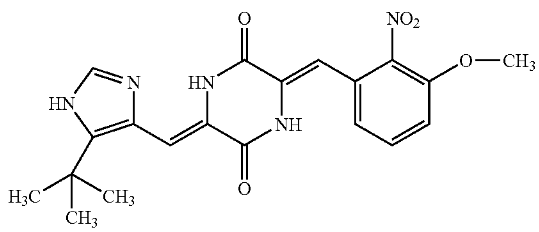 | KPU-92, tBu-delta-PLH-2-NO2-3-OMe; TFA Salt (MW) | 6.63E−07 | NA | 83 | NA | 2 |
| 2442 | 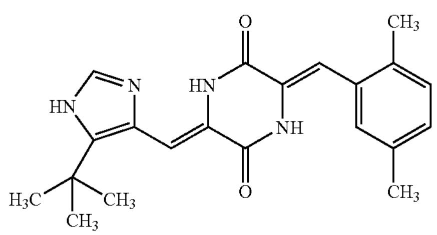 | KPU-93, tBu-delta-PLH-2,5-diMe; TFA Salt (MW) | 8.82E−08 | 1.40E−08 | 87 | 3 | 3 |
| 2455 | 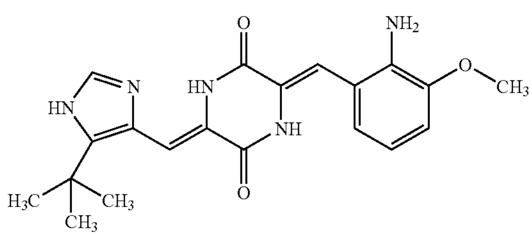 | KPU-94, tBu-delta-PLH-2-NH2-3-OMe; TFA Salt | 3.49E−07 | NA | 87 | NA | 2 |
| 2456 | 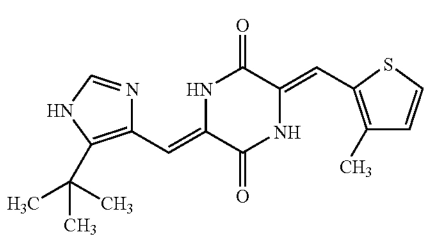 | KPU-95, tBu-delta-PLH-3-OMe-2-furyl; TFA Salt | 1.25E−07 | 3.68E−08 | 88 | 2 | 3 |
| 2457 | 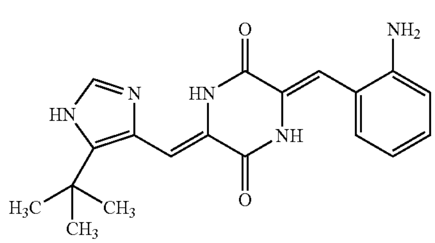 | KPU-96, tBu-delta-PLH-2-NH2; TFA Salt | 4.32E−07 | NA | 86 | NA | 2 |

TABLE 3.1-continued

Study of phenylahistin, dehydrophenylahistin and of additional dehydrophenylahistin derivatives

| NPI | Structure | Chemical name | EC$_{50}$ (M) Mean | SD | % cytotox Mean | SD | n |
|---|---|---|---|---|---|---|---|
| 2458 | 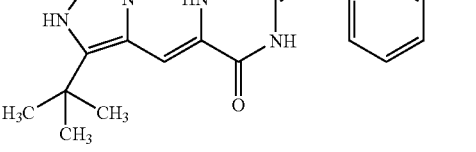 | KPU-97, tBu-delta-PLH-m-NH2; TFA Salt | 3.10E–08 | 1.71E–09 | 87 | 3 | 3 |
| 2459 | 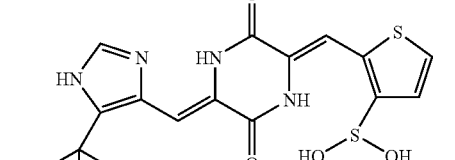 | KPU-98, tBu-delta-PLH-3-B(OH)2-2-thienyl; TFA Salt | 2.53E–08 | 4.31E–09 | 88 | 3 | 3 |
| 2460 | 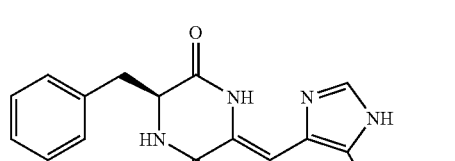 | (–)-tBu-PLH | 2.55E–07 | 1.24E–07 | 87 | 2 | 5 |

EXAMPLE 5

Other Dehydrophenylahistin Analogs

A. Modifications for the Synthesis of Dehydrophenylahistin Derivatives

Other derivatives of dehydrophenylahistin are synthesized using the foregoing techniques alone or in conjunction with other well known organic synthesis techniques.

Modifications to the diacyldiketopiperazine and the first and second aldehydes involved in the synthesis method vary according to the desired derivative to produce. Derivatives are synthesized that:

A) modify the phenyl ring and/or introduce other aromatic ring systems,

B) alter the position of the aromatic ring,

C) alter the imidazole aromatic ring system, and/or

D) modify the 5-position on the imidazole ring.

The figure below depicts regions of the dehydrophenylahistin compound modified to produce derivatives of dehydrophenylahistin. Non-limiting examples of modifications are disclosed, and based on this disclosure would be understood by those of skill in the art.

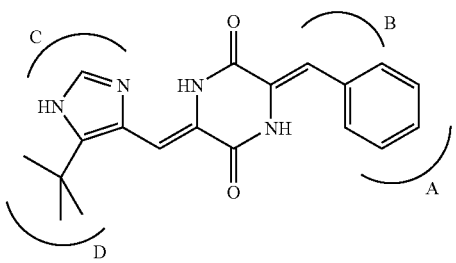

A 1) Modification of the phenyl ring besed on the structure of known anti-tubulin compounds Alkyl, Halogen, Alkoxy, Acetyl, Sulfonamide, Amino, Hydroxyl, Nitro, etc.

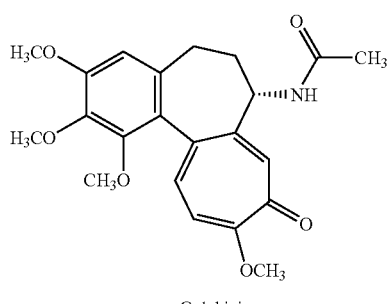

Colchicine

C Change to the other ring systems

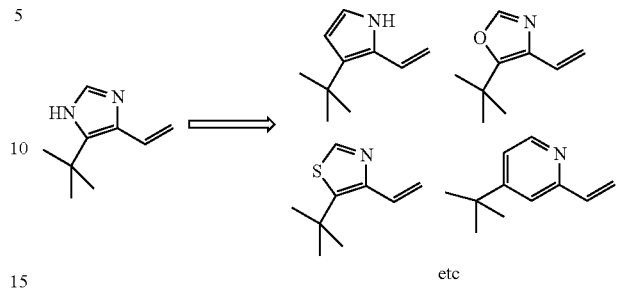

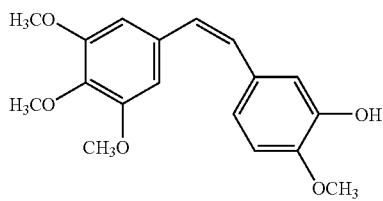

Combretastatin A-4

D Further modification of the 5-positin on the imidazole ring

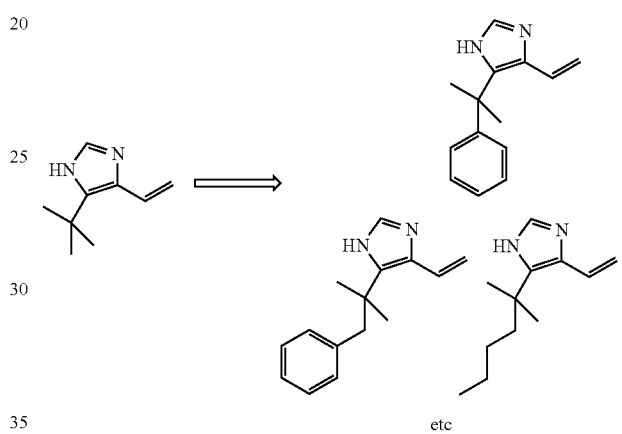

etc

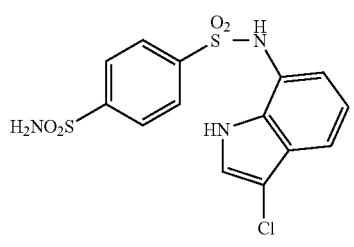

Mol. Wt.: 385.85

E7070
0.15 ug/mL
P-388 Phase II

2) Introduction of other aromatic ring systems

Expanding on the above modifications to the dehydrophenylahistin compound, derivatives of the compound may include the following substitutions at the phenyl ring (A): —$CF_3$, —$SO_2NH_2$ (—$SO_2NR_1R_2$), —$SO_3H$, —$CONH_2$ (—$CONR_1R_2$), —COOH, etc. Other ring systems (C) may also include the following:

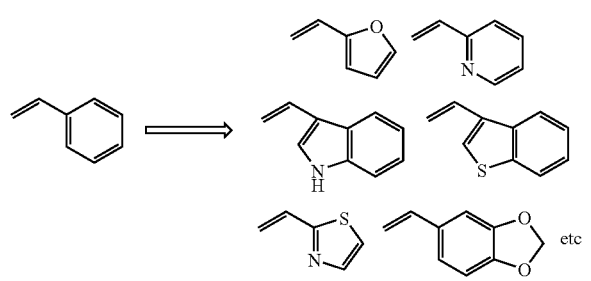

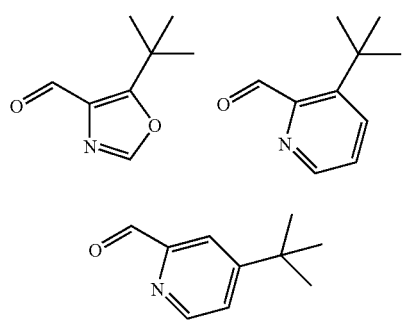

B Position of the aromatic ring

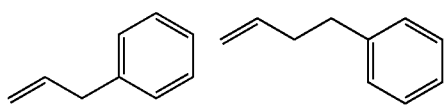

B. Examples of Synthesized Dehydrophenylahistin Derivatives

Additional examples of synthesized dehydrophenylahistin derivatives are disclosed in the Table 4.

TABLE 4

Additional synthesized derivatives of dehydrophenylahistin

| COMPOUNDS | STRUCTURE | SALT FORM | M.W. |
|---|---|---|---|
| KPU-20<br>tBu-ΔPLH-p-Cl | 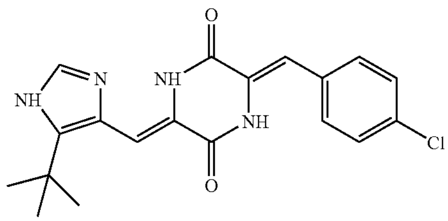 | TFA | 370.83<br>484.86<br>(+TFA) |
| KPU-30<br>tBu-ΔPLH-2,3-methylendioxy | 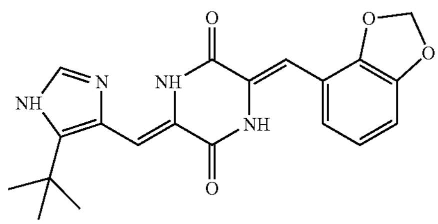 | TFA | 380.40<br>494.42<br>(+TFA) |
| KPU-31<br>tBu-ΔPLH-3-pyridyl | 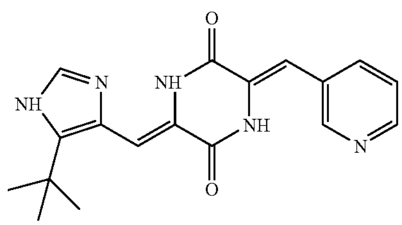 | 2TFA | 337.38<br>565.42<br>(+2TFA) |
| KPU-32<br>tBu-ΔPLH-o-Me | 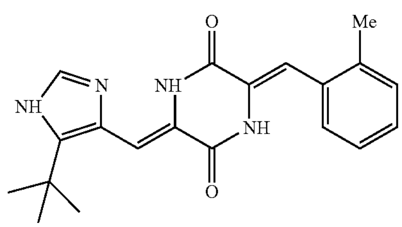 | TFA | 350.41<br>464.44<br>(+TFA) |
| KPU-33<br>tBu-ΔPLH-3-Me-2-pyridyl | 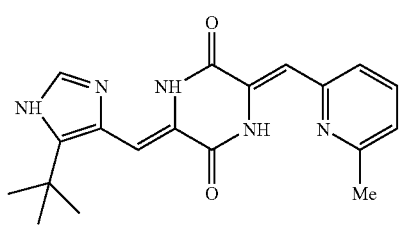 | 2TFA | 351.40<br>579.45<br>(+2TFA) |
| KPU-34<br>tBu-ΔPLH-4-F | 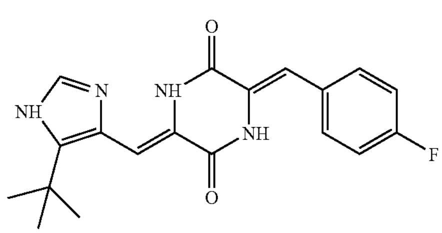 | TFA | 354.38<br>468.40<br>(+TFA) |

TABLE 4-continued

Additional synthesized derivatives of dehydrophenylahistin

| COMPOUNDS | STRUCTURE | SALT FORM | M.W. |
|---|---|---|---|
| KPU-35 tBu-ΔPLH-m-F | 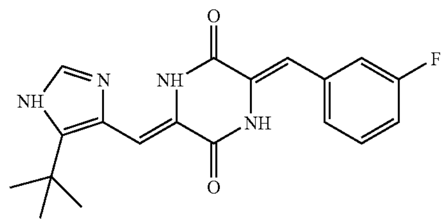 | TFA | 354.38 468.40 (+TFA) |
| KPU-36 tBu-ΔPLH-5-Me-4-im | 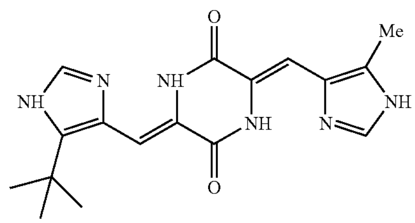 | 2TFA | 356.42 584.47 (+2TFA) |
| KPU-37 tBu-ΔPLH-o-F | 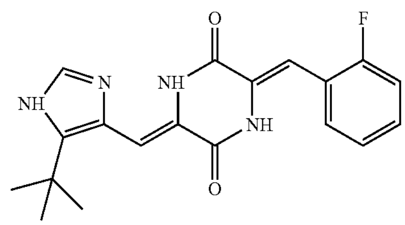 | TFA | 354.38 468.40 (+TFA) |
| KPU-38 tBu-ΔPLH-m-Me | 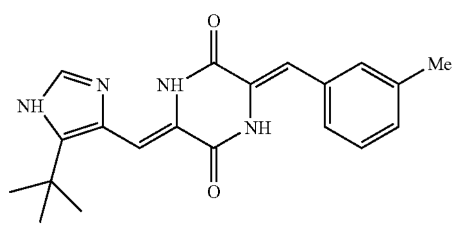 | TFA | 350.41 464.44 (+TFA) |
| KPU-39 tBu-ΔPLH-p-Me | 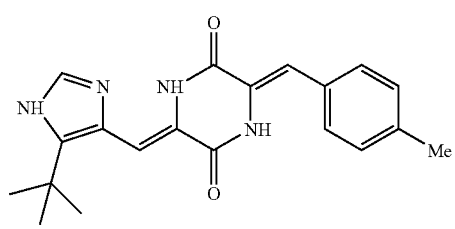 | TFA | 350.41 464.44 (+TFA) |
| KPU-40 tBu-ΔPLH-p-Br | 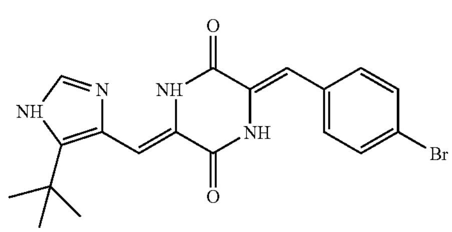 | TFA | 415.28 529.31 (+TFA) |

TABLE 4-continued

Additional synthesized derivatives of dehydrophenylahistin

| COMPOUNDS | STRUCTURE | SALT FORM | M.W. |
|---|---|---|---|
| KPU-41<br>tBu-ΔPLH-m-Br | 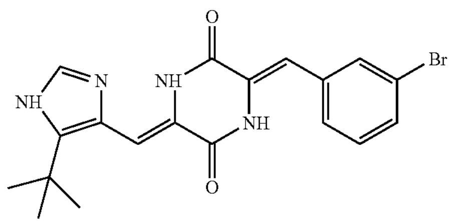 | TFA | 415.28<br>529.31<br>(+TFA) |
| KPU-42<br>tBu-ΔPLH-3-thienyl | 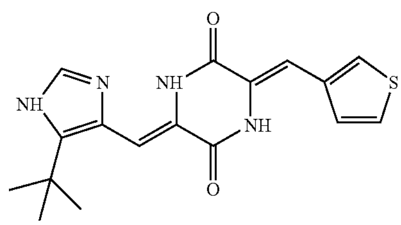 | TFA | 342.42<br>456.44<br>(+TFA) |
| KPU-43<br>tBu-ΔPLH-p-CN | 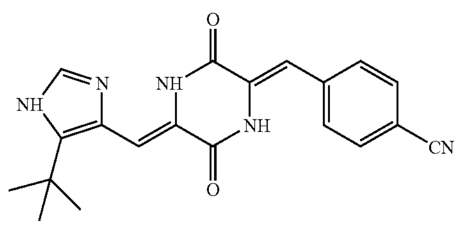 | TFA | 361.40<br>475.42<br>(+TFA) |
| KPU-44<br>tBu-ΔPLH-m-EtO | 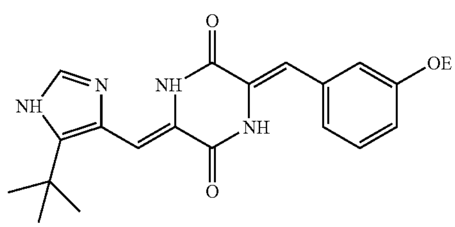 | TFA | 380.44<br>494.46<br>(+TFA) |
| KPU-45<br>tBu-ΔPLH-2,4,6-TriOMe | 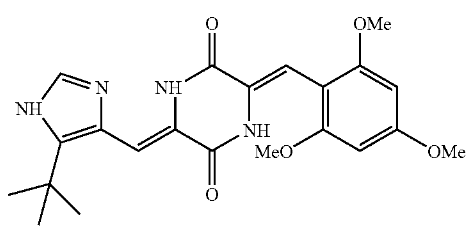 | TFA | 426.47<br>540.49<br>(+TFA) |
| KPU-46<br>tBu-ΔPLH-o-$NO_2$ | 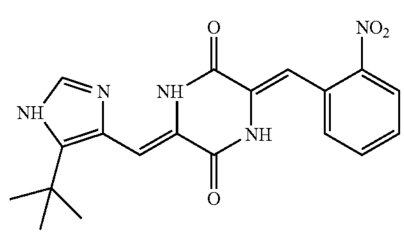 | TFA | 381.39<br>494.41<br>(+TFA) |

TABLE 4-continued

*Additional synthesized derivatives of dehydrophenylahistin*

| COMPOUNDS | STRUCTURE | SALT FORM | M.W. |
|---|---|---|---|
| KPU-47<br>tBu-ΔPLH-m-NO$_2$ | 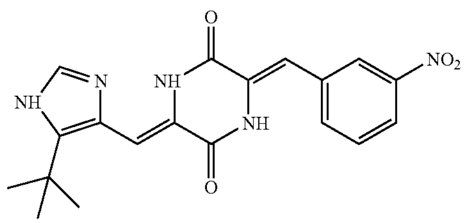 | TFA | 381.69<br>495.41<br>(+TFA) |
| KPU-48<br>tBu-ΔPLH-p-NO$_2$ | 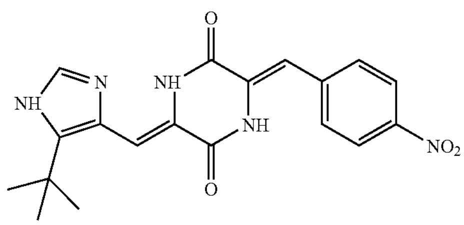 | TFA | 381.39<br>495.41<br>(+TFA) |
| KPU-49<br>tBu-ΔPLH-m-CN | 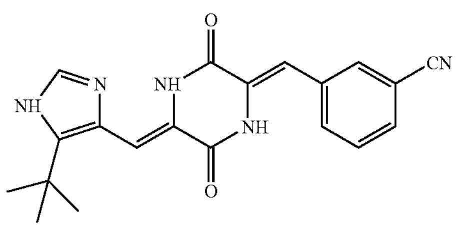 | TFA | 361.40<br>475.42<br>(+TFA) |
| LPU-50<br>tBu-ΔPLH-o-Br | 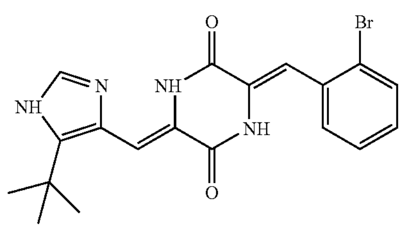 | TFA | 415.28<br>529.31<br>(+TFA) |
| KPU-51<br>tBu-ΔPLH-m-OH | 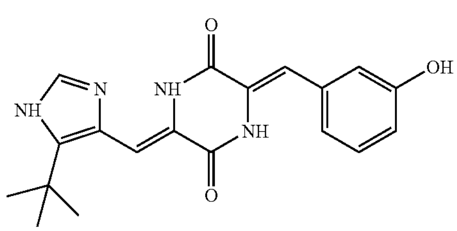 | TFA | 352.39<br>466.41<br>(+TFA) |
| KPU-52<br>tBu-ΔPLH-2-NO$_2$-5-Cl | 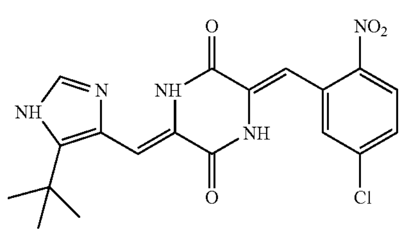 | TFA | 415.83<br>529.85<br>(+TFA) |

TABLE 4-continued

Additional synthesized derivatives of dehydrophenylahistin

| COMPOUNDS | STRUCTURE | SALT FORM | M.W. |
|---|---|---|---|
| KPU-53<br>tBu-ΔPLH-o-OH | 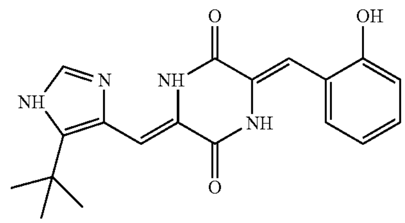 | TFA | 352.39<br>466.41<br>(+TFA) |
| KPU-54<br>tBu-ΔPLH-2-OH-5-OMe | 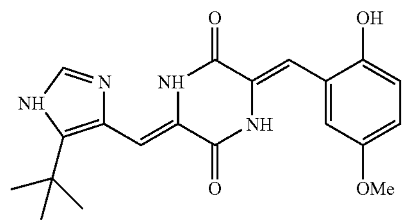 | TFA | 382.41<br>496.44<br>(+TFA) |
| KPU-55<br>tBu-ΔPLH-3-furanyl | 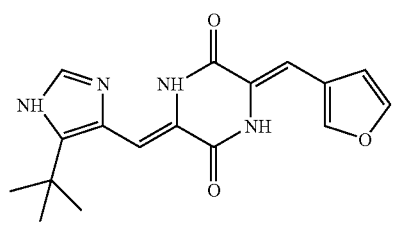 | TFA | 326.35<br>440.37<br>(+TFA) |
| KPU-56<br>tBu-ΔPLH-2-OH-5-Br | 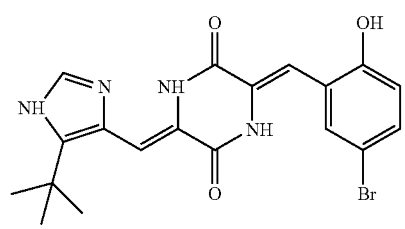 | TFA | 431.28<br>545.31<br>(+TFA) |
| KPU-57<br>tBu-ΔPLH-2-OH-4-OMe | 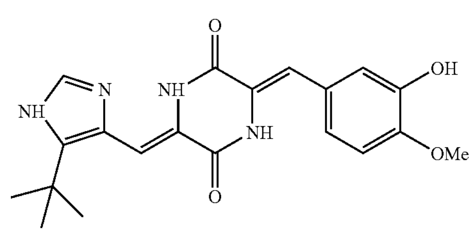 | TFA | 382.41<br>496.44<br>(+TFA) |
| KPU-58<br>tBu-ΔPLH-2-OH-4-OMe | 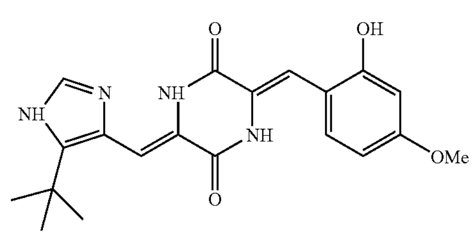 | TFA | 382.41<br>496.44<br>(+TFA) |

TABLE 4-continued

Additional synthesized derivatives of dehydrophenylahistin

| COMPOUNDS | STRUCTURE | SALT FORM | M.W. |
|---|---|---|---|
| KPU-59 tBu-ΔPLH-2-OH-5-Cl | | TFA | 386.83 (+TFA) 500.86 |
| KPU-60 tBu-ΔPLH-5-Me-2-furanyl | | TFA | 340.38 454.40 (+TFA) |
| KPU-61 tBu-ΔPLH-5-Cl-2-thionyl | | TFA | 376.86 490.88 (+TFA) |
| KPU-62 tBu-ΔPLH-2-thionyl | | TFA | 342.42 456.44 (+TFA) |
| KPU-63 tBu-ΔPLH-N-Me-2-pyrrole | | TFA | 339.39 453.42 (+TFA) |
| KPU-64 tBu-ΔPLH-3,5-diCl | | TFA | 405.27 |

TABLE 4-continued

Additional synthesized derivatives of dehydrophenylahistin

| COMPOUNDS | STRUCTURE | SALT FORM | M.W. |
|---|---|---|---|
| KPU-65<br>tBu-ΔPLH-m-CF$_3$ | | TFA | 404.39 |
| KPU-66<br>tBu-ΔPLH-1-Naphthalene | | TFA | 386.44 |
| KPU-67<br>tBu-ΔPLH-2-Naphthalene | | TFA | 386.44 |
| KPU-68<br>tBu-ΔPLH-2,3-diCl | | TFA | 405.27 |
| KPU-69<br>TBu-ΔPLH-m-Vinyl | | TFA | 362.42 |
| KPU-77<br>TBu-ΔPLH-2-F-5-I | | TFA | 480.28 |

TABLE 4-continued

Additional synthesized derivatives of dehydrophenylahistin

| COMPOUNDS | STRUCTURE | SALT FORM | M.W. |
|---|---|---|---|
| KPU-79<br>tBu-ΔPLH-2-(Methylthio) | | TFA | 368.45 |
| KPU-80<br>TBu-ΔPLH-m-OCF$_3$ | | TFA | 420.38 |
| KPU-81<br>TBu-ΔPLH-2-F-5-OMe | | TFA | 384.38 |
| KPU-82<br>TBu-ΔPLH-4-F-3-OMe | | TFA | 384.38 |
| KPU-83<br>TBu-ΔPLH-2-OH-5-tBu | | TFA | 408.39 |
| KPU-84<br>TBu-ΔPLH-cyclohexane | | TFA | 341.39 |

TABLE 4-continued

Additional synthesized derivatives of dehydrophenylahistin

| COMPOUNDS | STRUCTURE | SALT FORM | M.W. |
|---|---|---|---|
| KPU-86 TBu-ΔPLH-2-Me-3-F | | TFA | 368.39 |
| KPU-87 TBu-ΔPLH-2-F-5-Me | | TFA | 368.39 |
| KPU-88 TBu-ΔPLH-2-Cl-6-F | | TFA | 388.83 |
| KPU-89 TBu-ΔPLH-2,5-di-F | | TFA | 372.38 |
| KPU-90 TBu-ΔPLH-2,3-di-Me | | TFA | 364.38 |
| KPU-91 TBu-ΔPLH-2,6-di-Me | | TFA | 364.38 |

TABLE 4-continued

Additional synthesized derivatives of dehydrophenylahistin

| COMPOUNDS | STRUCTURE | SALT FORM | M.W. |
|---|---|---|---|
| KPU-92<br>tBu-ΔPLH-2-NO$_2$-3-OMe | 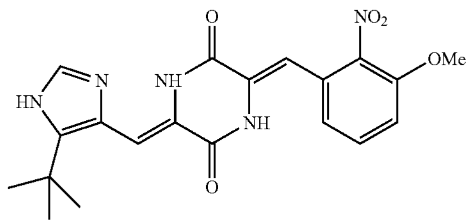 | TFA | 411.39 |
| KPU-93<br>TBu-ΔPLH-2,5-diMe | 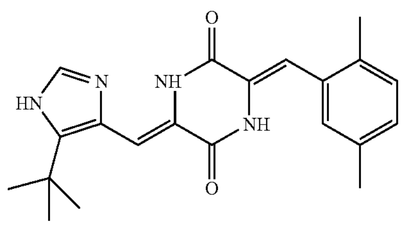 | TFA | 364.38 |
| KPU-94<br>tBu-ΔPLH-2-NH$_2$-3-OMe | 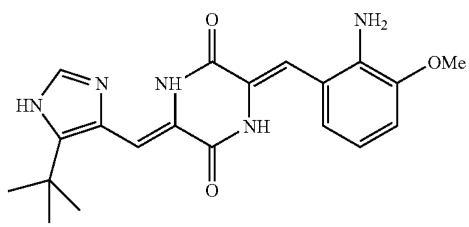 | TFA | 381.399 |
| KPU-96<br>TBu-ΔPLH-2-NH$_2$ | 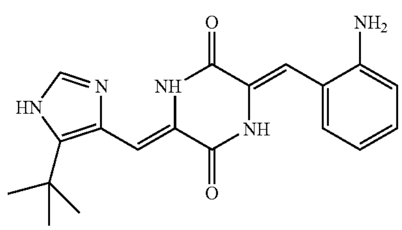 | TFA | 351.41 |
| KPU-97<br>TBu-ΔPLH-m-NH$_2$ | 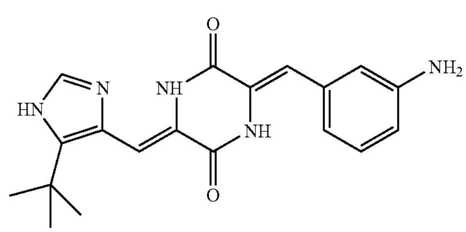 | TFA | 351.41 |

C. Evaluation of Dehydrophenylahistin Derivatives

Evaluation of derivatives described above is assessed according to the methods described in Example 3. Additional evaluation of the derivatives are extended to specific activities such as determining the inhibiting effect on cell proliferation, the effects on a specific cellular mechanism (i.e. microtuble function), effects on cell cycle progression, evaluating in vitro anti-tumor activity against cancer cell lines, etc. Some evaluation method protocols are given below.

1) Cell Proliferation Inhibiting Effect of Dehydrophenylahistin and its Analogs

Into each well of a 96-well microtiter plate, 100 µl of A-549 cells derived from human lung cancer prepared to $10^5$ cells/ml in a culture medium obtained by adding 10% bovine fetus serum to EMEM culture medium (Nissui Seiyaku Co., Ltd.) having antitumor effect against A-549 cells derived from human lung cancer are placed. Methanol solution of the derivative obtained by the above-listed examples are added to the wells of the uppermost row, specimens are diluted by the half-log dilution method and added, and the plate is incubated in a carbon dioxide gas incubator at 37° C. for 48 hours. The result is added in lots of 10 µl with MTT reagent (3-(4,5-dimethyl-2-thiazole)-2,5-diphenyl-2H-tetra bromide)(1 mg/ml·PBS), followed by incubation in a carbon dioxide gas incubator at 37° C. for 6 hours. The culture medium is discarded and the crystal of produced in the cells are dissolved in 100 µl/well of dimethylsulfoxide. Absorption of 595 nm light is then measured with a microplate reader. By comparing the light absorptions of the untreated cells to that of cells treated with a specimen of a known concentration, the specimen concentration that inhibited cell proliferation 50% ($IC_{50}$) is calculated.

2) Cell Cycle Inhibiting Activity of Dehydrophenylahistin and its Analogs

Cell strain A431 is derived from human lung cancer. EMEM culture medium containing 10% bovine fetal serum and 1% MEM nonessential amino acid solution (SIGMA M2025) is used to incubate A431 cells at 37° C. in an incubator saturated with 5% carbon dioxide gas and water vapor. The refined specimen of dehydrophenylahistin obtained by the methods above is added to the cells in the log-growth phase and progression of the cell cycle is analyzed by flow cytometer and microscopic observation.

Figure 42:
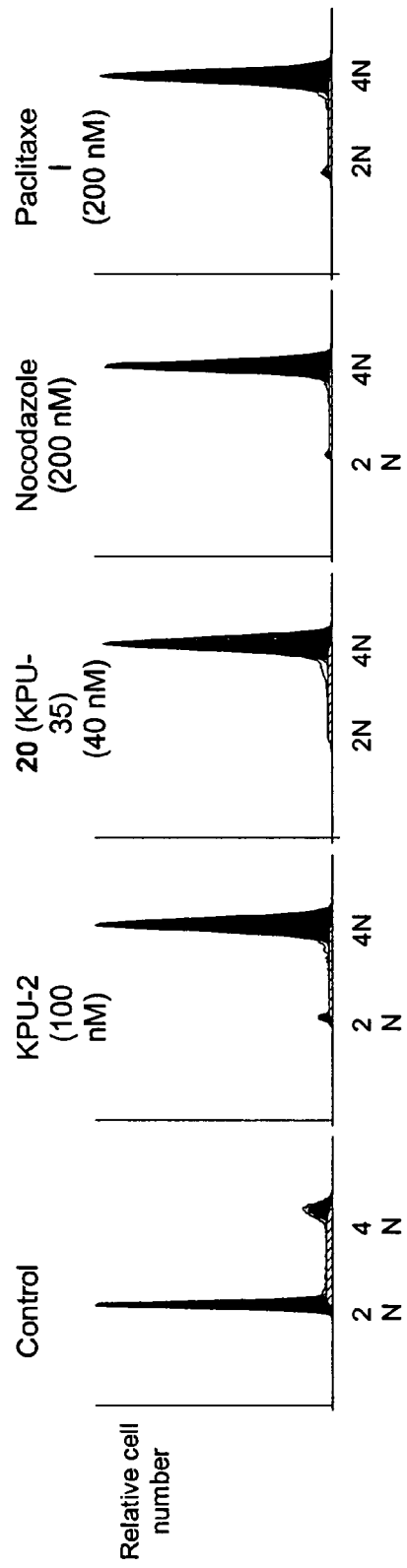
FIG. 42 depicts the effect on cell cycle progression of HeLa cells by tBu-dehydro-PLH (KPU-2) and KPU-35.

The effect on cell cycle progression of HeLa cells is depicted in FIG. 42.

EXAMPLE 6

Figure 5:
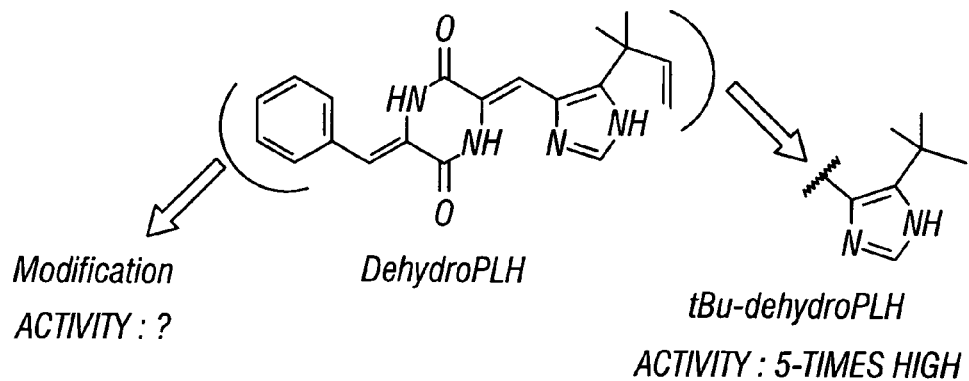
FIG. 5 illustrates two modification strategies for dehydro-PLH for potent cytotoxic activity.

Structure-Activity Relationship of Synthesized Dehydrophenylahistin (DehydroPLH) Derivatives 1) Overview in Derivative Syntheses Many, but not all, of the derivatives of dehydroPLH disclosed herein include one, two, or three modifications at the phenyl ring (FIG. 5 below). The derivatives were synthesized by the methods described above. As shown in Table 5, certain compounds showed more potent cytotoxic activity than dehydroPLH and tBu-dehydroPLH. The most potent compound exhibiting an EC50 value of 3 nM was KPU-90. This value was 16-times and 4-times higher than that of dehydroPLH and tBu-dehydroPLH, respectively. These derivatives have mono-substitution at the o- or m-position of the phenyl ring with the halogen atoms such as fluorine and chlorine atoms or the methyl, vinyl or methoxy group. Derivatives with substitutions to heteroaryl structures such as the npahthalene, thiophene and furan rings also elicited a potent activity. KPU-35, 42, 69, 80 and 81 also showed higher activity than tBu-dehydroPLH.

TABLE 5

Synthetic potent dehydroPLH derivatives

| Compound | Structure | $EC_{50}$ (nM) |
|---|---|---|
| KPU-9 | 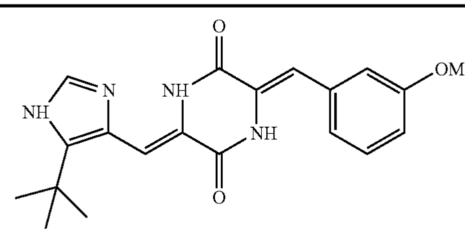 | 31 |
| KPU-35 | 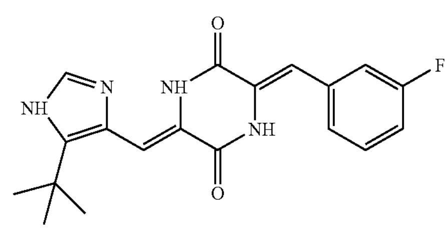 | 10 |
| KPU-18 | 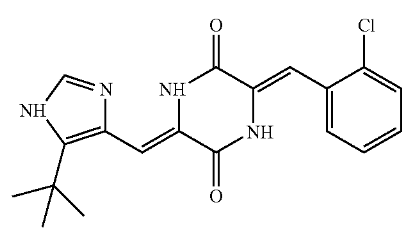 | 42 |
| KPU-19 | 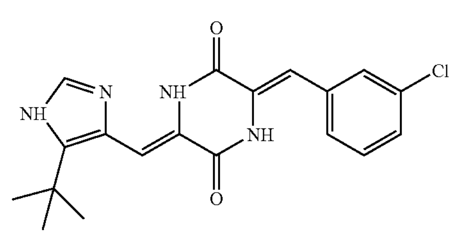 | 20 |

TABLE 5-continued

Synthetic potent dehydroPLH derivatives

| Compound | Structure | EC$_{50}$ (nM) |
|---|---|---|
| KPU-38 | 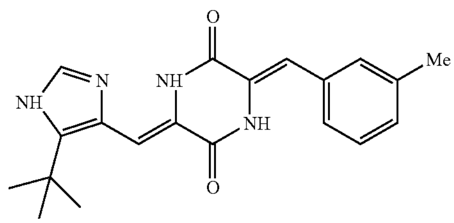 | 45 |
| KPU-37 | 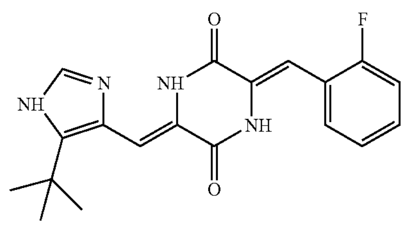 | 21 |
| KPU-41 | 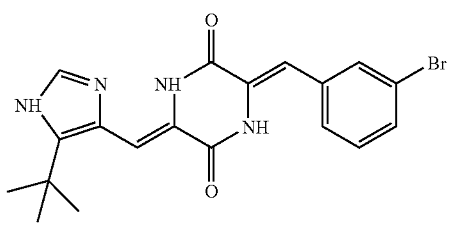 | 31 |
| KPU-29 | 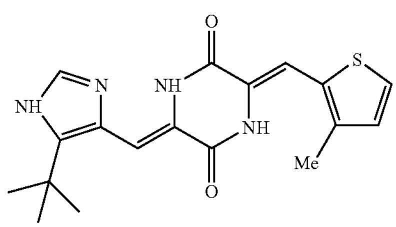 | 44 |
| KPU-16 | 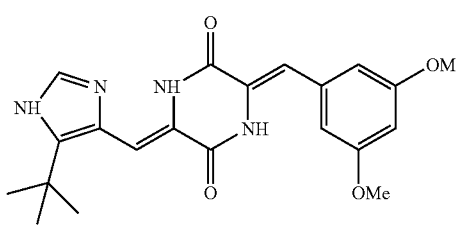 | 42 |
| KPU-32 | 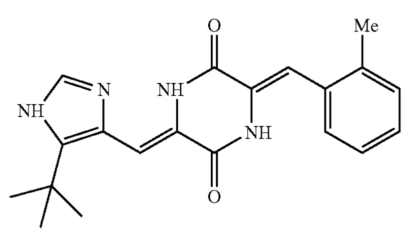 | 42 |

TABLE 5-continued

Synthetic potent dehydroPLH derivatives

| Compound | Structure | EC$_{50}$ (nM) |
| --- | --- | --- |
| KPU-42 | 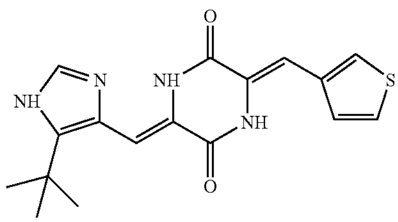 | 54 |
| KPU-46 | 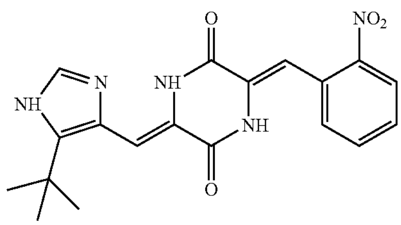 | 44 |
| KPU-44 | 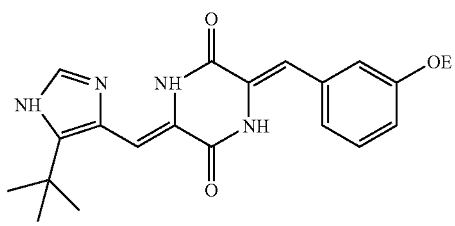 | 43 |
| tBu-ΔPLH (KPU-2) | 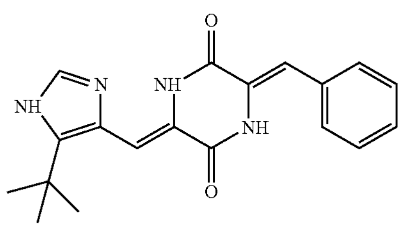 | 13 |
| KPU-69 | 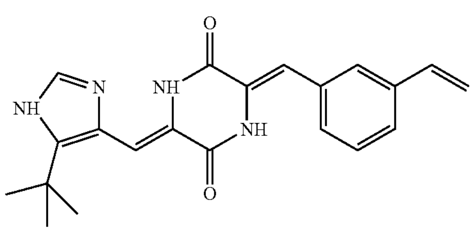 | 16 |
| KPU-80 | 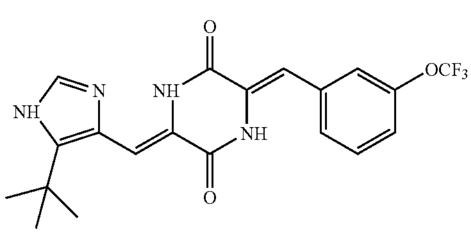 | 13 |

TABLE 5-continued

Synthetic potent dehydroPLH derivatives

| Compound | Structure | $EC_{50}$ (nM) |
| --- | --- | --- |
| KPU-81 | 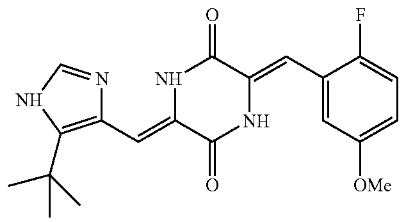 | 19 |
| KPU-90 | 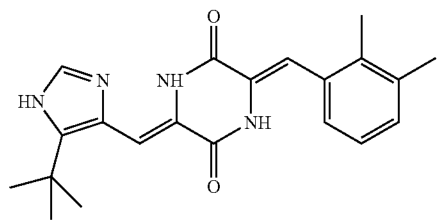 | 3 |
| DehydroPLH (KPU-1) | 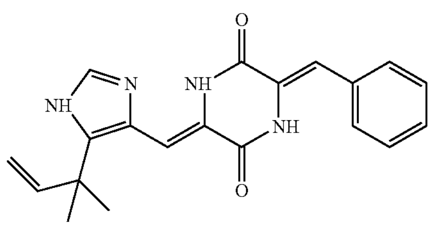 | 48 |

2) Introduction of the Methoxy Groups to the Phenyl Ring

Colchicine recognizes the same binding site on β-tubulin as PLH. Colchicine has four characteristic methoxy groups on its A and B rings. A series of substitutions with the single or multiple methoxy groups was performed and the results of cytotoxic activity are shown in Table 6.

TABLE 6

Effect of the methoxy group substitution on the proliferation of HT-29 cells

| Compound | Structure | EC50 (nM) |
| --- | --- | --- |
| DehydroPLH (KPU-1) | 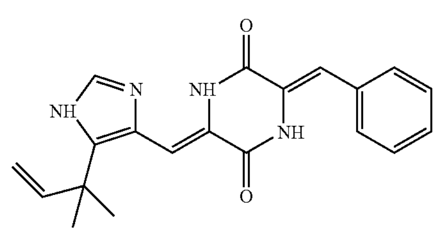 | 48 |
| tBuΔPLH (KPU-2) | 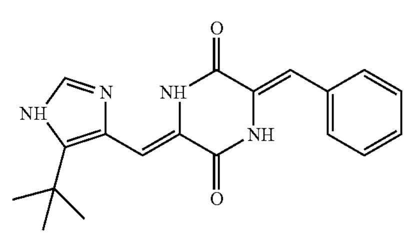 | 13 |

TABLE 6-continued

Effect of the methoxy group substitution on the proliferation of HT-29 cells

| Compound | Structure | EC50 (nM) |
|---|---|---|
| KPU-8 | 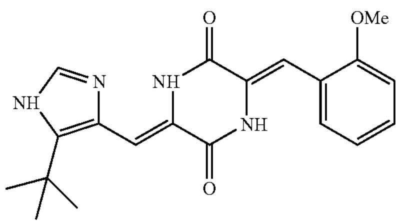 | 89 |
| KPU-9 | 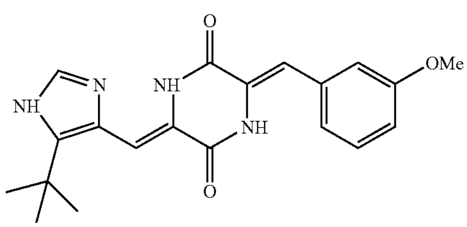 | 31 |
| KPU-6 | 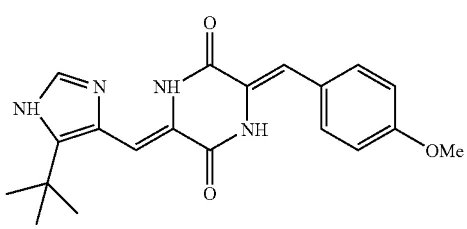 | 6730 |
| KPU-10 | 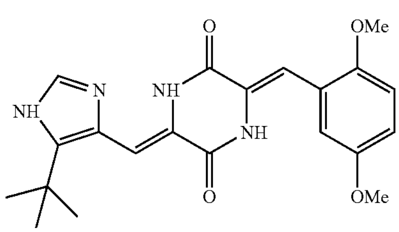 | 1350 |
| KPU-12 | 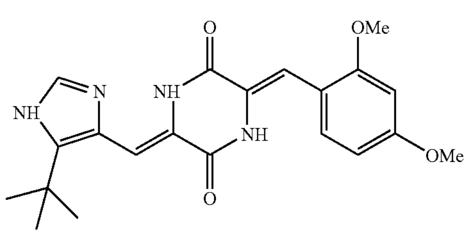 | 4980 |

TABLE 6-continued

Effect of the methoxy group substitution on the proliferation of HT-29 cells

| Compound | Structure | EC50 (nM) |
|---|---|---|
| KPU-13 | 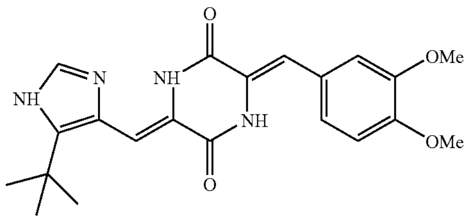 | 2130 |
| KPU-14 | 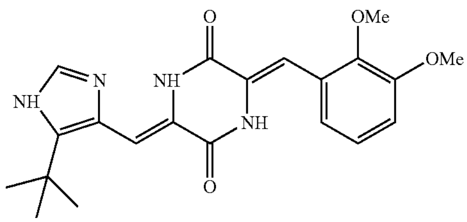 | 610 |
| KPU-15 | 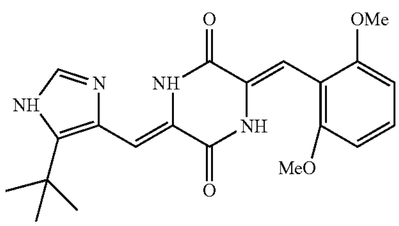 | 4430 |
| KPU-16 | 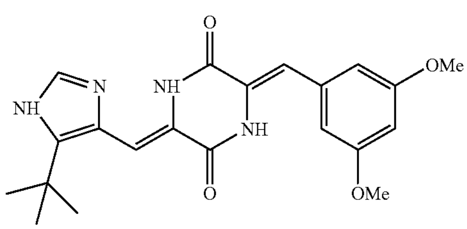 | 42 |
| KPU-24 | 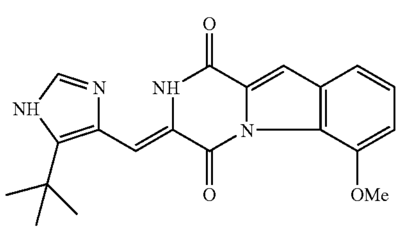 | 7040 |

The result demonstrated that substitutions at the m- or o-position increased cytotoxic activity against HT-29 cells. KPU-9 and 16 showed high activity. The methoxy-derivatives with triple substitution (KPU-11, 17 and 45) also showed activity. The structure of KPU-24 was assigned by MASS analysis.

3) Modification with the Electron-withdrawing Groups

To study more expanded structure-activity relationship on the phenyl ring, a series of different functional groups were introduced, which include both electron-withdrawing and -donating groups. The result of cytotoxicity against HT-29 cells is shown in Tables 7 and 8, respectively.

Substitution at the o- or m-position effectively increased activity. These results were well consistent with the case of the methoxy group.

TABLE 7

Effect of the electron-withdrawing group on proliferation of HT-29 cells

| Compound | Structure | $EC_{50}$ (nM) |
|---|---|---|
| KPU-18 | 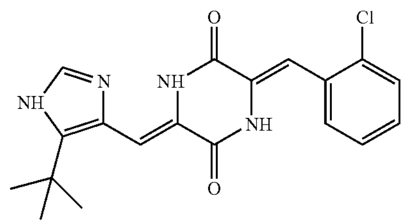 | 42 |
| KPU-19 | 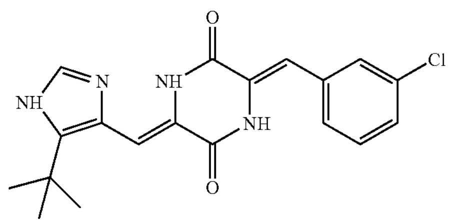 | 20 |
| KPU-20 | 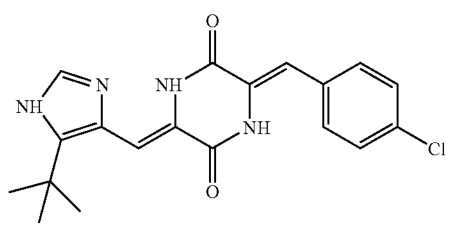 | 545 |
| KPU-21 | 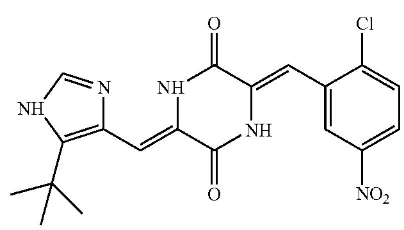 | 51 |
| KPU-52 | 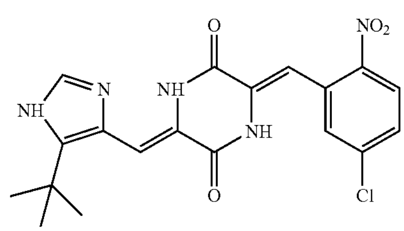 | 110 |
| KPU-37 | 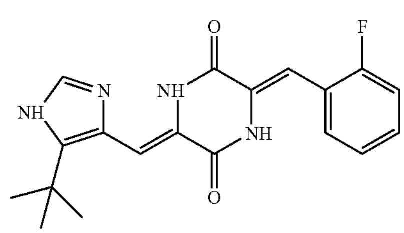 | 21 |

TABLE 7-continued

Effect of the electron-withdrawing group on proliferation of HT-29 cells

| Compound | Structure | EC$_{50}$ (nM) |
|---|---|---|
| KPU-35 | 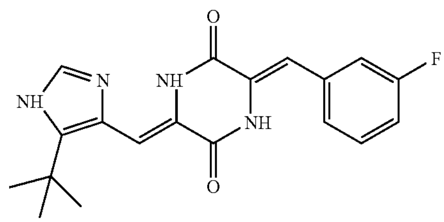 | 10 |
| KPU-34 | 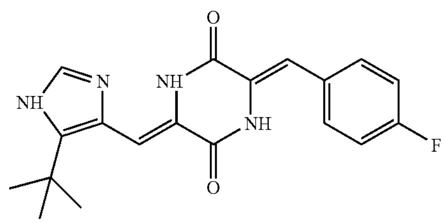 | 466 |
| KPU-50 | 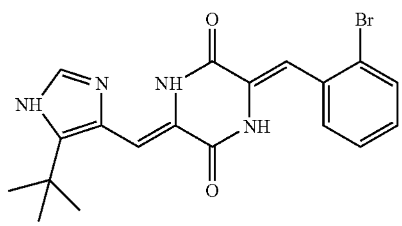 | 38 |
| KPU-41 | 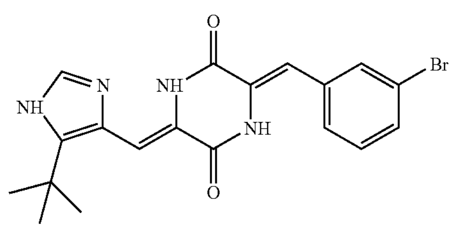 | 31 |
| KPU-40 | 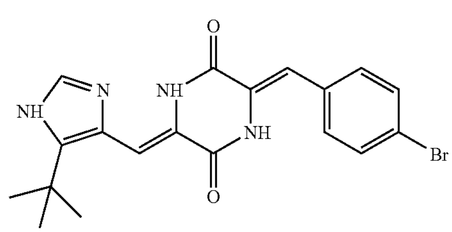 | 623 |
| KPU-46 | 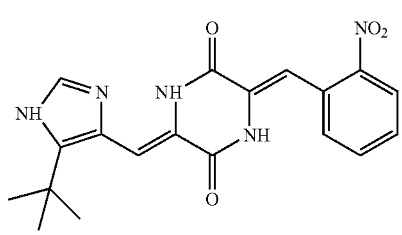 | 44 |

TABLE 7-continued
Effect of the electron-withdrawing group on proliferation of HT-29 cells
| Compound | Structure | EC$_{50}$ (nM) |
|---|---|---|
| KPU-47 | 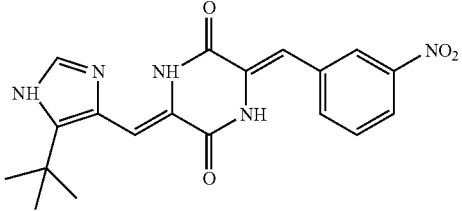 | 40 |
| KPU-48 | 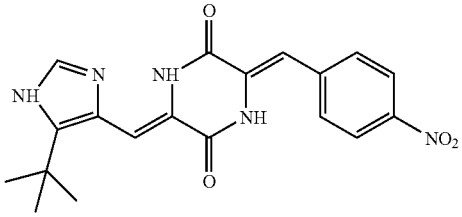 | >20 µM |
| KPU-49 | 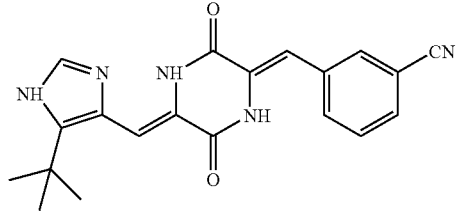 | 28 |
| KPU-43 | 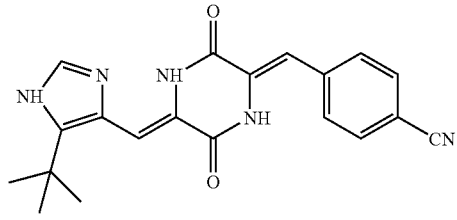 | >20 µM |
TABLE 8
Effect of the electron-donating group on proliferation of HT-29 cells
| Compound | Structure | EC$_{50}$ (nM) |
|---|---|---|
| KPU-8 | 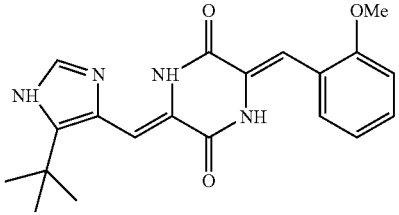 | 89 |

TABLE 8-continued

Effect of the electron-donating group on proliferation of HT-29 cells

| Compound | Structure | $EC_{50}$ (nM) |
|---|---|---|
| KPU-9 | 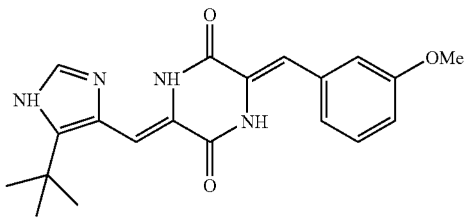 | 31 |
| KPU-6 | 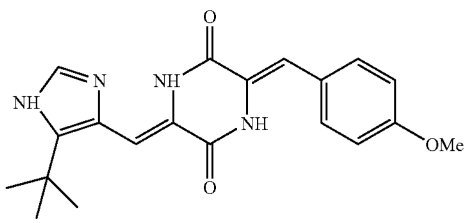 | 6730 |
| KPU-44 | 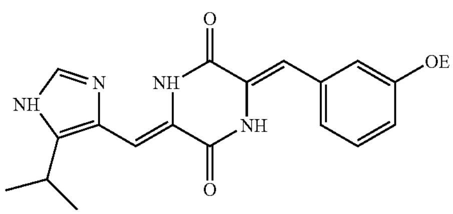 | 43 |
| KPU-30 | 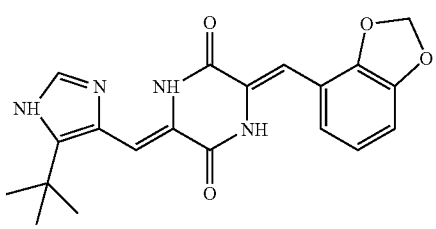 | 477 |
| KPU-22 | 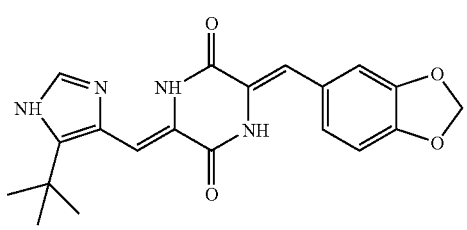 | 82 |
| KPU-32 | 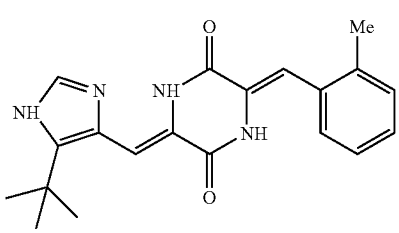 | 42 |

TABLE 8-continued

Effect of the electron-donating group on proliferation of HT-29 cells

| Compound | Structure | EC$_{50}$ (nM) |
|---|---|---|
| KPU-38 | 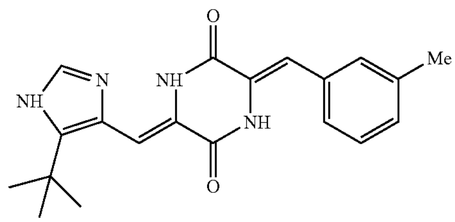 | 45 |
| KPU-39 | 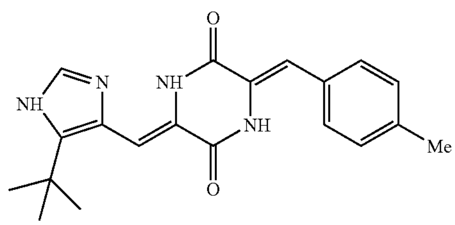 | 460 |
| KPU-53 | 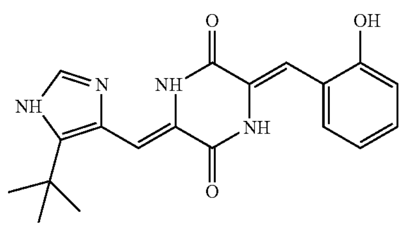 | >20 μM |
| KPU-51 | 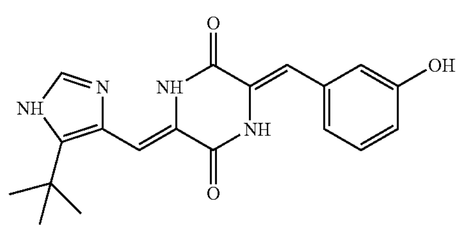 | 617 |
| KPU-23 | 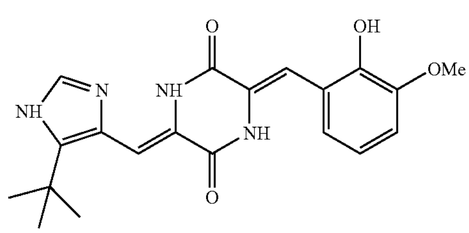 | 5870 |
| KPU-58 | 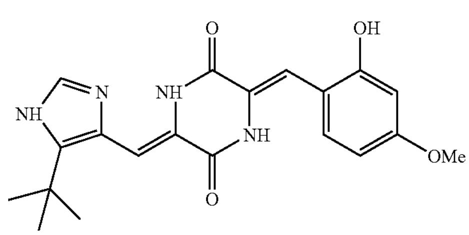 | >20 μM |

TABLE 8-continued

Effect of the electron-donating group on proliferation of HT-29 cells

| Compound | Structure | $EC_{50}$ (nM) |
|---|---|---|
| KPU-54 | (structure: tBu-imidazole-diketopiperazine-benzylidene with 2-OH, 5-OMe) | >20 μM |
| KPU-57 | (structure: tBu-imidazole-diketopiperazine-benzylidene with 3-OH, 4-OMe) | >20 μM |

The present disclosure is not bound by or limited to any particular scientific theory. Nonetheless, it is appreciated that persons of skill in the art may interpret the results presented herein to suggest that a relatively smaller functional group, affecting less steric hindrance, may be preferred to elicit more potent activity, and slightly large groups such as the ethoxy group (when compared to the methoxy group) or the Br atom (when compared to the Cl atom) may affect steric hindrance unfavorable to interaction with, for example, the tubulin binding site. Moreover, because the electrical property of these substituents did not affect the activity, it is suggested that these relatively small substituents do not directly interact with the binding site of β-tubulin, but restrict the conformation of dehydroPLH suitable for the binding. Or, as another possible hypothesis, the hydrophobic property may be a more important factor at the binding site for o- or m-position on β-tubulin, since introduction of the hydrophilic hydroxyl group, which can form the hydrogen bonding as a hydrogen-donor, drastically decreased the activity.

As shown in Table 9, the effect of the substituents in the cytotoxic activity at the opposition may be ordered, as in the case of m-position, as shown in Table 10. The compounds having effective functional groups, which showed higher activity than tBu-dehydroPLH, may also be further modified. And since the migration of the stereochemistry from Z to E under the visible light irradiation was observed, substituents that decrease the electron density in the conjugated double bonds may contribute to the reduction of Z to E migration by the light, results in more physicochemically stable structures. Temperature can also effect this migration.

Modification at two parts of the ring can be preferred for the development of potent but also biologically stable compounds. The phenyl ring of phenylahistin is oxidized by cytochrome P-450. Double modification that reduces the electron density of the phenyl ring may therefore be effective to avoid P-450 oxidation. Thus, the combination of the small electron withdrawing group such as the fluorine atom to the element that can increase the activity such as -OMe, -Me, —Cl, —F and Br, may result in more potent and biologically stable drug compounds.

TABLE 9

Summary of modification at the o-position

| Compound | Structure | $EC_{50}$ (nM) |
|---|---|---|
| KPU-2 | (structure: tBu-imidazole-diketopiperazine-benzylidene, unsubstituted phenyl) | 48 |
| KPU-8 | (structure: tBu-imidazole-diketopiperazine-benzylidene with 2-OMe) | 89 |
| KPU-37 | (structure: tBu-imidazole-diketopiperazine-benzylidene with 2-F) | 21 |

TABLE 9-continued

Summary of modification at the o-position

| Compound | Structure | EC$_{50}$ (nM) |
|---|---|---|
| KPU-18 | (2-Cl benzylidene diketopiperazine with tert-butyl imidazole) | 42 |
| KPU-50 | (2-Br benzylidene diketopiperazine with tert-butyl imidazole) | 38 |
| KPU-46 | (2-NO$_2$ benzylidene diketopiperazine with tert-butyl imidazole) | 44 |
| KPU-32 | (2-Me benzylidene diketopiperazine with tert-butyl imidazole) | 42 |
| KPU-53 | (2-OH benzylidene diketopiperazine with tert-butyl imidazole) | >20 μM |

TABLE 10

Summary of modification at the m-position

| Compound | Structure | EC$_{50}$ (nM) |
|---|---|---|
| KPU-2 | (benzylidene diketopiperazine with tert-butyl imidazole) | 48 |
| KPU-9 | (3-OMe benzylidene diketopiperazine with tert-butyl imidazole) | 31 |
| KPU-35 | (3-F benzylidene diketopiperazine with tert-butyl imidazole) | 10 |

TABLE 10-continued

Summary of modification at the m-position

| Compound | Structure | EC$_{50}$ (nM) |
|---|---|---|
| KPU-19 | 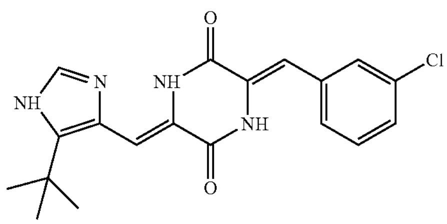 | 20 |
| KPU-41 | 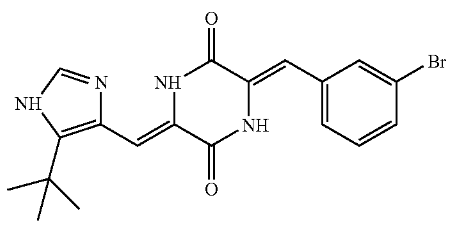 | 31 |
| KPU-47 | 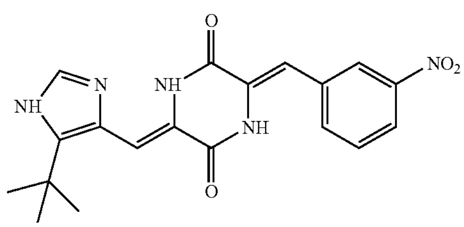 | 40 |
| KPU-38 | 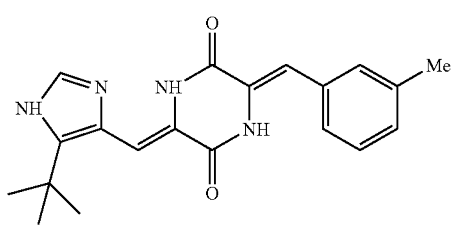 | 45 |
| KPU-51 | 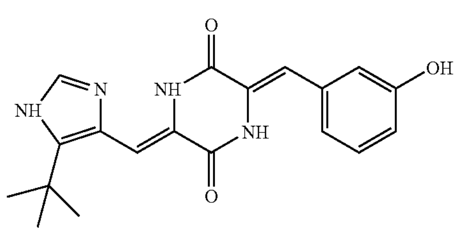 | 617 |
| KPU-49 | 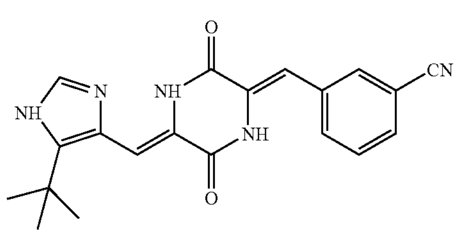 | 28 |

TABLE 10-continued

Summary of modification at the m-position

| Compound | Structure | EC$_{50}$ (nM) |
|---|---|---|
| KPU-44 | [structure] | 43 |

4) Substitution of the Phenyl Ring to Aryl-heterocycles

Figure 6:
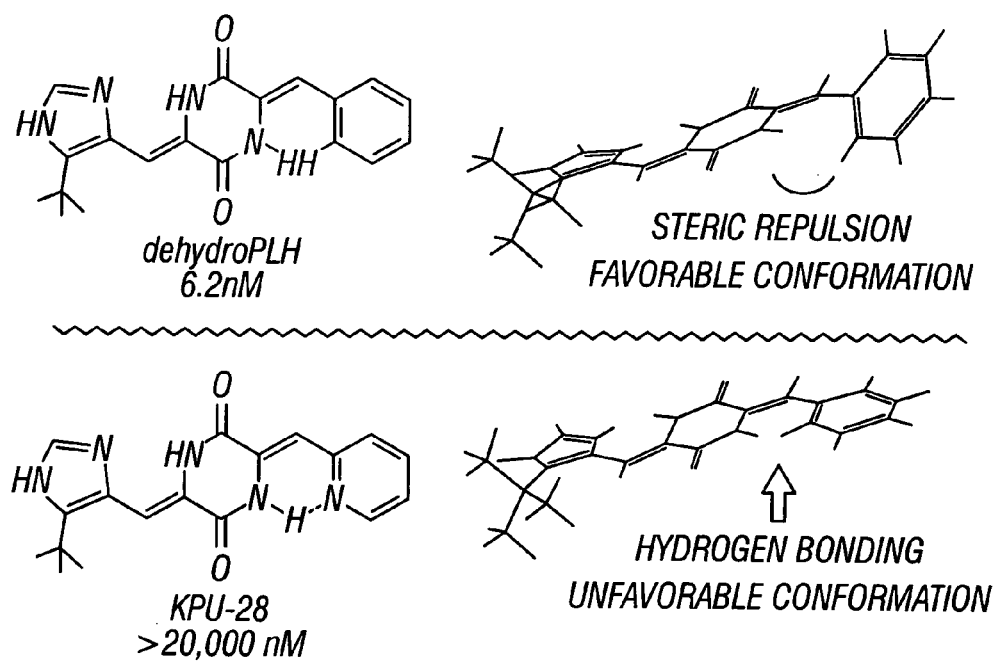
FIG. 6 depicts the putative active conformation of dehydroPLH at the phenyl moiety.
Figure 7:
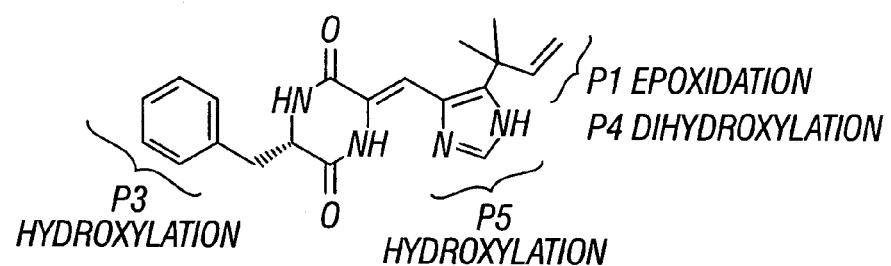
FIG. 7 depicts Cytochrome P450 metabolism of phenylahistin.
Figure 8:
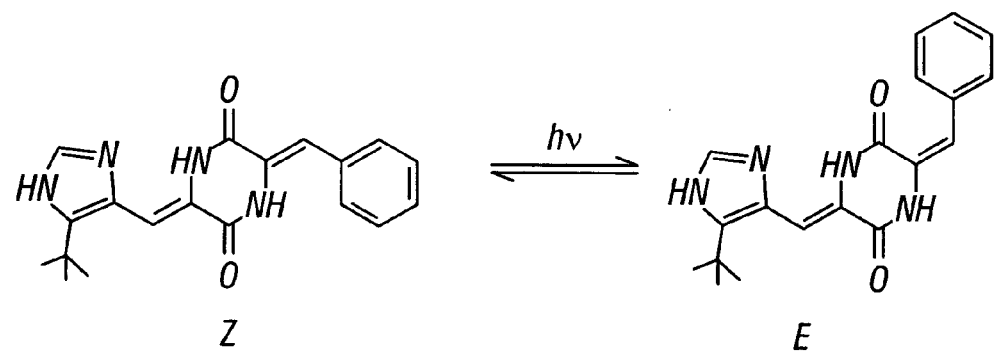
FIG. 8 illustrates the Z-E migration of tBu-dehydroPLH.

The phenyl ring may also be replaced by heteroaryl groups. The result of such replacements in terms of the cytotoxic activity is shown in Table 11. Since the arylic nitrogen atoms can form a hydrogen bonding with a NH group of the diketopiperazine ring and restrict the conformation of the molecule between pyridine and diketopiperazine rings to an uniplanar structure, the active conformation of dehydroPLH would be required a certain level of dihedral angle formed by the steric repulsion between an amide hydrogen atom of the diketopiperazine ring and an o-hydrogen atom of the phenyl ring (FIG. 6).

TABLE 11

Effect of the replacement with the heteroaryl ring on proliferation of HT-29 cells

| Compound | Structure | EC$_{50}$ (nM) |
|---|---|---|
| KPU-28 | [structure] | >20 µM |
| KPU-31 | [structure] | 96 |
| KPU-25 | [structure] | 544 |
| KPU-33 | [structure] | >20 µM |

TABLE 11-continued

Effect of the replacement with the heteroaryl ring on proliferation of HT-29 cells

| Compound | Structure | EC$_{50}$ (nM) |
|---|---|---|
| KPU-26 | 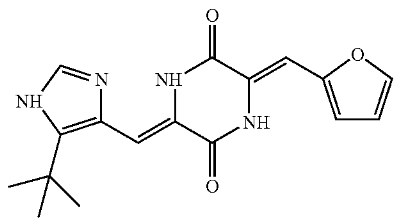 | 600 |
| KPU-60 | 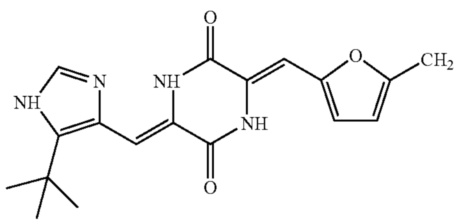 | 71 |
| KPU-42 | 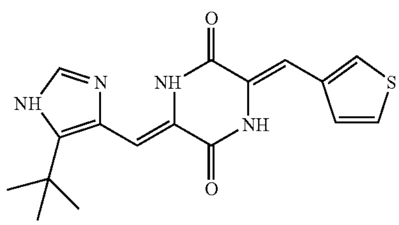 | 54 |
| KPU-27 | 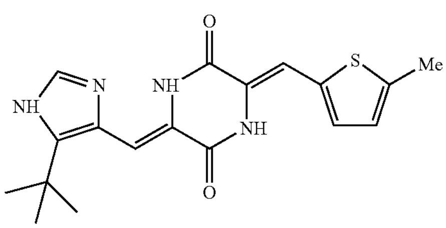 | 80 |
| KPU-29 | 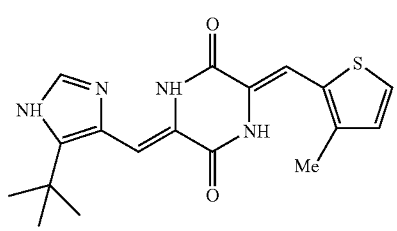 | 44 |
| KPU-61 | 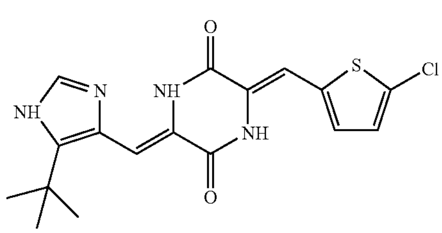 | 184 |

TABLE 11-continued

Effect of the replacement with the heteroaryl ring on proliferation of HT-29 cells

| Compound | Structure | $EC_{50}$ (nM) |
|---|---|---|
| KPU-36 | 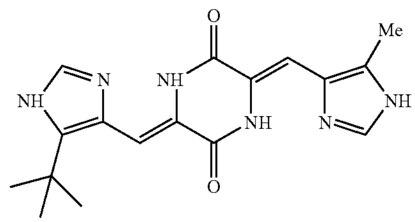 | 2790 |
| KPU-63 | 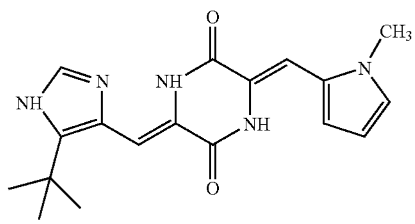 | 105 |

Replacing the phenyl ring with a smaller furan or thiophene ring, for example, KPU-29 or -42, exhibited activity. The phenyl ring can be changed to other aromatic structure while maintaining the potent activity.

5) Metabolism of Phenylahistin

In the recent his study, (±)-phenylahistin was treated with rat hepatic microsome or human hepatic P450s. In human case at least seven metabolites were detected, and two of them, i.e., P1 and P3, were major metabolites, represented more than 60% of the recovered metabolites.

Since there is no exo-olefin structure in tBu-dehydroPLH, present synthesized derivatives have no oxidization like P1 and P4. However, oxidizations such as P3 and P5 are formed during the hepatic metabolism. Various derivatives, which prevent such metabolism, are effective to avoid P450 oxidization at the phenyl ring. The imidazole ring can also be modified to avoid the unfavorable oxidation.

6) Physicochemical Stability of DehydroPLH

The physicochemical stability is one of the unfavorable problems of dehydroPLH. In phenylahistin, since there is no additional olefin structure at the benzyl part, there is no such problem. However, in dehydroPLH, the benzylidene moiety can be easily activated, probably with the visible light, and the Z to E migration frequently occurs due to the existence of longer conjugation of the double bond. This migration occurred even under normal room light. In the cytotoxic assay, some of the compounds migrate to E-form during the incubation, although this migration probably equilibrates at the 1:1 ratio in the case of dehydroPLH. This migration can be controlled. The Z to E migration is also known in combretastatin A4, a same type of tubulin inhibitor, and a few studies for improving this problem were reported.

7) Prodrug Synthesis

The E-form may also be used as a prodrug of dehydroPLH or of one or more of its analogs, including those analogs described herein. One of the undesired properties of anti-tubulin drugs involves its low selectivity between tumor and intact tissues, although these drugs belong to one of the molecular target therapies. This causes undesired side effects. However, if the compounds functions selectively only in tumor tissues, negative side effects of anti-microtubule drugs can be reduced. Since the dehydroPLH (Z-form) can be produced from its E-isomer by visible light irradiation, the E-form is administered and photo irradiation is performed only at the tumor site, then only the tumor is damaged by photo-produced Z-form and the adverse effect to the intact tissues is reduced.

The E-form can be protected chemically by the addition of a bulky but biodegradable acyl group, which is introduced into the diketopiperazine ring as a prodrug. This acyl group can be cleaved by the protease in the body. Therefore, the acylated-E-compound is maintained before administration, then after administration it is changed to the real E-form, which can migrate to the bioactive Z-form by the local photo irradiation.

Figure 9:
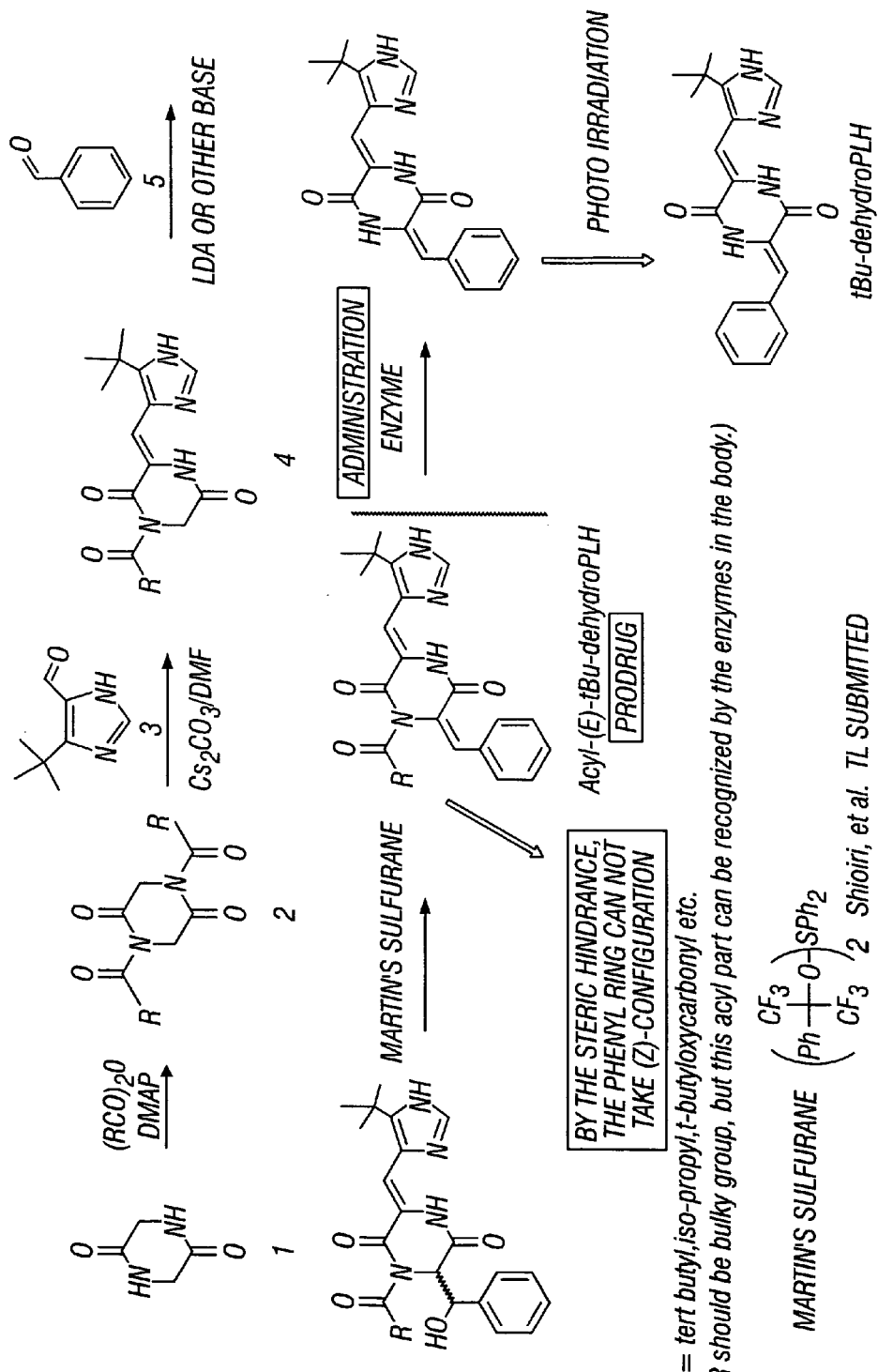
FIG. 9 depicts the synthesis and prodrug image of acyl-E-tBu-dehydroPLH.
Figure 10:
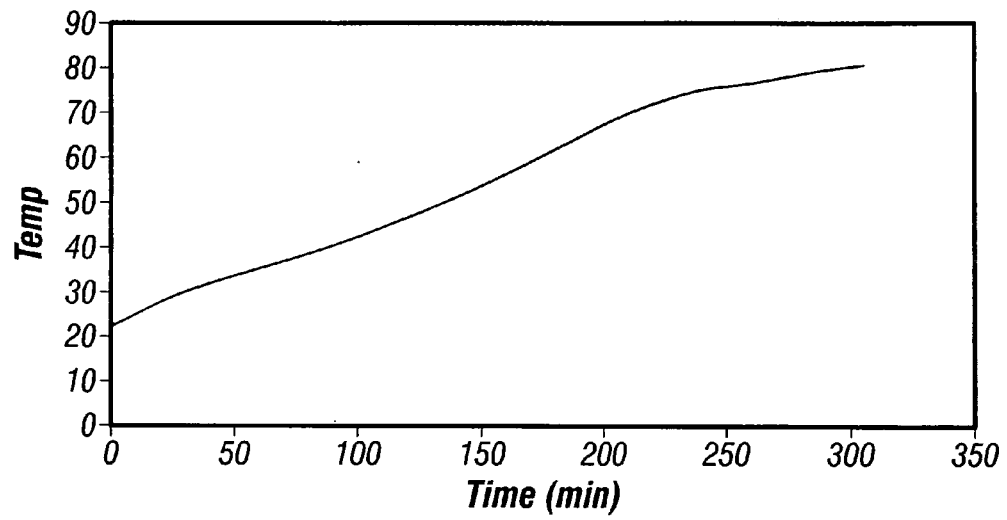
FIG. 10 depicts the temperature gradient of 3-Z-Benzylidene-6-[5"-(1,1-dimethylallyl)-1H-imidazol-4"-Z-ylmethylene]-piperazine-2,5-dione.
Figure 11:
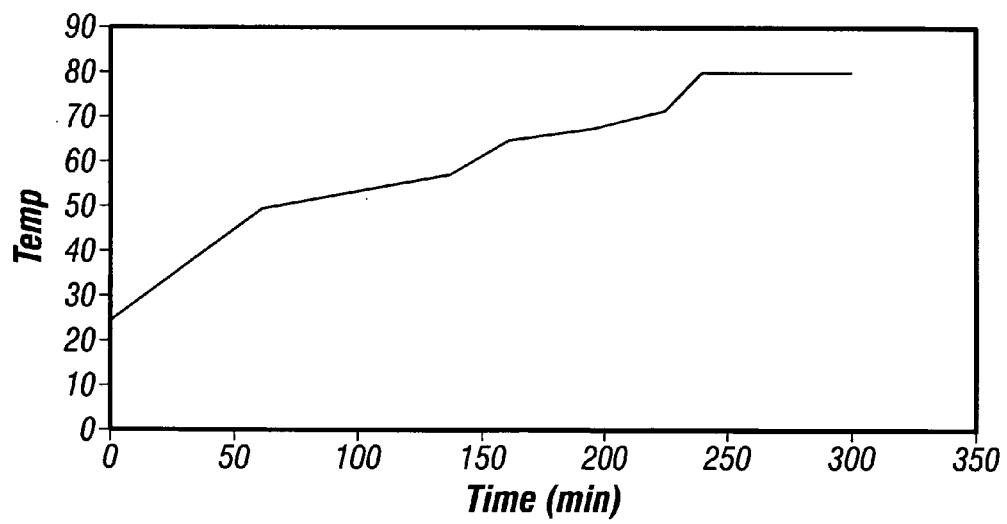
FIG. 11 depicts the temperature gradient of 3-Z-benzylidene-6-(5"-tert-butyl-1H-imidazol-4"-Z-ylmethylene)-piperazine-2,5-dione.

The synthetic scheme of this acyl-E-form of tBu-dehydroPLH is summarized in FIG. 9.

EXAMPLE 7

Pharmaceutical Formulations of the Synthesized Dehydrophenylahistins

1) Formulations Administered Intravenously, by Drip, Injection, Infusion or the Like Vials containing 5 g of powdered glucose are each added aseptically with 10 mg of a compound synthesized by the method and sealed. After being charged with nitrogen, helium or other inert gas, the vials are stored in a cool, dark place. Before use, the contents are dissolved in ethanol and added to 100 ml of a 0.85% physiological salt water solution. The resultant solution is administered as a method of inhibiting the growth of a cancerous tumor in a human diagnosed as having such a tumor at between approximately 10 ml/day to approximately 1000 ml/day, intravenously, by drip, or via a subcutaneous or intraperitoneal injection, as deemed appropriate by those of ordinary skill in the art.

2) Formulation to be Administered Orally or the Like

A mixture obtained by thoroughly blending 1 g of a compound synthesized by the method, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

3) Formulation to be Administered Topically

Administration to an individual of an effective amount of the compound can also be accomplished topically by administering the compound(s) directly to the affected area of the skin of the individual. For this purpose, the compound administered or applied is in the form of a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils. Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included. In addition, in certain instances, it is expected that the compound may be disposed within devices placed upon, in, or under the skin. Such devices include patches, implants, and injections which release the compound into the skin, by either passive or active release mechanisms.

EXAMPLE 8

In vitro Pharmacology of KPU-2, KPU-35 and t-butyl Phenylahistin

The in vitro efficacy studies performed with KPU-2, KPU-35 and t-butyl phenylahistin included: A) a panel of six tumor cell lines, B) studies in multidrug-resistant tumor cells, and C) studies to determine the mechanism of action.

A). Study of KPU-2, KPU-35 and t-butyl Phenylahistin in a Panel of Six Tumor Cell Lines The following cell lines (source in parentheses) were used: HT29 (human colon tumor; ATCC; HTB-38), PC3 (human prostate tumor; ATCC; CRL-1435), MDA-MB-231 (human breast tumor; ATCC; HTB-26), NCI-H292 (human non-small cell lung tumor; ATCC; CRL-1848), OVCAR-3 (human ovarian tumor; ATCC; HTB-161), B16-F10 (murine melanoma; ATCC; CRL-6475) and CCD-27sk (normal human fibroblast; ATCC; CRL-1475). Cells were maintained at subconfluent densities in their respective culture media.

Cytotoxicity assays were performed as described above in Example 4, using Resazurin fluorescence as an indicator of cell viability.

The disclosed compounds are effective agents against a variety of different and distinct tumor cell lines. Specifically, for example, KPU-2 and KPU-35 were most effective on the HT-29 tumor cell line, both in terms of potency (active in the low nanomolar range) and efficacy (most responsive in terms of the maximum cytotoxic effect); t-butyl-phenylahistin exhibited its greatest potency against the PC-3 tumor cell line, although the greatest efficacy was displayed against the HT-29 cell line; KPU-2 and KPU-35 were generally 10-40 fold more potent than t-butyl-phenylahistin whereas the efficacy was similar for all three compounds in the different tumor cell lines; the HT-29, PC-3, MDA-MB-231 and NCI-H292 tumor cell lines all responded similarly to the NPI compounds, whereas the B16-F10 appeared to be somewhat less sensitive. t-butyl-phenylahistin displayed a marked differential between normal fibroblasts and the tumor cell lines, with a ratio ranging from >20->100, except for the OVCAR-3 cell line.

TABLE 12

Activity of KPU-2, KPU-35 and t-butyl phenylahistin in the Tumor Panel Screen

| Cell Line | KPU-2 | | | KPU-35 | | | t-butyl-phenylahistin | | |
|---|---|---|---|---|---|---|---|---|---|
| | Mean | SD | n | Mean | SD | n | Mean | SD | n |
| HT-29 Colon | | | | | | | | | |
| IC50 nM | 9.8 | 2.4 | 4 | 8.2 | 2.0 | 4 | 420 | 473 | 3 |
| % Cytotoxicity | 82.5 | 5.3 | 4 | 81.3 | 4.0 | 4 | 88 | 0.2 | 3 |
| PC-3 Prostate | | | | | | | | | |
| IC50 nM | 13.4 | 0.7 | 4 | 13.2 | 2.5 | 4 | 174 | — | 2 |
| % Cytotoxicity | 60.3 | 2.1 | 4 | 56.8 | 1.0 | 4 | 59.5 | — | 2 |
| MDA-MB-231 Breast | | | | | | | | | |
| IC50 nM | 13.8 | 1.9 | 3 | 9.7 | 4.2 | 4 | 387 | — | 2 |
| % Cytotoxicity | 56.7 | 7.2 | 3 | 59.3 | 5.6 | 4 | 65.5 | — | 2 |
| NCI-H292 Lung | | | | | | | | | |
| IC50 nM | 17.5 | 1.1 | 4 | 15.9 | 1.1 | 4 | 384 | 194 | 3 |
| % Cytotoxicity | 70.5 | 2.9 | 4 | 68.5 | 2.9 | 4 | 65 | 5 | 3 |
| OVCAR-3 Ovary | | | | | | | | | |
| IC50 nM | >20,000 | — | 4 | >20,000 | — | 4 | >20,000 | — | 2 |
| % Cytotoxicity | 45.8 | 3.0 | 4 | 39 | 2.2 | 4 | 37 | — | 2 |
| B16-F10 Melanoma | | | | | | | | | |
| IC50 nM | 37.1 | 26.3 | 4 | 32.3 | 19.9 | 4 | 736 | 650 | 3 |
| % Cytotoxicity | 71.8 | 2.5 | 4 | 72.0 | 2.2 | 4 | 74 | 2 | 3 |

TABLE 12-continued

Activity of KPU-2, KPU-35 and t-butyl phenylahistin in the Tumor Panel Screen

| Cell Line | KPU-2 | | | KPU-35 | | | t-butyl-phenylahistin | | |
|---|---|---|---|---|---|---|---|---|---|
| | Mean | SD | n | Mean | SD | n | Mean | SD | n |
| CCD-27sk Fibroblast | | | | | | | | | |
| IC50 nM | 9.2 | 2.9 | 4 | 7.4 | 2.6 | 4 | >20,000 | — | 2 |
| % Cytotoxicity | 64.3 | 2.4 | 4 | 60.8 | 1.9 | 4 | 45 | — | 2 |

B). Studies in Drug Resistant Cell Lines

One of the major challenges in the use of chemotherapeutic agents in clinical oncology is the development of resistance to the drug effect by the tumor cells. There are several mechanisms for the development of resistance, each of which will have differential effects on chemotherapeutic drugs. These mechanisms include increased expression of ATP-dependent efflux pumps such as the P-glycoprotein encoded by MDR1 or the multidrug-resistance associated protein 1 encoded by MRP1. Reduced drug uptake, alteration of the drug's target, increasing repair of drug-induced DNA damage, alteration of the apoptotic pathway and the activation of cytochrome P450 enzymes are other examples of mechanisms by which cancer cells become resistant to anticancer drugs. The selected compounds were studied in three different cell lines that exhibit two different mechanisms of resistance; the overexpression of the P-glycoprotein and altered topoisomerase II activity.

1) Human Uterine Sarcoma Tumor Cell Line Pair: MES-SA (Taxol Sensitive) and MES-SA/Dx5 (Taxol Resistant).

This cell line expresses elevated mdr-1 mRNA and P-glycoprotein (an extrusion pump mechanism). Pretreatment with cyclosporin-A (CsA) blocks P-glycoprotein and reinstates activity in the resistant cell line for those compounds for which the resistance is due to elevated P-glycoprotein.

As can be seen from Table 13, KPU-2, and KPU-35 have the same potency in the resistant cell line as in the sensitive line and the potency of t-butyl-phenylahistin was only slightly reduced. Cyclosporin A (CsA) pretreatment did not alter the potency of the selected compounds. In contrast, taxol was virtually inactive in the MES-SA/Dx5 resistant cell line, whereas this compound was very potent in the sensitive cell line. CsA treatment restored the sensitivity to taxol of the MES-SA/Dx5 cell line. The MES-SA/Dx5 cell line also showed reduced susceptibility to etoposide (60 fold), doxorubicin (34 fold) and mitoxantrone (20 fold).

These data indicate that the effects of KPU-2, KPU-35 and t-butyl-phenylahistin are not susceptible to the taxol-related resistance mechanism (p-glycoprotein) in this cell line, and that cross-resistance from taxol does not occur to these selected compounds in this model.

TABLE 13

Activity of KPU-2, KPU-35, t-butyl-phenylahistin and Taxol in MES-SA Taxol Sensitive and MES-SA/DX5 Taxol Resistant Human Uterine Sarcoma Tumor Cell Lines

| | MES-SA Sensitive | | | MES-SA/DX5 Resistant | | | |
|---|---|---|---|---|---|---|---|
| | No CsA | CsA Pretreat | | No CsA | | CsA Pretreat | |
| Compound Study | IC50 nM | IC50 nM | Ratio No CsA | IC50 nM | Ratio MES-SA | IC50 nM | Ratio No CsA |
| KPU-2 | | | | | | | |
| Study I | 8.5 | — | — | 10.5 | 1.2 | — | — |
| Study II | 19.4 | 27.4 | 1.4 | 21.7 | 1.1 | 37.8 | 1.74 |
| KPU-35 | | | | | | | |
| Study I | 6.6 | — | — | 5.2 | 0.8 | — | — |
| Study III | 3.9 | 2.0 | 0.5 | 2.5 | 0.6 | 6.7 | 2.7 |
| t-butyl-phenylahistin | | | | | | | |
| Study I | 144 | — | — | 825 | 5.7 | — | — |
| Study III | 122 | 162 | 1.3 | 694 | 4.3 | 622 | 0.9 |
| Taxol | | | | | | | |
| Study I | 4.4 | — | — | >20,000 | >455 | — | — |
| Study II | 13.3 | 7.6 | 0.6 | >>100 | >>8 | 40 | <<0.25 |
| Study III | 7.3 | 2.8 | 0.4 | >24,000 | >3000 | 2.0 | <<0.001 |

See also the additional data presented in FIG. 43.

2) Human Acute Promyelocytic Leukemia Cell Line Pair: HL-60 (Mitoxantrone-Sensitive and HL-60/MX-2 (Mitoxantrone-Resistant)

This cell line is considered to have atypical drug resistance properties with altered topoisomerase II catalytic activity without overexpression of P-glycoprotein.

As can be seen in Table 14, these results indicate that the potencies of the selected novel compounds are very similar in the sensitive and resistant HL-60 cell lines. In contrast, Mitoxantrone loses efficacy by a factor of 24-fold in the resistant HL-60/MX-2 cell line.

Thus, KPU-2, KPU-35 and t-butyl-phenylahistin are not susceptible to the same resistance mechanisms as Mitoxantrone in this cell line, and there is no cross-resistance from Mitoxantrone to these selected novel compounds in this model.

TABLE 14

Activity of KPU-2, KPU-35, t-butyl-phenylahistin and Mitoxantrone in the HL-60 Human Acute Promyelocytic Leukemia Tumor Sensitive and Resistant Cell Line Pair

| Compound | HL-60 Sensitive IC50 nM | HL-60 Resistant IC50 nM | Ratio to Sensitive |
|---|---|---|---|
| KPU-2 | 6.4 | 8.17 | 1.28 |
| KPU-35 | 9.2 | 7.3 | 0.79 |
| t-butyl-phenylahistin | 255 | 175 | 0.69 |
| Mitoxantrone | 202 | 4870 | 24.1 |

3). Human Breast Carcinoma Cell Line Pair: MCF-7 (Taxol Sensitive) and MCF-7/ADR (Taxol Resistant)

This study involved KPU-2 in comparison to taxol. KPU-2 demonstrated similar potencies in both the sensitive and resistant members of this cell line pair. In contrast, taxol was virtually inactive in the resistant cell line whereas there was low nanomolar potency in the sensitive cell line (Table 15).

These studies confirm in a different human tumor cell line that taxol resistance does not transfer to KPU-2.

TABLE 15

Activity of KPU-2 and Taxol in the MCF-7 Human Breast Carcinoma Sensitive and Resistant Cell Line Pair

| Compound | MCF-7 Sensitive IC50 nM | MCF-7/ADR Resistant IC 50 nM | Ratio to Sensitive |
|---|---|---|---|
| KPU-2 | 39.6 | 27.4 | 0.69 |
| Taxol | 2.6 | >>100 | >>38 |

C) Studies of the Mechanism of Action

1). Action on Microtubule Function

Human umbilical vein endothelial cells (HuVEC from Cambrex) were used in this study, for evaluating the effects of KPU-2 and t-butyl-phenylahistin in comparison to colchicine and taxol on tubulin by staining for α-tubulin.

Thirty minutes exposure to KPU-2, t-butyl-phenylahistin or colchicine (all at 2 µM) induced microtubule depolymerization as was indicated by the lack of intact microtubule structure in contrast to that observed in the DMSO Control and cell membrane blebbing (a clear indication of apoptosis) in the HuVEC cells, whereas taxol did not induce microtubule depolymerization under these conditions. Colchicine is a known microtubule depolymerizing agent whereas taxol is a tubulin stabilizing agent. Similar results were obtained when CCD-27sk cells were exposed to KPU-2 or colchicine.

2). Induction of Apoptosis

Apoptosis and its dysregulation play an important role in oncology; the selective induction of the programmed cell death cycle in tumor cells is the goal of many chemotherapeutic drug discovery programs. This induction of apoptosis can be demonstrated by different methods including the characteristic cell membrane blebbing, DNA fragmentation, hyperphosphorylation of the antiapoptotic factor Bcl-2, activation of the caspase cascade and cleavage of poly (ADP ribose) polymerase (PARP).

The characteristic signs of apoptotic cell death include cell membrane blebbing, disruption of nuclei, cell shrinkage and condensation and finally cell death, very distinctive from necrotic cell death. KPU-2 induced the typical morphological changes associated with early stages of apoptosis in human prostate tumor cells. A similar finding was also clear in the treatment of HuVEC cells with KPU-2.

3). DNA Fragmentation

A late stage characteristic of apoptosis is internucleosomal DNA cleavage that results in a distinctive ladder pattern that can be visualized by gel electrophoresis. This approach was used to study the effect of KPU-2 on DNA laddering in Jurkat cells (human T cell leukemia line) in comparison to halimide and dehydrophenylahistin (KPU-1). KPU-2 induced DNA laddering at the 1 nM concentration whereas halimide and KPU-1 were much less potent.

4). Activation of the Caspase Cascade

Several enzymes in the caspase cascade are activated during apoptosis, including Caspase-3, -8 and -9. The activity of Caspase-3 was monitored in Jurkat cells following treatment with KPU-2, KPU-35 and t-butyl-phenylahistin.

The results indicate that caspase-3 was activated in a dose-dependent manner by treatment with all three compounds in a manner similar to halimide. The caspase-3 activation occurred over a similar concentration range as for the IC50s for cytotoxicity in the Jurkat cell line (Table 16).

TABLE 16

Cytotoxicity of KPU-2, KPU-35 and t-butyl-phenylahistin in Jurkat Cells

| NPI Compound | Cytotoxicity Potency IC50 nM | Efficacy % Cell Death |
|---|---|---|
| KPU-2 | 11 | 94 |
| KPU-35 | 5 | 93 |
| t-butyl-phenylahistin | 165 | 93 |
| Mitoxantrone | 41 | 99 |

5). Cleavage of Poly(ADP-ribose) Polymerase (PARP) in Jurkat Cells

In order to assess the ability of these compounds to induce apoptosis in Jurkat cells, cleavage of poly(ADP-ribose) polymerase (PARP) was monitored. PARP is a 116 kDa nuclear protein that is one of the main intracellular targets of Caspase-3. The cleavage of PARP generates a stable 89 kDa product, and this process can be easily monitored by western blotting. Cleavage of PARP by caspases is one of the hallmarks of apoptosis, and as such serves as an excellent marker for this process. KPU-2 at 100 nM induced cleavage of PARP in Jurkat cells 10 hours after exposure of the cells to the compound. KPU-2 appeared to be more active than either halimide or KPU-1.

6). Enhanced Vascular Permeability in HuVEC Cells

Compounds that depolymerize microtubules (e.g. combretastatin A-4-phosphate, ZD6126) have been shown to induce vascular collapse in tumors in vivo. This vascular collapse is preceded by a rapid induction of vascular cell permeability initially to electrolytes and soon after to large molecules. The enhanced permeability of HuVEC cells to a fluorescent-labeled dextran is used as a proxy assay for vascular collapse.

Figure 12:
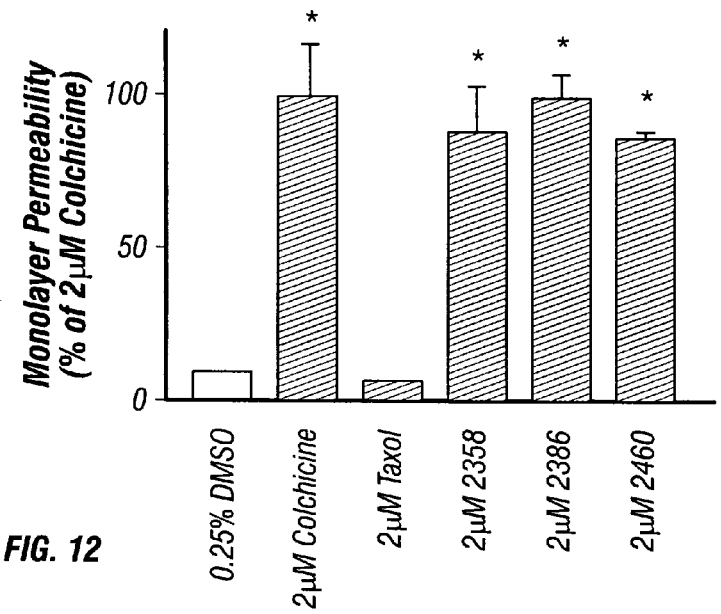
FIG. 12 depicts the effect of KPU-2, KPU-35 and t-butyl-phenylahistin in comparison to colchicine and taxol on HuVEC monolayer permeability to FITC-Dextran.

KPU-2, KPU-35 and t-butyl-phenylahistin all rapidly (within 1 hour) induced significant HuVEC monolayer permeability, to an extent similar to colchicine. The microtubule stabilizing agent taxol was inactive in this assay (FIG. 12).

7). Profile in a Broad Kinase Screen

KPU-2 was initially screened at a concentration of 10 μM in a panel of 60 different kinases; the ATP concentration was 10 μM. Four kinases were inhibited by greater than 50% in the primary screen and the IC50's determined in secondary screening are presented in Table 17. All of the IC50 values are in the low micromolar range, which indicates that inhibition of these kinases is not related to the low nanomolar activities observed for tumor cell cytotoxicity.

TABLE 17

Activity of KPU-2 against Selected Kinases

| Kinase | IC50 (μM) |
|---|---|
| CDK1/Cyclin B (human) | 10.1 |
| c-RAF (human) | 8.9 |
| JNK3 (rat) | 6.8 |
| Lyn (mouse) | 11.1 |

EXAMPLE 9

In vivo Pharmacology

Preliminary studies with KPU-2 were performed using the MX-1 (breast) and HT-29 (colon) xenograft models and the P-388 murine leukemia tumor model, in the mouse. Other tumor models selected on the basis of activity in the in vitro tumor panel were the DU-145 (prostate), MCF-7 (breast), and the A549 (lung) cell lines. The human pancreatic tumor (MiaPaCa-2) was also included. The novel compounds were studied as monotherapy and in combination with a clinically-used chemotherapeutic agent. The doses of the selected novel compounds were determined from the acute tolerability testing (Maximally Tolerated Dose, MTD) and were adjusted if necessary during each study. The doses of the clinically-used chemotherapeutic agents were selected on the basis of historical studies.

KPU-2 was the first compound to be studied in these five tumor models. Following the initial results from this study, all three compounds were compared in the HT-29 human colon tumor, the DU-145 human prostate and the MCF-7 human breast tumor xenograft models.

The above models all use the subcutaneous xenograft implantation technique and are potentially subject to selective effects of a compound on the subcutaneous vasculature producing a magnified (or apparent) antitumor activity. In order to circumvent this possibility, two other tumor models have been incorporated in the research. One of these is the observation of lung metastases following the intravenous injection of B16-F10 mouse melanoma tumor cells. The other model is the implantation of MDA-231 human breast tumor cells in the mouse mammary fat pad. While this latter model is a xenograft model, the subcutaneous vasculature does not play a role.

Methods

1). Xenograft Models

Animals used were (exceptions are indicated for individual studies): female nude mice (nu/nu) between 5 and 6 weeks of age (~20 g, Harlan); group size was 9-10 mice per group unless otherwise indicated.

Cell lines used for tumor implantation were: HT-29 human colon tumor; MCF-7 human breast tumor; A549 human non small cell lung tumor; MiaPaCa-2 human pancreas tumor; DU-145 human prostate tumor.

Selected novel compounds were administered as monotherapy via the intraperitoneal (i.p.) route at the doses indicated for the individual study; for the combination studies the selected reference chemotherapy agents were injected 15-30 min prior to the compound.

Vehicles used in these studies were: 12.5% DMSO, 5% Cremaphor and 82.5% peanut oil for the selected novel compounds; (1:3) Polysorbate 80:13% ethanol for taxotere; (1:1) Cremaphor:ethanol for paclitaxel; for CPT-11 each mL of solution contained 20 mg of irinotecan hydrochloride, 45 mg of sorbitol NF powder, and 0.9 mg of lactic acid, the pH being adjusted to 7.4 with NaOH or HCl. Saline dilutions are used to achieve the injection concentrations used for the reference compounds.

HT-29 Human Colon Tumor Model

Animals were implanted subcutaneously (s.c.) by trocar with fragments of HT-29 tumors harvested from s.c. growing tumors in nude mice hosts. When the tumor size reached 5 mm×5 mm (about 10-17 days) the animals were matched into treatment and control groups. Mice were weighed twice weekly and tumor measurements were obtained using calipers twice weekly, starting on Day 1. The tumor measurements were converted to estimated mg tumor weight using the formula $(W^2 \times L)/2$. When the estimated tumor weight of the control group reached an average of 1000 mg the mice were weighed, sacrificed and the tumor removed. The tumors were weighed and the mean tumor weight per group was calculated and the tumor growth inhibition (TGI) was determined for each group (100% minus the change in the mean treated tumor weight/the change in the mean control tumor weight×100.

In this model unless otherwise noted for the individual study, the selected novel compounds were injected intraperitoneally every third day for 15 days [1, 4, 8, 11 and 15 (q3d×5)]; CPT-11 was administered intraperitoneally on days 1, 8 and 15 (qw×3).

MCF-7 Human Breast Tumor Model

Female nude mice (~20 g) were implanted s.c. with 21-day release estrogen (0.25 mg) pellets 24 hours prior to the s.c. implantation with MCF-7 tumor fragments (harvested from s.c. tumors in nude mice hosts). The study then proceeded as described for the HT-29 model, using taxotere as the standard chemotherapy agent.

In this model unless otherwise noted for the individual study, the novel compounds were injected via the intraperitoneal route daily on Days 1-5, inclusive (qd×5); taxotere was administered intravenously on Days 1, 3 and 5 (qod×3).

A549 Human Lung Tumor Model

Animals were implanted s.c. by trocar with fragments of A549 tumors harvested from s.c. growing tumors in nude mice hosts. When the tumor size reached 5 mm×5 mm (about 10-17 days) the animals were matched into treatment and control groups. The rest of the study proceeded as described for the HT-29 model, using taxotere and CPT-11 as the standard chemotherapy agents.

In this model unless otherwise noted for the individual study, the tested compounds were administered via the intraperitoneal route on a q3d×5 dose schedule for the CPT-11 combination or on a qd×5 dose regimen for the combination with taxotere; CPT-11 was administered via the intraperitoneal route on a qw×3 schedule; taxotere was administered intravenously on a qod×3 dose regimen.

MiaPaCa-2 Human Pancreas Tumor Model

Animals were implanted s.c. by trocar with fragments of MiaPaCa-2 tumors harvested from s.c. growing tumors in nude mice hosts. When the tumor size reached 5 mm×5 mm (about 10-17 days) the animals were matched into treatment and control groups. The rest of the study proceeded as described for the HT-29 model, using gemcitabine as the standard chemotherapy agent.

In this model unless otherwise noted for the individual study, test compounds were administered every third day via the intraperitoneal route on Days 1, 4, 7, 10 and 15 (q3d×5); gemcitabine was administered via the intraperitoneal route on Days 1, 4, 7 and 10 (q3d×4).

DU-145 Human Prostate Tumor Model

Male mice were implanted s.c. by trocar with fragments of DU-145 tumors harvested from s.c. growing tumors in nude male mice hosts. When the tumors reached ~5 mm×5 mm (at about 13-17 days) the animals were matched into treatment and control groups. The remainder of the study proceeded as for the HT-29 model, using taxotere as the standard chemotherapy agent.

In this model unless otherwise noted for the individual study, test compounds were administered via the intraperitoneal route on Days 1, 3, 5, 8 and 11 (q3d×5); taxotere was administered intravenously on Days 1, 3 and 5 (q2d×3).

2). Non Subcutaneous Implantation Tumor Models

The animals used were: female nude mice (nu/nu) (MDA-231 study) or B6D2F1 (B16-F10 studies) mice between 5 and 6 weeks of age (~20 g, Harlan); group size was 10 mice per group unless otherwise indicated.

The cell lines used were: MDA-MB-231 human breast tumor and B16-F10 murine melanoma cells.

NPI compounds were administered as monotherapy via the intraperitoneal route at the doses indicated for the individual study; for the combination studies the selected reference chemotherapy agents were injected 15-30 min prior to the NPI compound.

MDA-231 Human Breast Tumor

Female nude mice were injected in the mammary fat pad with 2×10$^6$ MDA-231 cells harvested from in vitro cell culture. When the tumor size reached 5 mm×5 mm (about 14-28 days) the animals were matched into treatment and control groups. The study then proceeded as described for the HT-29 model, using paclitaxel as the standard chemotherapy agent.

In this model unless otherwise noted for the individual study, the test compounds were administered via the intraperitoneal route on Days 1, 4, 8, 11 and 15 (q3d×5); paclitaxel was administered via the intraperitoneal route on Days 1-5 (qd×5).

B16-F10 Metastatic Murine Melanoma Model

Mice received B16-F10 cells (prepared from an in vitro cell culture of B16-F10 cells) by the iv route on Day 0. On Day 1 mice were randomized into treatment and control groups and treatment commenced. Mice were weighed twice weekly, starting on Day 1. All mice are sacrificed on Day 16, the lungs removed, weighed and the surface colonies counted. Results are expressed as mean colonies of treated mice/mean colonies of control mice (T/C)×100%). The metastasis growth inhibition (MGD) is this number subtracted from 100%. Paclitaxel was the standard chemotherapy agent used in this study.

In this model unless otherwise noted for the individual study, the test compounds were administered via the intraperitoneal route on Days 1-5 (qd×5); paclitaxel was administered intravenously on Days 1-5(qd×5).

When appropriate (n≧3), results are presented as means ±SEM. Statistical analysis of studies with several groups was performed using ANOVA with Neuman-Keuls post test, unless otherwise indicated. A one-tailed t-test was also used based on the hypothesis that the compound or drug, or the combination, would reduce tumor growth.

Results

Studies in the HT-29 Human Colon Tumor Xenograft Model

1. In Vivo Evaluation of KPU-2+/−CPT-11 in the HT-29 Human Colon Tumor Xenograft Model This study assessed changes in dosage strength and dosing regimen for KPU-2 alone and in combination with a relevant chemotherapeutic CPT-11 in the HT-29 model.

Figure 13:
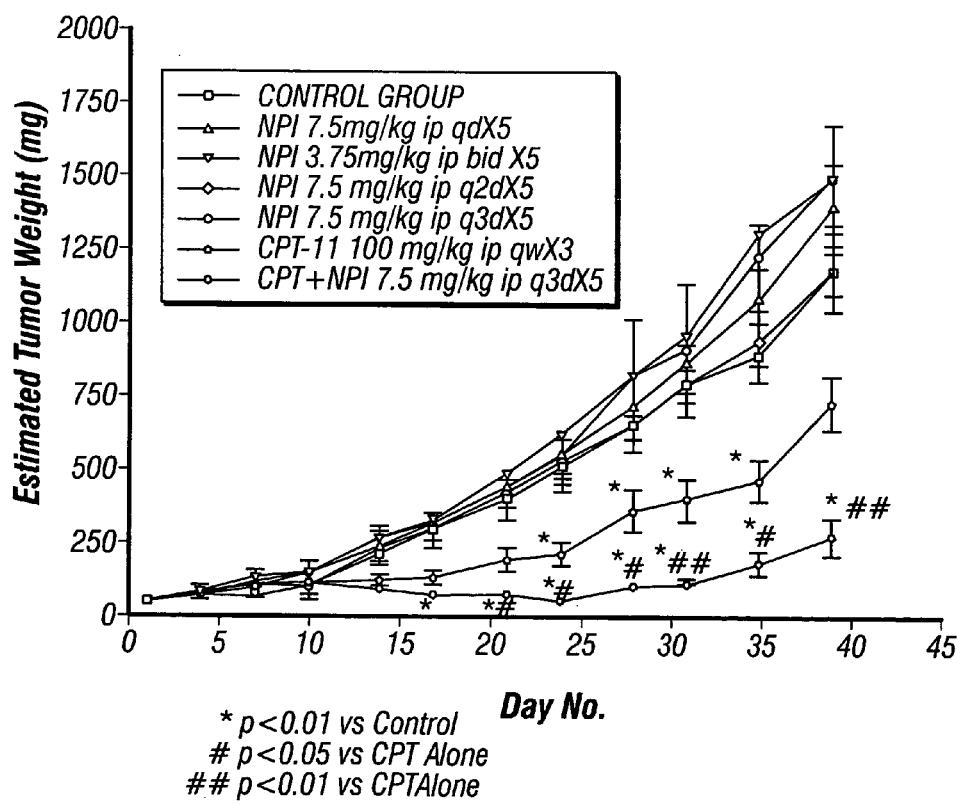
FIG. 13 depicts the effect of KPU-2 alone and in combination with CPT-11 on estimated tumor growth in the HT-29 Human Colon Tumor Xenograft model.
Figure 14:
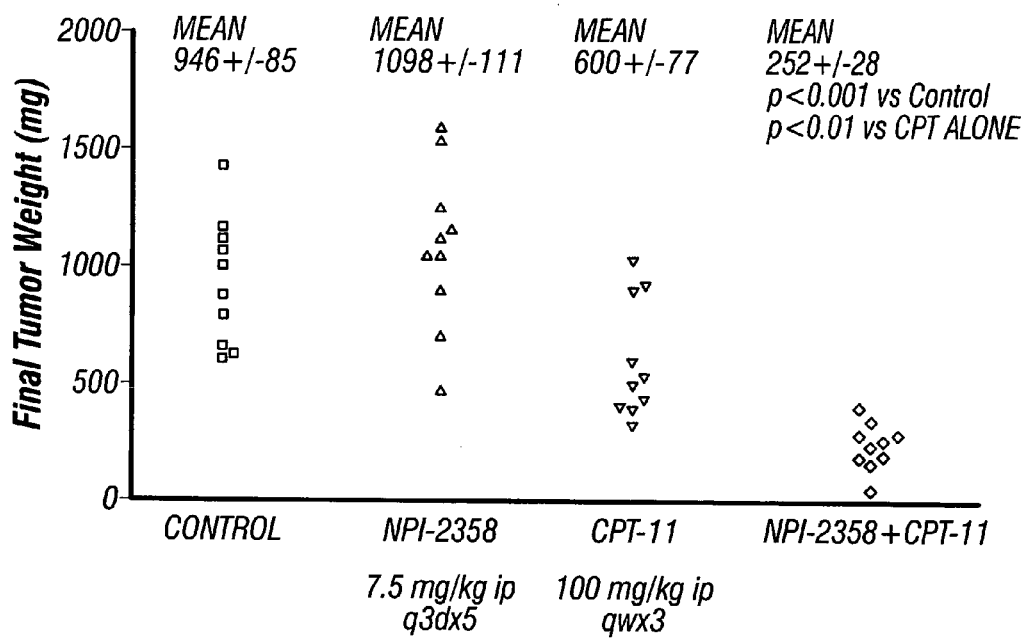
FIG. 14 depicts the effect of KPU-2 alone and in combination with CPT-11 on the weight of tumors excised at autopsy in individual mice in the HT-29 Human Colon Tumor Xenograft model.

KPU-2 was administered at doses of 7.5 mg/kg ip daily for five days (qd×5), 3.75 mg/kg ip bid for five days, 7.5 mg/kg ip every second day for 10 days (qod×5) and 7.5 mg/kg ip every third day for 15 days (q3d×5). The combination of CTP-11 with NPI-2358 at a dose of 7.5 mg/kg ip q3d×5 resulted in a significantly greater effect than for either compound alone, which lasted for the duration of the study (FIG. 13). These observations during the in-life portion of the study were confirmed by the mean group final tumor weights at autopsy for which only the combination group exhibited a statistically significant lower tumor weight than controls. In addition the difference between the mean tumor weights of the combination therapy and CPT-11 monotherapy groups was statistically significant (FIG. 14). When the individual final tumor weights at autopsy are examined the greater effect of cotherapy is clear (FIG. 14). The TGI of cotherapy was 78% as compared to 38.9% for CPT-11 alone. The TGI for the combined therapy group exceeds the NCI criterion of 58% for a positive result.

2. Study of KPU-2+/−Standard Chemotherapy vs. Five Human Tumor Xenograft Models

This study consists of five different arms, each with its own protocol, timing, dosing regimen and reference compound. Each arm will be considered within the presentation of the particular tumor model.

The aim of the HT-29 arm of the study was to investigate a slightly higher dose of KPU-2 (10 mg/kg ip q3d×5) in the HT-29 human colon tumor xenograft model as compared to those used in the study described above, in which a marked synergy was observed between KPU-2 (7.5 mg/kg ip q3d×5) and CPT-11 (100 mg/kg ip qw×3).

Figure 15:
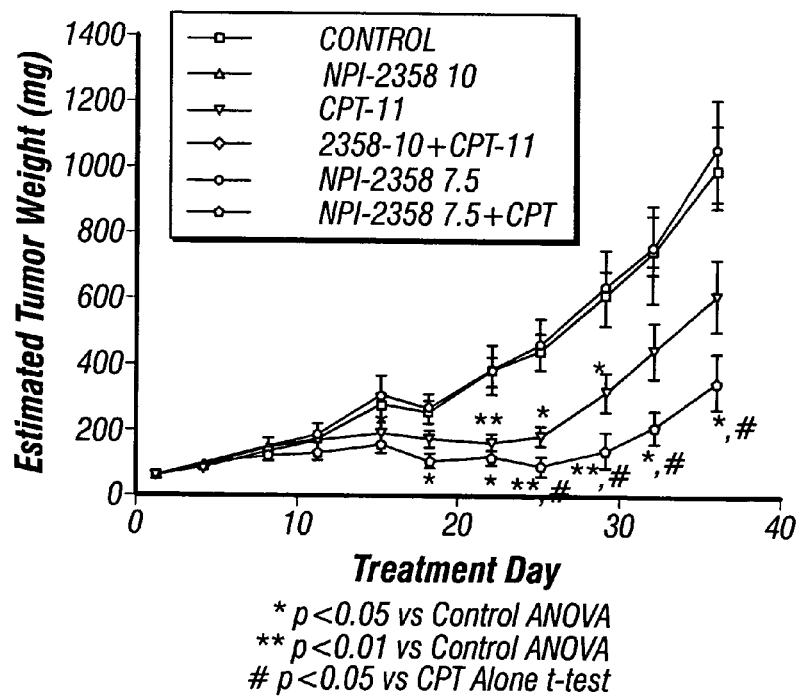
FIG. 15 depicts the effect of KPU-2 alone and in combination with CPT-11 on estimated tumor growth in the HT-29 Human Colon Tumor Xenograft model.

As can be observed in FIG. 15, the combination of KPU-2 and CPT-11 in this model resulted in a marked synergy in the inhibition of tumor growth, with the tumor growth being almost completely inhibited up to Treatment Day 29 in the combination therapy group. The combined therapy maintained efficacy and the estimated tumor growth for this group was significantly lower than for either monotherapy group. Accordingly, administration of KPU-2 and CPT-11 inhibited tumor growth and is an effective anti-tumor treatment.

Figure 16:
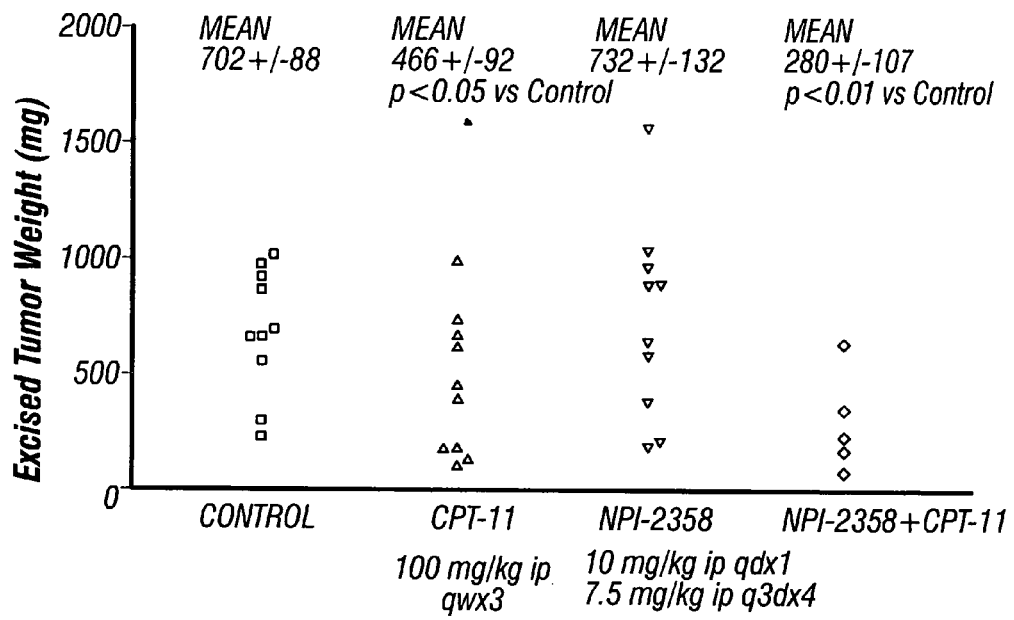
FIG. 16 depicts the effect of KPU-2 alone and in combination with CPT-11 on the weight of tumors excised at autopsy in individual mice in the HT-29 Human Colon Tumor Xenograft model.

The observations of the in-life portion of the study (estimated tumor growth, FIG. 15) are supported by measurement of the weights of the tumors excised at autopsy (FIG. 16). The tumor weights for the combination group was significantly less than the Controls (p<0.01), as were the tumor weights for CPT-11 alone (p<0.05).

When the individual final tumor weights are considered (FIG. 16), the tumor size for the combination group was generally smaller than for the other treated or control groups. The TGI of the combination group was 65.8%, indicating a positive effect by the NCI criterion, while monotherapy did not reach the NCI criterion of TGI>58%.

Figure 17A:
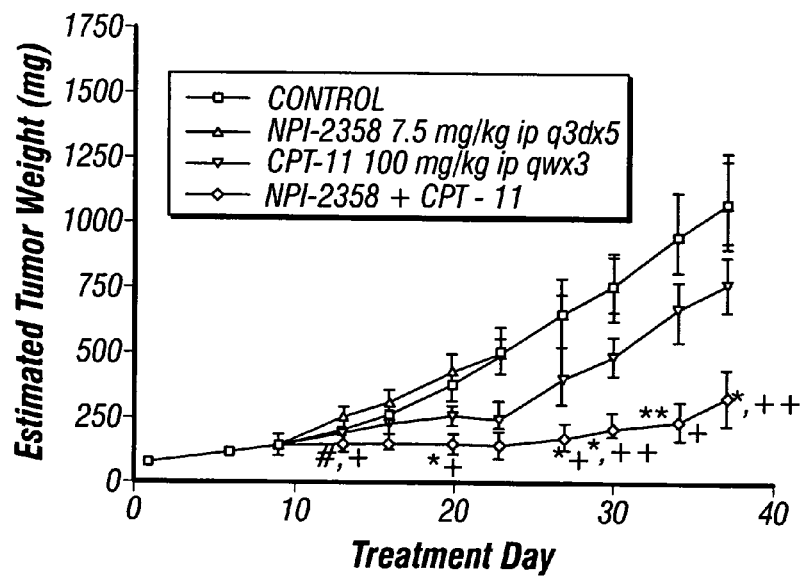
FIG. 17 depicts the effects of: A. KPU-2, B. KPU-35 and C. t-butyl-phenylahistin alone and in combination with CPT-11 on estimated tumor growth in the HT-29 human colon tumor xenograft model.
Figure 17B:
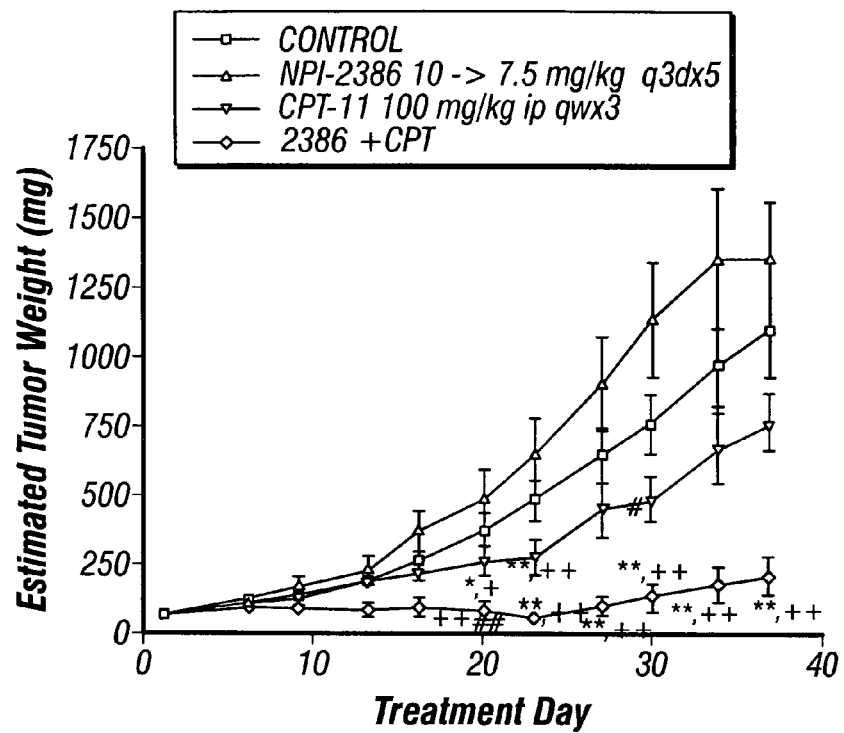
Figure 17C:
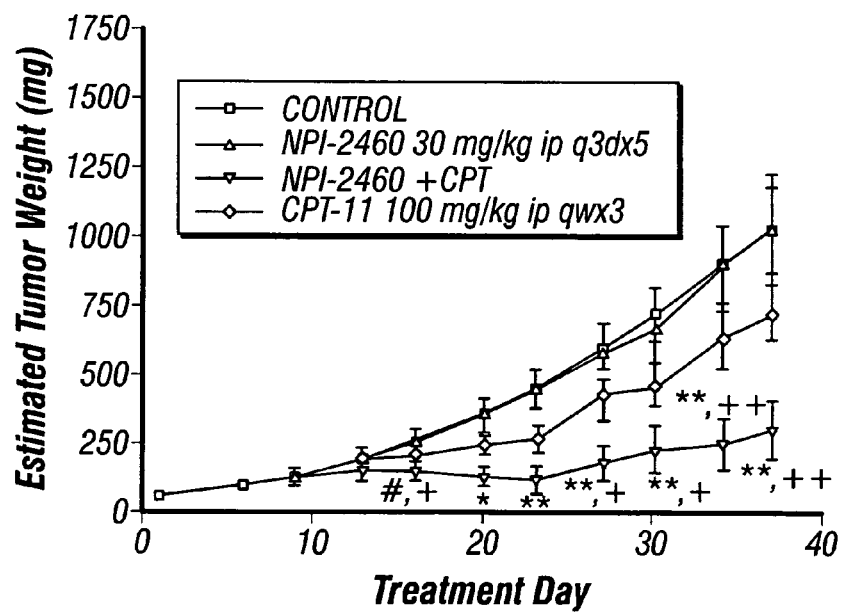
Figure 18A:
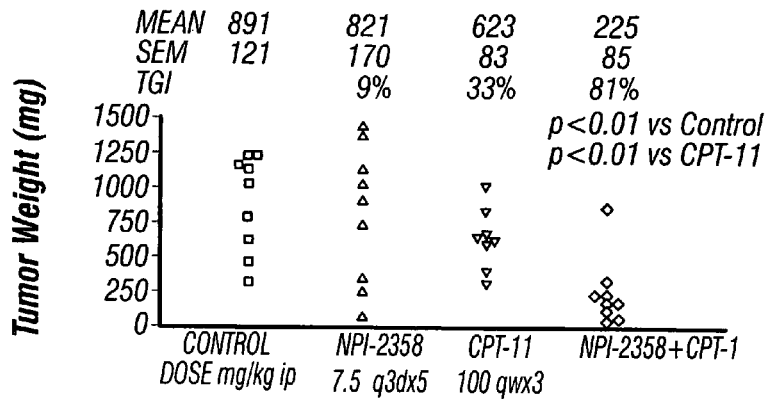
FIG. 18 depicts the effects of A. KPU-2, B. KPU-35 and C. t-butyl-phenylahistin alone and in combination with CPT-11 on the weight of tumors excised at autopsy in individual mice in the HT-29 Human Colon Tumor Xenograft model.
Figure 18B:
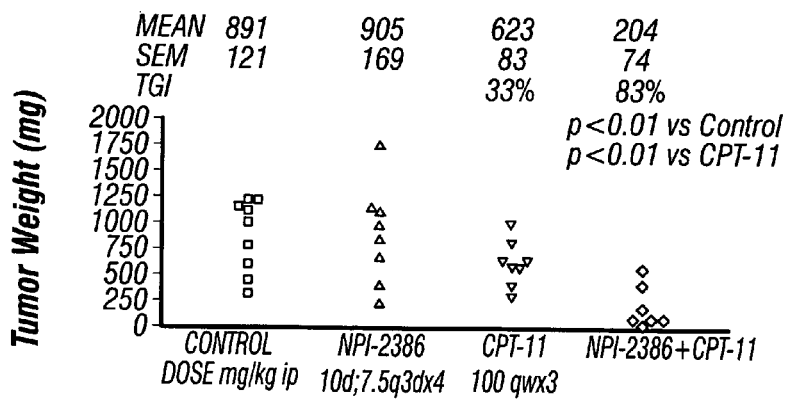
Figure 18C:
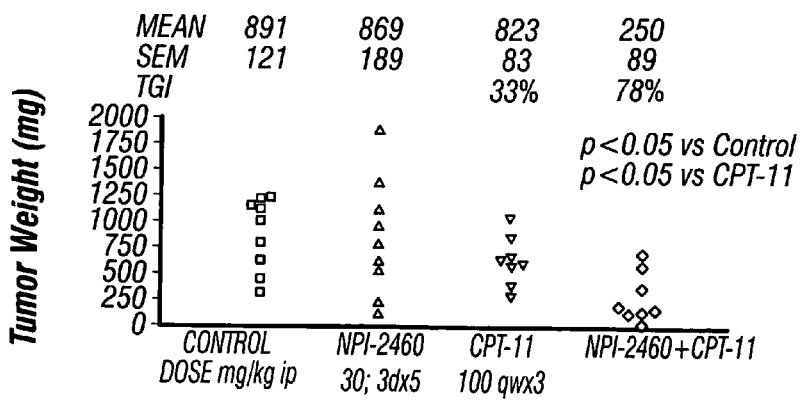

3. Study of Activity of KPU-2, KPU-35 and t-butyl-phenylahistin in the HT-29 Human Colon Tumor Xenograft Study The results of this study are presented in FIG. 17 and Table 18. The combination therapy groups all indicated a marked synergy between the novel compounds and CPT-11. The individual tumor weights demonstrate the effectiveness of the cotherapy treatment (FIG. 18). In each case the TGI for the combination group surpasses the NCI criterion for a positive effect, whereas the TGI for CPT-11 monotherapy did not reach this level.

TABLE 18

Summary of Studies Performed in the HT-29 Human Colon Tumor Model

| Study Description | | NPI-Compound | | Chemotherapeutic Agent | | | Combination Exceed NCI | |
| --- | --- | --- | --- | --- | --- | --- | --- | --- |
| Number Status | Endpoint | Number, mg/kg ip | Result TGI % | Name, Dose | Result TGI % | Results TGI % | Criterion (TGI ≧ 58%) | Comments |
| 2164 | TGI | KPU-2 7.5 qdx5 7.5 q3dx5 | No Effect No Effect | CPT-11 100 ip qwx3 | 39 * | 78 **; # | Combination | Synergy |
| 2288 | TGI | KPU-2 10→7.5 q3dx5 | No Effect | CPT-11 100 ip qwx3 | 36.5 * | 65.8 ** | Combination | Synergy See Text |
| 2139 | TGI | KPU-2 7.5 q3dx5 | No Effect | CPT-11 100 ip qwx3 | 32.7 | 80.7 **, # | Combination | Synergy |
| 2139 | TGI | KPU-35 10→7.5 q3dx5 | No Effect | CPT-11 100 ip qwx3 | 32.7 | 83.3 **, ## | Combination | Synergy 1 + Day 13 1 + Day 27 |
| 2139 | TGI | t-butyl-phenylahistin 30 q3dx5 | No Effect | CPT-11 100 ip qwx3 | 32.7 | 77.7 *, # | Combination | Synergy |

Figure 19A:
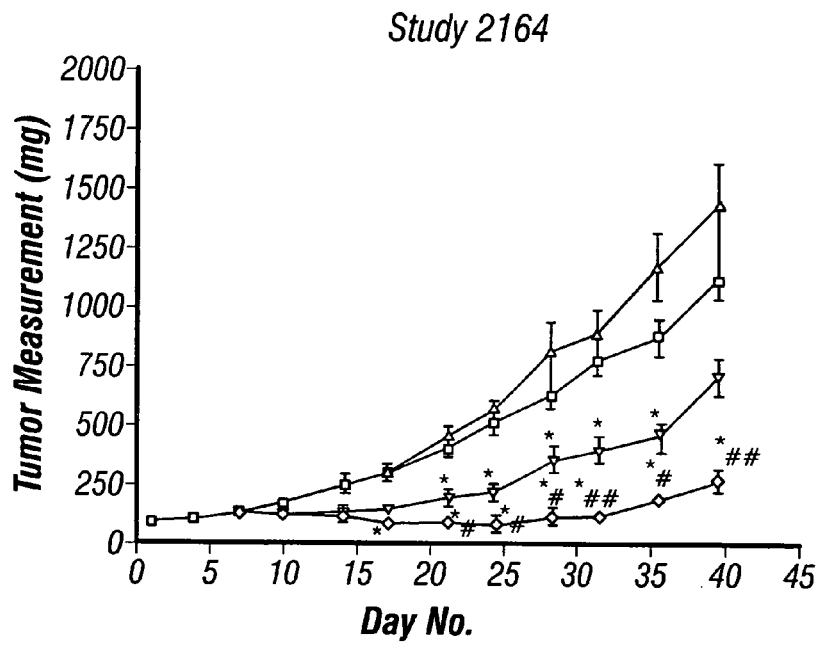
FIG. 19 depicts the effects of KPU-2 alone and in combination with CPT-11 on tumor growth in the HT-29 human colon tumor xenograft model: comparison of three studies.
Figure 19B:
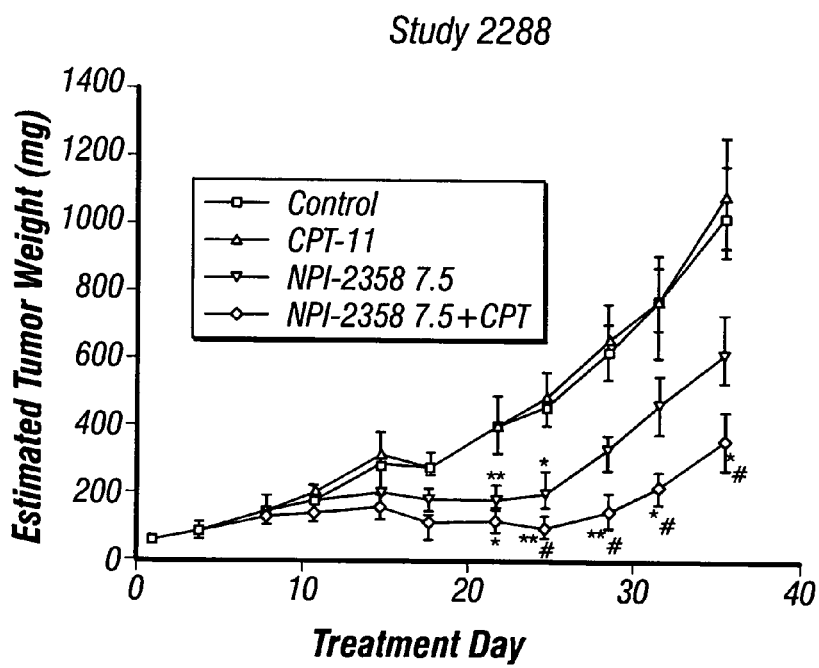
Figure 19C:
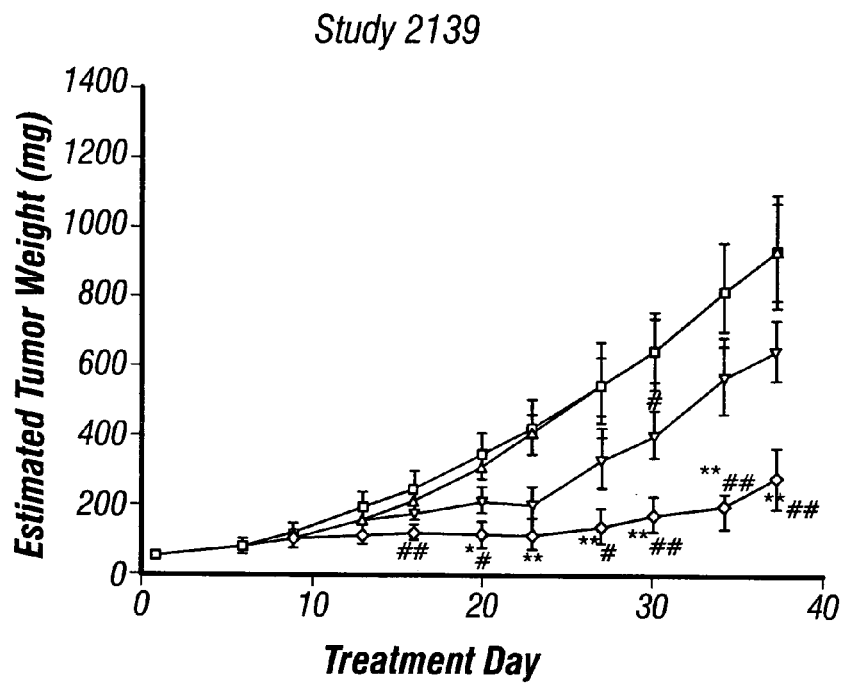
Figure 20A:
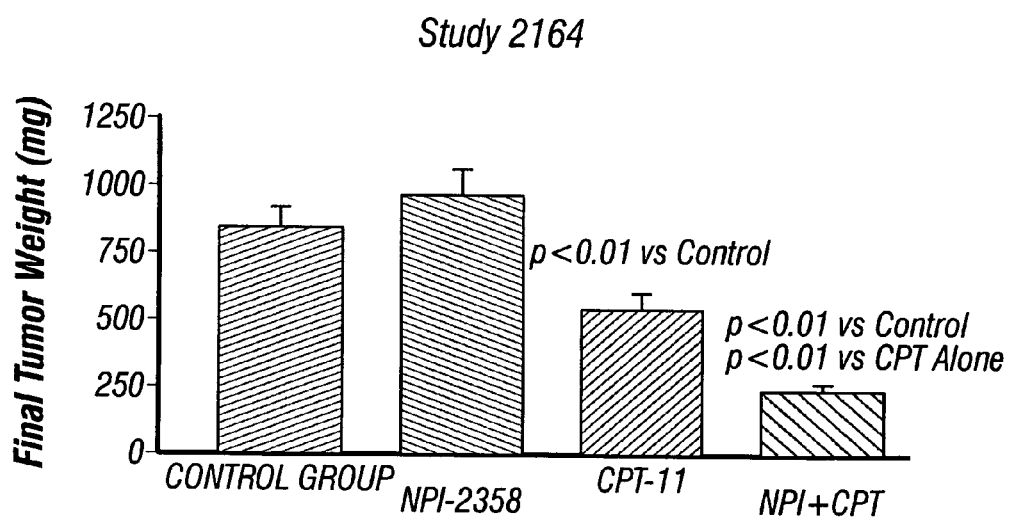
FIG. 20 depicts the effects of KPU-2 alone and in combination with CPT-11 on final tumor weights in the HT-29 human colon tumor xenograft model: comparison of three studies.
Figure 20B:
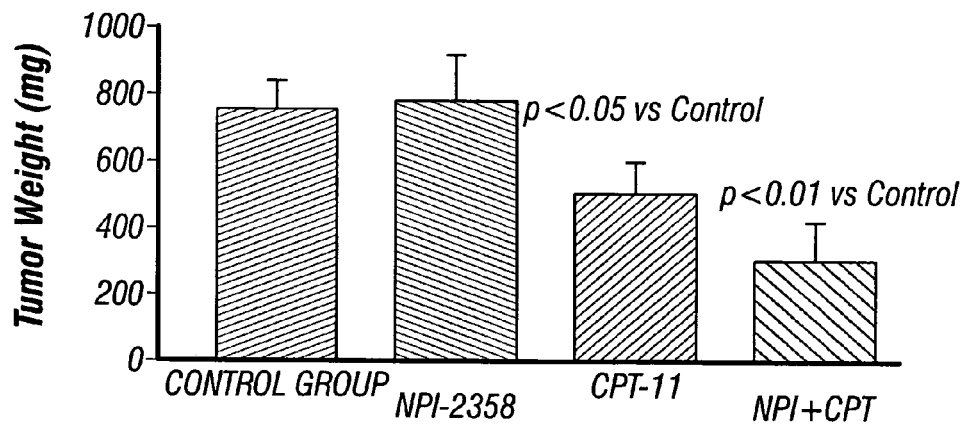
Figure 20C:
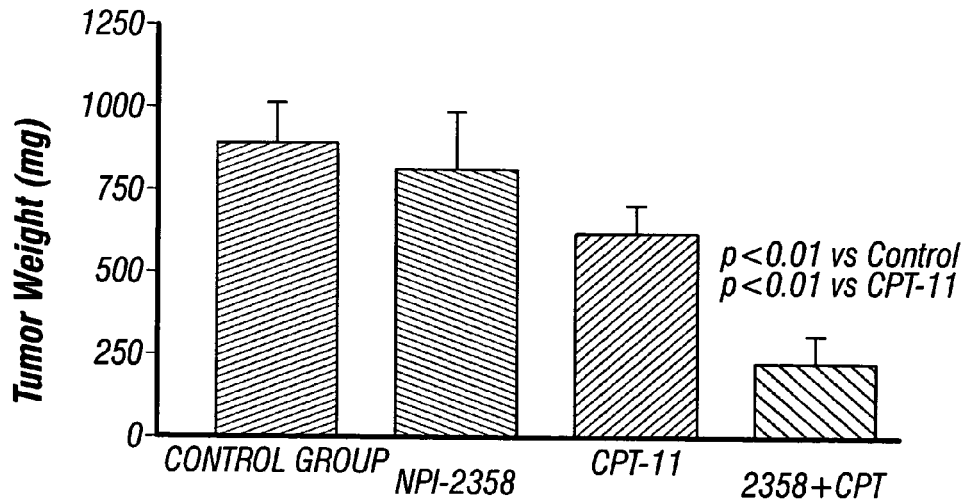

\* $p < 0.05$ vs Control;
\*\* $p < 0.01$ vs Control;
\# $p < 0.05$ vs CPT-11 Alone;
\#\# $p < 0.01$ vs CPT-11 Alone;
+ = Number of Deaths 4. Summary of the Effects of KPU-2, KPU-35 and t-butyl-phenylahistin in Combination with CPT-11 in the HT-29 Human Colon Tumor Xenograft Model When combined with CPT-11, KPU-2 enhanced the effect of CPT-11, the standard chemotherapeutic agent, to a level well in excess of the NCI criterion of a TGI≧58% for a positive effect. The results generated in the three studies are very comparable for both the in-life observations (FIG. 19) and for the weights of the tumors excised at autopsy (FIG. 20).

Studies in the DU-145 Human Prostate Tumor Xenograft Model

Two studies have been completed with this model: the first study involved KPU-2 alone and in combination with taxotere; the second study compared KPU-2, KPU-35 and t-butyl-phenylahistin alone and in combination with taxotere.

Figure 21:
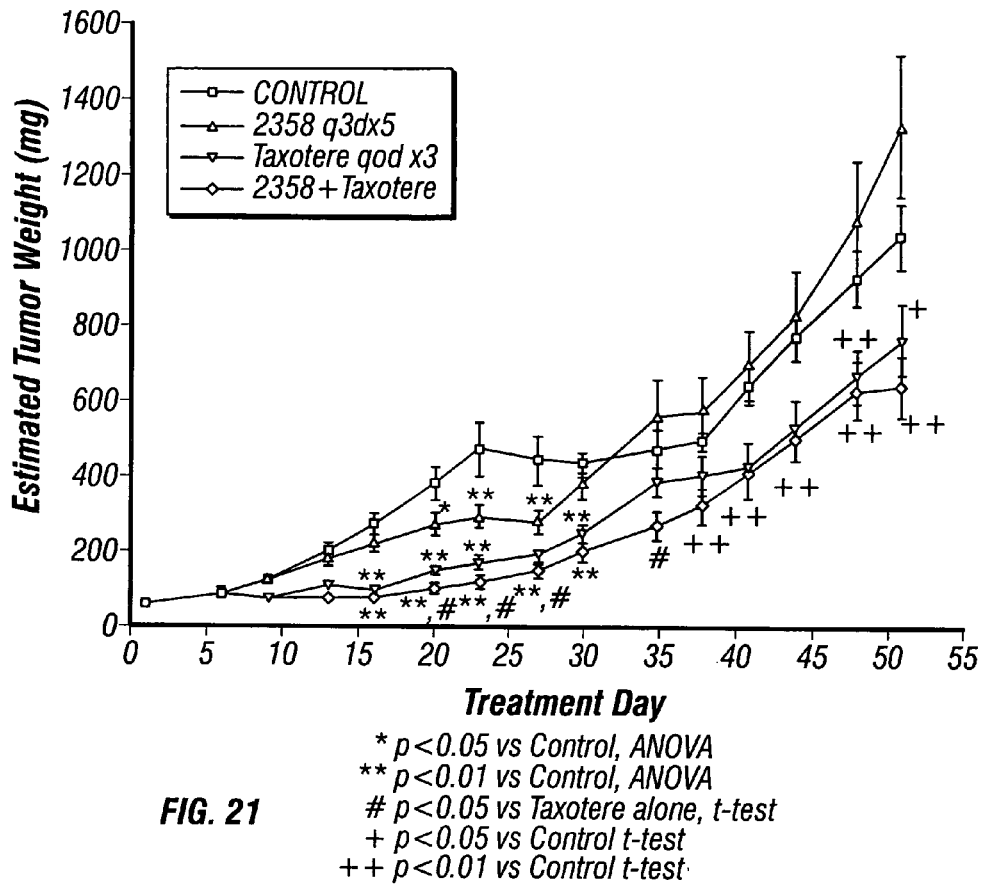
FIG. 21 depicts the effects of KPU-2 alone or in combination with Taxotere on estimated tumor growth in the DU-145 Human Prostate Tumor Xenograft Model.

1. Effect of KPU-2 in Combination with Taxotere in the DU-145 Human Prostate Tumor Xenograft Model As can be seen from the data obtained during the in-life portion of this study (FIG. 21), the most effective treatment of the DU-145 human prostate tumor was the combined therapy of KPU-2 plus taxotere. The treatment effect was most pronounced at the beginning of the study and appeared to be reduced as the study progressed. From treatment Days 20-27, the combination therapy did provide an apparent TGI that exceeded the NCI criterion (TGI >58%), and the estimated tumor weight of the combined therapy was significantly less than for either monotherapy.

2. Activity of KPU-2, KPU-35 and t-butyl-phenylahistin Alone or in Combination with Taxotere in the DU-145 Human Prostate Xenograft Model Based on the data obtained with KPU-2 in combination with taxotere in the Study described above a second study comparing KPU-2 to KPU-35 and t-butyl-phenylahistin alone and in combination with taxotere was initiated.

Figure 22A:
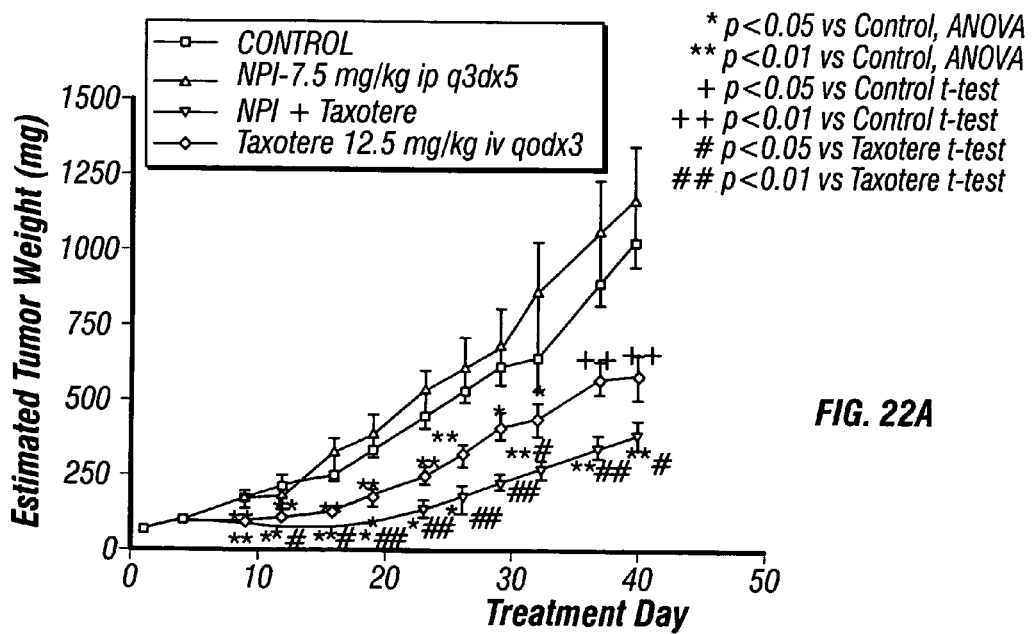
FIG. 22 depicts the effects of A. KPU-2, B. KPU-35 and C. t-butyl-phenylahistin alone and in combination with Taxotere on the estimated tumor growth based on observations made during the in-life portion of the DU-145 Human Prostate Tumor Xenograft Model.
Figure 22B:
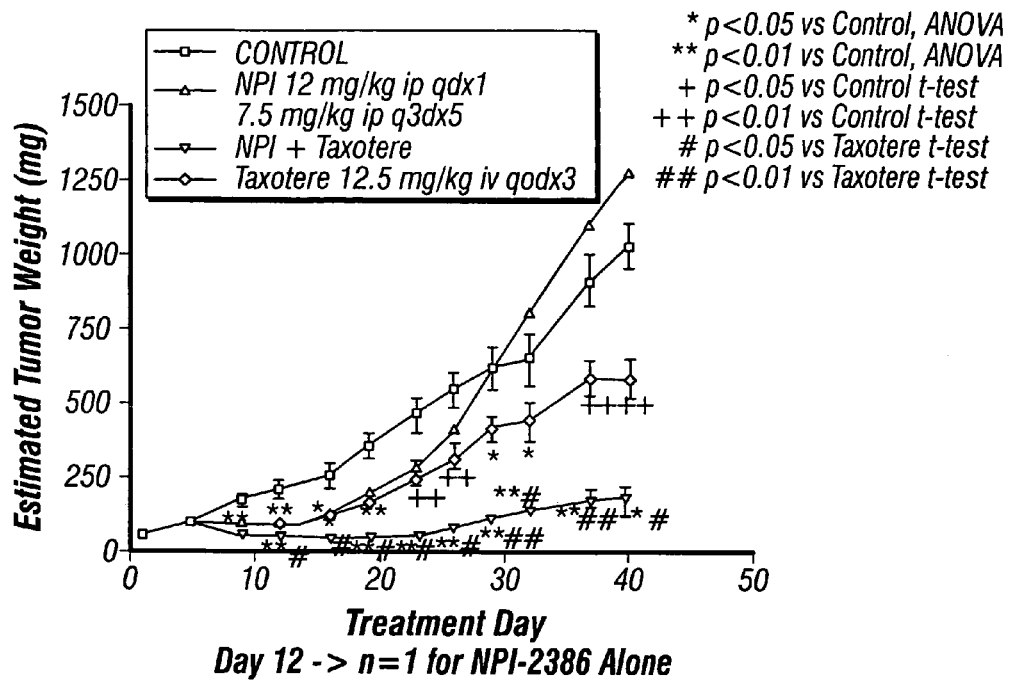
Figure 22C:
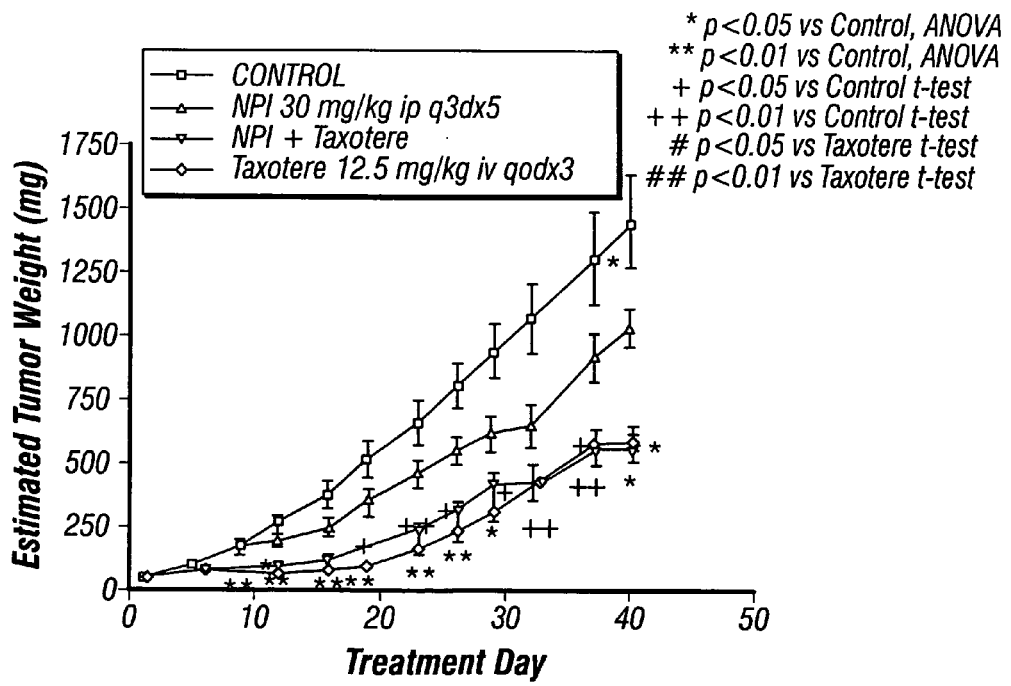

The observations made during the in-life portion of this study indicate that the combination of either KPU-2 or KPU-35 with taxotere has a greater reduction on tumor growth than for taxotere alone (FIG. 22). The tumor growth was almost completely blocked by KPU-35 in combination with taxotere.

Figure 23:
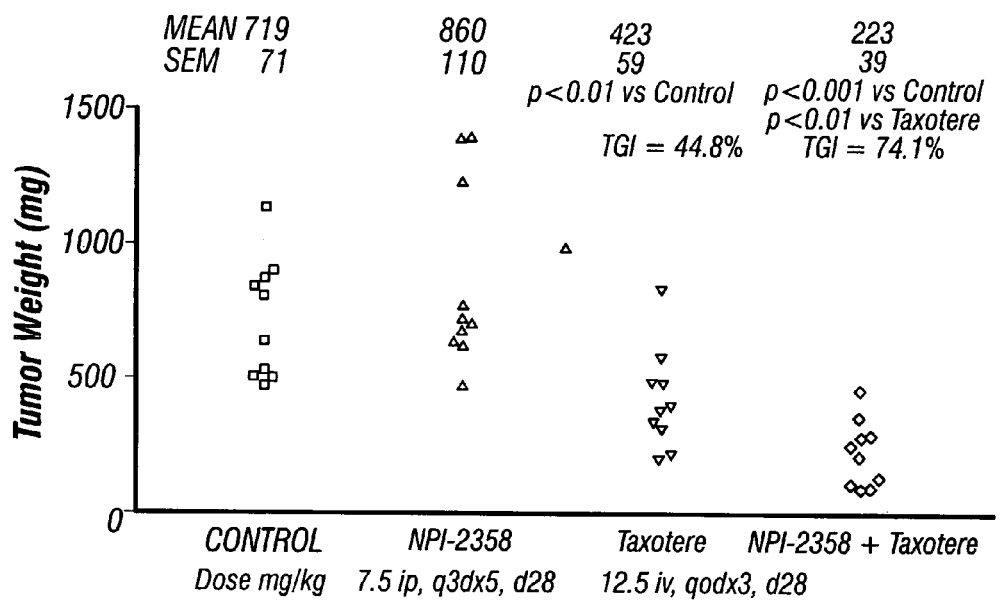
FIG. 23 depicts the effects of KPU-2 alone and in combination with Taxotere on the individual excised tumor weights at autopsy in the DU-145 Human Prostate Tumor Xenograft Model.
Figure 24:
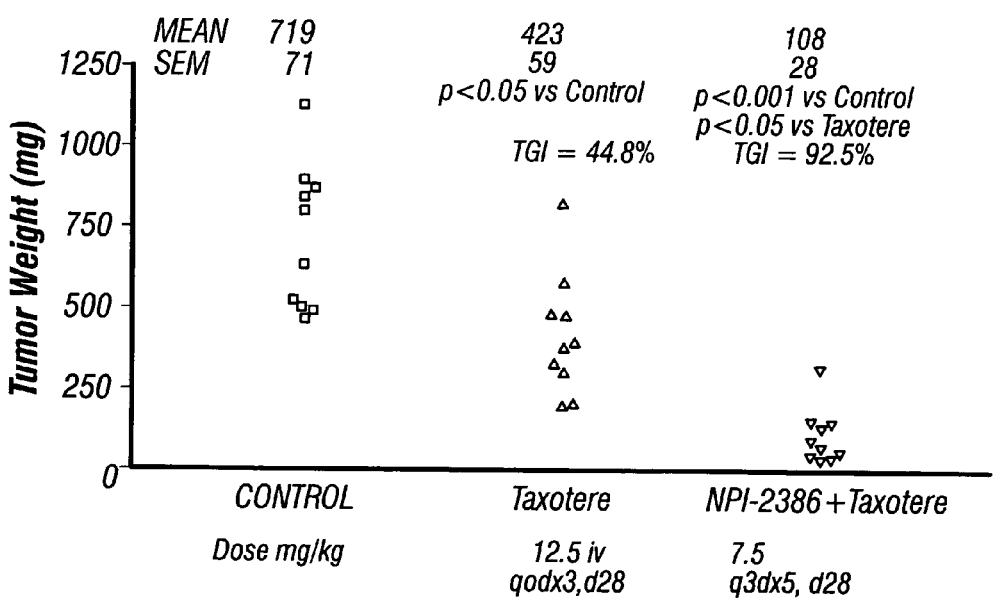
FIG. 24 depicts the effects of KPU-35 alone and in combination with Taxotere on the individual excised tumor weights at autopsy in the DU-145 Human Prostate Tumor Xenograft Model.

The excised tumor weights at autopsy confirmed the observations made during the in-life segment of the study. The combination of either KPU-2 (FIG. 23) or KPU-35 (FIG. 24) with taxotere was significantly more effective than taxotere alone in blocking tumor growth. In the case of KPU-35, three of ten mice showed evidence for tumor shrinkage. The tumor growth inhibition indices indicated a marked inhibition of tumor growth for KPU-2 (group mean=74.1%) and an almost total block for KPU-35 (group mean=92.5%). Taxotere alone did not reach the NCI established criterion for a positive effect (TGA≧58%).

5. Studies in the MCF-7 Human Breast Tumor Xenograft Model

This study compared the effects of KPU-2, KPU-35 and t-butyl-phenylahistin in the MCF-7 human breast tumor xenograft model. The doses of the compounds were administered on Days 1, 2, 3, 4, and 7; Taxotere was administered on Days 1, 3 and 7.

Figure 25A:
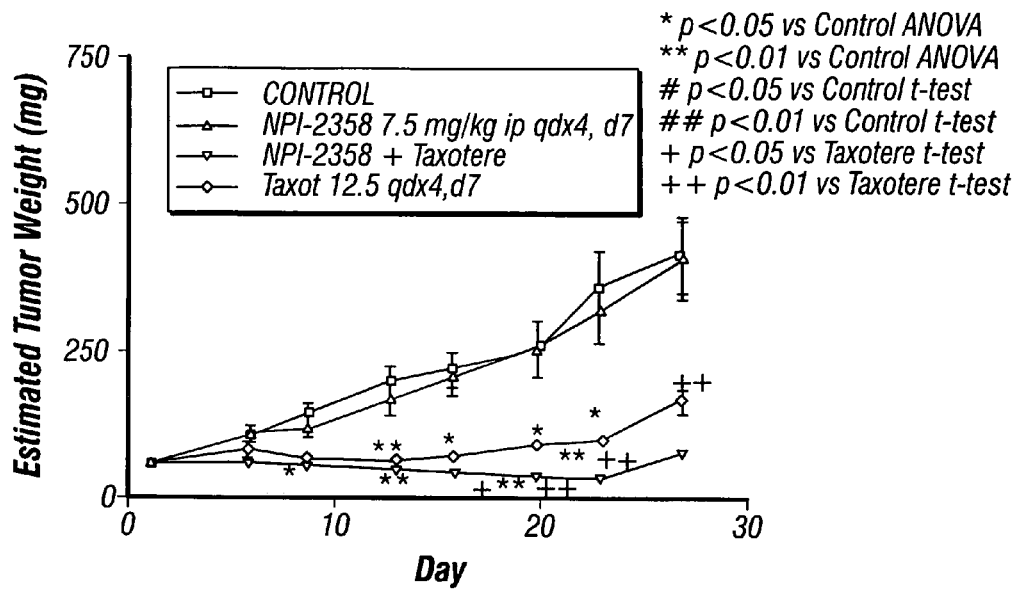
FIG. 25 depicts the effects of A. KPU-2, B. KPU-35 and C. t-butyl-phenylahistin alone and in combination with Taxotere in MCF-7 Human Breast Tumor Xenograft model.
Figure 25B:
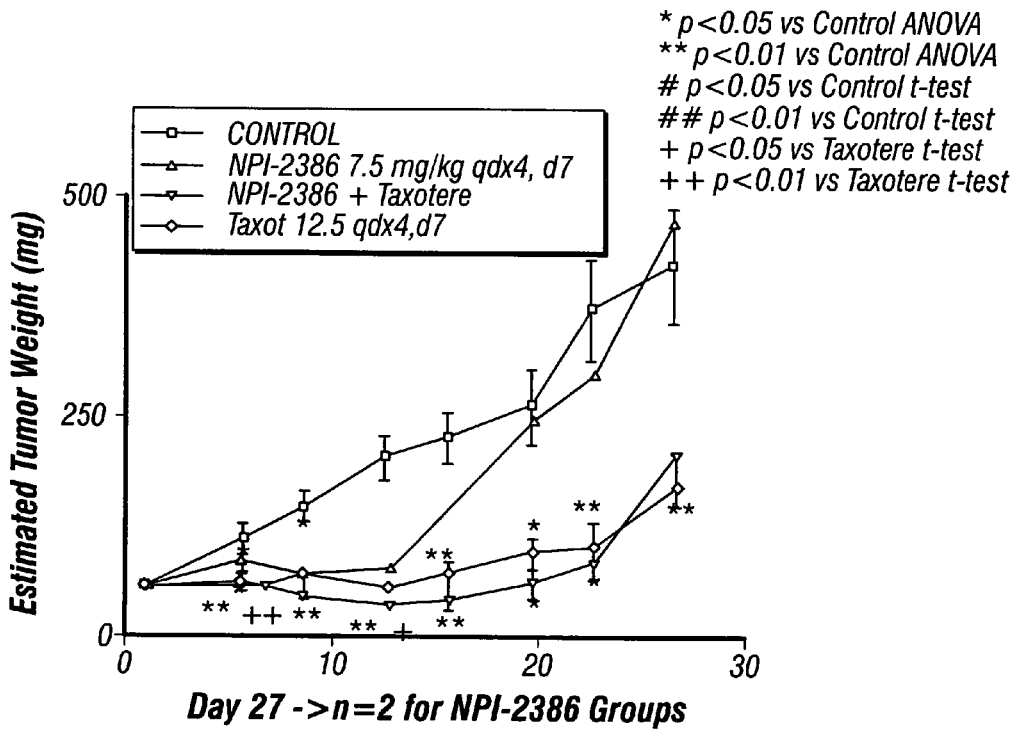
Figure 25C:
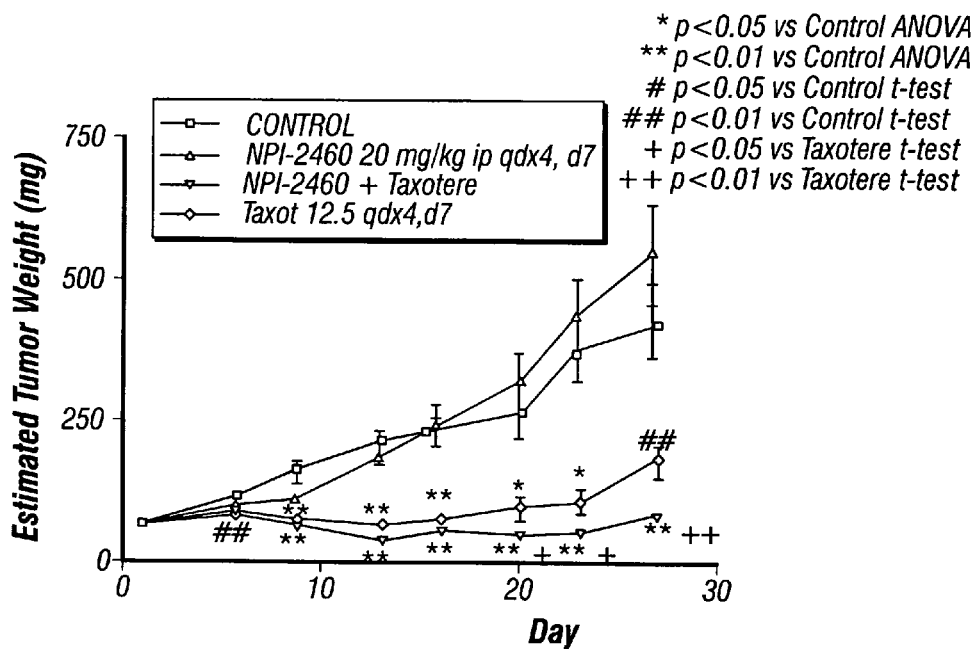

The selected novel compounds have early onset, statistically significant effects when used in combination with taxotere in this model, apparently almost completely blocking estimated tumor growth (FIG. 25). Of the three compounds, KPU-2 appeared to be the most effective, with t-butyl-phenylahistin also exhibiting a significant potentiation of taxotere.

6. Studies in the A549 Human Non Small Cell Lung Tumor Xenograft Model

Figure 26:
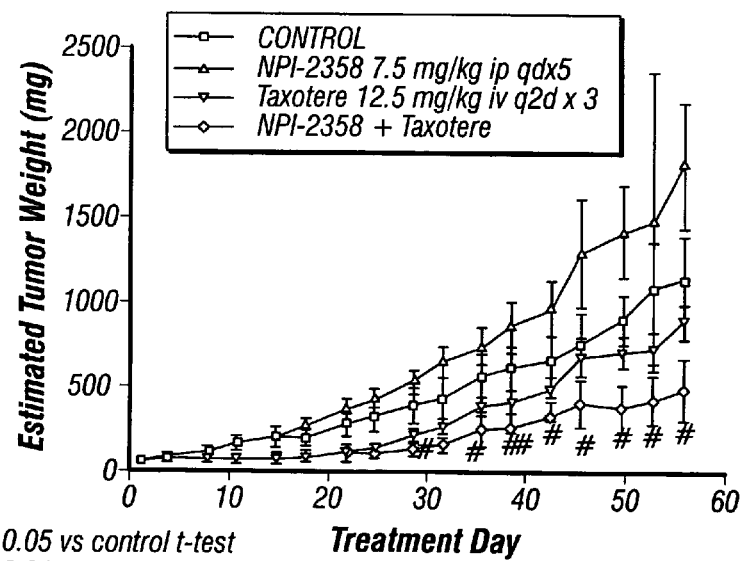
FIG. 26 depicts the effects of KPU-2 alone and in combination with Taxotere on estimated tumor growth in the A549 Human Lung Tumor Xenograft model.
Figure 27:
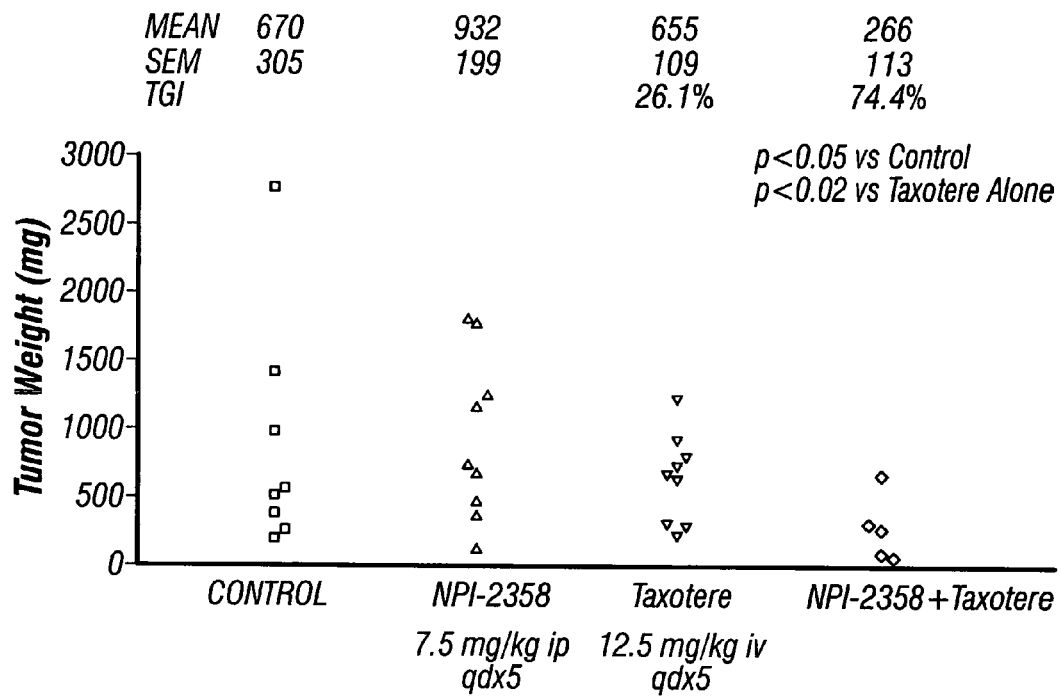
FIG. 27 depicts the effects of KPU-2 alone and in combination with Taxotere on the excised tumor weights at autopsy in the A549 Human Lung Tumor Xenograft model.

The in-life observations during this study (FIG. 26) indicated that the combination of KPU-2 (7.5 mg/kg ip, qdx5) with taxotere resulted in a marked inhibition of tumor growth as compared to the Control or either monotherapy group. This was confirmed by the autopsy tumor weights, as the mean of the cotherapy group was significantly less than that of taxotere alone or the Control group (FIG. 27). The cotherapy group tumor weights form a cluster of low tumor weights, indicating the consistency of the effect.

When the tumor growth index is calculated, the cotherapy group had a TGI of 74.4% as compared to the control group well in excess of the NCI criterion for a positive effect (TGI≧58%). Taxotere alone had a TGI of 26.1%.

7. Studies in the MDA-231 Human Breast Tumor Orthotopic Xenograft Model

This model involves the placement of the human tumor tissue into the mouse mammary fat pad, a surrogate of the natural environment. In this manner the possibility of a positive effect due to a specific action on the subcutaneous vascular bed is avoided. This study compared the effect of KPU-2 (7.5 mg/kg ip, q3d×5) alone and in combination with paclitaxel (16 mg/kg ip, qd×5).

Figure 28:
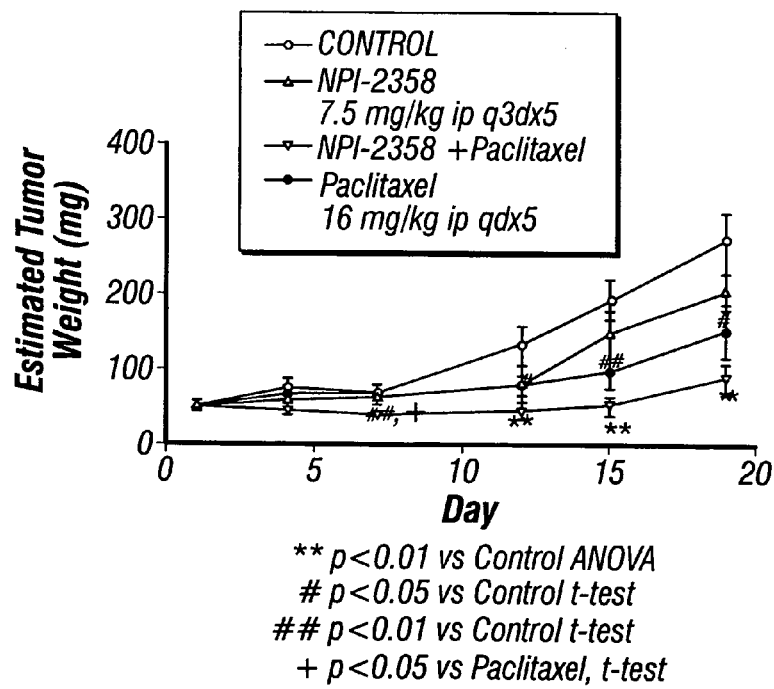
FIG. 28 depicts the effects of KPU-2 alone and in combination with Paclitaxel on estimated tumor weight in the murine mammary fat pad implanted MDA-231 Human Breast Tumor model.

Three weeks into the study there was a significant inhibition of tumor growth in the combination therapy group, a highly significant effect. This effect appeared to be more marked than for taxotere alone (FIG. 28).

8. Studies in the Murine Melanoma B16 F10 Metastatic Tumor Model

This study examined the effect of KPU-2, KPU-35 and t-butyl-phenylahistin alone and in combination with paclitaxel on the number of metastases appearing on the surface of the lung 16 days after the intravenous injection of B16 F10 melanoma cells to the mouse. This model is not a xenograft model; however, it does not involve a high degree of vascularization into the tumor mass.

Figure 29A:
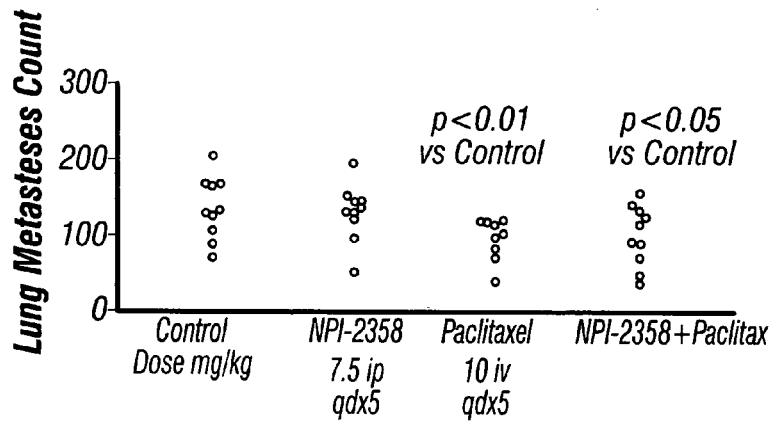
FIG. 29 depicts effects of A. KPU-2, B. KPU-35 and C. t-butyl-phenylahistin alone and in combination with Paclitaxel in the Murine Melanoma B16 F10 Metastatic Tumor Model.
Figure 29B:
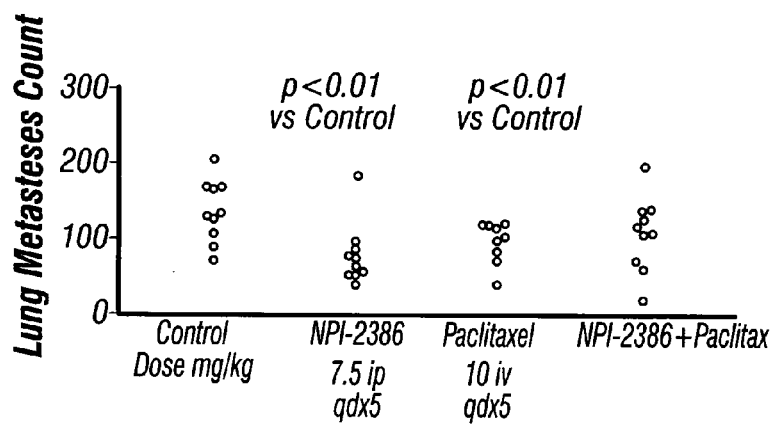
Figure 29C:
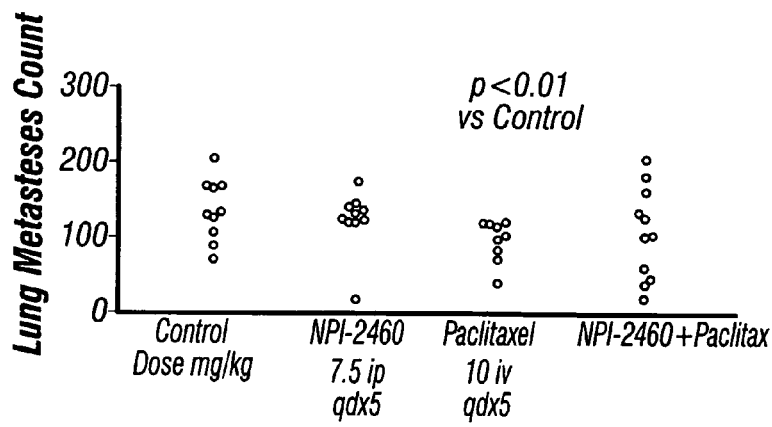
Figure 3D:
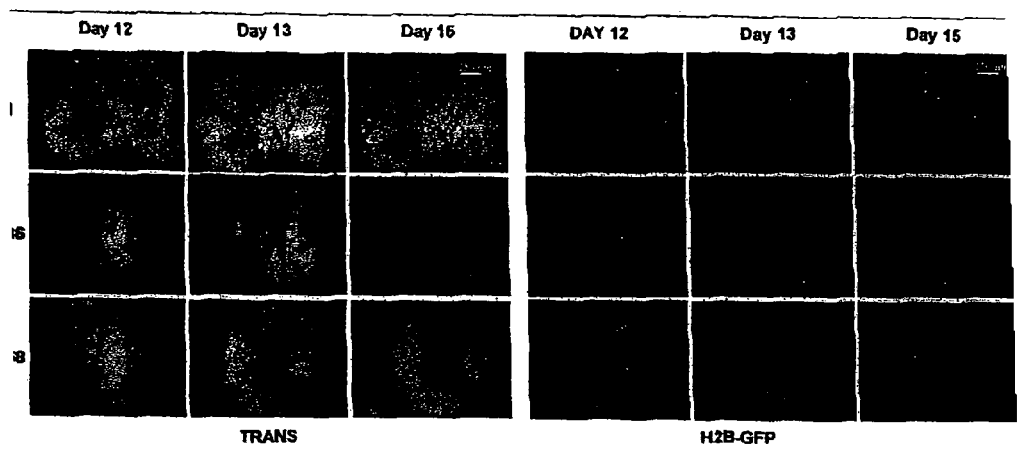
Figure 3:
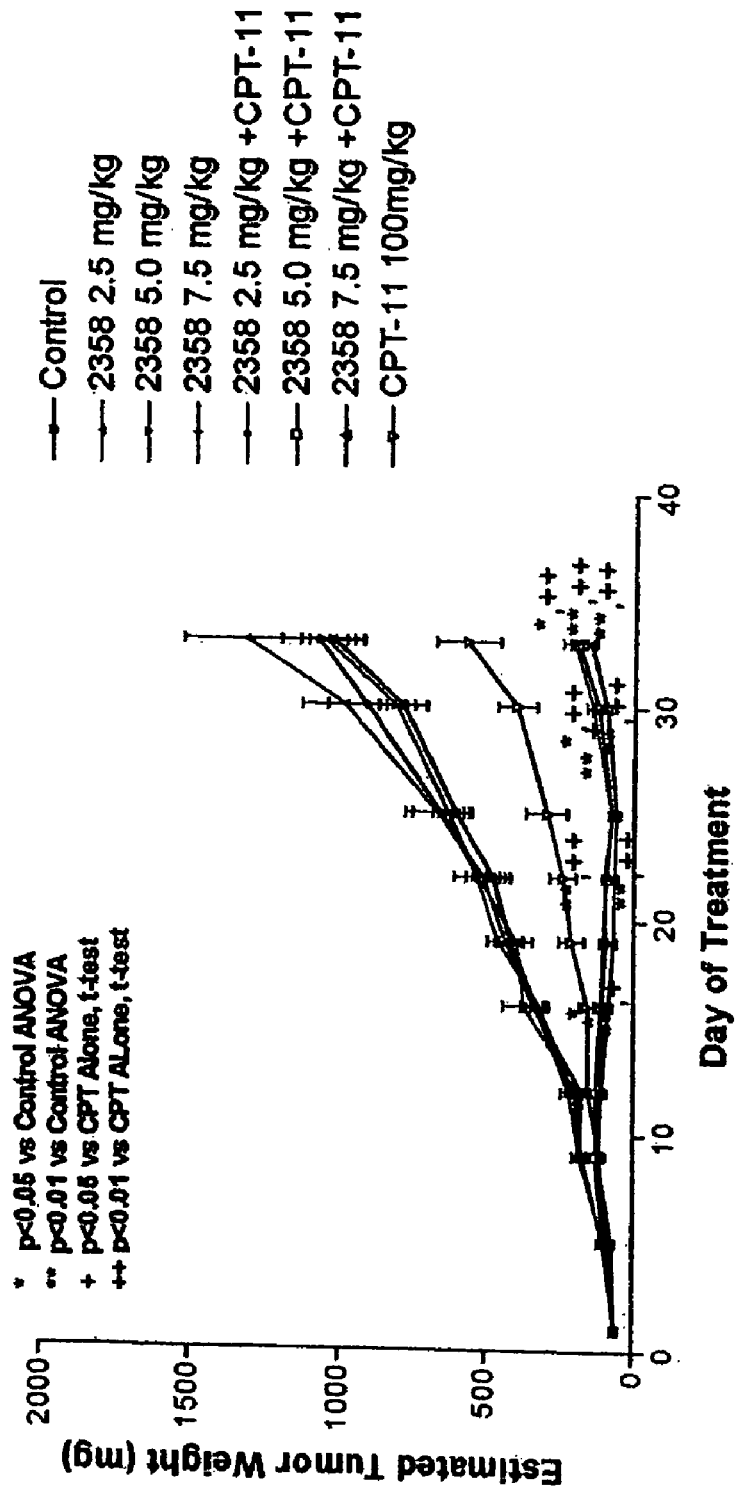

In this model the most effective treatment was KPU-2 alone (FIG. 29), having a mean metastases count about 10% less than that for paclitaxel (MGIs of 41.6% and 35.0%, respectively). While this study does not itself establish that combination therapy is more effective than monotherapy, it does indicate that KPU-2, KPU-35 and t-butyl-phenylahistin are most effective in highly vascularized tumors.

EXAMPLE 10

Assays for Activity Against Pathogenic Fungi

Comparative activity of a dehydrophenylahistin or its analog against a pathogenic fungus, relative to known antifungal compounds recited above, for use in determining the dehydrophenylahistin or its analog's AF/IS value is measured directly against the fungal organism, e.g. by microtiter plate adaptation of the NCCLS broth macrodilution method described in *Diagn Micro and Infect Diseases* 21:129-133 (1995). Antifungal activity can also be determined in whole-animal models of fungal infection. For instance, one may employ the steroid-treated mouse model of pulmonary mucormycosis (Goldaill, L. Z. & Sugar, A. M. 1994 *J Antimicrob Chemother* 33:369-372). By way of illustration, in such studies, a number of animals are given no dehydrophenylahistin or its analog, various doses of dehydrophenylahistin or its analog (and/or combinations with one or more other antifungal agents), or a positive control (e.g. Amphotericin B), respectively, beginning before, at the time of, or subsequent to infection with the fungus. Animals may be treated once every 24 hours with the selected dose of dehydrophenylahistin or its analog, positive control, or vehicle only. Treatment is continued for a predetermined number of days, e.g. up to ten days. Animals are observed for some time after the treatment period, e.g. for a total of three weeks, with mortality being assessed daily. Models can involve systemic, pulmonary, vaginal and other models of infection with or without other treatments (e.g. treatment with steroids) designed to mimic a human subject susceptible to infection.

To further illustrate, one method for determining the in vivo therapeutic efficacies ($ED_{50}$, e.g. expressed in mg dehydrophenylahistin or its analog/kg subject), is a rodent model system. For example, a mouse is infected with the fungal pathogen such as by intravenous infection with approximately 10 times the 50% lethal dose of the pathogen ($10^6$ *C. albicans* cells/mouse). Immediately after the fungal infection, dehydrophenylahistin compounds are given to the mouse at a predetermined dosed volume. The $ED_{50}$ is calculated by the method of Van der Waerden (*Arch Exp Pathol Pharmakol* 195:389-412, 1940) from the survival rate recorded on 20th day post-infection. Generally, untreated control animals die 7 to 13 days post-infection.

In another illustrative embodiment, *C. albicans* Wisconsin (C43) and *C. tropicalis* (C112), grown on Sabouraud dextrose agar (SDA) slants for 48 h at 28° C., are suspended in saline and adjusted to 46% transmission at 550 nm on a spectrophotometer. The inoculum is further adjusted by hemacytometer and confirmed by plate counts to be approximately 1 or $5×10^7$ CFU/ml. CF-1 mice are infected by injection 1 or $5×10^6$ CFU into the tail vein. Antifungal agents are administered intravenously or subcutaneously in ethanol:water (10:90), 4 h post infection and once daily thereafter for 3 or 4 more days. Survival is monitored daily. The $ED_{50}$ can be defined as that dose which allows for 50% survival of mice.

EXAMPLE 11

Evaluating Antimicotic Activity

Benzimidazoles and griseofulvin are anti-tubulin agents capable of binding to fungal microtubules. Once bound, these compounds interfere with cell division and intracellular transport in sensitive organisms, resulting in cell death. Commercially, benzimidazoles are used as fungicidal agents in veterinary medicine and plant disease control. A wide variety of fungal species, including *Botrytis cinerea, Beauveria bassiana, Helminthosporium solani, Saccharomyces cerevisiae* and *Aspergillus* are susceptible to these molecules. Toxicity concerns and increasing drug resistance, however, have negatively impacted their usage. Griseofulvin is used clinically to treat ringworm infections of the skin, hair and nails, caused by *Trichophyton* sp., *Microsporum* sp., and *Epidermophyton floccosum*. Its antifungal spectrum, however, is restricted to this class of fungal organisms. Genotoxicity is also a significant side effect. Terbinafine, while an alternative first-line treatment, is more costly. Further, clinical resistance recently has been observed in *Trichophyton rubrum* (the major causative agent for all derinatophyte infections).

In *Candida albicans*, microtubule/microfilament formation is affected where cells are exposed to the microtubule inhibitors nocodazole and chloropropham. These results further validate the exploration of cytoskeleton inhibitors as effective antimycotic agents. Accordingly, several of the compounds disclosed herein were evaluated for antimycotic activity.

Specifically, disclosed compounds were evaluated alongside commercially available microtubulin inhibitors as well as recognized antifungal agents. The test compounds and controls used in this study: (−)-Phenylahistin, KPU-1, KPU-2, KPU-11 and KPU-17, KPU-35, t-butyl phenylahistin, Colchicine (commercial microtubulin inhibitor tested versus 3 *Candida* isolates), Benomyl (commercial microtubulin inhibitor tested versus 3 *Candida* isolates), Griseofulvin (commercial microtubulin inhibitor and antibiotic control for testing versus 6 dermatophyte isolates), Amphotericin B (antibiotic control for testing versus 3 *Candida* isolates), Itraconazole (antibiotic control for testing versus 2 *Aspergillus* isolates).

Microorganisms against which these compounds were tested included: *Candida albicans, Candida glabrata, Aspergillus fumigatus, Trichophyton rubrum, Trichophyton mentagrophytes, Epidermophyton floccosum*. With the exception of *Candida glabrata* (one isolate), two isolates of each species were tested.

Antifungal susceptibility testing was accomplished according to the methods outlined in the National Committee for Clinical Laboratory Standards, M38-A "Reference Method for Broth Dilution Antifungal Susceptibility Testing of Conidium-Forming Filamentous Fungi; Approved Standard." This includes testing in RPMI-1640 with glutamine and without bicarbonate, an inoculum size of $0.4-5 \times 10^4$, and incubation at 30 or 35° C. for 48 hours. The minimum inhibitory concentration (MIC) was defined as the lowest concentration that resulted in an 80% reduction in turbidity as compared to a drug-free control tube. Drug concentrations were 0.03-16 µg/ml for the investigational compounds, 0.015-8 µg/ml for itraconazole and griseofulvin.

The minimum inhibitory concentration (MIC) at which a compound prevented the growth of the target microorganism was assessed according to the modified version of the NCCLS protocol. Minimum inhibitory concentrations (MIC) were determined at the first 24-hour interval where growth could be determined in the drug-free control tube. The defined MIC was the lowest concentration that exhibited an 80% reduction in turbidity as compared to the growth control. The minimum lethal concentration (MLC) was determined by plating 0.1 µl from the MIC concentration and each concentration above the MIC. The MLC was called at the first concentration that exhibited five or fewer colonies of fungal growth representing a 99.95% kill. When a MIC was obtained, a minimum fungicidal concentration (MFC) was determined to assess the fungistatic/fungicidal nature of the compound. This procedure entails diluting drug-treated cell samples (removed from test wells containing compound at and above the MIC) to compound concentrations significantly below the inhibitory concentration and depositing them on agar plates. The compound is scored as fungistatic if the cells are able to resume growth and fungicidal if no regrowth is possible because the compound had killed the organisms.

Compounds disclosed herein were shown to be effective against two *Trichophyton* species. *T. rubrum* is the principal causative agent for human dermatophytic infections, and would be the key organism to target in the development of a clinical agent.

Compounds KPU-2, KPU-11 and KPU-17, KPU-35 & t-butylphenylahistin were equivalent in potency or in some cases more potent than griseofulvin, a current, standard pharmaceutical agent used for treating dermatophytic infection.

Compounds (−)-Phenylahistin and KPU-1 were significantly less potent than the other compounds when tested versus *T. rubrum* and weaker but more comparable to the others versus the sensitive *T. mentagrophytes* isolate.

In those instances when an MFC could be determined, the results indicate that these compounds are fungistatic in nature (see Tables 19 and 20).

TABLE 19

Antifungal Activity of Dehydrophenylahistins and Analogs Thereof

MICs and MFCs, µg/ml

| Compound | C. albicans 90028 | | C. albicans 10231 | | C. glabrata | | A. fumigatus isolate #1 | | A. fumigatus isolate #2 | |
|---|---|---|---|---|---|---|---|---|---|---|
| | MIC | MFC | MIC | MFC | MIC | MFC | MIC | MFC | MIC | MFC |
| (−)-Phenylahistin | >70 | ND** | >70* | ND | >70 | ND | >16 | ND | >16 | ND |
| KPU-1 | >68* | ND | >68 | ND | >68 | ND | >16 | ND | >16 | ND |
| KPU-2 | >32 | ND | >32 | ND | >32 | ND | >16 | ND | >16 | ND |
| KPU-11 and KPU-17 | >32 | ND | >32 | ND | >32 | ND | >16 | ND | 0.06 | >16 |
| KPU-35 | >32 | ND | >32 | ND | >32 | ND | >16 | ND | <0.03 | 0.125 |
| t-butyl phenylahistin | >32 | ND | >32 | ND | >32 | ND | >16 | ND | <0.03 | 0.125 |
| amphotericin B | 0.5 | 0.5 | 0.5 | 0.5 | 1 | 1 | ND | ND | ND | ND |
| griseofulvin | ND | ND | ND | ND | ND | ND | ND | ND | 0.5 | ND |
| itraconazole | ND | ND | ND | ND | ND | ND | 1 | ND | ND | ND |
| colchicine | >128 | ND | >128 | ND | >128 | ND | ND | ND | ND | ND |
| benomyl | 64 | >512 | 64 | >512 | 64 | >512 | ND | ND | ND | ND |

TABLE 20

Antifungal Activity of Dehydrophenylahistins and Analogs Thereof

MICs and MFCs, µg/ml

| Compound | T. rubrum isolate #1 | | T. rubrum isolate #2 | | T. mentagrophytes isolate #1 | | T. mentagrophytes isolate #2 | | E. floccosum isolate #1 | | E. floccosum isolate #2 | |
|---|---|---|---|---|---|---|---|---|---|---|---|---|
| | MIC | MFC | MIC | MFC | MIC | MFC | MIC | MFC | MIC | MFC | | MFC |
| NPI2350 | >16 | ND | 0.16 | >16 | 16 | >16 | >16 | ND | >16 | ND | >16 | ND |
| NPI2352 | >16 | ND | 0.25 | >16 | 4 | >16 | >16 | ND | >16 | ND | >16 | ND |
| NPI2358 | >16 | ND | <0.03 | 0.125 | 2 | >16 | >16 | ND | >16 | ND | >16 | ND |
| NPI2362 | 0.06 | >16 | <0.03 | <0.03 | 1 | >16 | >16 | ND | >16 | ND | >16 | ND |
| NPI2386 | <0.03 | 0.125 | <0.03 | 0.06 | 1 | >16 | >16 | ND | >16 | ND | >16 | ND |
| NPI2460 | <0.03 | 0.125 | <0.03 | <0.03 | 4 | >16 | >16 | ND | >16 | ND | >16 | ND |
| amphotericin B | ND | ND | ND | ND | ND | ND | ND | ND | ND | ND | ND | ND |

TABLE 20-continued

Antifungal Activity of Dehydrophenylahistins and Analogs Thereof

MICs and MFCs, µg/ml

| Compound | T. rubrum isolate #1 | | T. rubrum isolate #2 | | T. mentagrophytes isolate #1 | | T. mentagrophytes isolate #2 | | E. floccosum isolate #1 | | E. floccosum isolate #2 |
|---|---|---|---|---|---|---|---|---|---|---|---|
| | MIC | MFC | MIC | MFC | MIC | MFC | MIC | MFC | MIC | MFC | MFC |
| griseofulvin | 0.5 | ND | <0.015 | ND | 1 | ND | 2 | ND | 2 | ND | 4 ND |
| itraconazole | ND | ND | ND | ND | ND | ND | ND | ND | ND | ND | ND ND |
| colchicine | ND | ND | ND | ND | ND | ND | ND | ND | ND | ND | ND ND |
| benomyl | ND | ND | ND | ND | ND | ND | ND | ND | ND | ND | ND ND |

EXAMPLE 12

Evaluating Vascular Targeting Activity

Tumors and neoplastic conditions can be treated using the compounds disclosed herein. The occlusion of the blood supply in tumors with vascular targeting agents (VTAs) induces regression of the tumors. The compounds disclosed herein, including NPU-02 and KPU-35, for example, can be as VTAs. Many VTAs exhibit their vascular effects by interacting at the colchicine-binding site on microtubules. This interaction induces a characteristic, rapid collapse and occlusion of established vasculature in the tumor and therefore compromises the integrity of existing vessels leading to necrosis.

Vascular collapse can occur, for example, within 30-60 minutes of exposure to the VTA and involves changing the shape of the immature and proliferating, but not the quiescent and mature, endothelial cells in the central portion of the tumor. This differential effect on vascular cells provides a rationale for the selective effects on the tumor due to the higher percentage of proliferating immature endothelial cells in the tumor blood vessels versus normal blood vessels. VTAs can be classified into three overlapping spectra of activity: (1) potent vascular and cytotoxic effects, (2) potent vascular with weak cytotoxic effects, and (3) potent cytotoxic with weak vascular effects.

In Vivo Vascular Targeting Activity of KPU-02 and KPU-35

Animal models are essential to investigate new therapies that inhibit tumor-induced angiogenesis, target the established tumor vasculature, and inhibit tumor growth.

A murine syngeneic "pseudo-orthotopic" breast cancer model was used to address these issues. Torres Filho et al., Microvascular Research (1995)49, 212-226, which is incorporated herein by reference in its entirety. To create the "pseudo-orthotopic milieu," the coverslip of a dorsal skinflap chamber was removed and small pieces of mammary fatpad from donor mice were implanted into the chamber. On top of the fatpad graft, tumor spheroids containing N202 mammary tumor cells transduced with Histone (H2B)-green fluorescent protein (GFP) were applied. The use of H2B-GFP transduced cells allows for visualizing tumor growth and monitoring mitosis and apoptosis.

Fluorescence video microscopy allows for the relatively non-invasive study of tumor microcirculation in conscious mice. This model can provide data regarding the effects of compounds on tumor vasculature, tumor growth, mitosis and apoptosis, and is useful to examine the activity of compounds either alone or in combination with other therapeutics. Utilizing this model, KPU-02 and KPU-35 were shown to induce a rapid vascular collapse leading to central necrosis, and the regression of established tumors after a single i.v. administration.

On day 12 of tumor growth, mice were treated i.v. with a 2-minute infusion of 5 mg/kg KPU-35, a 5 minute i.v. infusion of 10 mg/kg KPU-02, or bolus of vehicle (10% solutol (w/w) +2% DMSO in water). On day 13, 5-minute infusions of 10 mg/kg KPU-02, KPU-35 or vehicle were administered. Treatments with KPU-02 or KPU-35 were well tolerated. Mice were observed for two additional days. Tumor area, blood flow rate, and vascular density within and surrounding the tumor were visualized. Real-time observations were recorded at various time-points using still photos and video microscopy.

This study demonstrates the rapid collapse of the central vasculature after the single i.v. treatment with either KPU-02 or KPU-35. The changes in vascular functions resulted in a significant central tumor necrosis, without an observed effect on the vasculature in the surrounding fat pad or skin (FIG. 30). These observations support the selectivity and specificity of KPU-02 and KPU-35, which both individually can disrupt established tumor vasculature.

In Vivo Activity of KPU-02 in Human Tumor Xenografts

Figure 32:
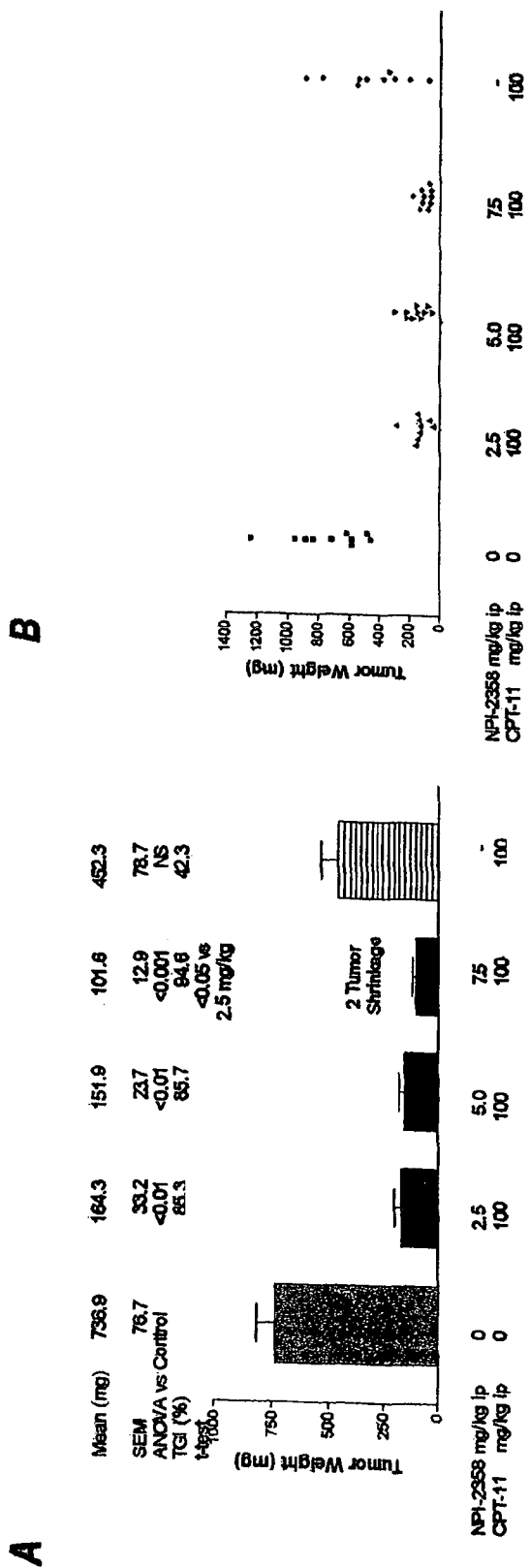
FIG. 32 depicts effect of KPU-02 in combination with CPT-11 on the excised tumor weight in the HT-29 human colon tumor xenograft model.
Figure 33:
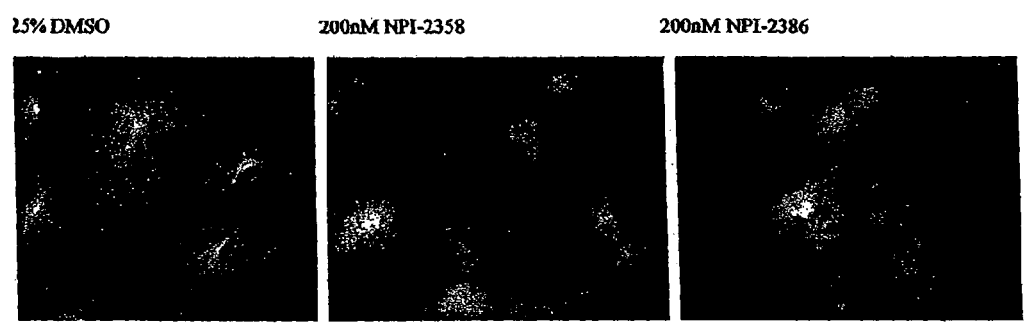
FIG. 33 depicts rapid tubulin depolymerization in HuVEC cells induced by KPU-02 and KPU-35.

When KPU-02 was administered with CPT-11 (Irinotecan), Taxotere or Paclitaxel, marked antitumor activity was seen in the human colon (HT-29), breast (MCF-7; MDA-MB231) and lung (A549) tumor xenograft models (Table 21). The effect of KPU-02 in the HT-29 model was robust, reproducible in three studies, and showed a dose-dependent effect i.e., 7.5 mg/kg was statistically greater than 2.5 mg/kg (FIGS. 32, 33).

In vitro Activity of KPU-02 and KPU-35 in HuVEC Cells

The above-described in vivo effects of KPU-02 and KPU-35 on tumor vasculature were supported by the in vitro effects of the same compounds in HuVEC cells. Human umbilical vein endothelial cells are considered a good in vitro model of tumor endothelium, which is considered "immature". Tumor endothelium lacks supporting vascular mural cells and is increasingly reliant on microtubule network for integrity of the tumor vasculature. Therefore, disruption of the microtubule network tumor causes vascular collapse.

KPU-02 Induces Rapid Tubulin Depolymerization in Hu VEC Cells.

Human umbilical vein endothelial cells (HuVECs; Cambrex CC2519A) were maintained at subconfluent densities in EGM-2 (Cambrex) media. The cells were cultured in an incubator at 37° C. in 5% $CO_2$ and 95% humidified air. For tubulin staining assays, HuVEC cells were seeded at a density of $3 \times 10^4$ cells/ml in EGM-2 on tissue culture compatible coverslips (Fisher). The plates were returned to the incubator for 2 days.

Stock (20 mM) solutions of the test compounds were prepared in 100% DMSO. 400× concentrated dilutions of the compounds were prepared in 100% DMSO. 5 µl volumes of the dilutions were added to individual wells resulting in a final concentration of 200 nM. The final concentration of DMSO was 0.25% in all samples. The plates were returned to the incubator for 30 minutes. HuVEC cells were treated for 30 min with 200 nM KPU-02 or KPU-35.

The cells were rinsed in dPBS before fixation in 10% (v/v) neutral buffered formalin for 10 minutes at room temperature. Following fixation, α-tubulin was visualized by indirect immunofluorescence. Specifically, the cells were permeabilized in 0.2% (v/v) triton X-100/dPBS for 10 minutes. The cells were washed prior to transferring the coverslips to a humidified chamber, the coverslips were blocked for two hours in antibody buffer (2% (w/v) BSA/0.1% (v/v) Tween 20/dPBS). The coverslips were incubated with 50 μl of 0.1 μg/ml mouse a-tubulin (Molecular Probes) in antibody buffer for 1 hour before washing and incubation with 50 μl of 1 μg/ml goat anti-mouse FITC (Jackson ImmunoResearch Laboratories) for one hour in the dark. Finally, the cells were washed and treated with 2 μg/ml DAPI (Molecular Probes) for 10 minutes before rinsing in $H_2O$ and mounting with Vectashield (Vector Labs) mounting media. The cells were imaged using a 60× oil immersion objective on an upright microscope (Olympus BX51). The images were digitally captured using a CCD camera and Magnafire 2.0 software (Olympus). Post image processing was performed in Photoshop Elements 2.0 (Adobe) and in Microsoft Powerpoint.

FIG. 33 shows that KPU-02 and KPU-35 rapidly induce tubulin depolymerization in HuVEC cells.

KPU-02 Induces Dose Dependent Monolayer Permeability in HuVEC Cells.

Human umbilical vein endothelial cells (HuVECs; Cambrex CC2519A) were maintained at subconfluent densities in EGM-2 (Cambrex) media. The cells were cultured in an incubator at 37° C. in 5% $CO_2$ and 95% humidified air. For monolayer permeability assays, HuVEC cells were seeded at $1 \times 10^5$ cells/ml in EGM-2 media on Fibronectin-coated 3.0 μm Fluoroblok inserts (Becton Dickinson) in 24-well plates. The plates were returned to the incubator for 4 days to allow the cells to reach confluency.

Stock solutions (20 mM) of the test compounds were prepared in 100% DMSO. 10× concentrated serial dilutions of the compounds were prepared in EGM-2. 10 μl volumes of the serial dilutions were added to the test inserts in duplicate resulting in final concentrations ranging from 2 μM to 2 nM. The final concentration of DMSO was 0.25% in all samples. The cells were treated with 2 nM-2 μM KPU-02 for 15 minutes.

FITC-Dextran (50 mg/ml) in dPBS (38.2 kDa; Sigma) was diluted 2.5 fold in EGM-2, 10 μl of FITC-Dextran was added to each insert. The final concentration of FITC-Dextran was 1 mg/ml. The plates were returned to the incubator and 30 minutes later the fluorescence of the lower chambers of the 24 well plates was read using a Fusion fluorimeter (Packard Bioscience) with $\lambda_{ex}$=485 nm and $\lambda_{em}$=530 nm filters.

Figure 34:
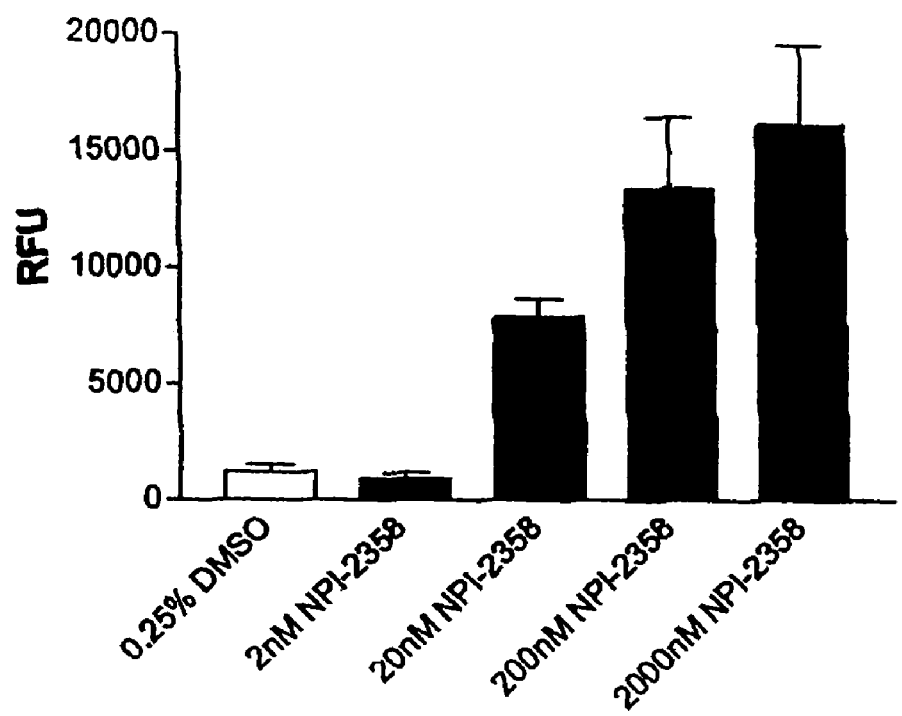
FIG. 34 depicts effect of KPU-02 on monolayer permeability in HuVEC cells.

FIG. 34 shows that KPU-02 is able to induce monolayer permeability in a dose dependent manner. The results shown in FIG. 34 represent the mean ±S.D. of three independent experiments.

Blood Flow in the P22 Rat Sarcoma Model with $^{125}$I-IAP

Figure 35:
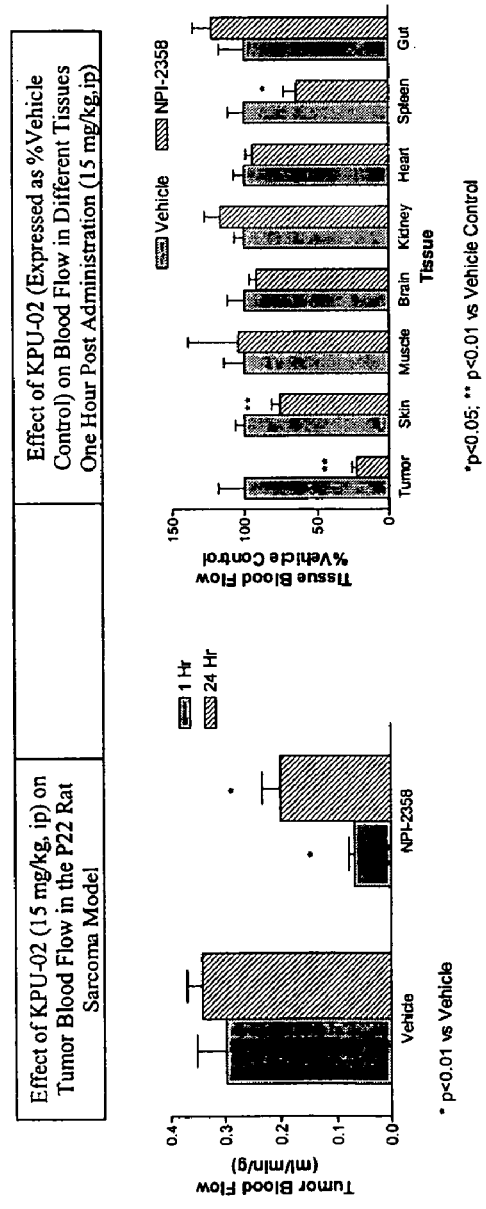
FIG. 35 depicts the effect of KPU-02 on tumor blood flow in the P22 rat sarcoma model using the 125I-IAP technique.

Tumor blood flow was assessed in a model using a quantitative $^{125}$I-iodoantipyrine (IAP) technique in rats bearing a P22 rat sarcoma. KPU-02 (15 mg/kg, IP) markedly and selectively reduced tumor blood flow to 23% of vehicle at 1 hour after administration; blood flow remained markedly reduced 24 hours later (59% vehicle). In contrast, blood flow in non-tumor tissues was affected to a much lesser extent at 1 hour (see FIG. 35).

Figure 36:
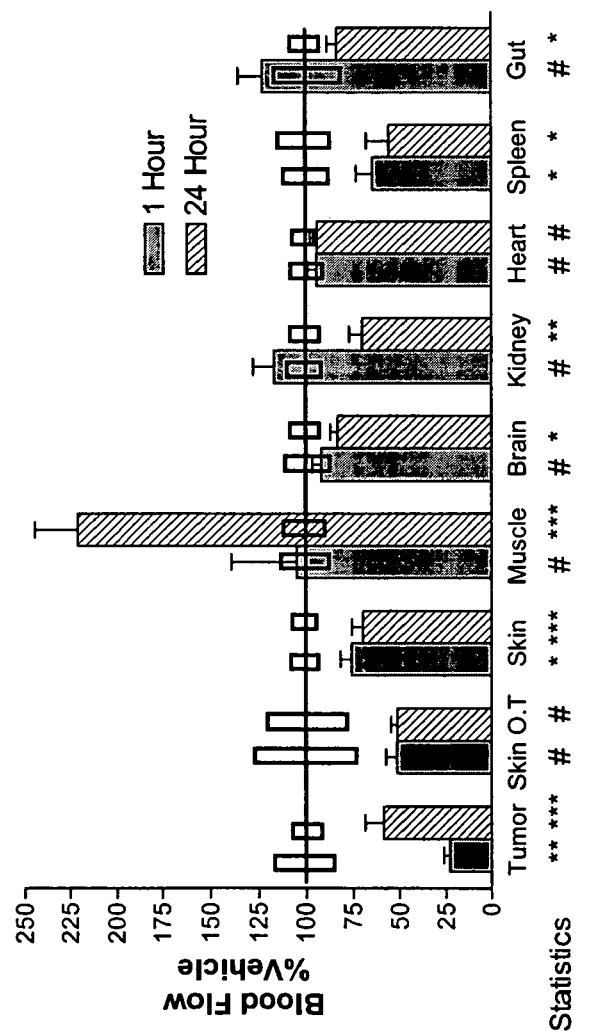
FIG. 36 depicts the effect of KPU-02 15 mg/kg IP (expressed as % vehicle control) on blood flow in different tissues 1 and 24 hours post-dose.

The reduction in blood flow at 24 hours post-dose was more variable between tissues for KPU-02 compared to vehicle, as shown in FIG. 36. The blood flow to the tumor was the most affected other tissues exhibited a small reduction in blood flow skeletal muscle blood flow appeared to be increased at 24 hours post-dose.

The effects of KPU-02 observed at 1 hour appear to be longer lasting and more selective for tumor blood flow than that previously reported for CA4P using the same technique.

Figure 37:
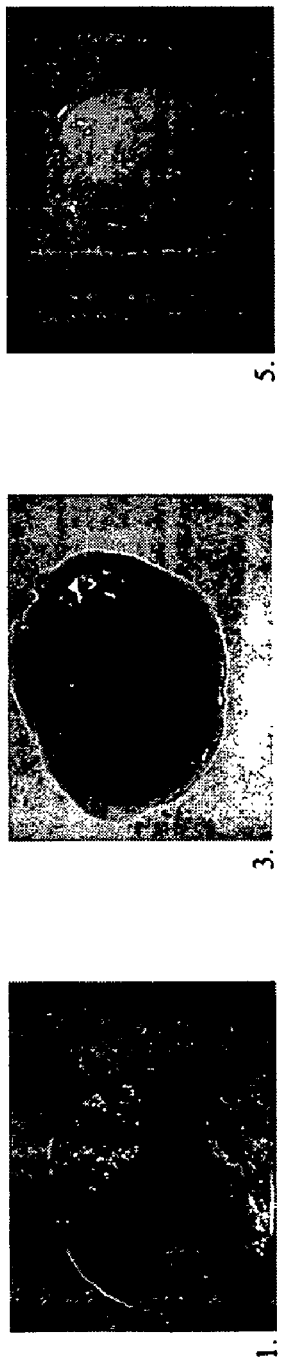
FIG. 37 depicts the tumor necrosis induced by KPU-02 7.5 and 15.0 mg/kg IP in the P22 rat sarcoma model FIG. 38 lists the activity of various tBu-dehydro-PLH derivatives at HT-29 cells.

In an experiment with the P22 rat sarcoma model, it was demonstrated that KPU-02 7.5 and 15 mg/kg IP (n=2 per dose) produced a dose-dependent tumor necrosis by 24 hours post-dose, with the highest dose resulting in an almost total necrosis of the tumor as shown in FIG. 37. All tumors in the KPU-02-treated rats showed evidence of necrosis, whereas tumors in vehicle-treated rats did not. The VTAs that have entered into the clinic (e.g., CA4P, ZD6126, AVE8062) show similar qualitative effects on tumor blood using the IAP methodology (or similar technology) to demonstrate reduced blood flow in the P22 rat sarcoma tumor and in humans using the dce-MRI technique. See Stevenson J P, Rosen M, Sun W, Gallagher M, Haller D G, Vaughn D, et al., "Phase I trial of the antivascular agent combretastatin A4 phosphate on a 5-day schedule to patients with cancer: magnetic resonance imaging evidence for altered tumor blood flow," *J Clin Oncol* 2003;21(23):4428-38; Evelhoch J L, LoRusso P M, He Z, DelProposto Z, Polin L, Corbett T H, et al., "Magnetic resonance imaging measurements of the response of murine and human tumors to the vascular-targeting agent ZD6126," *Clin Cancer Res* 2004;10(11):3650-7; and Gadgeel S M, LoRusso P M, Wozniak A J, Wheeler C. "A dose-escalation study of the novel vascular-targeting agent, ZD6126, in patients with solid tumors," *Proc Am Soc Clin Oncol* 2002;21:abstract 438; each of which is hereby incorporated by reference in its entirety.

Combination Therapy with Microtubule Targeting Agents

The findings that VTAs selectively damage the vasculature in the central part of the tumor versus the periphery, which recovers functionality, support using these agents in combination with chemotherapeutics (Taxol, Vinblastine and Cisplatin), radiation and angiogenesis inhibitors directed against VEGF and EGF. The new VTAs will supplement rather than supplant these therapies and should provide for greater antitumor activities.

Treatment of Other Conditions

In addition to cancer, other diseases may be treated using the VTAs disclosed herein. Conditions include other neoplasms, retinopathies, and any other condition or disease that relies upon blood supply, preferably blood supply from new vasculature in order to remain viable and/or proliferate.

Many conditions are associated with excessive or inappropriate vasculature. Examples of conditions associated with excessive vasculature include inflammatory disorders such as immune and non-immune inflammation, rheumatoid arthritis, chronic articular rheumatism and psoriasis; disorders associated with inappropriate or inopportune invasion of vessels such as diabetic retinopathy, neovascular glaucoma, retinopathy of prematurity, macular degeneration, corneal graft rejection, retrolental fibroplasia, rubeosis, capillary proliferation in atherosclerotic plaques and osteoporosis; and cancer associated disorders, including for example, solid tumors, tumor metastases, blood born tumors such as leukemias, angiofibromas, Kaposi sarcoma, benign tumors such as hemangiomas, acoustic neuromas, neurofibromas, trachomas, and pyogenic granulomas, as well as other cancers which require vascularization to support tumor growth. Additional examples of vasculature-dependent diseases include, for example, Osler-Webber Syndrome; myocardial angiogenesis; plaque neovascularization; telangiectasia; hemophiliac joints and wound granulation. Furthermore, excessive vasculature is also associated with clinical problems as part of biological and mechanical implants (tissue/organ implants, stents, etc.). The instant compounds and compositions can be used to target vasculature, in preferably to preferentially target disease vasculature over non disease tissue vasculature, and thus the compounds and compositions can be used in the treatment of such conditions. Other diseases in which vascularization plays a role, and to which the instant compounds and compositions can be used, are known by those of skill in the art.

Examples of retinopathies include age-related macular degeneration (ARMD), diabetic retinopathy, and the like. Pathological angiogenesis is a major contributing factor to a number of retinopathies that collectively are major cause of blindness in the developed world. Kahn and Hiller Am J Ophthalmol (1974) 78, 58-67, which is incorporated herein by reference in its entirety. For example, retinal and disk neovascularization occurs in 30-50% of patients with diabetic retinopathy for more than 20 years. Yanko et al Retina (2003) 23, 518-522, which is incorporated herein by reference in its entirety. Furthermore, subretinal neovascularization is a serious complication in ~10% of patients with macular degeneration. Ferris et al Arch Ophthalmol (1984), 102, 1640-1642, which is incorporated herein by reference in its entirety.

Vascular targeting agents such as Combretastatin A-4 (CA-4) have been shown to cause the disruption of neovessels in non-neoplastic tissue. Griggs et al Br J Cancer (2001) 84, 832-835, which is incorporated herein by reference in its entirety. Additionally, CA-4P was shown to inhibit the retinal neovascularization that occurs during proliferative retinopathy. Griggs et al Am J Path (2002) 160, 1097-1103, which is incorporated herein by reference in its entirety. Finally, CA-4P Phosphate was demonstrated to suppress the development of VEGF induced retinal neovascularization and inhibit the development and/or cause partial regression of choroidal neovascularization. Nambu et al Invest Ophthalmology & Visual Sci (2003) 44, 3650-3655, which is incorporated herein by reference in its entirety. The compounds disclosed herein can be used to treat retinopathies. For example, the methodologies of Griggs (2001 and 2002) and Nambu are used to treat retinopathies. Furthermore, the compounds and compositions disclosed herein can be used to treat such retinopathies by applying the compounds and/or compositions to the target area in an effective amount for reducing vascular density and/or vascular proliferation.

EXAMPLE 13

Structure-Activity Relationship

Figure 38:
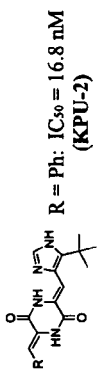

The effect of activity from various modifications on the phenyl ring of tBu-dehydroPLH is illustrated by the data in FIG. 38. It is apparent that substitution with relatively hydrophobic and smaller functional groups at the m- or o-position increased or maintained the cytotoxic activity at HT-29 cells while substitutions at the p-position decreased activity. While not being bound to any particular theory, this data suggests a rigorous recognition of the phenyl ring by tubulin.

Figure 40:
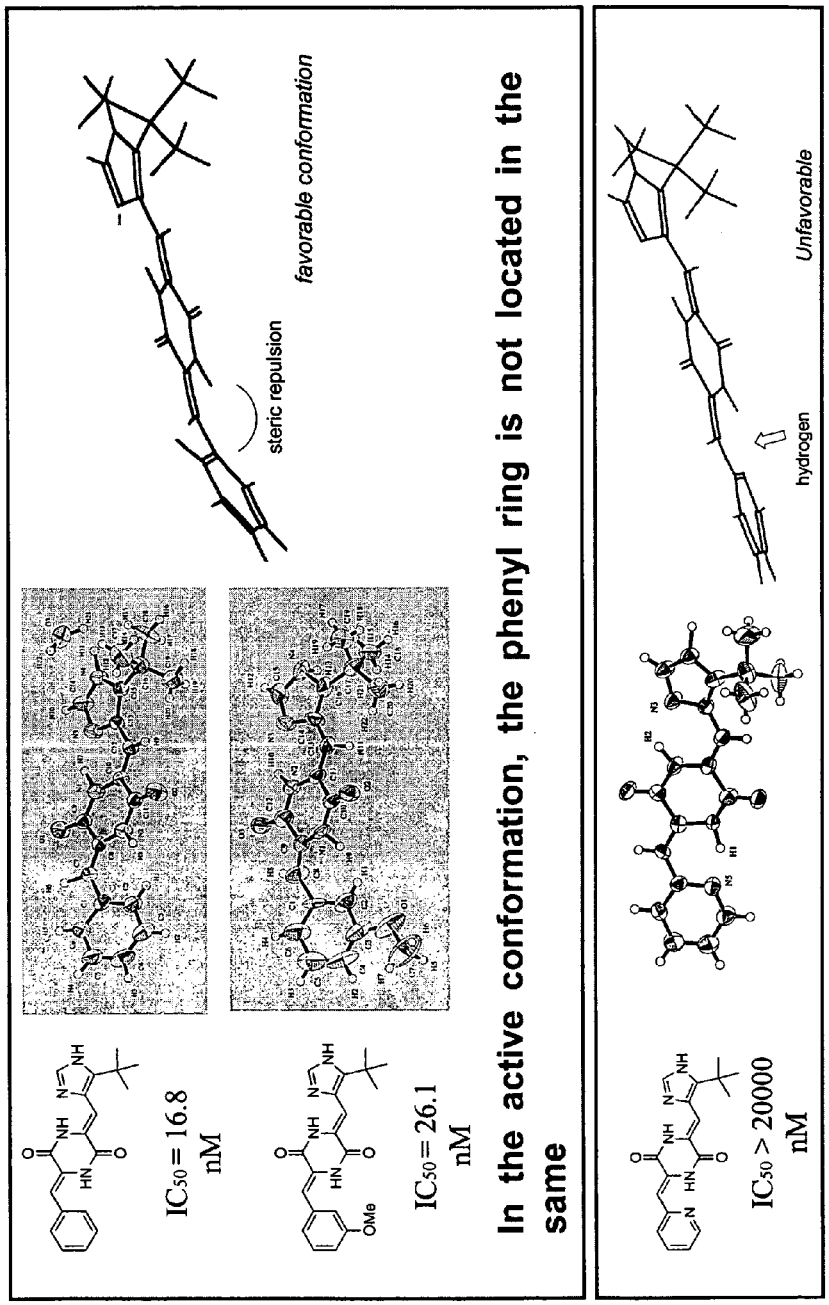
FIG. 40 depicts X-ray crystallographic analysis of tBu-dehydro-PLH derivatives.

3D-QSAR (CoMFA) analysis (see FIG. 39) also supports the existence of sterically favorable fields at m- and o-positions and sterically unfavorable fields exist at the p-position. X-ray crystal analysis (see FIG. 40) indicates that the conformation of potent derivatives require a certain amount of dihedral angle between the phenyl ring and the pseudo-tricyclic cor template formed by DKP and imidazole rings. Thus, modification with the appropriate conformational restriction of the phenyl ring may elicit potent activity. While not being bound to any particular theory, it may be that the binding mode of PLH derivatives at the chochicine binding site of tubulin is different from that of colchicines and its known homologues.

EXAMPLE 14

In Vitro Action on Microtubules

Purification of Microtubule Protein and Tubulin

Microtubule protein (MTP) was prepared as previously described (Farrell K W and Wilson L. (1987) Tubulin-colchicine complexes differentially poison opposite microtubule ends. *Biochemistry* 23(16):3741-8, which is incorporated herein by reference in its entirety). MTP preparations consisting of 70% tubulin and 30% microtubule-associated proteins (MAPs) were isolated from bovine brain by three cycles of warm polymerization and cold depolymerization in PEM100 (100 mM 1-4 piperazinediethansulfonic acid (Pipes), 1 mM MgSO$_4$, 1 mM EGTA, pH 6.8) and 1 mM GTP. MTP was drop-frozen in liquid nitrogen and stored at −70° C. until use. Tubulin was purified from microtubule protein by phosphocellulose chromatography (PC-tubulin) and stored in PEM50 (50 mM Pipes, 1 mM MgSO$_4$, 1 mM EGTA, pH 6.8). Protein concentration was determined by a Bradford assay

TABLE 21

Effect of KPU-02 in Combination with Chemotherapy in Human Tumor Xenograft Models

| Tumor Model (# Studies) | Dose KPU-02 (mg/kg ip) | Reference Chemotherapeutic Agent | Tumor Growth Inhibition (%) | | Tumor Regression (#/total) | |
|---|---|---|---|---|---|---|
| | | | Reference | KPU-02 + Reference | Reference Agent | NPI + Reference |
| Colon HT-29 (3) | 7.5 Days 1, 4, 8, 11, 15 | CPT-11 Days 1, 8, 15 | 37 ± 3 | 79 ± 8 | 0/30 | 4/30 |
| Breast MCF-7 (2) | 7.5 qdx5 | Taxotere Days 1, 3, 5 | 12; 58 | 26; 81 | 0/20 | 3/20 |
| Breast MDA- 231 (1) | 7.5 Days 1, 4, 8, 11, 15 | Paclitaxel qdx5 | 53 | 71 | 1/10 | 0/10 |
| Lung A549 (1) | 7.5 qdx5 | Taxotere Days 1, 3, 5 | 26 | 74 | 0/10 | 0/10 |

(Sigma Chemicals, St. Louis, Mo.) using bovine serum albumin as the standard (Bradford, 1976).

Test Agents

Stock solutions of KPU-02 were prepared at a concentration of 20 mM in DMSO. Stock solutions of Combretastatin A4 (National Cancer Institute, Bethesda, Md.) (CA4) was prepared at a concentration of 5 mM in DMSO. Colchicine (Sigma Chemicals, St. Louis, Mo.) (CLC) was prepared at a concentration of 3 mM in water. All agents were shielded from ambient light with amber Eppendorf tubes. Serial dilutions were made in DMSO and/or PEM50 to the desired concentrations.

Determination of Steady-State Microtubule Polymer Mass

MTP (2 mg/ml) was polymerized into microtubules in the presence of a range of drug concentrations in PEM100 containing 1 mM GTP and a final DMSO concentration of 0.5%. Samples were monitored by light scattering at 350 nm at 37° C. for 75 minutes.

Polymerization reactions were centrifuged and the microtubule protein concentrations in the supernatant, a measure of the soluble tubulin at steady state, and the pellet, a measure of the microtubule polymer, were used to calculate the inhibition of polymerization. After incubation, polymerized microtubules were separated and sedimented from unpolymerized MTP by centrifugation (150,000×g, 45 minutes, 37° C.). The supernatant was removed, and the microtubule pellets were depolymerized in deionized $H_2O$ (24 hours, 0° C.) before protein determination by the Bradford assay.

The percent inhibition was calculated in two ways and the values obtained from the two ways were compared. In one way, a ratio of the microtubule protein in the pellet, drug to no drug, was calculated. Another ratio of microtubule protein in the pellet to the supernatant, drug to no drug, was also calculated. The numbers were in close agreement and the former values were used because they were subject to less variance and experimental perturbation.

Microtubule Mean Length Distributions

Transmission electron microscopy was used to determine the mean length distribution of microtubules in the absence or presence of tested agent. At 75 minutes and prior to sedimentation, 10 μl aliquots from the polymer mass experiments were fixed by dilution into 290 μl PEM100-buffered 0.2% glutaraldehyde. Thirty microliters of fixed sample was settled onto formvar-coated 150 ICG mesh electron microscope grids for 90 seconds. Excess sample was wicked off with Whatman filter paper. Thirty microliters of cytochrome C (1 mg/ml) was applied for 30 seconds to enhance protofilament resolution and facilitate negative staining. Uranyl acetate (1.5%) was applied for 20 seconds and the excess was wicked off. Grids were viewed in a Jeol electron microscope-1200 EX11 at 2000× and 30,000× magnification. The Zeiss MOPIE was used to determine microtubule length distributions and mean lengths for at least 100 microtubules per sample.

CLC Competition Assays

PC-tubulin (0.2 mg/ml) was incubated in PEM50 with 1 mM GTP, 1% DMSO, 10 μM of tested agent and 7-25 μM [$^3$H] CLC for 120 minutes at 37° C. Measurement of [$^3$H] CLC binding was followed by DEAE-cellulose filter-binding assay as described previously (Wilson, 1970). This method depends on the adsorption of tubulin to filter paper impregnated with DEAE-cellulose. Whatman DE81 filter paper was pre-wet with PEM50 prior to sample application. The total 100 μl reaction volume was applied to 2.5 cm disks of filter paper, over parafilm, on ice. The paper disks were washed by immersion in five successive 50 ml changes of PEM50, 5 min/wash, 4° C., to remove all unbound colchicine. The paper disks with adhering tubulin-bound colchicine were then counted directly in a scintillation vial containing 2 ml of Beckman Coulter Ready Protein solution (Fullerton, Calif.). All of the disks were washed together. Negligible binding of unbound CLC to the paper disks occurred in controls, either in the presence of absence of tubulin.

The $K_i$ values were calculated by linear regression of a double reciprocal plot of the experimental data in Microsoft Excel. The $K_m$ value of tubulin for CLC under the experimental conditions was first determined, with x intercept equal to $-1/K_m$. $K_{m\,app}$, $K_m$ in the presence of drug, was determined experimentally. The $K_i$ was determined using the relationship $K_{m\,app}=\alpha K_m$, and for competitive inhibition $\alpha=K_m(1+[I]/K_i)$.

Fluorescence Spectroscopy

Fluorescence measurements were performed using a Perkin-Elmer LS50B spectrofluorimeter. PC-tubulin (0.2 mg/ml) was incubated in PEM50, 2 mM GTP, 3% DMSO, with 0-30 μM KPU-02. The interaction of KPU-02 with tubulin was reported by 4,4'-dianilino-1,1'-binaphthyl-5,5'-disulfonic acid, dipotassium salt (bis-ANS; Molecular Probes, Eugene, Oreg.) fluorescence, with an excitation wavelength of 395 nm and an emission wavelength maximum of 487 nm. Excitation and emission band passes were 10 nm. This experiment was performed twice.

The bis-ANS fluorophore probes the hydrophobic surface of proteins and a change in intensity of the bis-ANS fluorescence signal is a result of a change in the solvent accessible surface area of a protein. If there is some conformational change that changes the tubulin-bis-ANS interaction upon ligand binding, then bis-ANS can be used to report binding.

PC-tubulin (0.2 mg/ml) was incubated with 0-30 μM KPU-02 at 25° C. for 20 minutes. Bis-ANS (25 μM) was then added and relative fluorescence intensities of samples were measured at 25° C. within 15 minutes. Buffer blank spectra were collected and showed that KPU-02 plus bis-ANS produced negligible fluorescence in the experimental wavelength range.

The $K_d$ was determined by fitting experimental data in Sigmaplot and Microsoft Excel using the equation $F=((-F_{max}\times L)/(K_d+L))+F_0$ where F is the fluorescence intensity of bis-ANS-tubulin in the presence of total ligand concentration L, $F_{max}$ is the bis-ANS fluorescence intensity of fully liganded tubulin, and $F_0$ is bis-ANS fluorescence in the absence of drug. $F_{max}$ was determined by plotting $1/(F_0-F)$ versus $1/L$ and extrapolating to $1/L=0$. The fraction of binding sites B occupied by KPU-02 was determined using the following relationship: $B=(F_0-F)/(F_0-F_{max})$. The concentration of free ligand was determined with Lfree=L−B[C] in which [C] is the molar concentration of ligand-binding sites, assuming a single binding site per tubulin dimer.

Inhibition of Microtubule Polymerization by KPU-02

KPU-02, CA4, and CLC were assayed for their ability to alter the polymerization of MAP-rich tubulin (MTP) (2 mg/ml) in a cell-free system in vitro. Initially, inhibition of polymerization was assayed using phosphocellulose-purified, microtubule-associated protein-free tubulin (data not shown). KPU-02 was a more potent inhibitor towards MTs assembled with glycerol and DMSO seeds as compared to MTs assembled in the presence of MAPs that copurify with tubulin. Although microtubule polymer in the absence of stabilizing MAPs did not reach steady state over a 2-hour period, these assays demonstrated that KPU-02 interacts directly with purified tubulin and that it does not exert its primary effect through a MAP.

Figure 44A:
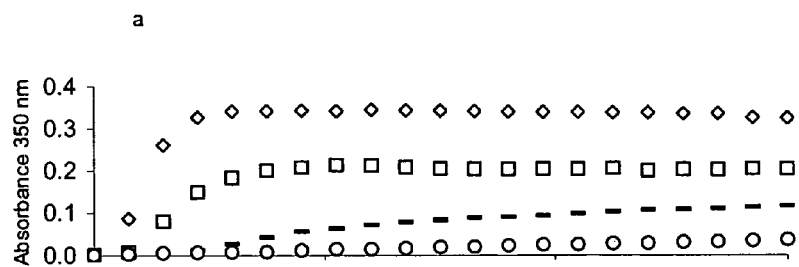
FIG. 44A depicts turbidity spectra of microtubule protein polymerization in the presence of DMSO drug vehicle (◇), 1.25 μM (□), 2.5 μM (−), and 5 μM (○) KPU-02.
Figure 44B:
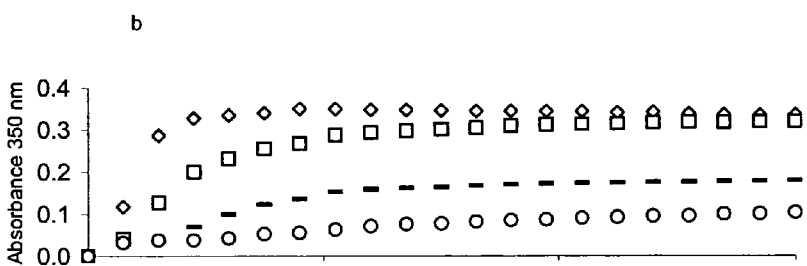
FIG. 44B depicts turbidity spectra of microtubule protein polymerization in the presence of DMSO drug vehicle (◇), 1.25 μM (□), 2.5 μM (−), and 5 μM (○) CA4.
Figure 44C:
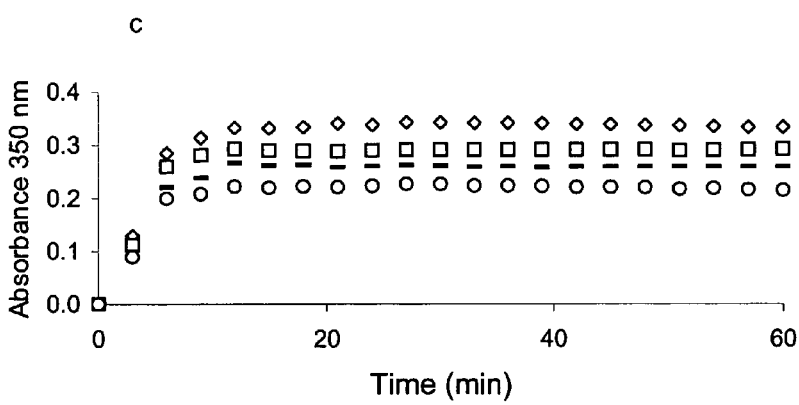
FIG. 44C depicts turbidity spectra of microtubule protein polymerization in the presence of DMSO drug vehicle (◇), 1.25 μM (□), 2.5 μM (−), and 5 μM (○) CLC.
Figure 45:
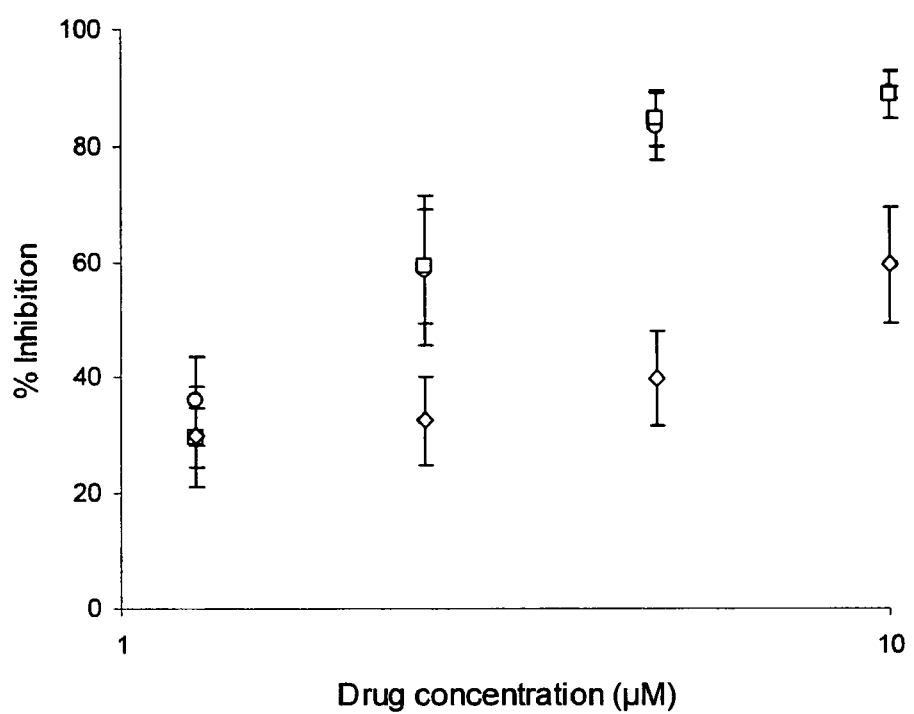
FIG. 45 depicts inhibition of MT in the absence or presence of a range of KPU-02 (○), CA4 (□), and colchicine (◇) concentrations.

KPU-02 and CA4 inhibited MT polymerization more powerfully than CLC as measured by light scattering (FIG. 44) and sedimentation analysis (FIG. 45). MTP (2 mg/ml) was polymerized into microtubules in the presence of a range of drug concentrations and allowed to reach steady state as monitored by light scattering at 350 nm. FIG. 41 depicts turbidity spectra of microtubule protein polymerization in the presence of DMSO drug vehicle (◇), 1.25 µM (□), 2.5 µM (—), and 5 µM (○) NPI-2358 (a), CA4 (b) and CLC (c) KPU-02 and CA4 inhibited MT polymerization with comparable potencies. FIG. 45 depicts inhibition of microtubule polymerization in the absence or presence of a range of KPU-02 (○), CA4 (□), and colchicine (◇) concentrations. The total polymer mass after 75 minutes of assembly was determined by sedimentation. Error bars are standard deviation values from three experiments. The concentration at which polymerization was inhibited 50% ($IC_{50}$), is 2.4±0.4 µM for KPU-02, 2.2±0.3 µM for CA4, and 7.6≠2.4 µM for CLC (Table 22). (Variances obtained by statistical analysis are reported as standard deviation values unless stated otherwise). At concentrations over the $IC_{50}$ for in vitro polymerization of MAP-rich tubulin, MTP displays aggregation kinetics, suggesting that KPU-02 and CA4 sequester protein to prevent microtubule assembly.

TABLE 22

Microtubule polymerization inhibition concentrations.

| Compound | Polymer Mass Ave. IC50 ± sd (µM) | n |
|---|---|---|
| KPU-02 | 2.4 ± 0.4 | 4 |
| CA4 | 2.2 ± 0.3 | 3 |
| CLC | 7.6 ± 2.4 | 3 |

As shown in FIG. 44, all three of the tested agents produced a concentration dependent inhibition of the extent of microtubule polymerization from 1.25-5 EM. There are two important differences to note among the spectra. First, the initial rate of increase in absorbance over time decreases with increasing drug concentration (FIGS. 44A and 44B). The spectra indicate that there is a lag period for MT formation in the presence of KPU-02 and CA4. Drugs that significantly and rapidly reduce the soluble, assembly-competent pool of tubulin would decrease the initial rate of polymerization. In contrast, the initial rate of polymerization is unchanged at all concentrations of CLC (FIG. 44C). Second, MTP in the presence of KPU-02 or CA4 does not reach steady state at high drug concentrations (above 5 µM), as shown by the absorbance values that increase linearly with time (FIGS. 44A and 44B). In contrast, MTP in the presence of CLC reaches steady state at high drug concentrations (FIG. 44C).

The amount of drug required to inhibit polymerization by 50% ($IC_{50}$) was determined from the analysis of the linear relationship between the decrease in microtubule polymer sedimented by centrifugation with the increase in drug concentration (FIG. 45). The error bars in FIG. 45 represent standard deviation values from at least three independent experiments.

Figure 46B:
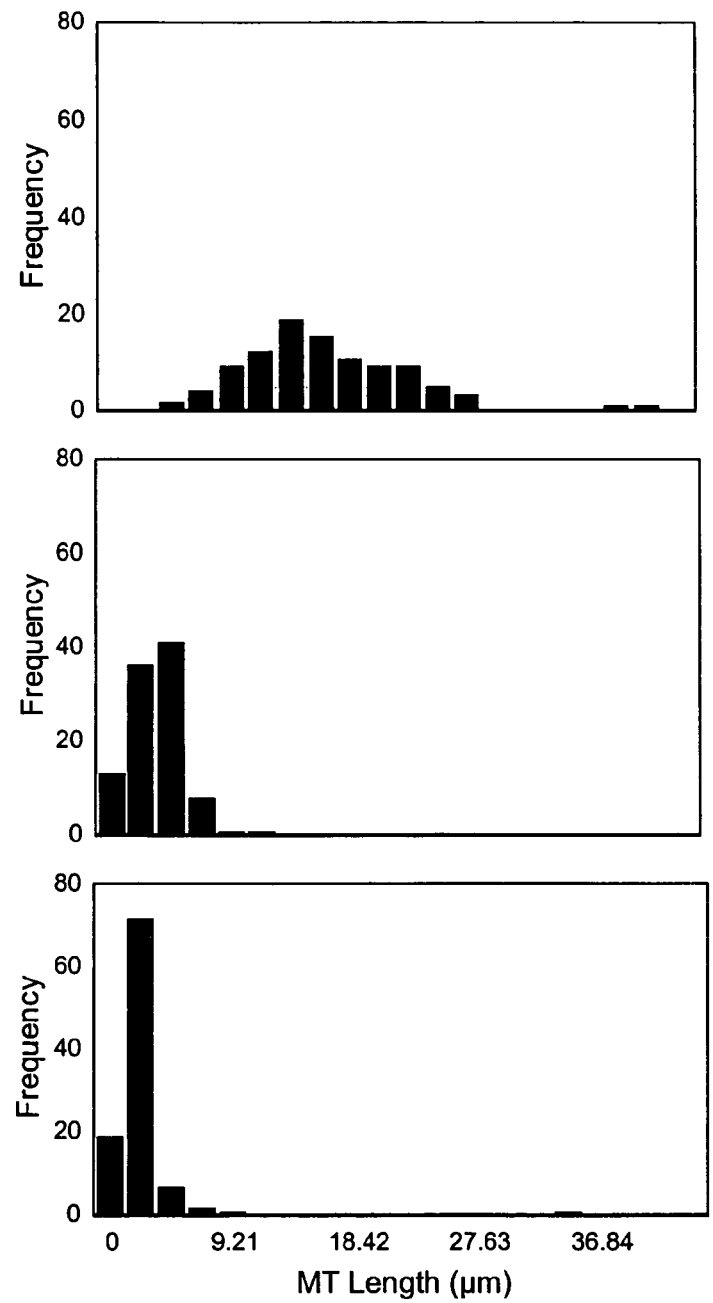
FIG. 46B depicts frequency histograms of mean microtubule lengths in vitro at steady state in the presence of CA4.
Figure 46C:
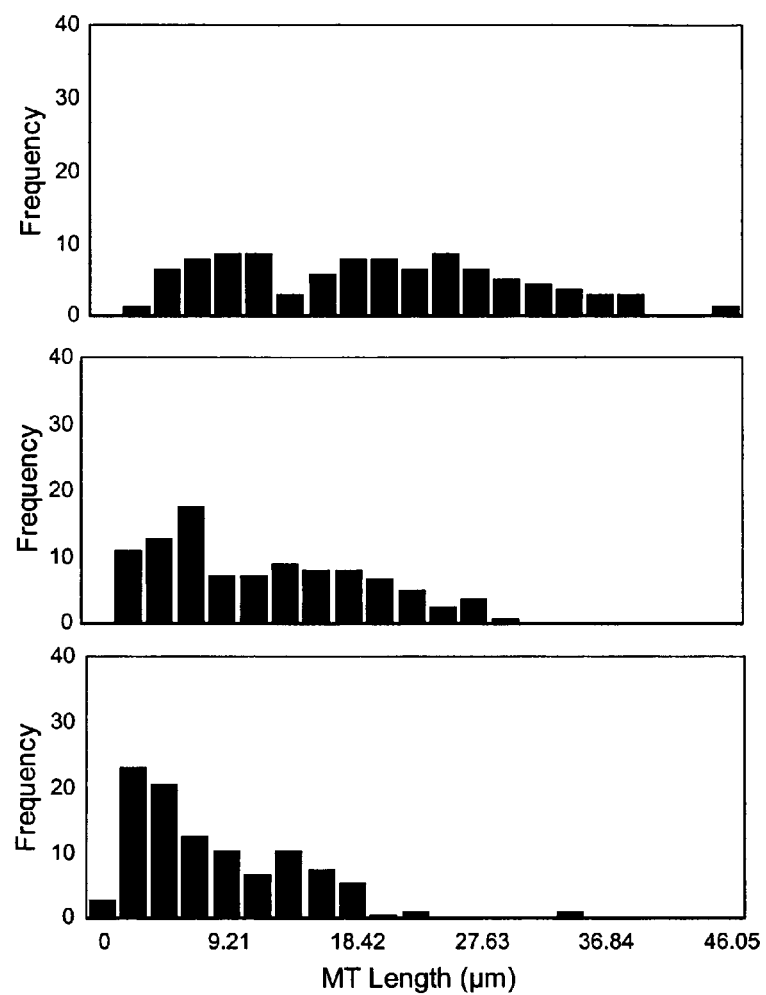
FIG. 46C depicts frequency histograms of mean microtubule lengths in vitro at steady state in the presence of CLC.
Figure 47A:
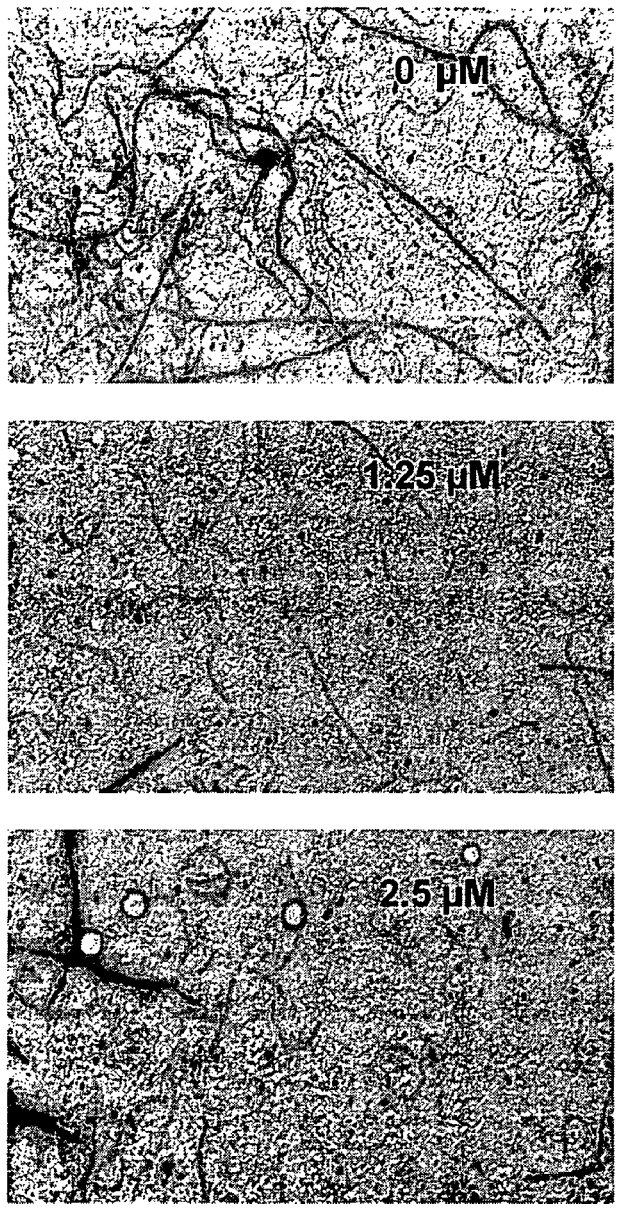
FIG. 47A depicts electron micrographs of MAP-rich microtubules formed in vitro at steady state in the presence of KPU-02.
Figure 47B:
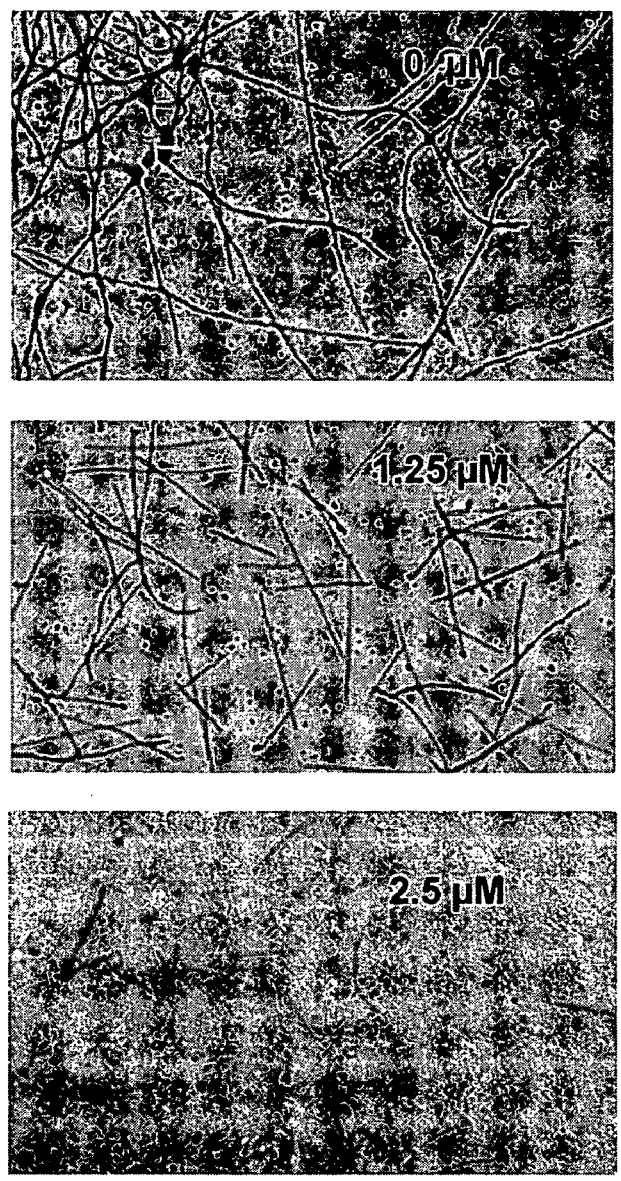
FIG. 47B depicts electron micrographs of MAP-rich microtubules formed in vitro at steady state in the presence of CA4.
Figure 48:
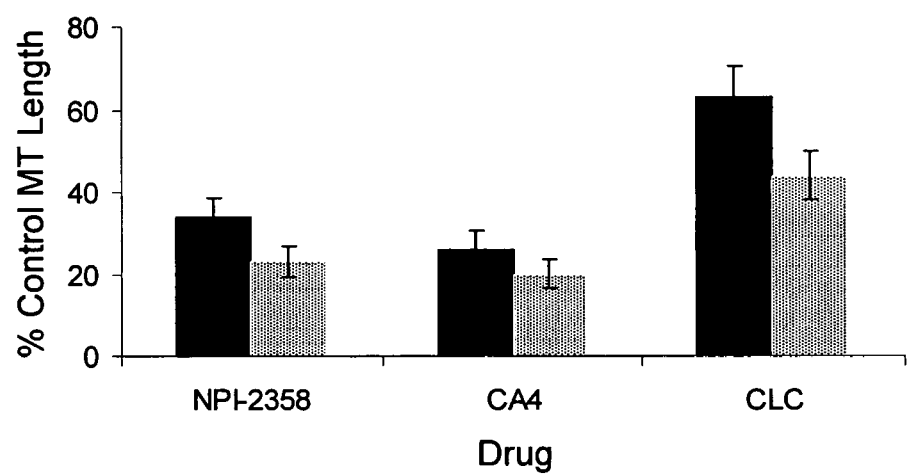
FIG. 48 depicts a graphical summary of MT length decrease at steady state in the presence of KPU-02, CA4, and colchicine.

Decrease in Mean Microtubule Length Measured by Transmission Electron Microscopy Transmission electron microscopy was performed on agent-microtubule polymerization reactions to describe the polymer formed at steady state and to evaluate conclusions drawn from the light scattering spectra. KPU-02, CA4, and CLC all decreased the lengths of the microtubules formed at steady state. MTs were progressively shorter with increasing drug concentration (FIGS. 46, 47 and 48). FIG. 46 depicts frequency histograms of mean microtubule lengths in vitro at steady state in the presence of (A) KPU-02, (B) CA4, and (C) CLC. The Zeiss MOPIE was used to determine microtubule length distributions and mean lengths. At least 100 microtubules per drug concentration were counted. FIG. 47 depicts electron microscopy used to record microtubules in the absence or presence of tested compounds. At 75 minutes, samples from polymer mass experiments were fixed and stained and viewed in a Jeol electron microscope-1200 EX11 at 2000× magnification. Representative electron micrographs of MAP-rich microtubules formed in vitro at steady state in the presence of (A) KPU-02, (b) CA4, and (C) CLC. Scale bar, 10 µM. FIG. 48 depicts a graphical summary of MT length decrease at steady state in the presence of KPU-02, CA4, and colchicine. Black bars, 1.25 µM, and shaded bars, 2.5 µM drug. In the presence of KPU-02, and CA4, MTs are progressively shorter with increasing drug concentration, until the drug concentration at which MTP displays aggregation kinetics as detected by turbidity, and no MTs are observed. Error bars are standard deviation values from the measurement of at least 100 microtubules.

KPU-02, CA4 and CLC did not affect MT nucleation. The numerous, short microtubules formed in the polymerization reactions evidence that the presence of KPU-02, CA4, or CLC does not affect nucleation. If nucleation were affected, then fewer, longer microtubules, as opposed to numerous, shorter microtubules would have been observed in drug-treated versus control samples.

KPU-02 and CA4 were comparably potent in decreasing the average MT length. At 1.25 µM, the lowest drug concentration analyzed by electron microscopy, KPU-02 and CA4 decreased mean MT length by approximately 70%, and CLC by 40% (FIG. 48).

At drug concentrations over the $IC_{50}$ for in vitro microtubule polymerization, microtubules are not observed by electron microscopy for KPU-02 and CA4. In contrast, microtubules were observed by electron microscopy for all concentrations of CLC assayed. At concentrations over the $IC_{50}$, microtubule protein in the presence of KPU-02 and CA4 displays aggregation kinetics, characterized by a linear increase in light absorbance over time (FIGS. 44A and 44B), whereas in the presence of CLC, light scattering polymer reaches steady state (FIG. 44C). Despite the observation that MTP with KPU-02 or CA4 increases absorbance at 350 nm over time, drug-specific protein aggregates were not observed.

Fluorescence Spectroscopy

Figure 49A:
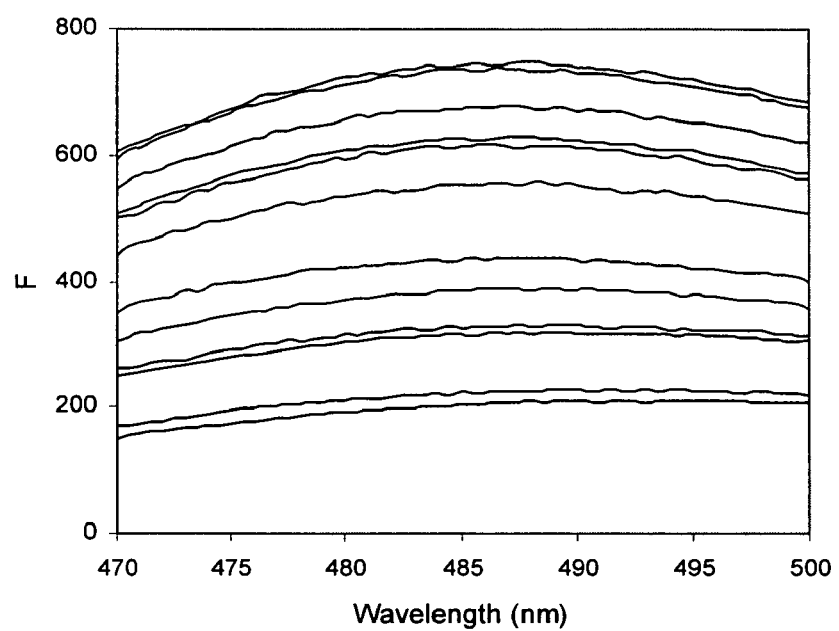
FIG. 49A depicts fluorescence emission spectra of tubulin in the presence of increasing KPU-02.
Figure 49B:
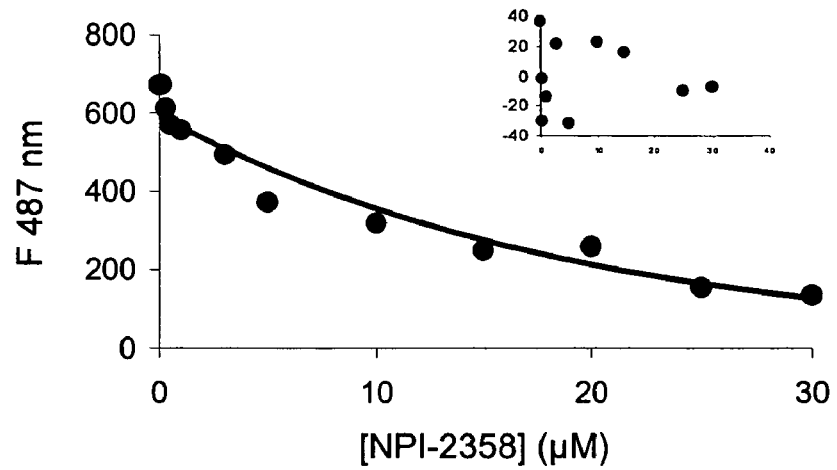
FIG. 49B depicts a fit to fluorescence emission maxima at 487 nm to obtain the $K_d$ of tubulin for KPU-02. The inset depicts residuals.
Figure 49C:
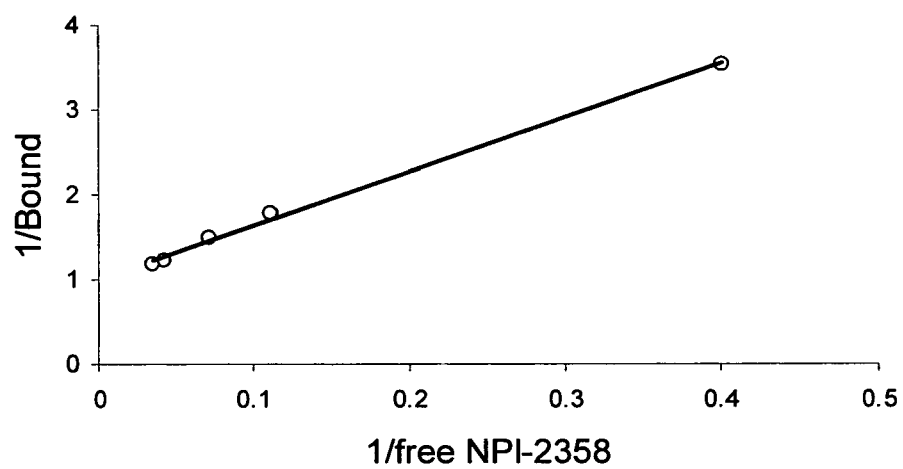
FIG. 49C depicts double reciprocal transformation of the binding data.

Tubulin (0.2 mg/ml) was incubated with a range of KPU-02 concentrations for 20 minutes at 25° C. in PEM50 and 2 mM GTP. KPU-02 quenched bis-ANS fluorescence in a concentration-dependent manner (FIG. 49A). For KPU-02 and tubulin as measured by non-linear regression analysis of bis-ANS fluorescence intensity at the emission maximum, $K_d$=10±1.6 µM (standard error) (FIG. 49B). The double reciprocal plot of the binding data, assuming a single binding site for KPU-02 per tubulin dimer, yielded a dissociation constant of 6.4 EM (FIG. 49C). The two different $K_d$ values obtained by nonlinear and linear regression analysis methods were sufficiently close and the values were considered approximately equivalent. FIG. 49A depicts fluorescence emission spectra of tubulin in the presence of increasing KPU-02. Drug binding results in quenching of bis-ANS fluorescence. FIG. 49B depicts fluorescence emission maxima at 487 nm fit to obtain the $K_d$ of tubulin for KPU-02, 10 µM, standard deviation 1.6 µM. Inset, residuals. FIG. 49C depicts the double reciprocal transformation of the binding data assuming a one mole drug/mole tubulin dimer.

Competitive Inhibition of CLC Binding

Figure 50:
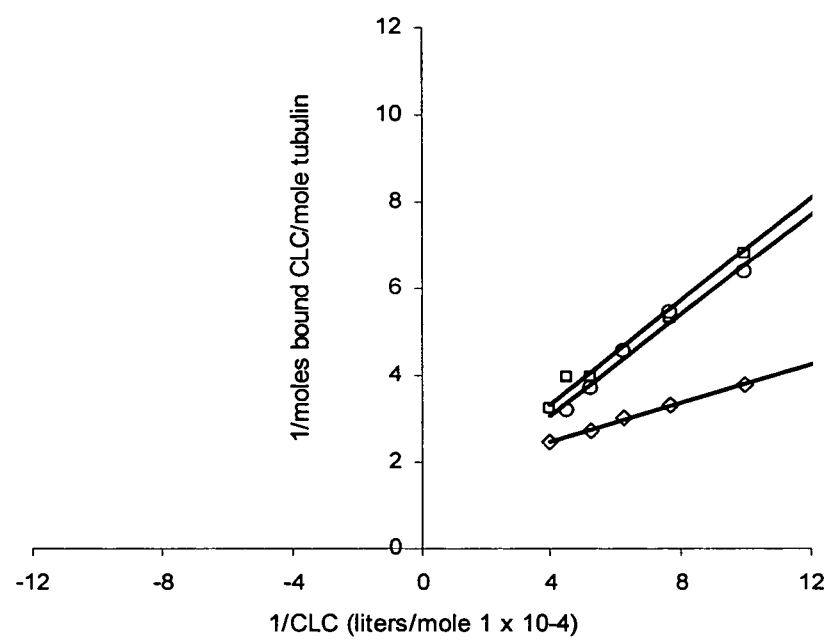
FIG. 50 depicts the graphical results of a competitive inhibition assay of colchicine binding to tubulin with various concentrations of [$^3$H]CLC in the absence (◇), or presence of 10 μM KPU-02 (○) or 10 μM CA4 (□).

KPU-02 and CA4 competitively inhibited CLC binding to tubulin (FIG. 50). FIG. 50 depicts the results of an inhibition assay where phosphocellulose-purified tubulin (0.2 mg/ml) was incubated with various concentrations of [$^3$H]CLC in the absence (0), or presence of 10 µM KPU-02 (○) or 10 µM CA4 (□). Tubulin-CLC Km was 11±4.4 µM and inhibition constants for KPU-02 and CA4 were 3.2±1.7 µM and 2.4±0.3 µM, respectively. Constants were calculated from three independent experiments. The colchicine-tubulin binding reaction is time and temperature dependent and the binding dissociation constant is $K_d$=0.1-1 µM, depending on the conditions of the assay (Wilson L and Meza I. (1973) The mechanism of action of colchicine. Colchicine binding properties of sea urchin sperm tail outer doublet tubulin. *Journal of Cell Biology* 58(3):709-19, which is incorporated herein by reference in its entirety). Under the test conditions, the $K_m$ of tubulin for CLC is 11±4.4 µM. The $K_m$ may be considered the overall $K_d$ of tubulin for CLC, however, due to the time-dependence of CLC binding, the $K_m$ is greater than the reported values for the $K_d$. The $K_i$ for KPU-02 and CA4 was 3.2±1.7 µM and 2.4±0.3 µM, respectively. The $K_i$ is defined as the amount of drug required to inhibit CLC binding by 50% and it is based on the amount of radioactive CLC bound to tubulin. The $K_i$ is a measure of the drugs' ability to compete with CLC; it is not a direct measurement of drug-tubulin binding dissociation because of the method in which binding affinity is reported.

Results

At all concentrations of CLC assayed, MAP-rich tubulin reached steady state. In contrast, at higher KPU-02 or CA4 drug concentrations, MAP-rich tubulin did not polymerize to steady state and microtubules were not observed by electron microscopy. KPU-02 and CA4 effectively decreased the concentration of available tubulin. This decrease in the pool of soluble tubulin increased the MT critical concentration and prevented polymerization. The stoichiometric amounts of KPU-02 and CA4 required to decrease in vitro polymer mass coupled with the data that microtubule protein did not reach steady state above those concentrations, suggesting that KPU-02 and CA4 act by a sequestering mechanism in which soluble tubulin is bound and prevented from polymerization.

Observations by electron microscopy on the steady state, MAP-rich microtubules formed in the presence of the tested agents were consistent with the proposed mechanism that KPU-02 and CA4 sequester tubulin. There was a concentration-dependent decrease in the average microtubule length in the presence of KPU-02, CA4, and CLC. In the presence of KPU-02 and CA4, there was a drug concentration dependent decrease in the initial rate of polymerization, indicating that these drugs reduce the tubulin available for elongation. This decrease in the initial polymerization rate was not seen with CLC due to its slow association with tubulin. Furthermore, microtubules were formed at CLC concentrations over its $IC_{50}$ for polymerization, but microtubules were not formed at KPU-02 or CA4 concentrations over their $IC_{50}$ for polymerization. While not being bound by any particular theory, the concentration of soluble tubulin bound by KPU-02 or CA4 must be under the critical concentration required for tubulin polymerization to proceed.

Binding studies indicated that tubulin has a lower affinity for KPU-02 than it has for CLC. Inhibition of CLC binding to tubulin by KPU-02 and CA4 occurred within a 20-minute incubation period, indicating that KPU-02 and CA4 association with tubulin approaches equilibrium relatively faster than for CLC (data not shown). KPU-02 competitively inhibited CLC binding to tubulin at a site overlapping with the CLC-binding site, consistent with studies characterizing phenylahistin (halimide) (Kanoh K, Kohno S, Kataka J, Takahashi J and Uno I. (1999) (−)-Phenylahistin arrests cells in mitosis by inhibiting tubulin polymerization. *The Journal of Antibiotics* 52(2):134-141, which is incorporated herein by reference in its entirety). CA4, a structural analog of CLC, also competitively inhibited CLC binding. Without being bound to any particular theory, it appears that despite sharing a tubulin binding region with CLC, KPU-02 and CA4 interact with tubulin and inhibit microtubules by a mechanism distinct from that of CLC.

EXAMPLE 15

In Vivo Action on Microtubules

Cell Culture Studies

MCF7 human breast carcinoma cells (American Type Culture Collection, Manassas, Va.) stably transfected with GFP-alpha-tubulin (Clontech, Palo Alto, Calif.) were cultured in Dulbecco's modified Eagle's medium supplemented with 5% fetal bovine serum, 0.1% penicillin/streptomycin and nonessential amino acids (Sigma) in 250-ml tissue culture flasks or 35-mm six-well plates (doubling time, 29 hours) at 37° C. in 5% $CO_2$. Cells were incubated with KPU-02, CA4, or CLC, prepared as described in Example 14, by replacing the original medium with an equal volume of medium containing the required concentration of tested agent or DMSO vehicle, and incubation was continued at 37° C. for 20 hours.

Mitotic Progression

The fraction of cells in mitosis at a given drug concentration (mitotic index) was determined in the breast cancer cell line MCF7. Cells were plated at a density of $3 \times 10^4$ cells/ml in six-well plates. After 24 hours, cells were incubated in the absence or presence of drug over a range of concentrations (1 nM to 1 µM) for 20 hours. Media were collected and cells were rinsed with versene (137 mM NaCl, 2.7 mM KCl, 1.5 mM $KH_2PO_4$, 8.1 mM $Na_2PO_4$, and 0.5 mM EDTA), detached with trypsin, and added back to the media to ensure that floating and poorly attached mitotic cells were included in the analysis. Cells were fixed with 10% formalin in PBS overnight at 37° C., permeabilized in methanol for 10 minutes, and stained with 4,6-diamidino-phenylindole (DAPI) to visualize nuclei. Stained cells were spread on coverslips in Vectashield mounting media (Burlingame, Calif.) and sealed onto slides with nail polish. Fluorescence microscopy was used to determine mitotic indices. Results were the mean and standard deviation of 4-7 experiments in which 300 cells were counted for each concentration. The $IC_{50}$ was the drug concentration that experimentally induced 50% of the maximal mitotic accumulation at 20 hours.

Immunofluorescence Microscopy

Cells were prepared as for mitotic progression, except that cells were seeded onto poly-L-lysine (50 µg/ml, Sigma) treated coverslips. On the day of staining, cells were rinsed in PBS and fixed in 10% formalin overnight at 37° C. Cells were rinsed in PBS, permeabilized in methanol at −20° C., and hydrated with PBS. Coverslips were treated with 20% normal goat serum in PBS/BSA (1%) for 1 h at room temperature. Cells were incubated in a mouse monoclonal cocktail of anti-alpha- and beta-tubulin, DM1A/DM1B diluted in PBS/BSA for 1 hour at room temperature, then stained with FITC-conjugated secondary antibody and DAPI. Coverslips were mounted using Prolong antifade media (Molecular Probes, Eugene Oreg.).

Preparation of Cells for Analysis of Microtubule Dynamics

Cells were prepared as for mitotic progression, except that to promote cell spreading, cells were seeded onto glass coverslips that had been pretreated with poly-L-lysine (50 μg/ml, Sigma) for 2 hours, followed by laminin and fibronectin (10 μg/ml, Sigma) for 1 hour at 37° C. Cells were incubated with drug or DMSO for 20 hours and serum-starved. Before analysis, coverslips were transferred to recording media (culture media lacking phenol red and sodium bicarbonate buffered with 25 mM HEPES and supplemented with 3.5 g/L sucrose). To prevent photobleaching, Oxyrase (30 μl/ml, Oxyrase Inc., Mansfield, Ohio) was added to the recording media immediately before sealing cells in a double coverslip-enclosed chamber.

Time-lapse Microscopy and Image Acquisition

Microtubules were observed using a Nikon Eclipse E800 fluorescence microscope with a plan apochromat 1.4 N.A.× 100 objective lens. The stage was enclosed in a Pyrex box and maintained at 36±1° C. by a forced air heating system. Thirty images of each cell were acquired at 4-s intervals using a Photometrics CoolSNAP HQ digital camera (Tucson, Ariz.) driven by Metamorph software (Universal Imaging, Media, Pa.) at 10 MHz, with a 300 ms exposure time, a gain of 2, and 2×2 binning to enhance brightness.

Analysis of Microtubule Dynamics

The positions of the plus ends of microtubules over time were tracked using the Metamorph Track Points application exported to Microsoft Excel and analyzed using Real Time Measurement software. The lengths of individual microtubules were graphed as a function of time. Individual growth and shortening rates were determined by linear regression. Changes of $\geq 0.5$ μm between two points were considered to be growth or shortening events, and changes of <0.5 μm between two points were considered to be periods of attenuated dynamics or pause. At least 25 microtubules were analyzed for each condition. Results are the mean and standard deviation of at least three independent experiments.

The time-based catastrophe frequency for each microtubule was calculated by dividing the number of catastrophes per microtubule by the time spent in growth or attenuation. The time-based rescue frequency per microtubule was calculated by dividing the total number of rescues per microtubule by the time spent shortening. The distance-based catastrophe and rescue frequencies were calculated similarly by dividing the number of transitions by the length grown or shortened, respectively. Microtubules that were visible for $\leq 2$ min were included in the frequency analysis. Dynamicity per microtubule was calculated as the length grown and shortened divided by the total life span of the microtubule. Microtubules that were visible for $\geq 0.3$ min were included in the dynamicity analysis.

Cell Cycle Progression Blocked at Prometaphase

Figure 51:
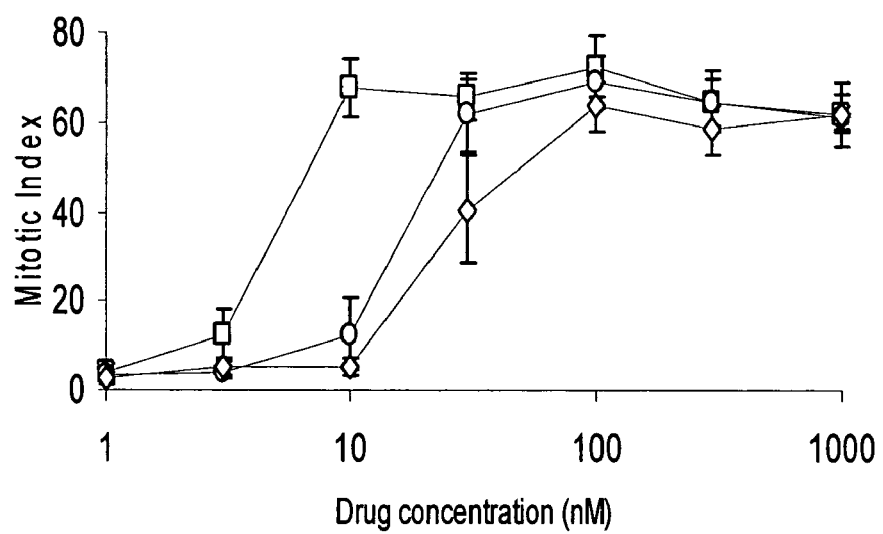
FIG. 51 depicts log [compound] response curves for mitotic progression inhibition by KPU-02, CA4, and CLC in MCF7 cells cultured in the presence of KPU-02 (○), CA4 (□), and colchicine (◇).

The concentration range for KPU-02, CA4 and CLC over which cells accumulate in mitosis were determined. After 20 hours, 60-70% of cells were inhibited at prometaphase, compared to 30-40% of cells at metaphase in studies on MT depolymerizers such as the vinca alkaloids and 2-methoxyestradiol, and MT stabilizers such as taxol, epothilone B, and discodermolide (Jordan M A (2002) Mechanism of action of antitumor drugs that interact with microtubules and tubulin. *Current Medicinal Chemistry—Anti-Cancer Agents* 2: 1-17, which is incorporated herein by reference in its entirety). The drug concentration necessary for 50% maximal mitotic block ($IC_{50}$) was evaluated between 1 nM and 1 μM drug (FIG. 51). FIG. 51 depicts log [Drug] response curves for mitotic progression inhibition by KPU-02, CA4, and CLC. MCF7 cells were cultured in the presence of NPI-2358 (○), CA4 (□), and colchicine (◇). To evaluate mitotic indices, MCF7 cells were plated at a density of 3×10⁴ cells/ml in six-well plates. After 24 hours, cells were incubated in the absence or presence of drug over a range of concentrations (1 nM to 1 μM) for 20 hours. Cells were fixed and stained with DAPI to visualize nuclei. Fluorescence microscopy was used to determine mitotic indices. Results are the mean and standard deviation of three or four experiments in which 300 cells were counted for each drug concentration. The mitotic block $IC_{50}$ for KPU-02 was 17.4±1.2 nM, CA4 was 5.4±0.7 nM, and CLC was 23.8±3.1 nM (Table 23).

TABLE 23

Inhibition of mitotic progression.

| Compound | Mitotic block Ave. IC50 ± sd (nM) | n |
|---|---|---|
| KPU-02 | 17.4 ± 1.2 | 4 |
| CA4 | 5.4 ± 0.7 | 3 |
| CLC | 23.8 ± 3.1 | 4 |

Most MT-targeting agents block mitosis at the metaphase to anaphase transition. Mitotic block at the metaphase to anaphase transition is associated with suppression of MT dynamics. Without being bound to any particular theory, the earlier prometaphase block, together with the depletion of MT polymer, suggests a distinct mechanism of action for KPU-02 as compared with other MT depolymerizing drugs, e.g., vinblastine, which at low concentrations stabilize MT dynamics.

Depolymerization of the Mitotic Spindle and the Interphase Array MTs

Figure 52:
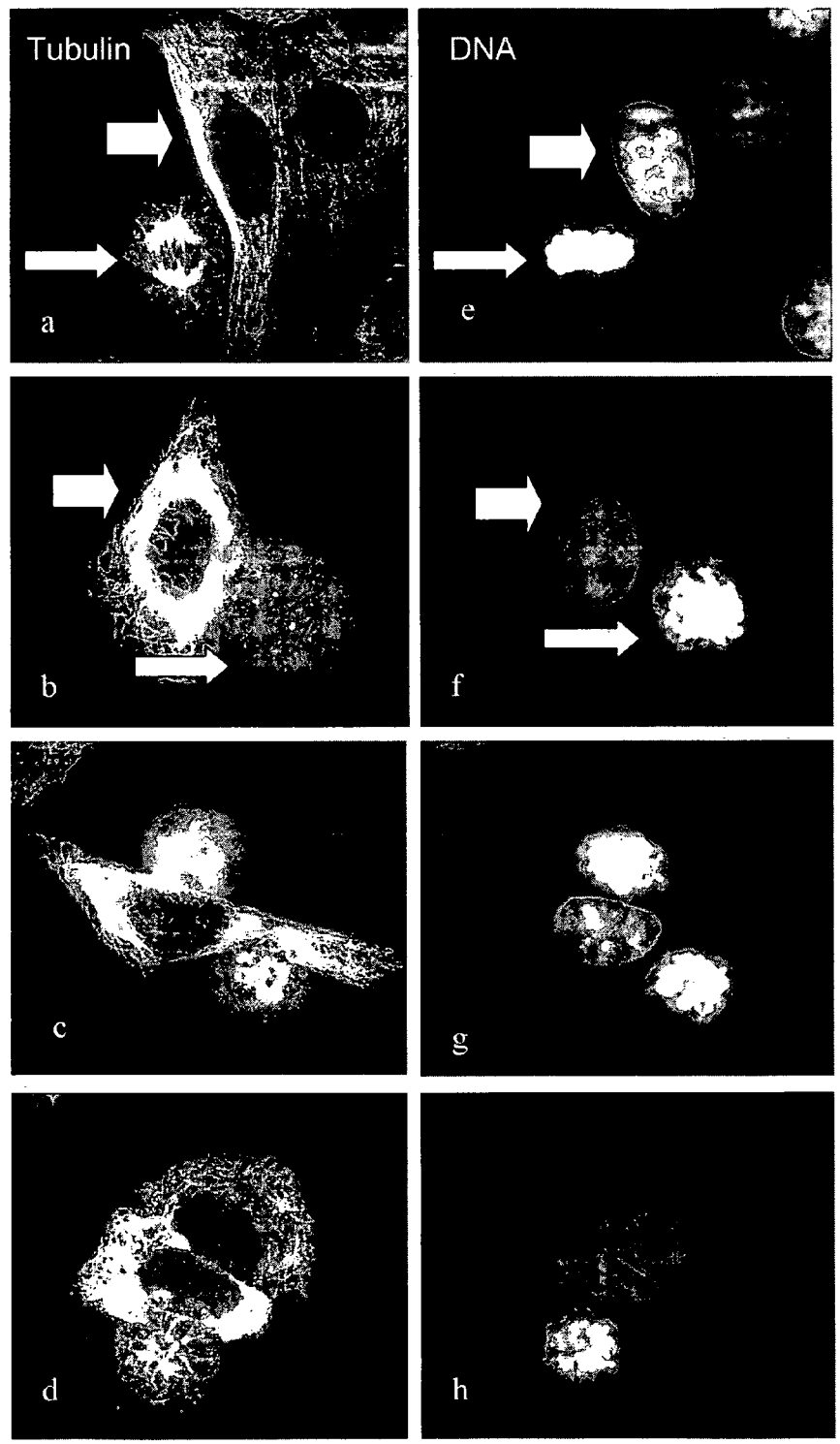
FIG. 52 depicts immunofluorescence microscopy images of MCF7 cells. a-d: Tubulin in control—(a) Tubulin in control, (b) KPU-02, (c) CA4, and (d) CLC treated cells; e-h: DNA in control—(e) DNA in control, (f) KPU-02, (g) CA4, and (h) CLC treated cells.

KPU-02, CA4, and CLC were observed to be potent microtubule depolymerizers in MCF7 cells. Although mitotic spindle microtubules are more susceptible to depolymerization and/or inhibition of polymerization than interphase array microtubules, both microtubule populations were affected (FIG. 52). FIG. 52 depicts immunofluorescence microscopy images of MCF7 cells. Interphase arrays are relatively more stable to depolymerization by KPU-02, CA4 and CLC than mitotic spindles. Cells were prepared and seeded as for mitotic progression and treated with the mitotic block $IC_{50}$ for each drug for 20 hours. Cells were incubated in a mouse monoclonal cocktail of anti-alpha- and beta-tubulin, DM1A/DM1B then stained with FITC-conjugated secondary antibody and DAPI. a-d, Tubulin in control (a), KPU-02 (b), CA4 (c), and CLC (d) treated cells, and e-h, DNA in control (e), KPU-02 (f), CA4 (g), and CLC (h) treated cells. Narrow arrows indicate mitotic spindle polymer and mitotic chromosomes and thicker arrows indicate interphase arrays and nuclei.

Figure 53A:
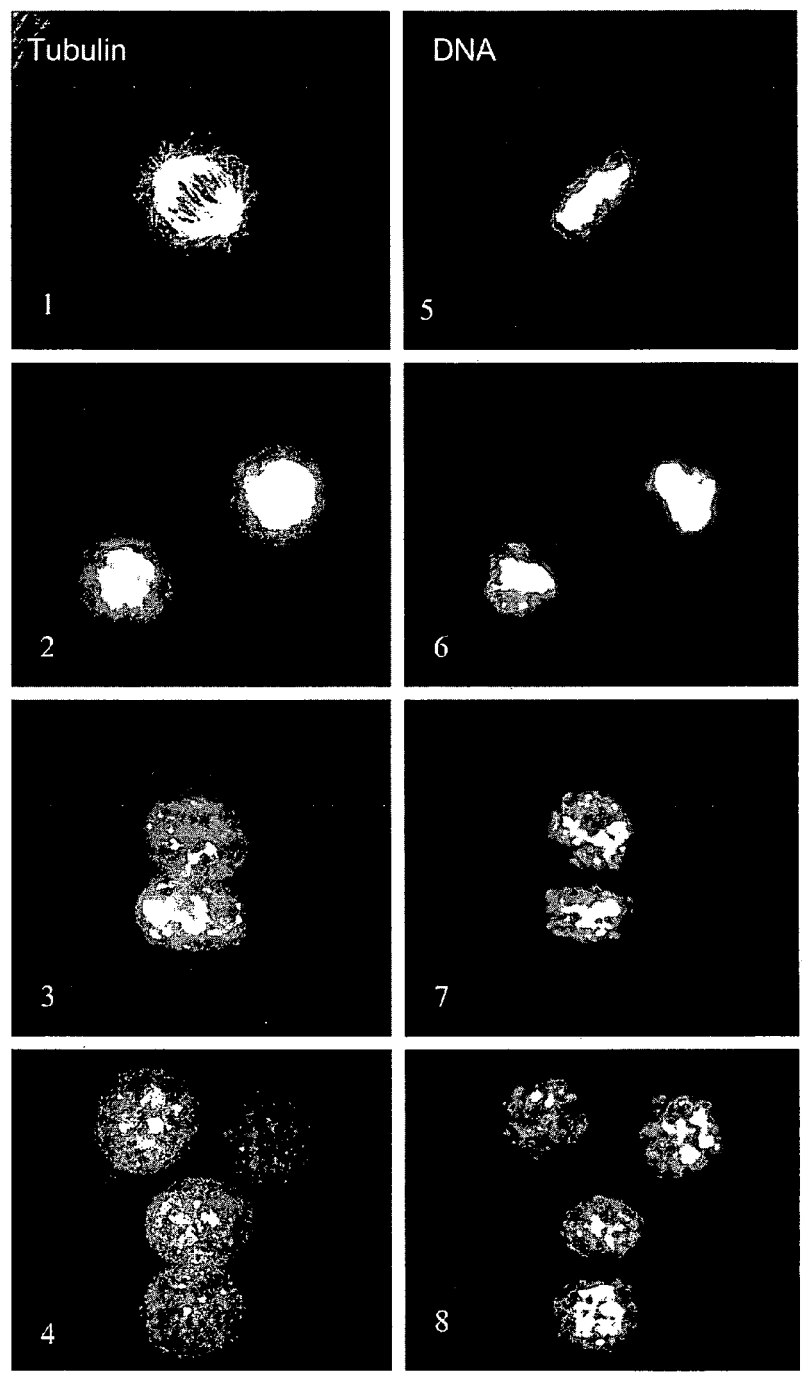
FIG. 53A depicts immunofluorescence microscopy images of MCF7 cells treated with KPU-02
Figure 53B:
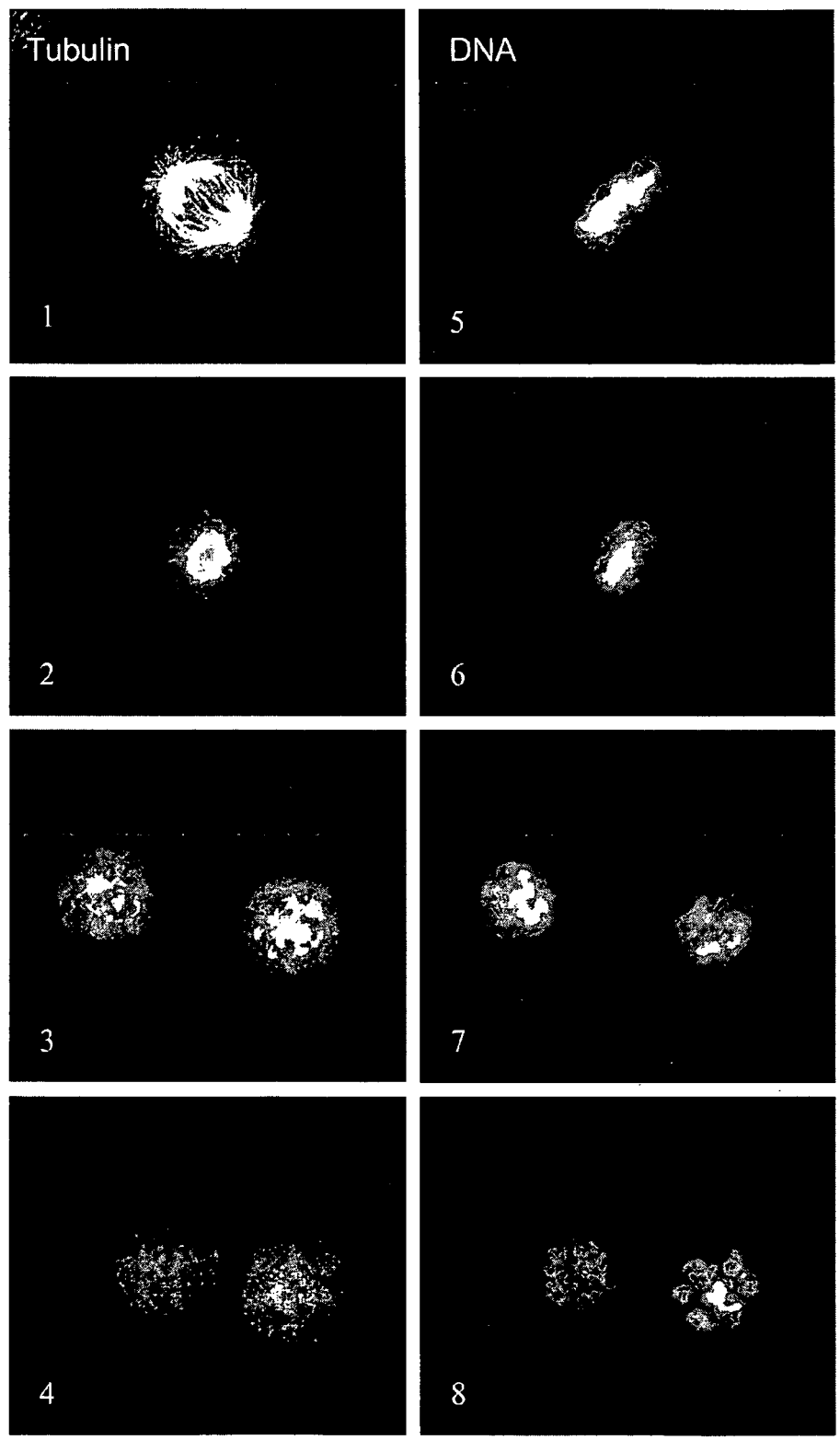
FIG. 53B depicts immunofluorescence microscopy images of MCF7 cells treated with CA4.
Figure 53C:
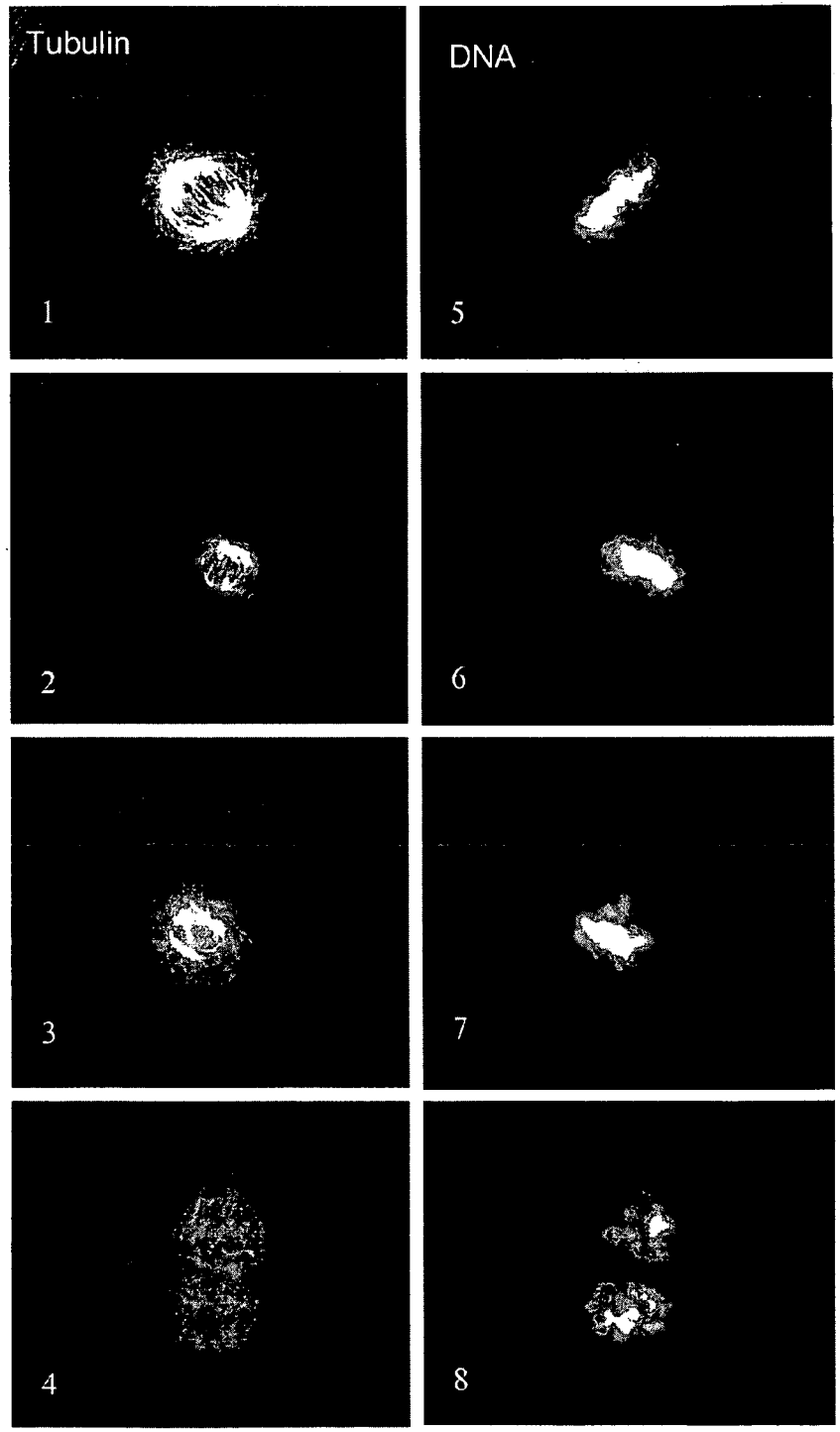
FIG. 53C depicts immunofluorescence microscopy images of MCF7 cells treated with CLC.

At the $IC_{25}$ for mitotic block, KPU-02 dramatically altered spindle morphology. FIG. 53A-C depicts immunofluorescence microscopy images of MCF7 cells treated with KPU-02 (A), CA4 (B), and CLC (C) for 20 hours. Mitotic spindle destruction with increasing drug concentration. 1-4, Alpha and beta tubulin in control (1), a concentration of $IC_{25}$ for mitotic block (2), the $IC_{50}$ for mitotic block (3), and twice the $IC_{50}$ for mitotic block (4); 5-8, corresponding images of DNA for the adjoining panels. There were no normal, bipolar spindles at the $IC_{25}$ for KPU-02 or CA4 (FIGS. 53A and B). Compound-treated cells had monopolar or bipolar spindles with uncongressed chromosomes. In contrast, normal bipolar spindles persist at the $IC_{25}$ for CLC (FIG. 53C). At the $IC_{50}$ for KPU-02, 75% of the mitotic cells contained asters or foci of tubulin, and the remaining cells had no detectable mitotic polymer. In the presence of CLC, half of the cells were bipolar with uncongressed chromosomes and the remaining half were monopolar. At concentrations of twice the $IC_{50}$ for mitotic block, there was little detectable MT polymer in mitotic cells treated with KPU-02, CA4, or CLC.

Figure 54A:
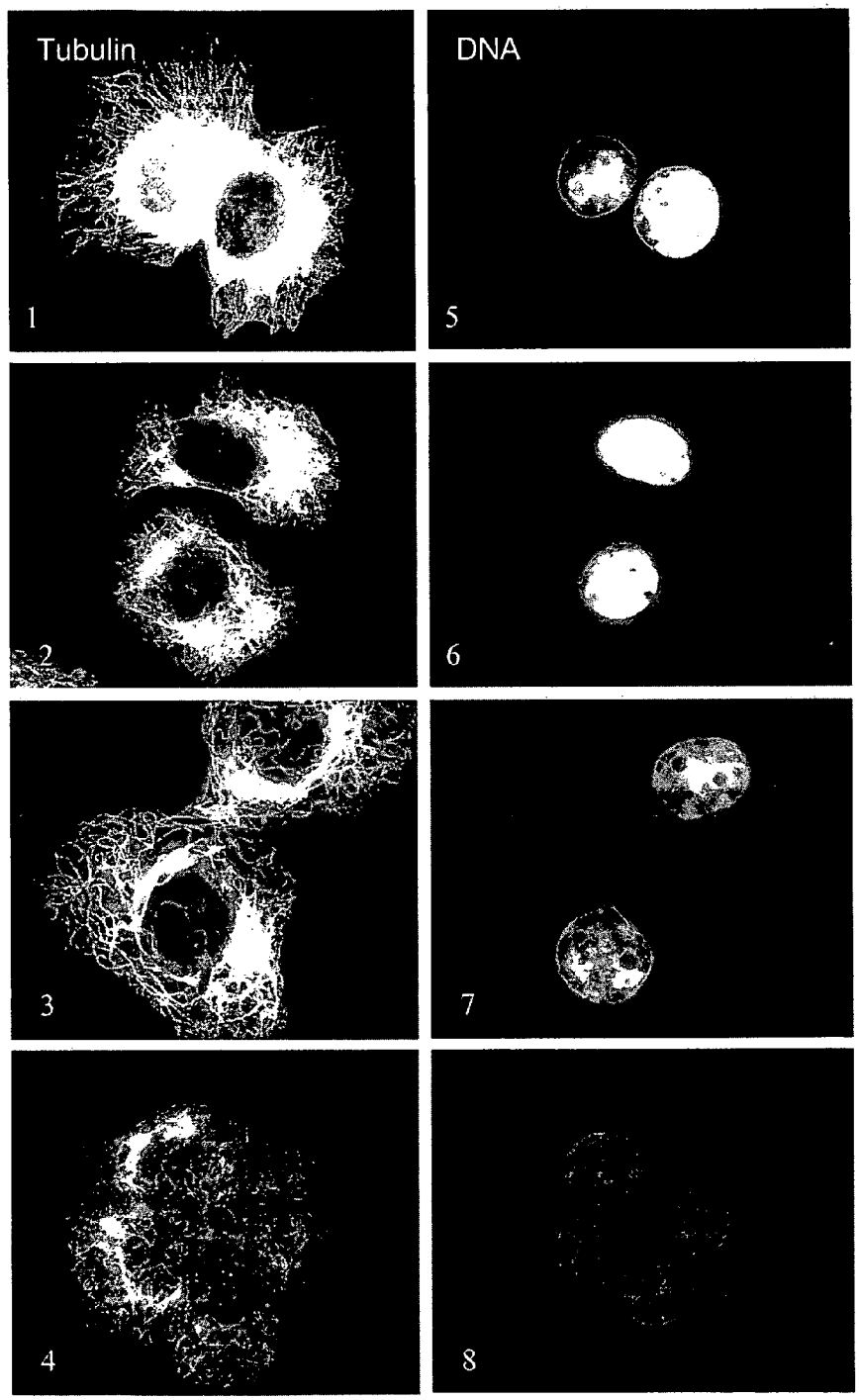
FIG. 54A depicts immunofluorescence microscopy images of MCF7 cells treated with KPU-02
Figure 54B:
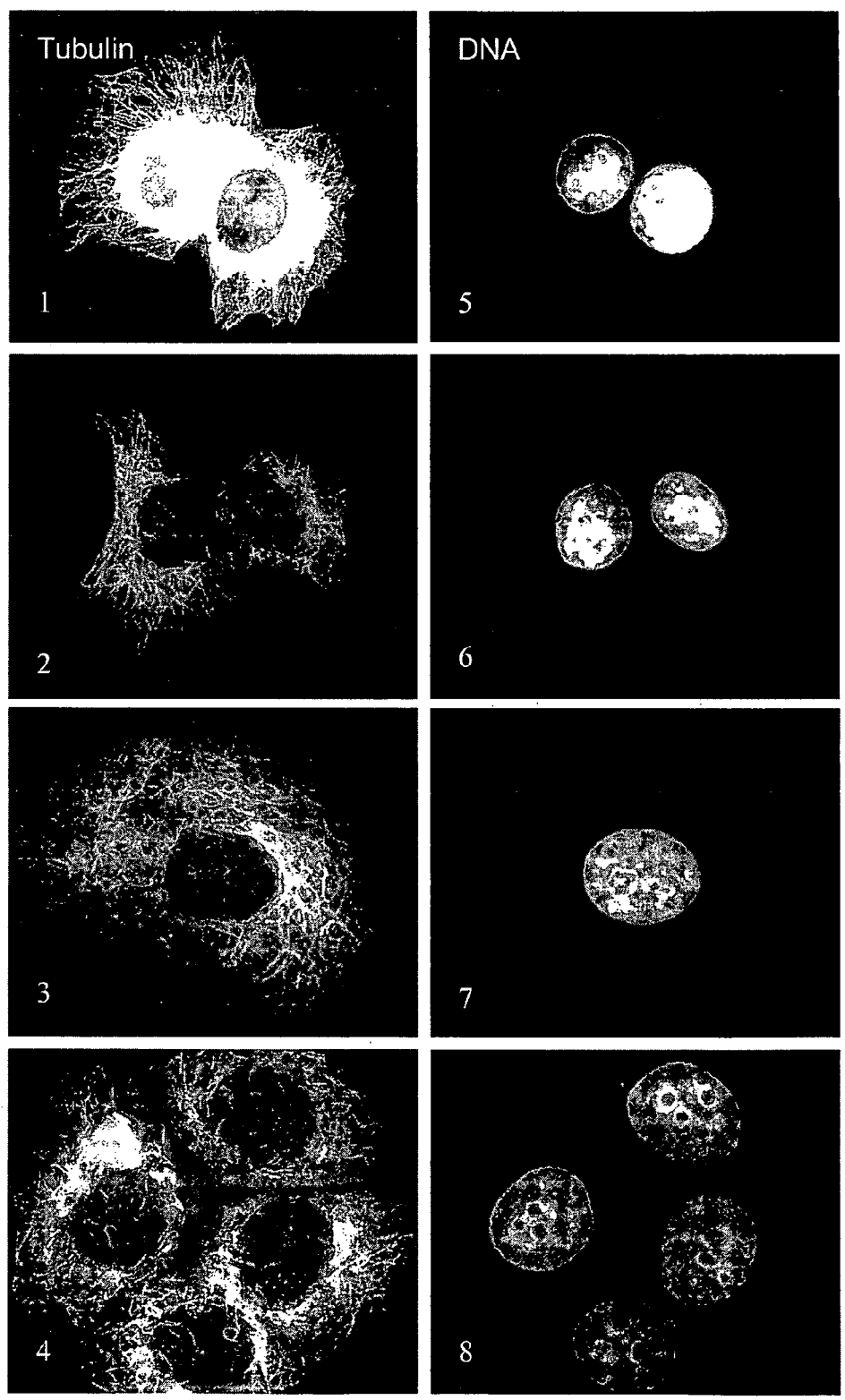
FIG. 54B depicts immunofluorescence microscopy images of MCF7 cells treated with CA4.
Figure 54C:
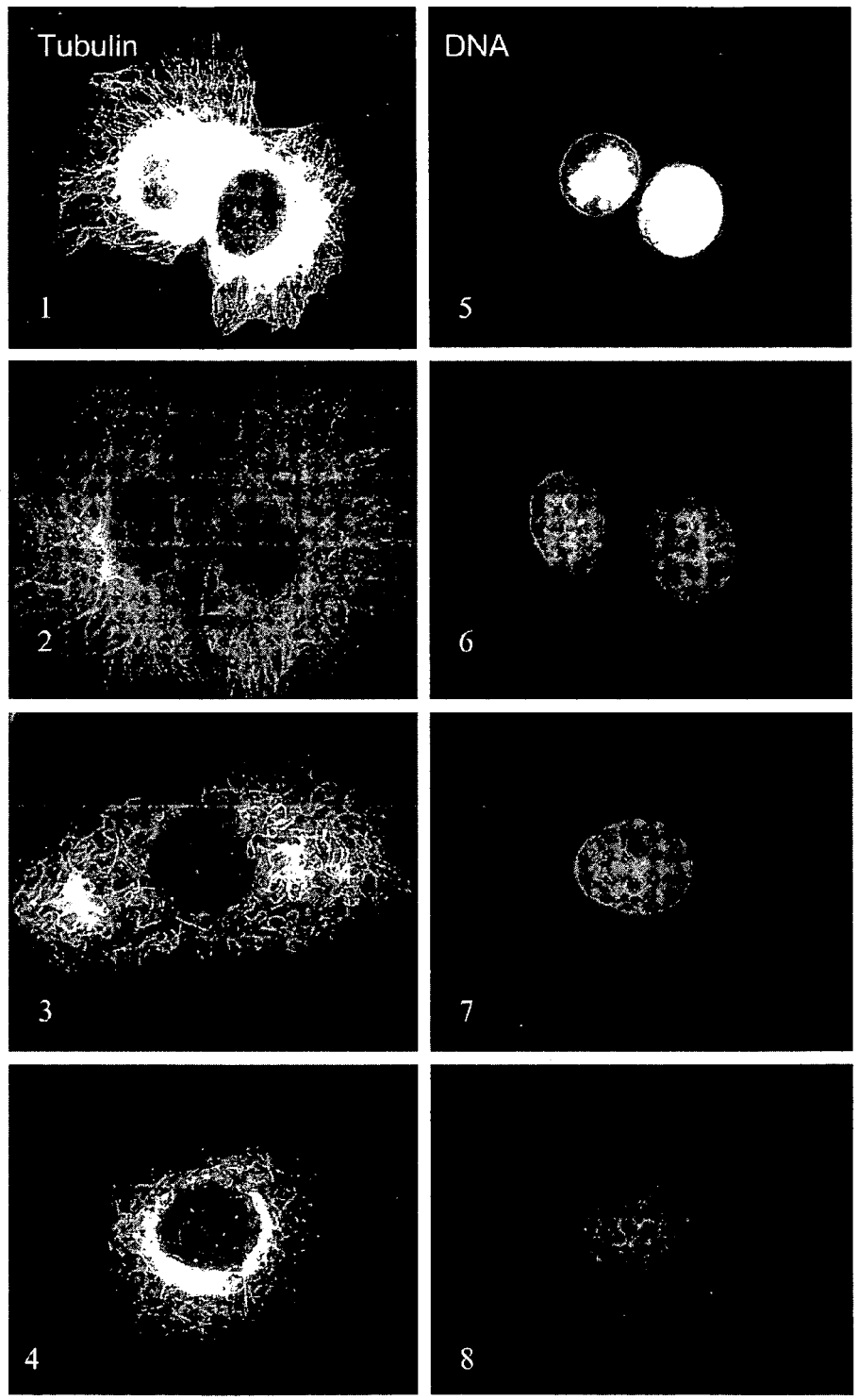
FIG. 54C depicts immunofluorescence microscopy images of MCF7 cells treated with CLC.

Microtubule interphase arrays were more resistant to depolymerization than mitotic spindles for all of the compounds examined (FIG. 52). However, a qualitative decrease in polymer was observed in a dose-dependent manner for all three compounds (FIG. 54 A-C). FIG. 54A-C depicts immunofluorescence microscopy images of MCF7 cells treated with KPU-02 (a), CA4 (b), and CLC (c) for 20 hours. Interphase MT depolymerization with increasing drug concentration. 1-4, Alpha and beta tubulin in control (1), a concentration of $IC_{25}$ for mitotic block (2), the $IC_{50}$ for mitotic block (3), and $2 \times IC_{50}$ for mitotic block (4); 5-8, corresponding images of DNA for the adjoining panels. Presumably, tubulin is sequestered in these interphase cells, despite the presence of intracellular stabilizing MAPs, just as MAP-rich tubulin is sequestered in in vitro polymer mass assays.

Lack of Suppression or Modulation of MT Dynamic Instability in Living MCF7 Cells KPU-02, as well as CA4, did not have a measurable effect on MT dynamic instability at concentrations effecting 25% (Table 24) or 50% (Table 25) of the maximal mitotic block in MCF7 cells. Without being bound by any particular theory, these data suggest that the antiproliferative mechanism of action of KPU-02 (and CA4) is primarily due to inhibition of MT polymerization, rather than suppression of microtubule dynamics.

TABLE 24

MT dynamic instability at the mitotic block.

|  | Control | sd | NPI-2358 | sd | CA4 | sd | CLC | sd |
|---|---|---|---|---|---|---|---|---|
| Mean rates (μm/min) |  |  |  |  |  |  |  |  |
| Growth | 9.03 | 4.66 | 11.89 | 6.23 | 10.59 | 4.75 | 11.31 | 8.46 |
| Shortening | 32.85 | 18.06 | 31.87 | 15.12 | 40.21 | 18.90 | 29.17 | 17.13 |
| Mean duration (min) |  |  |  |  |  |  |  |  |
| Growth | 0.41 | 0.27 | 0.31 | 0.15 | 0.27 | 0.12 | 0.26 | 0.14 |
| Shortening | 0.20 | 0.07 | 0.20 | 0.07 | 0.21 | 0.09 | 0.23 | 0.29 |
| Attenuation | 0.58 | 0.38 | 0.73 | 0.36 | 0.45 | 0.32 | 0.56 | 0.43 |
| % time spent |  |  |  |  |  |  |  |  |
| Growth | 41.83 |  | 29.66 |  | 35.31 |  | 33.07 |  |
| Shortening | 18.57 |  | 20.53 |  | 25.19 |  | 25.96 |  |
| Attenuation | 39.60 |  | 49.81 |  | 39.50 |  | 40.97 |  |
| Freq. of (min-1) |  |  |  |  |  |  |  |  |
| Catastrophe | 1.15 |  | 1.27 |  | 1.52 |  | 1.57 |  |
| Rescue | 3.05 |  | 2.79 |  | 1.90 |  | 2.95 |  |
| Dyn. (μm/min) | 9.87 |  | 10.07 |  | 13.87 |  | 11.31 |  |
| MTs/cells | 16/30 |  | 11/33 |  | 13/39 |  | 8/26 |  |
| Minutes | 40.66 |  | 43.69 |  | 39.62 |  | 35.29 |  |

TABLE 25

MT dynamic instability at the mitotic block.

|  | Control | sd | NPI-2358 | sd | CA4 | sd |
|---|---|---|---|---|---|---|
| Mean rates (μm/min) |  |  |  |  |  |  |
| Growth | 9.03 | 4.66 | 10.63 | 6.78 | 11.21 | 5.64 |
| Shortening | 32.85 | 18.06 | 34.06 | 12.84 | 29.88 | 18.87 |
| Mean duration (min) |  |  |  |  |  |  |
| Growth | 0.41 | 0.27 | 0.30 | 0.18 | 0.33 | 0.18 |
| Shortening | 0.20 | 0.07 | 0.22 | 0.08 | 0.22 | 0.08 |
| Attenuation | 0.58 | 0.38 | 0.61 | 0.41 | 0.55 | 0.44 |
| % time spent |  |  |  |  |  |  |
| Growth | 41.83 |  | 33.02 |  | 43.64 |  |
| Shortening | 18.57 |  | 20.92 |  | 20.13 |  |
| Attenuation | 39.60 |  | 46.06 |  | 36.23 |  |
| Freq. of (min-1) |  |  |  |  |  |  |
| Catastrophe | 1.15 |  | 1.22 |  | 1.09 |  |
| Rescue | 3.05 |  | 2.60 |  | 2.79 |  |
| Dynamicity (μm/min) | 9.87 |  | 10.64 |  | 10.91 |  |
| MTs/cells | 30/16 |  | 25/11 |  | 29/9 |  |
| Minutes | 40.66 |  | 33.13 |  | 39.14 |  |

The examples described above are set forth solely to assist in the understanding of the invention. Thus, those skilled in the art will appreciate that the disclosed methods and compounds encompass and may otherwise provide further derivatives of dehydrophenylahistins.

One skilled in the art would readily appreciate that the present invention is well adapted to obtain, for example, the ends and advantages mentioned, as well as others inherent. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the invention disclosed herein without departing from the scope and spirit of the invention.

As noted above, all patents and publications mentioned in the specification are indicative of the levels of those skilled in the art to which the invention pertains. All patents and publications are hereby incorporated by reference herein to the extent allowable by law, such that each individual patent and publication may be treated as specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

The invention claimed is:

1. A method for treating a condition in an animal, comprising administering to the animal a compound in an amount that is effective to reduce vascular proliferation or in an amount that is effective to reduce vascular density, wherein the condition is selected from the group consisting of breast cancer, colon cancer, lung cancer, prostate cancer, melanoma, angiofibroma, Kaposi sarcoma, hemangioma, acoustic neuroma, and neurofibroma, wherein the compound has the structure of Formula (I)

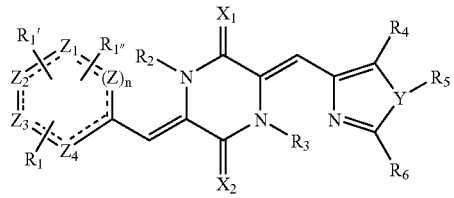

wherein
- $R_1$ is selected from the group consisting of a hydrogen atom, a halogen atom, hydroxy, and cyano, or selected from the group consisting of saturated $C_1$-$C_{24}$ alkyl, unsaturated $C_1$-$C_{24}$ alkenyl, cycloalkyl, cycloalkenyl, alkoxy, cycloalkoxy, aryl, amino, nitro, azido, phenyl, carboxy, —CO—O—$R_7$, alkylthio, halogenated alkyl including polyhalogenated alkyl, halogenated carbonyl, and carbonyl —CCO—$R_7$, each optionally substituted with one or more of alkoxy, cycloalkyl, cycloalkenyl, acyl, aclyamino, acyloxy, amino, aminoacyl, aminoacyloxy, oxyacylamino, cyano, halogen, hydroxy, carboxy, carboxyalkyl, aryl, arlyoxy, hydroxyamino, alkoxyamino, nitro, —SO-alkyl, —SO-aryl, —$SO_2$-alkyl, and —$SO_2$-aryl;
- $R_7$ is selected from a hydrogen atom or a halogen atom or selected from the group consisting of saturated $C_1$-$C_{24}$ alkyl, unsaturated $C_1$-$C_{24}$ alkenyl, cycloalkyl, cycloalkenyl, alkoxy, cycloalkoxy, aryl, amino, substituted amino, nitro, azido, and phenyl groups, each optionally substituted with one or more of alkoxy, cycloalkyl, cycloalkenyl, acyl, aclyamino, acyloxy, amino, aminoacyl, aminoacyloxy, oxyacylamino, cyano, halogen, hydroxy, carboxy, carboxyalkyl, aryl, arlyoxy, hydroxyamino, alkoxyamino, nitro, —SO-alkyl, —SO-aryl, —$SO_2$-alkyl, and —$SO_2$-aryl;
- $R_4$ is a branched alkyl or branched alkenyl group;
- $R_1'$ and $R_1''$ are each independently selected from the group consisting of a hydrogen atom, a halogen atom, hydroxy, and cyano, or independently selected from the group consisting of saturated $C_1$-$C_{24}$ alkyl, unsaturated $C_1$-$C_{24}$ alkenyl, cycloalkyl, cycloalkenyl, alkoxy, cycloalkoxy, aryl, amino, nitro, azido, phenyl, carboxy, —CO—O—$R_7$, alkylthio, halogenated alkyl including polyhalogenated alkyl, halogenated carbonyl, and carbonyl —CCO—$R_7$, each optionally substituted with one or more of alkoxy, cycloalkyl, cycloalkenyl, acyl, aclyamino, acyloxy, amino, aminoacyl, aminoacyloxy, oxyacylamino, cyano, halogen, hydroxy, carboxy, carboxyalkyl, aryl, arlyoxy, hydroxyamino, alkoxyamino, nitro, —SO-alkyl, —SO- aryl, —$SO_2$-alkyl, and —$SO_2$-aryl;
- R, $R_1'$ and $R_1''$ are either covalently bound to one another or are not covalently bound to one another;
- $R_2$, $R_3$, $R_5$, and $R_6$ are hydrogen;
- $X_1$ and $X_2$ are oxygen;
- Y is a nitrogen atom;
- n is an integer equal to one;
- Z, $Z_1$, $Z_2$, $Z_3$ and $Z_4$ are each a carbon atom; and
- the dashed bonds may be either single or double bonds.

2. The method of claim 1, wherein said animal is a human.

3. The method of claim 1, wherein the compound is

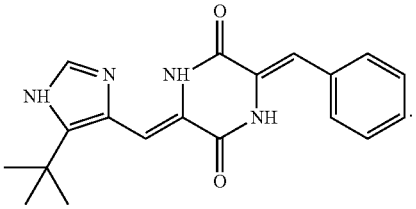

4. The method of claim 1, wherein
$R_1$ is selected from the group consisting of a hydrogen atom, a halogen atom, hydroxy, and cyano, or selected from the group consisting of saturated $C_1$-$C_{24}$ alkyl, unsaturated $C_1$-$C_{24}$ alkenyl, alkoxy, aryl, amino, azido, phenyl, carboxy, —CO—O—$R_7$, alkylthio, halogenated alkyl including polyhalogenated alkyl, halogenated carbonyl, and carbonyl —CCO—$R_7$, each optionally substituted with one or more of alkoxy, cycloalkyl, cycloalkenyl, acyl, aclyamino, acyloxy, amino, aminoacyl, aminoacyloxy, oxyacylamino, cyano, halogen, hydroxy, carboxy, carboxyalkyl, aryl, arlyoxy, hydroxyamino, alkoxyamino, nitro, —SO-alkyl, —SO-aryl, —$SO_2$-alkyl, and —$SO_2$-aryl; and $R_1'$ and $R_1''$ are each independently selected from the group consisting of a hydrogen atom, a halogen atom, hydroxy, and cyano, or independently selected from the group consisting of saturated $C_1$-$C_{24}$ alkyl, unsaturated $C_1$-$C_{24}$ alkenyl, alkoxy, aryl, amino, nitro, azido, phenyl, carboxy, —CO—O—$R_7$, alkylthio, halogenated alkyl including polyhalogenated alkyl, halogenated carbonyl, and carbonyl —CCO—$R_7$, each optionally substituted with one or more of alkoxy, cycloalkyl, cycloalkenyl, acyl, aclyamino, acyloxy, amino, aminoacyl, aminoacyloxy, oxyacylamino, cyano, halogen, hydroxy, carboxy, carboxyalkyl, aryl, arlyoxy, hydroxyamino, alkoxyamino, nitro, —SO-alkyl, —SO- aryl, —$SO_2$-alkyl, and —$SO_2$-aryl.

5. The method of claim 1, wherein
$R_1$ is selected from the group consisting of a hydrogen atom, a halogen atom, hydroxy, and cyano, or selected from the group consisting of saturated $C_1$-$C_{24}$ alkyl, unsaturated $C_1$-$C_{24}$ alkenyl, alkoxy, aryl, amino, azido, phenyl, carboxy, —CO—O—$R_7$, alkylthio, halogenated alkyl including polyhalogenated alkyl, halogenated carbonyl, and carbonyl —CCO—$R_7$, each optionally substituted with one or more of alkoxy, cycloalkyl, cycloalkenyl, acyl, aclyamino, acyloxy, amino, aminoacyl, aminoacyloxy, oxyacylamino, cyano, halogen, hydroxy, carboxy, carboxyalkyl, aryl, arlyoxy, hydroxyamino, alkoxyamino, nitro, —SO-alkyl, —SO-aryl, —$SO_2$-alkyl, and —$SO_2$-aryl; and $R_1'$ and $R_1''$ are hydrogen.

6. The method of claim 1, wherein $R_4$ is tert-butyl.

7. The method of claim 1, wherein $R_4$ is 2-methyl-butenyl.

* * * * *